(12) United States Patent
Tartaglia et al.

(10) Patent No.: US 10,954,268 B2
(45) Date of Patent: *Mar. 23, 2021

(54) METHOD OF TREATING MELANOCORTIN-4 RECEPTOR-ASSOCIATED DISORDERS IN HETEROZYGOUS CARRIERS

(71) Applicant: RHYTHM PHARMACEUTICALS, INC., Boston, MA (US)

(72) Inventors: Louis Anthony Tartaglia, Newton, MA (US); Bart Henderson, Belmont, MA (US); Leonardus H. T. Van Der Ploeg, Newton, MA (US)

(73) Assignee: RHYTHM PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,889

(22) Filed: Apr. 15, 2019

(65) Prior Publication Data

US 2020/0017546 A1 Jan. 16, 2020

Related U.S. Application Data

(63) Continuation of application No. 16/117,767, filed on Aug. 30, 2018, now abandoned, which is a continuation of application No. 15/789,118, filed on Oct. 20, 2017, now Pat. No. 10,167,312, which is a continuation of application No. 14/369,116, filed as application No. PCT/US2012/072026 on Dec. 28, 2012, now Pat. No. 9,845,339.

(60) Provisional application No. 61/581,391, filed on Dec. 29, 2011.

(51) Int. Cl.
*A61K 38/00* (2006.01)
*C07K 5/08* (2006.01)
*A61K 38/08* (2019.01)
*C07K 14/68* (2006.01)
*C07K 14/72* (2006.01)
*C07K 7/06* (2006.01)

(52) U.S. Cl.
CPC ............ *C07K 5/0802* (2013.01); *A61K 38/08* (2013.01); *C07K 7/06* (2013.01); *C07K 14/68* (2013.01); *C07K 14/723* (2013.01)

(58) Field of Classification Search
None
See application file for complete search history.

(56) References Cited

U.S. PATENT DOCUMENTS

| | | | |
|---|---|---|---|
| 7,968,548 B2 | 6/2011 | Sharma et al. | |
| 8,039,435 B2 | 10/2011 | Dong et al. | |
| 8,114,844 B2 | 2/2012 | Sharma et al. | |
| 8,247,530 B2 | 8/2012 | Sharma et al. | |
| 8,263,608 B2 | 9/2012 | Shi et al. | |
| 8,349,797 B2 | 1/2013 | Dong et al. | |
| 8,563,000 B2 | 10/2013 | Dong et al. | |
| 9,155,777 B2 | 10/2015 | Halem et al. | |
| 9,845,339 B2 | 12/2017 | Tartaglia et al. | |
| 10,167,312 B2 | 1/2019 | Tartaglia et al. | |
| 2005/0267147 A1 | 12/2005 | Poitout et al. | |
| 2006/0173036 A1 | 8/2006 | Poitout et al. | |
| 2006/0281784 A1 | 12/2006 | Poitout et al. | |
| 2007/0021433 A1 | 1/2007 | Fan et al. | |
| 2009/0176712 A1 | 7/2009 | Haskell-Luevano | |
| 2009/0209531 A1 | 8/2009 | Poitout et al. | |
| 2010/0120783 A1 | 5/2010 | Lee et al. | |
| 2010/0173834 A1 | 7/2010 | Dong | |
| 2010/0184646 A1 | 7/2010 | Dong et al. | |
| 2010/0190793 A1 | 7/2010 | Weber et al. | |
| 2010/0279922 A1 | 11/2010 | Dong et al. | |
| 2010/0280079 A1 | 11/2010 | Eisinger et al. | |
| 2010/0311647 A1 | 12/2010 | Halem et al. | |
| 2010/0311648 A1 | 12/2010 | Dodd et al. | |
| 2011/0065652 A1 | 3/2011 | Shi et al. | |
| 2011/0183886 A1 | 7/2011 | Dong et al. | |
| 2011/0263490 A1 | 10/2011 | Kaplan et al. | |
| 2012/0135923 A1 | 5/2012 | Halem et al. | |
| 2012/0225816 A1 | 9/2012 | Dong et al. | |
| 2012/0226018 A1 | 9/2012 | Dong | |
| 2014/0127303 A1 | 5/2014 | Richard et al. | |
| 2015/0157719 A1 | 6/2015 | Baronnet et al. | |
| 2016/0022764 A1 | 1/2016 | Sharma et al. | |
| 2018/0311309 A1 | 11/2018 | Ploeg et al. | |

FOREIGN PATENT DOCUMENTS

| | | |
|---|---|---|
| WO | 2005/000339 A2 | 1/2005 |
| WO | 2007/008684 A2 | 1/2007 |
| WO | 2007/008704 A2 | 1/2007 |
| WO | 2008/087186 A2 | 7/2008 |
| WO | 2008/087187 A1 | 7/2008 |
| WO | 2008/087188 A2 | 7/2008 |
| WO | 2008/087189 A2 | 7/2008 |

(Continued)

OTHER PUBLICATIONS

Extended European Search Report from Application No. 19158126.3 dated Jun. 18, 2019.

(Continued)

*Primary Examiner* — Jeanette M Lieb

(74) *Attorney, Agent, or Firm* — Lando & Anastasi, LLP

(57) ABSTRACT

A method of treating a disorder in a subject. The method comprises administering to said subject an effective amount of an agonist of the melanocortin-4 receptor (MC4R). The subject is a heterozygous carrier of an MC4R mutation, and the disorder results from an attenuated response of MC4R to α-melanocortin stimulating hormone (α-MSH).

18 Claims, 4 Drawing Sheets

Specification includes a Sequence Listing.

(56) References Cited

FOREIGN PATENT DOCUMENTS

| | | | |
|---|---|---|---|
| WO | 2008/116665 | A1 | 10/2008 |
| WO | 2008/147556 | A2 | 12/2008 |
| WO | 2008/156677 | A2 | 12/2008 |
| WO | 2009/010299 | A1 | 1/2009 |
| WO | 2009/061411 | A2 | 5/2009 |
| WO | 2009/151383 | A1 | 12/2009 |
| WO | 2009/152079 | A1 | 12/2009 |
| WO | 2010/015972 | A1 | 2/2010 |
| WO | 2010/025142 | A1 | 3/2010 |
| WO | 2010/034500 | A1 | 4/2010 |
| WO | 2010/037081 | A1 | 4/2010 |
| WO | 2010/052255 | A1 | 5/2010 |
| WO | 2010/052256 | A1 | 5/2010 |
| WO | 2010/060901 | A1 | 6/2010 |
| WO | 2010/065799 | A2 | 6/2010 |
| WO | 2010/065800 | A1 | 6/2010 |
| WO | 2010/065801 | A1 | 6/2010 |
| WO | 2010/065802 | A2 | 6/2010 |
| WO | 2010/081666 | A1 | 7/2010 |
| WO | 2010/096854 | A1 | 9/2010 |
| WO | 2010/144341 | A2 | 12/2010 |
| WO | 2010/144344 | A2 | 12/2010 |
| WO | 2011017209 | A1 | 2/2011 |
| WO | 2011/026015 | A2 | 3/2011 |
| WO | 2011/060352 | A1 | 5/2011 |
| WO | 2011/104378 | A1 | 9/2011 |
| WO | 2011/104379 | A1 | 9/2011 |
| WO | 2012/172433 | A2 | 12/2012 |
| WO | 2013/182653 | A1 | 12/2013 |
| WO | 2014/144260 | A1 | 9/2014 |
| WO | 2014/144842 | A2 | 9/2014 |
| WO | 2019/099735 | A1 | 5/2019 |

OTHER PUBLICATIONS

Baker et al. "Childhood Body-Mass Index and the Risk of Coronary Heart Disease in Adulthood," The New England Journal of Medicine (2007) vol. 357. No. 23, pp. 2329-2337.

Farooqi et al. "Dominant and recessive inheritance of morbid obesity associated with melanocortin 4 receptor deficieincy", The Journal of Clinical Investigation (2000) vol. 106, No. 2, pp. 271-279.

International Search Report for PCT/US2012/072026 filing date Dec. 28, 2012.

Online Mendelian Inheritance in Man (OMIM), a database of human genes and genetic disorders, under the accession No. 155541 (MC4R) (more precisely, accession Nos. 155541.0001-155541.0023) at the URL <http://omim.org/entry/155541>; created on Oct. 1, 1993; last edited on Jun. 23, 2015.

Reinehr et al. "Lifestyle Intervention in Obese Children With Variations in the Melanocortin 4 Receptor Gene," Obesity Journal (2009), vol. 17 No. 2.

Vaisse et al. "Melanocortin-4 receptor mutations are a frequent and heterogeneous cause of morbid obesity", The Journal of Clinical Investigation (2000) vol. 106, No. 2, pp. 253-262.

Xiang et al. "Pharmacological characterization of 30 human melanocortin-4 receptor polymorphisms with the endogenous proopiomelanocortin-derived agonists, synthetic agonists, and the endogenous agouti-related protein antagonist." Biochemistry (2010), No. 49(22), pp. 4583-4600.

Partial European Search Report from 12863862.4 dated Sep. 21, 2015.

Govaerts et al., "Obesity-associated mutations in the melanocortin 4 receptor provide novel insights into its function" Peptides (2005) vol. 26 pp. 1909-1919.

Extended European Search Report for PCT/US2012072026 dated Apr. 18, 2016.

Table 1

Sequence variants of *MC4R* detected in 243 subjects with severe early-onset obesity

| Sequence Variant | Number of obese subjects with mutation[A] | Number of controls with mutation[B] | Number of subjects previously described |
|---|---|---|---|
| GT insertion at codon 279 | 2 | 0 | None |
| C deletion 28-bp downstream of stop codon | 1 | 0 | None |
| N62S | 1 (hom) | 0 | None |
| T112M | 1 | 0 | 2 (11, 12) |
| R165Q | 1 | 0 | None |
| V253I | 1 | 0 | None |
| C271Y | 1 | 0 | None |
| I251L | 7 | 3 | 1 (12) |
| V103I | 3 | 1 | 2 (11, 12) |

FIG. 2A

Table 2

MC4-R mutation screening in morbidly obese patients and nonobese controls

| Base change | Effect on amino acid sequence | Morbidly obese (n = 209) | Control 1 (n = 254) | Control 2 (n = 112) |
|---|---|---|---|---|
| A-307-G | Val103 Ile | 8 | 8 | 3 |
| A-751-C | Ile251Leu | 3 | 3 | 0 |
| C-593-T | Silent | 1 | ND | 1 |
| 47-48insG | 16 + 12 amino-acids | 1 | 0 | 0 |
| A-31-G | Thr11Ser | 1 | 0 | 0 |
| C-52-T | Arg18Cys | 1 | 0 | 0 |
| C-449-T | Thr150Ile | 1 | 0 | 0 |
| A-508-G | Ile170Val | 1 | 0 | 0 |
| C-493-T | Arg165Trp | 1 | 0 | 0 |
| T-749-A | Leu250Gln | 1 | 0 | 0 |
| T-902-C | Ile301Thr | 1 | 0 | 0 |

The morbidly obese and the control 2 populations were screened by PCR-SSCP. The control 1 population was screened by PCT-RFLP for every functionally relevant mutation detected in the morbidly obese population. ND, not determined.

FIG. 2B

METHOD OF TREATING MELANOCORTIN-4 RECEPTOR-ASSOCIATED DISORDERS IN HETEROZYGOUS CARRIERS

RELATED APPLICATIONS

The present application is a continuation of U.S. application Ser. No. 16/117,767, filed Aug. 30, 2018, which is a continuation of U.S. application Ser. No. 15/789,118, now U.S. Pat. No. 10,167,312, filed Oct. 20, 2017, which is a continuation of U.S. application Ser. No. 14/369,116, now U.S. Pat. No. 9,845,339, filed Jun. 26, 2014, which is a U.S. national stage application under 35 U.S.C. § 371 of International Application No. PCT/US2012/072026, filed Dec. 28, 2012, which claims the benefit of U.S. Provisional Application No. 61/581,391, filed Dec. 29, 2011. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 46051001.txt; created Dec. 26, 2012, 314 KB in size.

BACKGROUND OF THE INVENTION

Melanocortin 4 receptor (MC4R) mutations can result in genetically derived cause of human obesity or metabolic syndrome. MC4R receptor is a heterotrimeric G-protein-coupled receptor, which transduces signals by activating adenylate cyclase. Expressed in hypothalamic nuclei and other neuronal and non-neuronal tissues, controlling feeding behavior and energy homeostasis, MC4R integrates an agonist (anorexigenic) signal provided by the α-melanocyte stimulating hormone (α-MSH), and an antagonist (orexigenic) signal provided by the agouti-related peptide (AGPR).

As shown in FIG. 1, MC4R is a part of the leptin-melanocortin pathway. Leptin is released from adipose tissue and binds to leptin receptors (LEPR) on AGPR- and pro-opiomelanocortin (POMC)-releasing neurons in the arcuate nucleus (ARC) of the hypothalamus. Leptin binding inhibits AGPR release and stimulates the release of POMC, which undergoes post-translational modification by the prohormone convertase PC1/3 to generate a range of peptides, including α-MSH. AGPR binding to MC4R suppresses MC4R activity, while α-MSH binding stimulates the MC4R. Suppressed receptor activity generates orexigenic signal, whereas stimulated receptor activity generates anorexigenic signal. Signals from MC4R modulate feeding behavior through secondary effector neurons.

Humans affected by a monogenic MC4R-caused disorders, e.g., obesity, are mostly heterozygous carriers of mutant human MC4R (hMC4R) gene with an autosomal dominant inheritance and penetrance and expressivity that varies with age and generational influences. The functional consequences of hMC4R mutations can be schematically divided into the following categories: nonfunctional receptor (e.g. due to missense or frameshift mutations), intracellular retention of the expressed receptor, altered basal activity of the receptor, and altered α-MSH stimulation of the receptor.

SUMMARY OF THE INVENTION

The need exists for a method of treating disorders associated with MC4R mutations. It has now been discovered that certain individuals that carry an MC4R mutations can respond to pharmacological agents that activate MC4R-mediated signaling pathway. These individuals are heterozygous carriers of an MC4R mutation. Based on this discovery, it is now possible to treat MC4R-mediated disorders in a class of patients that was previously considered unresponsive to MC4R agonists.

Accordingly, an example embodiment of the present invention is a method of treating a disorder in a subject in need thereof. The method comprises administering to said subject an effective amount of an agonist of the melanocortin-4 receptor (MC4R). The subject is a heterozygous carrier of an MC4R mutation, and the disorder results from an attenuated response of MC4R to α-melanocortin stimulating hormone (α-MSH).

In a particular embodiment, the disorder is obesity (for example, obesity caused by an MC4R mutation, such as loss of function) and the subject is heterozygous with respect to the MC4R gene. In this embodiment, treatment of such a subject with a pharmacological agent that activates MC4R-mediated signaling pathway, such as described herein, may confer a number of unexpected advantages and benefits. For instance, most subjects heterozygous for MC4R may respond to treatment with sustained weight loss. A proportion of subjects may have MC4R functionality restored to wild type levels, resulting in body weight and body composition normalization. Additional benefits may include overcoming hyperinsulinemia, and improving glucose control and hyperphagia. A further benefit may be that weight loss is sustained throughout the treatment period as well as for prolonged periods of time on treatment cessation.

Additional unexpected benefits of treating an MC4R-mediated obesity in an MC4R-heterozygous subject by a pharmacological agent that activates MC4R-mediated signaling pathway, when compared to an obese subject that is wild-type with respect to MC4R, may include one or more of: an unexpectedly long ability to sustain a drug holiday, without gaining weight; a more profound improvement in insulin and glucose management; a longer lasting and sustained reduction in meal size and food intake; a more profound effect on reducing sleep apnea and increasing quality of sleep; an unexpected and more profound improvement effect on parameters of male or female sexual dysfunction; a more profound reduction in the incidence of obesity-associated cancers; a more profoundly reduced incidence in obesity-associated inflammatory disease including rheumatoid arthritis and endothelial and micro-vascular dysfunction; a more profoundly reduced incidence of heart attack and stroke; more profound improvements in cardiovascular parameters including heart rate and blood pressure.

There are additional benefits to treatment of an MC4R-mediated obesity in an MC4R-heterozygous subject (MC4R+/−) by a pharmacological agent that activates MC4R-mediated signaling pathway, when compared to an obese subject that is wild-type with respect to MC4R. MC4R+/− obese individuals are more at risk than wild type obese individuals of the consequences of obesity because of the intractability of their obesity, and the duration of the MC4R-mediated obesity, that often has a high rate of childhood onset. For example, MC4+/− obese individuals are resistant to weight management by diet/exercise regimens. (Reinhhr et. al, "Lifestyle Intervention in Obese Children With Variations in the Melanocortin 4 Receptor Gene," Obesity Journal, Vol. 17 No. 2, 2009). It is well-established, however, that higher childhood body-mass index (BMI) values elevate the risk of having a Coronary Heart Disease event in adulthood. (Baker et al., "Childhood Body-Mass Index and the Risk of Coronary Heart Disease in Adulthood," N. Engl. J. Med 2007; 357:2329-2337 (2007).) Treatment of this higher risk patient group may provide a treatment option not previously available (e.g., a treatment that achieves long term weight management).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2A and 2B show Tables 1 and 2 which list examples of the MC4R mutations that cause obesity in humans.

DETAILED DESCRIPTION OF THE INVENTION

Figure 1:
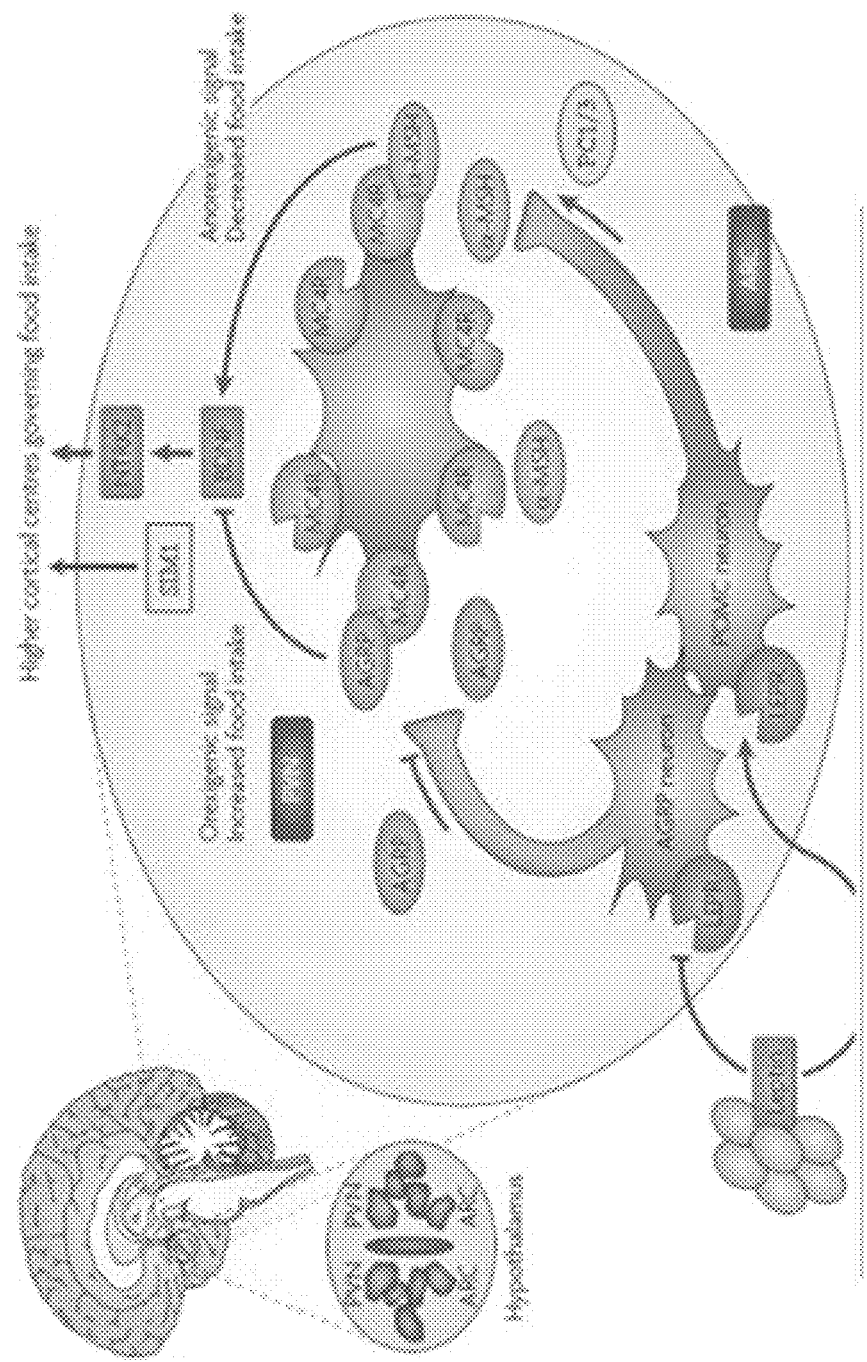
FIG. 1 is a schematic diagram of the leptin-melanocortin pathway.

A description of example embodiments of the invention follows.

The present invention relates to a method of treating a disorder in a subject suffering from an attenuated response of MC4R to α-melanocortin stimulating hormone (α-MSH). The method comprises administering an effective amount of an agonist of the melanocortin-4 receptor (MC4R). In an example embodiment, the subject is a heterozygous carrier of an MC4R mutation resulting in the attenuated response of MC4R to α-melanocortin stimulating hormone (α-MSH). Because heterozygous carriers retain an ability to respond to the natural ligand of MC4R, treating MC4R-associated disorders in heterozygous carriers by administration of an MC4R agonist does not rely on the knowledge of the type of the MC4R mutation.

In one example embodiment, the disorder is obesity, for example, MC4R-associated obesity. In another example embodiment, the disorder is metabolic syndrome.

As used herein, the term "obese" refers to a subject having a body mass index (BMI) within the ranges defined as "obese" by the Center for Disease Control. See, URL http://www.cdc.gov/obesity/defining.html, last accessed on Oct. 28, 2011. For example, an adult who has a BMI of 30 or higher is considered obese, As used herein, the term "metabolic syndrome" refers to a group of symptoms that occur together and increase the risk for coronary artery disease, stroke, and type 2 diabetes. According to the American Heart Association and the National Heart, Lung, and Blood Institute, metabolic syndrome also referred to as Syndrome X) is present if a subject has three or more of the following signs:
1) Blood pressure equal to or higher than 130/85 mmHg;
2) Fasting blood sugar (glucose) equal to or higher than 100 mg/dL;
3) Large waist circumference (length around the waist):
    Men—40 inches or more;
    Women—35 inches or more;
4) Low HDL cholesterol:
    Men—under 40 mg/dL;
    Women—under 50 mg/dL;
5) Triglycerides equal to or higher than 150 mg/dL.

Metabolic syndrome can be diagnosed by testing subject's blood pressure, blood glucose level, HDL cholesterol level, LDL cholesterol level, total cholesterol level, and triglyceride level.

As used herein, the phrase "attenuated response" refers to reduction, but not complete abrogation, of a signaling activity of a receptor in response to its cognate naturally occurring or synthetic ligand.

As used herein, the term "agonist" refers to any chemical compound, either naturally occurring or synthetic, that, upon interacting with (e.g., binding to) its target, here, MC4R, raises the signaling activity of MC4R above its basal level. An agonist can be a superagonist (i.e. a compound that is capable of producing a greater maximal response than the endogenous agonist for the target receptor, and thus has an efficacy of more than 100%), a full agonist (i.e. a compound that elicits a maximal response following receptor occupation and activation) or a partial agonist (i.e. a compounds that can activate receptors but are unable to elicit the maximal response of the receptor system).

Examples of naturally occurring MC4R agonists include α-MSH, β-MSH, γ-MSH and adenocorticitropic hormone (ACTH) or a functional fragment thereof. Examples of synthetic MC4R agonists will be described in detail below.

As used herein, an "effective amount" is a therapeutically or prophylactically sufficient amount of the MC4R agonist to treat the target disorder. Examples of effective amounts typically range from about from 0.005 mg/kg of body weight to 500 mg/kg of body weight. In other examples, effective amounts range from about from 0.01 mg/kg of body weight to 50 mg/kg of body weight, or from 0.01 mg/kg of body weight to 20 mg/kg of body weight.

As used herein "treating" includes achieving, partially or substantially, one or more of the following results: partially or totally reducing the body weight (as measured, for example, by a body mass index, BMI); ameliorating or improving a clinical symptom or indicators associated with obesity, such as type-II diabetes, pre-diabetic condition, blood level of haemoglobin A1C (Hb1Ac) above 6%, hyperinsulimenia, hyperlipidemia, insulin insensitivity, glucose intolerance etc; delaying, inhibiting or preventing the progression of obesity and obesity related indication; or partially or totally delaying, inhibiting or preventing the onset or development of obesity or obesity related indication. Delaying, inhibiting or preventing the progression of the obesity includes for example, delaying, inhibiting or preventing the progression of a subject having normal weight to obesity.

The term "treating" further includes partially or totally reducing the risk for coronary artery disease, stroke, and type 2 diabetes associated with the metabolic syndrome as well as ameliorating or improving a clinical symptom or signs of metabolic syndrome associated with metabolic syndrome, such as any one or more of the five indicators listed above. For example, the term "treating" includes delaying, inhibiting or preventing the progression of parameters associated with the metabolic syndrome, including insulin resistance, glucose clearance and parameters of cardiovascular disease including heart rate and blood pressure.

"Prophylactic treatment" refers to treatment before onset of obesity to prevent, inhibit or reduce its occurrence.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

hMC4R is a well-characterized protein encoded by a genomic sequence having GenBank accession number CH471077.

Mutations in the MC4R receptor are an associated cause of severe childhood obesity. The carrier prevalence for MC4R mutations in a juvenile-onset obese population has been noted to be around 2.5% with a highest prevalence of 6% among severe obese children. Humans with MC4R mutations show a more or less similar phenotype as has been described for mice with mutations in the MC4 receptor gene. Those people show clear hyperphagia, hyperinsulinaemia, increased fat mass, accompanied by lean body mass, bone mineral density and linear growth rate, with no changes in cortisol levels, gonadotropin, thyroid and sex steroid levels. In contrast to MC4 receptor deletion, hyperphagia and hyperinsulinaemia tends to subside with age in human subjects. Similar to the MC4R knockout mice, the phenotype in heterozygote carriers is intermediate in comparison to homozygote carriers. The exhibited hyperphagia observed upon a test meal is less severe than that observed in people with a leptin deficiency. The severity of MC4 receptor dysfunction seen in assays in vitro can predict the amount of food ingested at a test meal by the subject harboring that particular mutation and correlates with the onset and severity of the obese phenotype. At east 90 different MC4 receptor mutations have been associated with obesity and additional mutations in the MC4 receptor are likely to be discovered, leading to a similar obesity phenotype.

Examples of the MC4R mutations that cause obesity in humans are shown in FIGS. 2A and 2B as Table 1 and Table 2 (adopted from Farooqi et al., *The Journal of Clinical Investigation*, July 2000, vol. 106 (2), pp. 271-279 and Vaisse et al., *The Journal of Clinical Investigation*, July 2000, vol. 106 (2), pp. 253-262, the relevant portions of which are incorporated herein by reference).

Additional mutations that potentially cause obesity in humans include, R18H, R18L, S36Y, P48S, V50M, F51L, E61K, I69T, D90N, S94R, G98R, I121T, A154D, Y157S, W174C, G181D, F202L, A219 V, I226T, G231S, G238D, N240S, C271R, S295P, P299L, E308K, I317V, L325F, and 750DelGA, as described in Xiang et al., "Pharmacological characterization of 30 human melanocortin-4 receptor polymorphisms with the endogenous proopiomelanocortin-derived agonists, synthetic agonists, and the endogenous agouti-related protein antagonist." Biochemistry, 2010 Jun. 8; 49(22):4583-600, the relevant portions of which are incorporated herein by reference.

Further examples of mutations that potentially cause obesity in humans are those listed in Online Mendelian Inheritance in Man (OMIM), a database of human genes and genetic disorders, under the accession number 155541 (MC4R) (more precisely, accession nos. 155541.0001-155541.0023) at the URL http://omim.org/entry/155541. Representative examples include 4-BP DEL, NT631; 4-BP INS, NT732; TYR35TER; ASP37VAL; SER58CYS; ILE102SER; ASN274SER; 1-BP INS, 112A; 4-BP DEL, 211CTCT; ILE125LYS; ALA175THR; ILE316SER; TYR287TER; ASN97ASP; 15-BP DEL (delta88-92 codons); and SER127LEU. The relevant portions of the OMIM database are incorporated herein by reference.

In example embodiments, the MC4R mutation results in retention of the MC4R signaling activity.

Mutations in the genomic sequence encoding MC4R can be detected by the methods that are well known to a person of ordinary skill in the art. For example, the genomic sequence can be cloned using nucleotide primers, such as e.g., the primers described in Farooqi et al., The Journal of Clinical Investigation, July 2000, vol. 106 (2), pp. 271-279 and Vaisse et al., The Journal of Clinical Investigation, July 2000, vol. 106 (2), pp. 253-262, and the cloned sequence analyzed using commercially available sequencers and software.

Activity of MC4R can be measured by the methods well known to a person of ordinary skill in the art. For example, cells can be transiently transfected with the cloned MC4R DNA, the transfected cells contacted by an agonist of MC4R (e.g. α-MSH), and the intracellular level of cAMP, the secondary messenger of MC4R, measured by an electrochemiluminescence assay described, e.g., in Roubert et al., Journal of Endocrinology (2010) 207, pp. 177-183. A reduction in MC4R signaling can be ascertained by comparing the intracellular level of cAMP produced in response to a given agonist by a wild type MC4R to that produced by a mutant MC4R.

In an example embodiment, an agonist employed by the methods of the present invention can be any known agonist of MC4R. In some example embodiment, the MC4R agonist is not an adrenocorticotropic hormone (ACTH) or a fragment thereof.

In an example embodiment, an MC4R agonist is any of the peptides disclosed in International Application published as WO/2005/000339. Specifically, examples include peptides of the following structural formula:

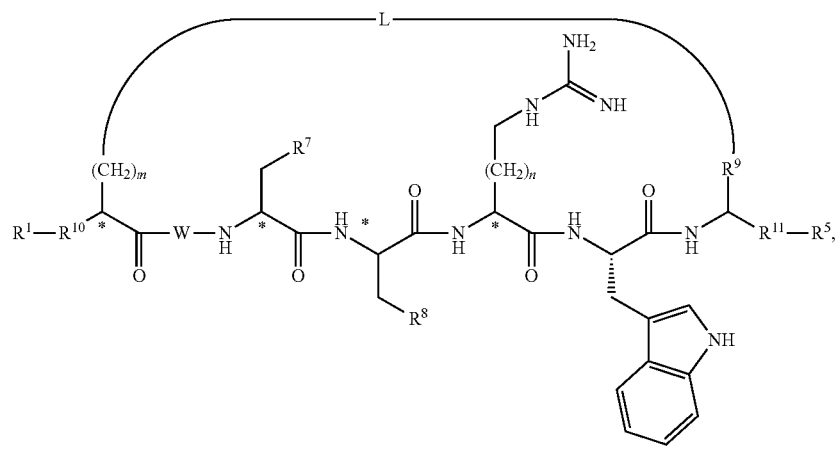

wherein

W is Glu, Gln, Asp, Asn, Ala, Gly, Thr, Ser, Pro, Met, Ile, Val, Arg, His, Tyr, Trp, Phe, Lys, Leu, Cya, or is absent;

R$^1$ is —H, —C(O)CH$_3$, —C(O)(CH$_2$)$_{1-4}$ CH$_3$, —C(O)(CH$_2$)$_{1-4}$ NHC(NH)NH$_2$, Tyr-βArg-, Ac-Tyr-β-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, R$^6$—SO$_2$NHC(O)CH$_2$CH$_2$C(O)—, R$^6$—SO$_2$NHC(O)CH$_2$CH$_2$C(O)Arg-, R$^6$—SO$_2$NHCH$_2$CH$_2$CH$_2$C(O)—, C$_3$-C$_7$ cycloalkylcarbonyl, pheylsulfonyl, C$_8$-C$_{14}$ bicyclic arylsulfonyl, phenyl-(CH$_2$)$_q$C(O)—, C$_8$-C$_{14}$ bicyclic aryl-(CH$_2$)$_q$C(O)—,

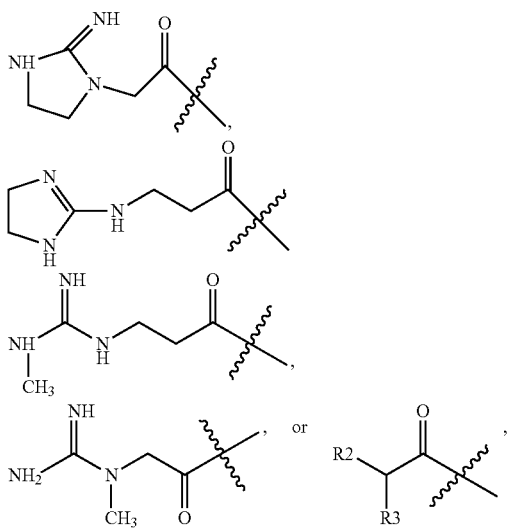

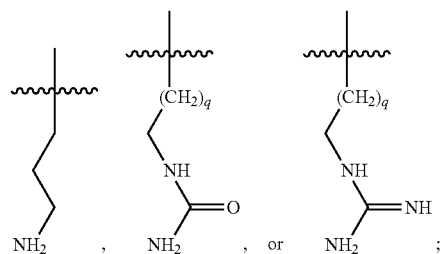

q is 0, 1, 2, or 3;
R$^6$ is a phenyl or C$_8$-C$_{14}$ bicyclic aryl;
m is 1 or 2;
n is 1, 2, 3, or 4;
R$^9$ is (CH$_2$)$_p$ or (CH$_3$)$_2$C—;
p is 1 or 2;
R$^{10}$ is NH— or is absent;
R$^7$ is a 5- or 6-membered heteroaryl or a 5- or 6-membered heteroaryl ring optionally substituted with R$^4$;
R$^4$ is H, C$_1$-C$_4$ straight or branched alkyl, phenyl, benzyl, or (C$_6$H$_5$)—CH$_2$—O—CH$_2$—;
R$^8$ is phenyl, a phenyl ring optionally substituted with X, or cyclohexyl;
X is H, Cl, F, Br, methyl, or methoxy;
R$^{11}$ is —C(O) or —CH$_2$;
R$^5$ is —NH$_2$, —OH, glycinol, NH$_2$-Pro-Ser-, NH$_2$-Pro-Lys-, HO-Ser-, HO-Pro-Ser-, HO-Lys-, Ser alcohol, -Ser-Pro alcohol, -Lys-Pro alcohol, HOCH$_2$CH$_2$—O—CH$_2$CH$_2$NH—, NH$_2$-Phe-Arg-, NH$_2$-Glu-, NH$_2$CH$_2$RCH$_2$NH—, RHN—, RO— where R is a C$_1$-C$_4$ straight or branched alkyl; and
L is —S—S— or —S—CH$_2$—S—.

Other examples of MC4R agonists include peptides of the following structural formula:

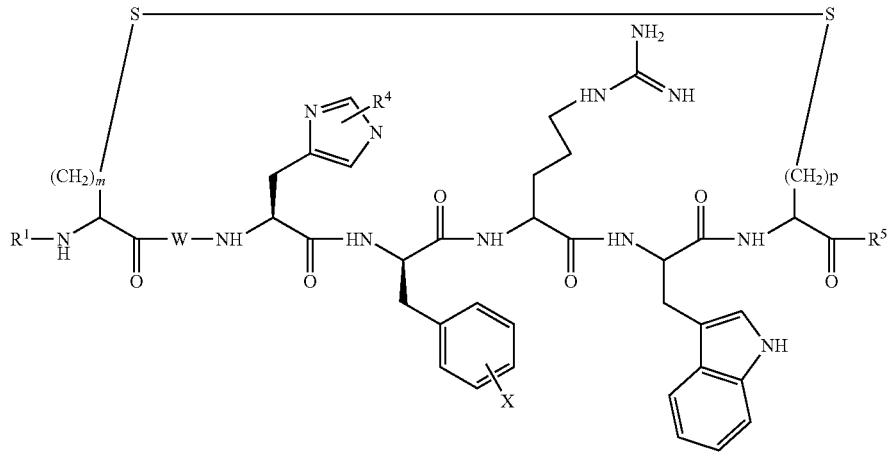

wherein
R$^2$ is —H, —NH$_2$, —NHC(O)CH$_3$, —NHC(O)(CH$_2$)$_{1-4}$ CH$_3$, —NH-TyrC(O)CH$_3$, R$^6$SO$_2$NH—, Ac-Cya-NH—, Tyr-NH—, HO—(C$_6$H$_5$)—CH$_2$CH$_2$C(O)NH—, or CH$_3$—(C$_6$H$_5$)—C(O)CH$_2$CH$_2$C(O)NH—;
R$^3$ is C$_1$-C$_4$ straight or branched alkyl, NH$_2$—CH$_2$—(CH$_2$)$_q$—, HO—CH$_2$—, (CH$_3$)$_2$CHNH(CH$_2$)$_4$—, R$^6$(CH$_2$)$_q$—, R$^6$SO$_2$NH—, Ser, Ile, wherein:
W is a single bond, Glu, Gln, Asp, Asn, Ala, Gly, Thr, Ser, Pro, Met, Ile, Val, Arg, His, Tyr, Trp, or Phe;
R$^1$ is —H, —C(O)CH$_3$, —C(O)(CH$_2$)$_{1-4}$ CH$_3$, —C(O)(CH$_2$)$_{1-4}$—NHC(NH)NH$_2$, Tyr-βArg, gluconoyl-Tyr-Arg, Ac-Dab, Ac-Dap, N-succinyl-Tyr-Arg, N-propionyl, N-valeryl, N-glutaryl-Tyr-Arg, N-butyryl,

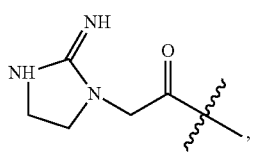

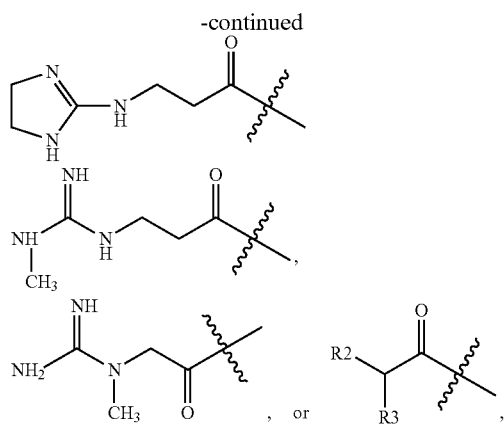

wherein
R² is —H, —NH₂, —NHC(O)CH₃, —NHC(O)(CH₂)₁₋₄ CH₃, or —NH-TyrC(O)CH₃;
R³ is C₁-C₄ straight or branched alkyl, Ser, Ile,

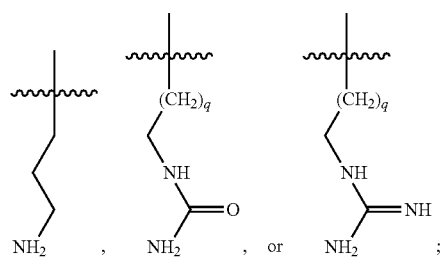

q is 0, 1, 2, or 3;
m is 1 or 2;
p is 1 or 2;

R⁴ is H or C₁-C₄ straight or branched alkyl;
X is H, Cl, F, Br, methyl, or methoxy; and
R⁵ is —NH₂, —OH, glycinol, -Ser-Pro-NH₂, -Lys-Pro-NH₂, -Ser-OH, -Ser-Pro-OH, -Lys-Pro-OH-Arg-Phe-NH₂, -Glu-NH₂, —NHR, or —OR, where R is a C₁-C₄ straight or branched alkyl.

In yet another example embodiment, the MC4R agonist can be represented by the following structural formula:

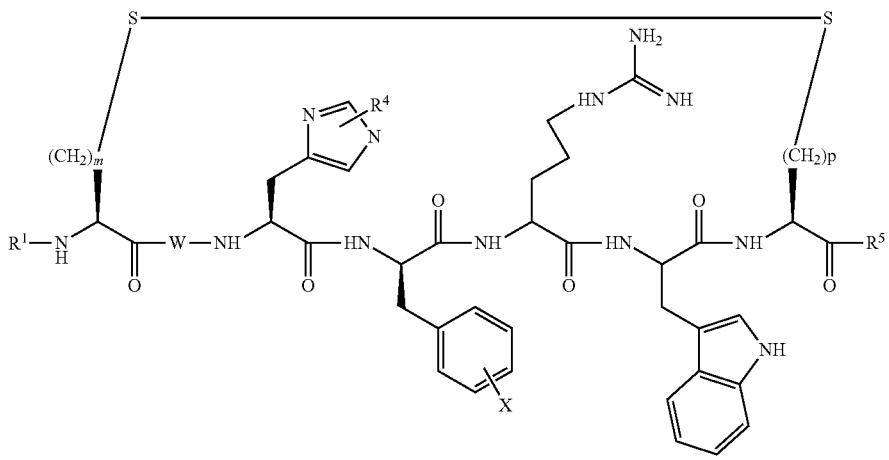

wherein
W is Glu, Gln, Asp, Ala, Gly, Thr, Ser, Pro, Met, Ile, Val, Arg, His, Tyr, Trp, Phe, Lys, Leu, Cya, or is absent;
R¹ is —H, —C(O)CH₃, —C(O)(CH₂)₁₋₄ CH₃, —C(O)(CH₂)₁₋₄ NHC(NH)NH₂, Tyr-βArg-, Ac-Tyr-β-hArg-, gluconoyl-Tyr-Arg-, Ac-diaminobutyryl-, Ac-diaminopropionyl-, N-propionyl-, N-butyryl-, N-valeryl-, N-methyl-Tyr-Arg-, N-glutaryl-Tyr-Arg-, N-succinyl-Tyr-Arg-, R⁶—SO₂NHC(O)CH₂CH₂C(O)—, R⁶—SO₂NHC(O)CH₂CH₂C(O)Arg-, R⁶—SO₂NHCH₂CH₂CH₂C(O)—, C₃-C₇ cycloalkylcarbonyl, phenylsulfonyl, C₈-C₁₄ bicyclic arylsulfonyl, phenyl-(CH₂)qC(O)—, C₅-C₁₄ bicyclic aryl-(CH₂)qC(O)—,

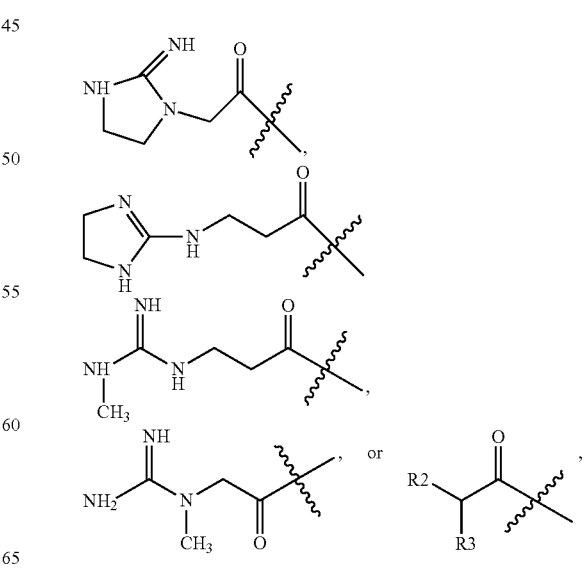

wherein

R² is —H, —NH₂, —NHC(O)CH₃, —NHC(O)(CH₂)₁₋₄CH₃, —NH-TyrC(O)CH₃, R⁶SO₂NH—, Ac-Cya-NH—, Tyr-NH—, HO—(C₆H₅)—CH₂CH₂C(O)NH—, or CH₃—(C₆H₅)—C(O)CH₂CH₂C(O)NH—;

R³ is C₁-C₄ straight or branched alkyl, NH₂—CH₂—(CH₂)$_q$—, HO—CH₂—, (CH₃)₂CHNH(CH₂)₄—, R⁶(CH₂)$_q$—, R⁶SO₂NH—, Ser, Ile,

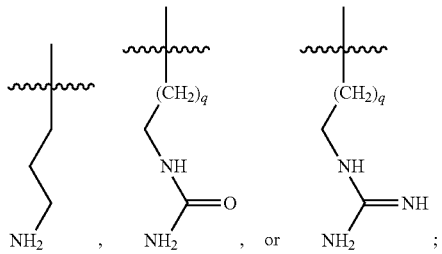

q is 0, 1, 2, or 3;
R⁶ is a phenyl or C₈-C₁₄ bicyclic aryl;
m is 1 or 2;
p is 1 or 2;
R⁴ is H, C₁-C₄ straight or branched alkyl, phenyl, benzyl, or (C₆H₅)—CH₂—O—CH₂—;
X is H, Cl, F, Br, methyl, or methoxy; and
R⁵ is —NH₂, —OH, glycinol, NH₂-Pro-Ser-, NH₂-Pro-Lys-, HO-Ser-, HO-Pro-Ser-, HO-Lys-, -Ser alcohol, -Ser Pro alcohol, -Lys-Pro alcohol, HOCH₂CH₂—O—CH₂CH₂NH—, NH₂-Phe-Arg-, NH₂-Glu-, NH₂CH₂RCH₂NH—, or RO— where R is a C₁-C₄ straight or branched alkyl.

Additional examples of MC4R agonists useful to practice the present invention are found in WO2011104378; WO2011104379; WO201060901; WO200887189; WO200887188, WO200887187, WO200887186; US20110065652; WO2010144341; WO2010144344; WO201065799; WO201065800; WO201065801; WO201065802; WO201037081; WO2009152079; WO2009151383; US20100311648; US20100280079; WO201081666; WO201034500; WO200910299; WO2008116665; WO201052256; WO201052255; WO201126015; US20100120783; WO201096854; US20100190793; WO201025142; and WO201015972. Further examples of MC4R agonists useful to practice the present invention are found in U.S. Pat. Nos. 8,263,608; 8,247,530; 8,114,844; and 7,968,548. The entire teachings of these publications are incorporated herein by reference.

In one example embodiment, the agonist of MC4R is a tripeptide D-Phe-Arg-Trp (SEQ ID NO: 560) or a pharmaceutical salt thereof. In another example, the agonist is any peptide that includes SEQ ID NO: 560 or a pharmaceutical salt thereof. In yet another example, the MC4R agonist is an acetylated tripeptide Ac-D-Phe-Arg-Trp-NH₂ (SEQ ID NO: 561) or a pharmaceutical salt thereof.

In an example embodiment, the agonists of MC4R are those of Formula (I) or a pharmaceutically acceptable salt, hydrate, solvate or a prodrug thereof (see International Patent Application Publication Number WO 2007/008704, incorporated herein by reference in its entirety):

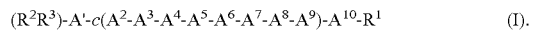

(R²R³)-A¹-c(A²-A³-A⁴-A⁵-A⁶-A⁷-A⁸-A⁹)-A¹⁰-R¹  (I).

In Formula (I):
A¹ is Acc, HN—(CH₂)$_m$—C(O), L- or D-amino acid, or deleted;

A² is Cys, D-Cys, hCys, D-hCys, Pen, D-Pen, Asp, or Glu;

A³ is Gly, Ala, β-Ala, Gaba, Aib, D-amino acid, or deleted;

A⁴ is His, 2-Pal, 3-Pal, 4-Pal, Taz, 2-Thi, 3-Thi, or (X¹, X², X³, X⁴, X⁵)Phe;

A⁵ is D-Phe, D-1-Nal, D-2-Nal, D-Trp, D-Bal, D-(X¹, X², X³, X⁴, X⁵)Phe, L-Phe or D-(Et)Tyr;

A⁶ is Arg, hArg, Dab, Dap, Lys, Orn, or HN—CH₄CH₂)$_n$—N(R⁴R⁵))—C(O);

A⁷ is Trp, 1-Nal, 2-Nal, Bal, Bip, D-Trp, D-2-Nal, D-Bal or D-Bip;

A⁸ is Gly, D-Ala, Acc, Ala, β-Ala, Gaba, Apn, Ahx, Aha, HN—(CH₂)$_s$—C(O), or deleted;

A⁹ is Cys, D-Cys, hCys, D-hCys, Pen, D-Pen, Dab, Dap, Orn, or Lys;

A¹⁰ is Acc, HN—(CH₂)$_t$—C(O), L- or D-amino acid, or deleted;

R¹ is OH or NH₂;

each of R² and R³ is, independently for each occurrence, selected from the group consisting of H, (C₁-C₃₀)alkyl, (C₁-C₃₀)heteroalkyl, (C₁-C₃₀)acyl, (C₂-C₃₀)alkenyl, (C₂-C₃₀)alkynyl, aryl(C₁-C₃₀)alkyl, aryl(C₁-C₃₀)acyl, substituted (C₁-C₃₀)alkyl, substituted (C₁-C₃₀)heteroalkyl, substituted (C₁-C₃₀)acyl, substituted (C₂-C₃₀)alkenyl, substituted (C₂-C₃₀)alkynyl, substituted aryl(C₁-C₃₀)alkyl, and substituted aryl(C₁-C₃₀)acyl;

each of R⁴ and R⁵ is, independently for each occurrence, H, (C₁-C₄₀)alkyl, (C₁-C₄₀)heteroalkyl, (C₁-C₄₀)acyl, (C₂-C₄₀)alkenyl, (C₂-C₄₀)alkynyl, aryl(C₁-C₄₀)alkyl, aryl(C₁-C₄₀)acyl, substituted (C₁-C₄₀)alkyl, substituted (C₁-C₄₀)heteroalkyl, substituted (C₁-C₄₀)acyl, substituted (C₂-C₄₀)alkenyl, substituted (C₂-C₄₀)alkynyl, substituted aryl(C₁-C₄₀)alkyl, substituted aryl(C₁-C₄₀)acyl, (C₁-C₄₀)alkylsulfonyl, or —C(NH)—NH₂;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

t is, independently for each occurrence, 1, 2, 3, 4, 5, 6, or 7;

X¹, X², X³, X⁴, and X⁸ each is, independently for each occurrence, H, F, Cl, Br, I, (C₁₋₁₀)alkyl, substituted (C₁₋₁₀)alkyl, (C₂₋₁₀)alkenyl, substituted (C₂₋₁₀)alkenyl, (C₂₋₁₀)alkynyl, substituted (C₂₋₁₀)alkynyl, aryl, substituted aryl, OH, NH₂, NO₂, or CN.

In exemplary embodiments of the agonists of Formula (I):
(I) when R⁴ is (C₁-C₄₀)acyl, aryl(C₁-C₄₀)acyl, substituted (C₁-C₄₀)acyl, substituted aryl(C₁-C₄₀)acyl, (C₁-C₄₀)alkylsulfonyl, or —C(NH)—NH₂, then R⁵ is H or (C₁-C₄₀)alkyl, (C₁-C₄₀)heteroalkyl, (C₂-C₄₀)alkenyl, (C₂-C₄₀)alkynyl, aryl(C₁-C₄₀)alkyl, substituted (C₁-C₄₀)alkyl, substituted (C₁-C₄₀)heteroalkyl, substituted (C₂-C₄₀)alkenyl, substituted (C₂-C₄₀)alkynyl, or substituted aryl(C₁-C₄₀)alkyl;

(II) when R² is (C₁-C₃₀)acyl, aryl(C₁-C₃₀)acyl, substituted (C₁-C₃₀)acyl, or substituted aryl(C₁-C₃₀)acyl, then R³ is H, (C₁-C₃₀)alkyl, (C₁-C₃₀)heteroalkyl, (C₂-C₃₀)alkenyl, (C₂-C₃₀)alkynyl, aryl(C₁-C₃₀)alkyl, substituted (C₁-C₃₀)alkyl, substituted (C₁-C₃₀)heteroalkyl, substituted (C₂-C₃₀)alkenyl, substituted (C₂-C₃₀)alkynyl, or substituted aryl(C₁-C₃₀)alkyl;

(III) either A³ or A⁸ or both must be present in said compound;

(IV) when A² is Cys, D-Cys, hCys, D-hCys, Pen, or D-Pen, then A⁹ is Cys, D-Cys, hCys, D-hCys, Pen, or D-Pen;

(V) when A² is Asp or Glu, then A⁹ is Dab, Dap, Orn, or Lys;

(VI) when A⁸ is Ala or Gly, then A¹ is not Nle; and (VII) when A¹ is deleted, then R² and R³ cannot both be H.

In an example embodiment, the agonists employed by the methods described herein are the compounds of Formula I, wherein:

A¹ is A6c, Arg, D-Arg, Cha, D-Cha, hCha, Chg, D-Chg, Gaba, Ile, Leu, hLeu, Met, β-hMet, 2-Nal, D-2-Nal, Nip, Nle, Oic, Phe, D-Phe, hPhe, hPro, Val, or deleted;

A² is Asp, Cys, D-Cys, hCys, D-hCys, Glu, Pen, or D-Pen;

A³ is D-Abu, Aib, Ala, β-Ala, D-Ala, D-Cha, Gaba, D-Glu, Gly, D-Ile, D-Leu, D-Tle, D-Val, or deleted;

A⁴ is His or 3-Pal;

A⁵ is D-Bal, D-1-Nal, D-2-Nal, D-Phe, D-Trp, or D-(Et)Tyr;

A⁶ is Arg, or hArg;

A⁷ is Bal, Bip, 1-Nal, 2-Nal, Trp, D-Trp;

A⁸ is A6c, D-Ala, Aha, Ahx, Ala, β-Ala, Apn, Gaba, Gly or deleted;

A⁹ is Cys, D-Cys, hCys, D-hCys, Lys, Pen, or D-Pen;

A¹⁰ is Thr, or deleted, wherein at least one of A³ or A⁸ is deleted, but not both, or pharmaceutically acceptable salts thereof.

In an example embodiments, agonists of Formula (I) useful in practicing the invention described herein are compounds of the following formula or a pharmaceutically acceptable salt thereof:

SEQ ID NO: 1
Ac-Nle-c(Asp-His-D-Phe-Arg-Trp-β-Ala-Lys)-NH₂;

SEQ ID NO: 2
Ac-Nle-c(Asp-His-D-Phe-Arg-Trp-A6c-Lys)-NH₂;

SEQ ID NO: 3
Ac-Nle-c(Cys-His-D-Phe-Arg-Trp-Ahx-Cys)-NH₂;

SEQ ID NO: 4
D-Phe-c(Cys-His-D-Phe-Arg-Trp-Ala-D-Cys)-Thr-NH₂;

SEQ ID NO: 5
D-Phe-c(Cys-His-D-Phe-Arg-Trp-β-Ala-D-Cys)-Thr-NH₂;

SEQ ID NO: 6
D-Phe-c(Cys-His-D-Phe-Arg-Trp-Gaba-D-Cys)-Thr-NH₂;

SEQ ID NO: 7
Ac-Nle-c(Cys-His-D-Phe-Arg-Trp-Apn-Cys)-NH₂;

SEQ ID NO: 8
Ac-Nle-c(Asp-His-D-Phe-Arg-Trp-Apn-Lys)-NH₂;

SEQ ID NO: 9
Ac-A6c-c(Asp-His-D-Phe-Arg-Trp-Gaba-Lys)-NH₂;

SEQ ID NO: 10
Ac-D-2-Nal-c(Asp-His-D-Phe-Arg-Trp-Gaba-Lys)-NH₂;

SEQ ID NO: 11
Ac-Cha-c(Asp-His-D-Phe-Arg-Trp-Gaba-Lys)-NH₂;

SEQ ID NO: 12
Ac-Nle-c(Asp-His-D-Phe-Arg-Trp-Gaba-Lys)-NH₂;

SEQ ID NO: 13
Ac-Nle-c(Cys-D-Ala-His-D-Phe-Arg-Trp-Cys)-NH₂;

SEQ ID NO: 14
Ac-Nle-c(Cys-β-Ala-His-D-Phe-Arg-Trp-Cys)-NH₂;

SEQ ID NO: 15
Ac-Nle-c(Cys-Gaba-His-D-Phe-Arg-Trp-Cys)-NH₂;

SEQ ID NO: 16
Ac-Nle-c(Cys-Aib-His-D-Phe-Arg-Trp-Cys)-NH₂;

SEQ ID NO: 17
Ac-Nle-c(Cys-Gly-His-D-Phe-Arg-Trp-Cys)-NH₂;

SEQ ID NO: 18
Ac-Nle-c(D-Cys-Ala-His-D-Phe-Arg-Trp-Cys)-NH₂;

SEQ ID NO: 19
Ac-Nle-c(D-Cys-D-Ala-His-D-Phe-Arg-Trp-Cys)-NH₂;

SEQ ID NO: 20
Ac-Nle-c(D-Cys-β-Ala-His-D-Phe-Arg-Trp-Cys)-NH₂;

SEQ ID NO: 21
Ac-Nle-c(D-Cys-Gaba-His-D-Phe-Arg-Trp-Cys)-NH₂;

SEQ ID NO: 22
Ac-Nle-c(D-Cys-Aib-His-D-Phe-Arg-Trp-Cys)-NH₂;

SEQ ID NO: 23
Ac-Nle-c(D-Cys-Gly-His-D-Phe-Arg-Trp-Cys)-NH₂;

SEQ ID NO: 24
Ac-Nle-c(Cys-D-Ala-His-D-Phe-Arg-Trp-D-Cys)-NH₂;

SEQ ID NO: 25
Ac-Nle-c(Cys-β-Ala-His-D-Phe-Arg-Trp-D-Cys)-NH₂;

SEQ ID NO: 26
Ac-Nle-c(Cys-Gaba-His-D-Phe-Arg-Trp-D-Cys)-NH₂;

SEQ ID NO: 27
Ac-Nle-c(Cys-Aib-His-D-Phe-Arg-Trp-D-Cys)-NH₂;

SEQ ID NO: 28
Ac-Nle-c(Cys-Gly-His-D-Phe-Arg-Trp-D-Cys)-NH₂;

SEQ ID NO: 29
Ac-Nle-c(D-Cys-Ala-His-D-Phe-Arg-Trp-D-Cys)-NH₂;

SEQ ID NO: 30
Ac-Nle-c(D-Cys-D-Ala-His-D-Phe-Arg-Trp-D-Cys)-NH₂;

SEQ ID NO: 31
Ac-Nle-c(D-Cys-β-Ala-His-D-Phe-Arg-Trp-D-Cys)-NH₂;

SEQ ID NO: 32
Ac-Nle-c(D-Cys-Gaba-His-D-Phe-Arg-Trp-D-Cys)-NH₂;

SEQ ID NO: 33
Ac-Nle-c(D-Cys-Aib-His-D-Phe-Arg-Trp-D-Cys)-NH₂;

SEQ ID NO: 34
Ac-Oic-c(Asp-His-D-Phe-Arg-Trp-Gaba-Lys)-NH₂;

SEQ ID NO: 35
Ac-Chg-c(Asp-His-D-Phe-Arg-Trp-Gaba-Lys)-NH₂;

SEQ ID NO: 36
Ac-hCha-c(Asp-His-D-Phe-Arg-Trp-Gaba-Lys)-NH₂;

SEQ ID NO: 37
Ac-D-Cha-c(Asp-His-D-Phe-Arg-Trp-Gaba-Lys)-NH₂;

SEQ ID NO: 38
Ac-D-hCha-c(Asp-His-D-Phe-Arg-Trp-Gaba-Lys)-NH₂;

SEQ ID NO: 39
Ac-Nip-c(Asp-His-D-Phe-Arg-Trp-Gaba-Lys)-NH₂;

SEQ ID NO: 40
Ac-hPro-c(Asp-His-D-Phe-Arg-Trp-Gaba-Lys)-NH₂;

SEQ ID NO: 41
Ac-hLeu-c(Asp-His-D-Phe-Arg-Trp-Gaba-Lys)-NH$_2$;

SEQ ID NO: 42
Ac-Phe-c(Asp-His-D-Phe-Arg-Trp-Gaba-Lys)-NH$_2$;

SEQ ID NO: 43
Ac-D-Phe-c(Asp-His-D-Phe-Arg-Trp-Gaba-Lys)-NH$_2$;

SEQ ID NO: 44
Ac-D-Chg-c(Asp-His-D-Phe-Arg-Trp-Gaba-Lys)-NH$_2$;

SEQ ID NO: 45
n-butanoyl-Cha-c(Asp-His-D-Phe-Arg-Trp-Gaba-Lys)-NH$_2$;

SEQ ID NO: 46
n-butyryl-Cha-c(Asp-His-D-Phe-Arg-Trp-Gaba-Lys)-NH$_2$;

SEQ ID NO: 47
Ac-hPhe-c(Asp-His-D-Phe-Arg-Trp-Gaba-Lys)-NH$_2$;

SEQ ID NO: 48
Ac-β-hMet-c(Asp-His-D-Phe-Arg-Trp-Gaba-Lys)-NH$_2$;

SEQ ID NO: 49
Ac-Gaba-c(Asp-His-D-Phe-Arg-Trp-Gaba-Lys)-NH$_2$;

SEQ ID NO: 50
Ac-Cha-c(Asp-His-D-Phe-Arg-D-Trp-Ala-Lys)-NH$_2$;

SEQ ID NO: 51
Ac-hCha-c(Asp-His-D-Phe-Arg-D-Trp-Ala-Lys)-NH$_2$;

SEQ ID NO: 52
Ac-Leu-c(Asp-His-D-Phe-Arg-D-Trp-Ala-Lys)-NH$_2$;

SEQ ID NO: 53
Ac-hLeu-c(Asp-His-D-Phe-Arg-D-Trp-Ala-Lys)-NH$_2$;

SEQ ID NO: 54
Ac-Phe-c(Asp-His-D-Phe-Arg-D-Trp-Ala-Lys)-NH$_2$;

SEQ ID NO: 55
Ac-Nle-c(Asp-His-D-Phe-Arg-D-Trp-D-Ala-Lys)-NH$_2$;

SEQ ID NO: 56
Ac-Nle-c(Asp-His-D-Phe-Arg-D-Trp-β-Ala-Lys)-NH$_2$;

SEQ ID NO: 57
Ac-Nle-c(Asp-His-D-Phe-Arg-D-Trp-Gaba-Lys)-NH$_2$;

SEQ ID NO: 58
Ac-Nle-c(Asp-His-D-Phe-Arg-D-Trp-Aha-Lys)-NH$_2$;

SEQ ID NO: 59
Ac-Nle-c(Asp-His-D-Phe-Arg-D-Trp-Apn-Lys)-NH$_2$;

SEQ ID NO: 60
Ac-Nle-c(Cys-His-D-Phe-Arg-D-Trp-Apn-Cys)-NH$_2$;

SEQ ID NO: 61
Ac-Nle-c(Cys-His-D-Phe-Arg-D-Trp-Gaba-Cys)-NH$_2$;

SEQ ID NO: 62
Ac-Nle-c(Cys-His-D-Phe-Arg-D-Trp-Ahx-Cys)-NH$_2$;

SEQ ID NO: 63
Ac-Nle-c(Cys-His-D-Phe-Arg-D-Trp-β-Ala-Cys)-NH$_2$;

SEQ ID NO: 64
Ac-Nle-c(Cys-His-D-Phe-Arg-D-Trp-D-Ala-Cys)-NH$_2$;

SEQ ID NO: 65
Ac-Nle-c(Cys-D-Ala-His-D-2-Nal-Arg-Trp-Cys)-NH$_2$;

SEQ ID NO: 66
Ac-Nle-c(Cys-D-Ala-His-D-2-Nal-Arg-2-Nal-Cys)-NH$_2$;

SEQ ID NO: 67
Ac-Nle-c(Cys-D-Ala-His-D-2-Nal-Arg-1-Nal-Cys)-NH$_2$;

SEQ ID NO: 68
n-butanoyl-Nle-c(Cys-D-Ala-His-D-Phe-Arg-2-Nal-Cys)-NH$_2$;

SEQ ID NO: 69
n-butanoyl-Nle-c(Cys-D-Ala-His-D-Phe-Arg-Trp-Cys)-NH$_2$;

SEQ ID NO: 70
Ac-Nle-c(Cys-D-Ala-His-D-Phe-Arg-2-Nal-Cys)-NH$_2$;

SEQ ID NO: 71
Ac-Nle-c(Cys-D-Ala-His-D-Phe-Arg-1-Nal-Cys)-NH$_2$;

SEQ ID NO: 72
Ac-Nle-c(Cys-D-Ala-His-D-Phe-Arg-Bal-Cys)-NH$_2$;

SEQ ID NO: 73
Ac-Nle-c(Cys-D-Glu-His-D-Phe-Arg-Trp-Cys)-NH$_2$;

SEQ ID NO: 74
Ac-Nle-c(Asp-His-D-Phe-Arg-Trp-D-Ala-Lys)-NH$_2$;

SEQ ID NO: 75
Ac-Nle-c(Cys-D-Ala-His-D-2-Nal-Arg-Bal-Cys)-NH$_2$;

SEQ ID NO: 76
Ac-Nle-c(Pen-D-Ala-His-D-Phe-Arg-Trp-Cys)-NH$_2$;

SEQ ID NO: 77
Ac-Nle-c(Cys-D-Ala-His-D-Phe-Arg-Trp-Pen)-NH$_2$;

SEQ ID NO: 78
Ac-Nle-c(Pen-D-Ala-His-D-Phe-Arg-Trp-Pen)-NH$_2$;

SEQ ID NO: 79
D-Phe-c(Cys-His-D-Phe-hArg-Trp-β-Ala-D-Cys)-Thr-NH$_2$;

SEQ ID NO: 80
D-Phe-c(Cys-His-D-(Et)Tyr-Arg-Trp-β-Ala-D-Cys)-Thr-NH$_2$;

SEQ ID NO: 81
D-Phe-c(Cys-His-D-Phe-Arg-Bip-β-Ala-D-Cys)-Thr-NH$_2$;

SEQ ID NO: 82
D-Phe-c(Cys-His-D-(Et)Tyr-hArg-Trp-β-Ala-D-Cys)-Thr-NH$_2$;

SEQ ID NO: 83
D-Phe-c(Cys-His-D-Phe-hArg-Bip-β-Ala-D-Cys)-Thr-NH$_2$;

SEQ ID NO: 84
D-Phe-c(Cys-His-D-(Et)Tyr-hArg-Bip-β-Ala-D-Cys)-Thr-NH$_2$;

SEQ ID NO: 85
Nle-c(Cys-His-D-Phe-Arg-Trp-Apn-Cys)-NH$_2$;

SEQ ID NO: 86
Ac-Nle-c(Asp-D-Ala-His-D-Phe-Arg-Trp-Lys)-NH$_2$;

SEQ ID NO: 87
Ac-Nle-c(Asp-D-Ala-His-D-Phe-Arg-Bal-Lys)-NH$_2$;

-continued

SEQ ID NO: 88
Ac-Nle-c(Cys-D-Ala-His-D-Phe-Arg-Trp-Pen)-OH;

SEQ ID NO: 89
Ac-Nle-c(Cys-D-Abu-His-D-Phe-Arg-Trp-Cys)-NH$_2$;

SEQ ID NO: 90
Ac-Nle-c(Cys-D-Val-His-D-Phe-Arg-Trp-Cys)-NH$_2$;

SEQ ID NO: 91
Ac-Nle-c(Cys-D-Ile-His-D-Phe-Arg-Trp-Cys)-NH$_2$;

SEQ ID NO: 92
Ac-Nle-c(Cys-D-Leu-His-D-Phe-Arg-Trp-Cys)-NH$_2$;

SEQ ID NO: 93
Ac-Nle-c(Cys-D-Tle-His-D-Phe-Arg-Trp-Cys)-NH$_2$;

SEQ ID NO: 94
Ac-Nle-c(Cys-D-Cha-His-D-Phe-Arg-Trp-Cys)-NH$_2$;

SEQ ID NO: 95
Ac-Nle-c(Pen-His-D-Phe-Arg-Trp-Gaba-Cys)-NH$_2$;

SEQ ID NO: 96
Ac-Nle-c(Cys-His-D-Phe-Arg-Trp-Gaba-Pen)-NH$_2$;

SEQ ID NO: 97
Ac-Nle-c(Pen-His-D-Phe-Arg-Trp-Gaba-Pen)-NH$_2$;

SEQ ID NO: 98
Ac-Leu-c(Cys-His-D-Phe-Arg-Trp-Gaba-Cys)-NH$_2$;

SEQ ID NO: 99
Ac-Cha-c(Cys-His-D-Phe-Arg-Trp-Gaba-Cys)-NH$_2$;

SEQ ID NO: 100
Ac-Ile-c(Cys-His-D-Phe-Arg-Trp-Gaba-Cys)-NH$_2$;

SEQ ID NO: 101
Ac-Phe-c(Cys-His-D-Phe-Arg-Trp-Gaba-Cys)-NH$_2$;

SEQ ID NO: 102
Ac-Val-c(Cys-His-D-Phe-Arg-Trp-Gaba-Cys)-NH$_2$;

SEQ ID NO: 103
Ac-2-Nal-c(Cys-His-D-Phe-Arg-Trp-Gaba-Cys)-NH$_2$;

SEQ ID NO: 104
Nle-c(Cys-His-D-Phe-Arg-Trp-Gaba-Cys)-NH$_2$;

SEQ ID NO: 105
Phe-c(Cys-His-D-Phe-Arg-Trp-Gaba-Cys)-NH$_2$;

SEQ ID NO: 106
Ac-Nle-c(Cys-3-Pal-D-Phe-Arg-Trp-Gaba-Cys)-NH$_2$;

SEQ ID NO: 107
Ac-Nle-c(Cys-D-Ala-His-D-Phe-Arg-Trp-Cys)-OH;

SEQ ID NO: 108
Ac-Nle-c(Cys-His-Phe-Arg-D-Trp-Gaba-Cys)-NH$_2$;

SEQ ID NO: 109
Ac-Nle-c(Asp-His-D-2-Nal-Arg-Trp-Ala-Lys)-NH$_2$;

SEQ ID NO: 110
Ac-Nle-c(Asp-His-D-2-Nal-Arg-Trp-β-Ala-Lys)-NH$_2$;

SEQ ID NO: 111
Ac-Nle-c(Cys-His-D-2-Nal-Arg-Trp-Gaba-Cys)-NH$_2$;

SEQ ID NO: 112
Ac-Nle-c(Cys-His-D-2-Nal-Arg-Trp-Ahx-Cys)-NH$_2$;

SEQ ID NO: 113
Ac-hPhe-c(Asp-His-D-2-Nal-Arg-Trp-Gaba-Lys)-NH$_2$;

SEQ ID NO: 114
Ac-Cha-c(Asp-His-D-2-Nal-Arg-Trp-Gaba-Lys)-NH$_2$;

SEQ ID NO: 115
Ac-Nle-c(Asp-His-D-Phe-Arg-Trp-β-Ala-Lys)-OH;

SEQ ID NO: 116
Ac-Nle-c(Cys-His-D-Phe-Arg-Trp-Ahx-Cys)-OH;

SEQ ID NO: 117
D-Phe-c(Cys-His-D-Phe-Arg-Trp-Ala-D-Cys)-Thr-OH;

SEQ ID NO: 118
D-Phe-c(Cys-His-D-Phe-Arg-Trp-β-Ala-D-Cys)-Thr-OH;

SEQ ID NO: 119
D-Phe-c(Cys-His-D-Phe-Arg-Trp-Gaba-D-Cys)-Thr-OH;

SEQ ID NO: 120
Ac-Nle-c(Cys-His-D-Phe-Arg-Trp-Apn-Cys)-OH;

SEQ ID NO: 121
Ac-Nle-c(Asp-His-D-Phe-Arg-Trp-Apn-Lys)-OH;

SEQ ID NO: 122
Ac-Cha-c(Asp-His-D-Phe-Arg-Trp-Gaba-Lys)-OH;

SEQ ID NO: 123
Ac-Nle-c(Asp-His-D-Phe-Arg-Trp-Gaba-Lys)-OH;

SEQ ID NO: 124
Ac-Chg-c(Asp-His-D-Phe-Arg-Trp-Gaba-Lys)-OH;

SEQ ID NO: 125
Ac-D-Cha-c(Asp-His-D-Phe-Arg-Trp-Gaba-Lys)-OH;

SEQ ID NO: 126
Ac-hCha-c(Asp-His-D-Phe-Arg-Trp-Gaba-Lys)-OH;

SEQ ID NO: 127
Ac-D-Chg-c(Asp-His-D-Phe-Arg-Trp-Gaba-Lys)-OH;

SEQ ID NO: 128
Ac-hPhe-c(Asp-His-D-Phe-Arg-Trp-Gaba-Lys)-OH;

SEQ ID NO: 129
Ac-Nle-c(Cys-His-D-Phe-Arg-D-Trp-Gaba-Cys)-OH;

SEQ ID NO: 130
Ac-Nle-c(Cys-His-D-Phe-Arg-D-Trp-Ahx-Cys)-OH;

SEQ ID NO: 131
Ac-Nle-c(Cys-His-D-Phe-Arg-D-Trp-β-Ala-Cys)-OH;

SEQ ID NO: 132
Ac-Nle-c(Cys-His-D-Phe-Arg-D-Trp-D-Ala-Cys)-OH;

SEQ ID NO: 133
Ac-Nle-c(Cys-D-Ala-His-D-2-Nal-Arg-Trp-Cys)-OH;

SEQ ID NO: 134
Ac-Nle-c(Cys-D-Ala-His-D-2-Nal-Arg-2-Nal-Cys)-OH;

SEQ ID NO: 135
Ac-Nle-c(Cys-D-Ala-His-D-2-Nal-Arg-1-Nal-Cys)-OH;

SEQ ID NO: 136
Ac-Nle-c(Cys-D-Ala-His-D-2-Nal-Arg-Bal-Cys)-OH;

SEQ ID NO: 137
Ac-Nle-c(Pen-D-Ala-His-D-Phe-Arg-Trp-Cys)-OH;

SEQ ID NO: 138
Ac-Nle-c(Cys-His-D-Phe-Arg-Trp-Gaba-Pen)-OH;

SEQ ID NO: 139
Ac-Arg-c(Cys-D-Ala-His-D-2-Nal-Arg-Trp-Cys)-NH$_2$;

SEQ ID NO: 140
Ac-Arg-c(Cys-D-Ala-His-D-Phe-Arg-Trp-Cys)-NH$_2$;

SEQ ID NO: 141
Ac-D-Arg-c(Cys-D-Ala-His-D-Phe-Arg-Trp-Cys)-NH$_2$;

```
                                               SEQ ID NO: 142
Ac-D-Arg-c(Cys-D-Ala-His-D-Phe-Arg-Trp-Pen)-NH2;

SEQ ID NO: 143
Ac-D-Arg-c(Cys-His-D-Phe-Arg-Trp-Gaba-Pen)-NH2;

SEQ ID NO: 144
Ac-Arg-c(Cys-His-D-Phe-Arg-Trp-Gaba-Pen)-NH2;

SEQ ID NO: 145
Ac-Arg-c(Cys-D-Ala-His-D-Phe-Arg-Trp-Pen)-NH2;

SEQ ID NO: 146
Ac-D-Arg-c(Asp-His-D-Phe-Arg-Trp-Ala-Lys)-NH2;
or
                                               SEQ ID NO: 147
Ac-Arg-c(Asp-His-D-Phe-Arg-Trp-Ala-Lys)-NH2;
``` or pharmaceutically acceptable salts thereof.

In an example embodiment, an agonist of MC4R receptor useful for practicing methods described herein is any of the compounds described by Formula (II) or a pharmaceutically acceptable salt, hydrate, solvate or a prodrug thereof (see International Patent Application Publication Number WO 2007/008704 incorporated herein by reference in its entirety):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}NH_2 \qquad (II)$$

In formula (II):
$A^1$ is Nle or deleted;
$A^2$ is Cys or Asp;
$A^3$ is Glu or D-Ala;
$A^4$ is His;
$A^5$ is D-Phe;
$A^6$ is Arg;
$A^7$ is Trp, 2-Nal or Bal;
$A^8$ is Gly, Ala, D-Ala, β-Ala, Gaba or Apn;
$A^9$ is Cys or Lys;
each of $R^2$ and $R^3$ is independently selected from the group consisting of H or $(C_1\text{-}C_6)$acyl.

In exemplary embodiments of Formula (II):
(I) when $R^2$ is $(C_1\text{-}C_6)$acyl, then $R^3$ is H; and
(II) when $A^2$ is Cys, then $A^9$ is Cys.

In alternative example embodiments of the present invention, the compounds useful for practicing the methods disclosed herein are:

```
                                               SEQ ID NO: 148
Ac-Nle-c(Cys-D-Ala-His-D-Phe-Arg-Trp-Gly-Cys)-NH2;

SEQ ID NO: 149
Ac-Nle-c(Cys-D-Ala-His-D-Phe-Arg-Trp-D-Ala-Cys)-
NH2;

SEQ ID NO: 150
Ac-Nle-c(Cys-D-Ala-His-D-Phe-Arg-Trp-β-Ala-Cys)-
NH2;

SEQ ID NO: 151
Ac-Nle-c(Cys-D-Ala-His-D-Phe-Arg-Trp-Gaba-Cys)-
NH2;

SEQ ID NO: 152
Ac-Nle-c(Cys-D-Ala-His-D-Phe-Arg-Trp-Apn-Cys)-NH2;

SEQ ID NO: 153
Ac-c(Cys-Glu-His-D-Phe-Arg-Trp-Ala-Cys)-NH2;

SEQ ID NO: 154
Ac-c(Cys-Glu-His-D-Phe-Arg-2-Nal-Ala-Cys)-NH2;

SEQ ID NO: 155
Ac-c(Cys-D-Ala-His-D-Phe-Arg-Trp-Ala-Cys)-NH2;

SEQ ID NO: 156
Ac-c(Cys-D-Ala-His-D-Phe-Arg-2-Nal-Ala-Cys)-NH2;

SEQ ID NO: 157
Ac-Nle-c(Cys-D-Ala-His-D-Phe-Arg-Trp-Ala-Cys)-NH2;
or
                                               SEQ ID NO: 158
Ac-Nle-c(Asp-D-Ala-His-D-Phe-Arg-Bal-Ala-Lys)-NH2;
``` or a pharmaceutically acceptable salt thereof.

In an exemplary embodiment, the agonists of MC4R useful for practicing the methods described herein is any of the compounds of Formula (III), or a pharmaceutically acceptable salt, hydrate, solvate or a prodrug thereof (see International Application Publication Number WO 2007/008684, incorporated herein by reference in its entirety):

$$(R^2R^3)\text{-}B^1\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}A^{11}\text{-}A^{12}\text{-}A^{13}\text{-}B^2\text{-}B^3\text{-}R^1 \qquad (III).$$

In Formula (III):
$B^1$ is a peptide moiety which contains 5, 6, 7, 8, 9, 10, 11, 12, 13, 14, or 15 amino acids, wherein at least 5 amino acids are independently selected from the group consisting of L-Arg, D-Arg, L-hArg and D-hArg, or $B^1$ is optionally deleted;
$A^1$ is Acc, $HN\text{—}(CH_2)_m\text{—}C(O)$, L- or D-amino acid or deleted;
$A^2$ is Cys, D-Cys, hCys, D-hCys, Pen, D-Pen, Asp or Glu;
$A^3$ is Gly, Glu, Ala, β-Ala, Gaba, Aib, D-amino acid or deleted;
$A^4$ is His, 2-Pal, 3-Pal, 4-Pal, Taz, 2-Thi, 3-Thi or $(X^1, X^2, X^3, X^4, X^5)$Phe;
$A^5$ is D-Phe, D-1-Nal, D-2-Nal, D-Trp, D-Bal, D-$(X^1, X^2, X^3, X^4, X^5)$Phe, D-(Et)Tyr, D-Dip, D-Bip or D-Bpa;
$A^6$ is Arg, hArg, Dab, Dap, Lys, Orn or $HN\text{—}CH((CH_2)_n\text{—}N(R^4R^5))\text{—}C(O)$;
$A^7$ is Trp, 1-Nal, 2-Nal, Bal, Bip, Dip, Bpa, D-Trp, D-1-Nal, D-2-Nal, D-Bal, D-Bip, D-Dip or D-Bpa;
$A^8$ is Gly, D-Ala, Acc, Ala, β-Ala, Gaba, Apn, Ahx, Aha, $HN\text{—}(CH_2)_s\text{—}C(O)$ or deleted;
$A^9$ is Cys, D-Cys, hCys, D-hCys, Pen, D-Pen, Dab, Dap, Orn or Lys;
$A^{10}$ is Acc, $HN\text{—}(CH_2)_t\text{—}C(O)$, Pro, hPro, 3-Hyp, 4-Hyp, Thr, an L- or D-amino acid or deleted;
$A^{11}$ is Pro, hPro, 3-Hyp, 4-Hyp or deleted;
$A^{12}$ is Lys, Dab, Dap, Arg, hArg or deleted;
$A^{13}$ is Asp, Glu or deleted;
$B^2$ is a peptide moiety containing 1, 2, 3, 4, or 5 amino acids or deleted,
$B^3$ is a peptide moiety which contains 5, 6, 7, 8, 9, 10, 11, 12, 13, 14 or 15 amino acids wherein at least 5 amino acids are independently selected from the group consisting of L-Arg, D-Arg, L-hArg and D-hArg, or is deleted;
$R^1$ is OH or $NH_2$;
$R^2$ and $R^3$ each is, independently for each occurrence, selected from the group consisting of H, $(C_1\text{-}C_{30})$alkyl, $(C_1\text{-}C_{30})$heteroalkyl, $(C_1\text{-}C_{30})$acyl, $(C_2\text{-}C_{30})$alkenyl, $(C_2\text{-}C_{30})$alkynyl, aryl$(C_1\text{-}C_{30})$alkyl, aryl$(C_1\text{-}C_{30})$acyl, substituted $(C_1\text{-}C_{30})$alkyl, substituted $(C_1\text{-}C_{30})$heteroalkyl, substituted $(C_1\text{-}C_{30})$acyl, substituted $(C_2\text{-}C_{30})$alkenyl, substituted $(C_2\text{-}C_{30})$alkynyl, substituted aryl$(C_1\text{-}C_{30})$alkyl and substituted aryl$(C_1\text{-}C_{30})$acyl;

$R^4$ and $R^5$ each is, independently for each occurrence, H, $(C_1-C_{40})$alkyl, $(C_1-C_{40})$heteroalkyl, $(C_1-C_{40})$acyl, $(C_2-C_{40})$alkenyl, $(C_2-C_{40})$alkynyl, aryl$(C_1-C_{40})$alkyl, aryl$(C_1-C_{40})$acyl, substituted $(C_1-C_{40})$alkyl, substituted $(C_1-C_{40})$heteroalkyl, substituted $(C_1-C_{40})$acyl, substituted $(C_2-C_{40})$alkenyl, substituted $(C_2-C_{40})$alkynyl, substituted aryl$(C_1-C_{40})$alkyl, substituted aryl$(C_1-C_{40})$acyl, $(C_1-C_{40})$alkylsulfonyl or C(NH)—NH$_2$;

n is, independently for each occurrence, 1, 2, 3, 4 or 5;

m is, independently for each occurrence, 1, 2, 3, 4, 5, 6 or 7;

s is, independently for each occurrence, 1, 2, 3, 4, 5, 6 or 7;

t is, independently for each occurrence, 1, 2, 3, 4, 5, 6 or 7;

$X^1$, $X^2$, $X^3$, $X^4$ and $X^5$ each is, independently for each occurrence, H, F, Cl, Br, I, $(C_{1-10})$alkyl, substituted $(C_{1-10})$alkyl, $(C_{2-10})$alkenyl, substituted $(C_{2-10})$alkenyl, $(C_{2-10})$alkynyl, substituted $(C_{2-10})$alkynyl, aryl, substituted aryl, OH, NH$_2$, NO$_2$ or CN.

In an example embodiments of Formula (III):

(I) when $R^4$ is $(C_1-C_{40})$acyl, aryl$(C_1-C_{40})$acyl, substituted $(C_1-C_{40})$acyl, substituted aryl$(C_1-C_{40})$acyl, $(C_1-C_{40})$alkylsulfonyl or C(NH)—NH$_2$, then $R^5$ is H, $(C_1-C_{40})$alkyl, $(C_1-C_{40})$heteroalkyl, $(C_2-C_{40})$alkenyl, $(C_2-C_{40})$alkynyl, aryl $(C_1-C_{40})$alkyl, substituted $(C_1-C_{40})$alkyl, substituted $(C_1-C_{40})$heteroalkyl, substituted $(C_2-C_{40})$alkenyl, substituted $(C_2-C_{40})$alkynyl or substituted aryl$(C_1-C_{40})$alkyl;

(II) when $R^2$ is $(C_1-C_{30})$acyl, aryl$(C_1-C_{30})$acyl, substituted $(C_1-C_{30})$acyl or substituted aryl$(C_1-C_{30})$acyl, then $R^3$ is H, $(C_1-C_{30})$alkyl, $(C_1-C_{30})$heteroalkyl, $(C_2-C_{30})$alkenyl, $(C_2-C_{30})$alkynyl, aryl$(C_1-C_{30})$alkyl, substituted $(C_1-C_{30})$alkyl, substituted $(C_1-C_{30})$heteroalkyl, substituted $(C_2-C_{30})$alkenyl, substituted $(C_2-C_{30})$alkynyl or substituted aryl$(C_1-C_{30})$alkyl;

(III) neither $B^1$ nor $B^2$ contains one or more of the following amino acid sequences: Arg-(Lys)$_2$-(Arg)$_2$-Gln-(Arg)$_3$, Tyr-Ala-Arg-Lys-Ala-(Arg)$_2$-Gln-Ala-(Arg)$_2$, Tyr-Ala-Arg-(Ala)$_2$-(Arg)$_2$-(Ala)$_2$-(Arg)$_2$, Tyr-Ala-(Arg)$_9$, Tyr-(Ala)$_3$-(Arg)$_7$, Tyr-Ala-Arg-Ala-Pro-(Arg)$_2$-Ala-(Arg)$_3$ or Tyr-Ala-Arg-Ala-Pro-(Arg)$_2$-Pro-(Arg)$_2$;

(IV) either $B^1$ or $B^2$ or both must be present in said compound;

(V) when $A^2$ is Cys, D-Cys, hCys, D-hCys, Pen or D-Pen, then $A^9$ is Cys, D-Cys, hCys, D-hCys, Pen or D-Pen; and (VI) when $A^2$ is Asp or Glu, then $A^9$ is Dab, Dap, Orn or Lys.

In exemplary embodiments, in Formula (III):

$B^1$ is Arg-Lys-Gln-Lys-(Arg)$_5$, Arg-(Lys)$_2$-Arg-Gln-(Arg)$_4$, Arg-(Lys)$_2$-(Arg)$_3$-Gln-(Arg)$_2$, Arg-(Lys)$_2$-(Arg)$_4$-Gln-Arg, Arg-(Lys)$_2$-(Arg)$_5$-Gln, Arg-(Lys)$_2$-Gln-(Arg)$_5$, Arg-Gln-(Lys)$_2$-(Arg)$_5$, Arg-Gln-(Arg)$_7$, Arg-Gln-(Arg)$_8$, (Arg)$_2$-Gln-(Arg)$_6$, (Arg)$_2$-Gln-(Arg)$_7$, (Arg)$_3$-Gln-(Arg)$_5$, (Arg)$_3$-Gln-(Arg)$_6$, (Arg)$_4$-Gln-(Arg)$_4$, (Arg)$_4$-Gln-(Arg)$_5$, (Arg)$_5$, (Arg)$_5$-Gln-(Arg)$_3$, (Arg)$_5$-Gln-(Arg)$_4$, (Arg)$_6$, (Arg)$_6$-Gln-(Arg)$_3$, (Arg)$_7$, (Arg)$_7$-Gln-(Arg)$_2$, (Arg)$_8$, (Arg)$_s$-Gln-Arg, (Arg)$_9$, (Arg)$_9$-Gln, (D-Arg)$_5$, (D-Arg)$_6$, (D-Arg)$_7$, (D-Arg)$_8$, (D-Arg)$_9$, Gln-Arg-(Lys)$_2$-(Arg)$_5$, Gln-(Arg)$_8$, Gln-(Arg)$_9$, Tyr-Gly-Arg-(Lys)$_2$-(Arg)$_2$-Gln-(Arg)$_3$, Tyr-Gly-Arg-(Lys)$_2$-(Arg)$_2$-Gln-(Arg)$_3$-Doc; or deleted;

$B^2$ is β-Ala, β-Ala-Gly, β-Ala-Tyr, β-Ala-Tyr-Gly, (β-Ala)$_2$, (β-Ala)$_2$-Gly, (β-Ala)$_2$-Tyr, (β-Ala)$_2$-Tyr-Gly, Doc, Doc-Gly, Doc-Tyr, Doc-Tyr-Gly, (Doc)$_2$, (Doc)$_2$-Gly, (Doc)$_2$-Tyr, Doc)$_2$-Tyr-Gly, or deleted;

$B^3$ is Arg-Lys-Gln-Lys-(Arg)$_5$, Arg-Lys-(Arg)$_3$-Gln-(Arg)$_3$, Arg-(Lys)$_2$-Arg-Gln-(Arg)$_4$, Arg-(Lys)$_2$-Gln-(Arg)$_5$, Arg-(Lys)$_2$-(Arg)$_2$-Gln-(Arg)$_3$, Arg-(Lys)$_2$-(Arg)$_3$-Gln-(Arg)$_2$, Arg-(Lys)$_2$-(Arg)$_4$-Gln-Arg, Arg-(Lys)$_2$-(Arg)$_5$-Gln, Arg-Gln-(Lys)$_2$-(Arg)$_5$, Arg-Gln-(Arg)$_7$, Arg-Gln-(Arg)$_s$, (Arg)$_2$-Lys-(Arg)$_2$-Gln-(Arg)$_3$, (Arg)$_2$-Gln-(Arg)$_6$, (Arg)$_2$-Gln-(Arg)$_7$, (Arg)$_3$-Gln-(Arg)$_5$, (Arg)$_3$-Gln-(Arg)$_6$, (Arg)$_4$-Gln-(Arg)$_4$, (Arg)$_4$-Gln-(Arg)$_5$, (Arg)$_5$, (Arg)$_s$-Gln-(Arg)$_3$, (Arg)$_5$-Gln-(Arg)$_4$, (Arg)$_6$, (Arg)$_6$-Gln-(Arg)$_3$, (Arg)$_7$, (Arg)$_7$-Gln-(Arg)$_2$, (Arg)$_8$, (Arg)$_s$-Gln-Arg, (Arg)$_9$, (Arg)$_9$-Gln, (D-Arg)$_5$, (D-Arg)$_6$, (D-Arg)$_7$, (D-Arg)$_8$, (D-Arg)$_9$, Gln-Arg-(Lys)$_2$-(Arg)$_s$, Gln-(Arg)$_8$, Gln-(Arg)$_9$, or deleted;

$A^1$ is A6c, Cha, hCha, Chg, D-Chg, hChg, Gaba, hLeu, Met, β-hMet, D-2-Nal, Nip, Nle, Oic, Phe, D-Phe, hPhe, hPro, or deleted;

$A^2$ is Cys;

$A^3$ is D-Abu, Aib, Ala, β-Ala, D-Ala, D-Cha, Gaba, Glu, Gly, D-Ile, D-Leu, D-Met, D-Nle, D-Phe, D-Tle, D-Trp, D-Tyr, D-Val, or deleted;

$A^4$ is H;

$A^5$ is D-Bal, D-1-Nal, D-2-Nal, D-Phe, D-($X^1$, $X^2$, $X^3$, $X^4$, $X^5$)Phe, D-Trp, or D-(Et)Tyr;

$A^6$ is Arg or hArg;

$A^7$ is Bal, Bip, 1-Nal, 2-Nal, Trp, or D-Trp;

$A^8$ is A5c, A6c, Aha, Ahx, Ala, β-Ala, Apn, Gaba, Gly, or deleted;

$A^9$ is Cys, D-Cys, hCys, D-hCys, Lys, Pen, or D-Pen;

$A^{10}$ is Pro, Thr or deleted;

$A^{11}$ is Pro or deleted;

$A^{12}$ is arg, Lys, or deleted;

$A^{13}$ is Asp or deleted;

each of $R^2$ and $R^3$ is, independently, H or acyl;

or pharmaceutically acceptable salts thereof.

In exemplary embodiments, the MC4R agonists useful for practicing the methods of the present invention are at least one of the following compounds:

(SEQ ID NO: 159)
Tyr-Gly-Arg-(Lys)$_2$-(Arg)$_2$-Gln-(Arg)$_3$-Nle-c(Asp-His-D-2-Nal-Arg-Trp-Lys)-NH$_2$;

(SEQ ID NO: 160)
Tyr-Gly-Arg-(Lys)$_2$-(Arg)$_2$-Gln-(Arg)$_3$-Doc-Nle-c(Asp-His-D-2-Nal-Arg-Trp-Lys)-NH$_2$;

(SEQ ID NO: 161)
Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

-continued

```
                                                 (SEQ ID NO: 162)
Ac-Nle-c(Asp-His-D-2-Nal-Arg-Trp-Lys)-β-Ala-Tyr-Gly-Arg-(Lys)2-

(Arg)2-Gln-(Arg)3-NH2;

(SEQ ID NO: 163)
Nle-c(Asp-His-D-2-Nal-Arg-Trp-Lys)-(Doc)2-Tyr-Gly-Arg-(Lys)2-(Arg)2-

Gln-(Arg)3-NH2;

(SEQ ID NO: 164)
Ac-Nle-c(Asp-His-D-2-Nal-Arg-Trp-Lys)-(Pro)2-Lys-Asp-Tyr-Gly-Arg- (Lys)2-(Arg)2-Gln-(Arg)3-NH2;

(SEQ ID NO: 165)
Ac-c(Cys-Glu-His-D-2-Nal-Arg-Trp-Gly-Cys)-(Pro)2-Lys-Asp-Tyr-Gly-

Arg-(Lys)2-(Arg)2-Gln-(Arg)3-NH2;

(SEQ ID NO: 166)
Ac-Nle-c(Asp-His-D-2-Nal-Arg-Trp-Lys)-(β-Ala)2-Tyr-Gly-Arg-(Lys)2-

(Arg)2-Gln-(Arg)3-NH2;

(SEQ ID NO: 167)
Ac-Nle-c(Asp-His-D-2-Nal-Arg-Trp-Lys)-(Pro)2-Lys-Asp-Doc-Tyr-Gly-

Arg-(Lys)2-(Arg)2-Gln-(Arg)3-NH2;

(SEQ ID NO: 168)
Ac-c(Cys-Glu-His-D-2-Nal-Arg-Trp-Gly-Cys)-(Pro)2-Lys-Asp-Doc-Tyr-

Gly-Arg-(Lys)2-(Arg)2-Gln-(Arg)3-NH2;

(SEQ ID NO: 169)
Ac-c(Cys-Glu-His-D-2-Nal-Arg-Trp-Ala-Cys)-(Pro)2-Lys-Asp-β-Ala-Tyr-

Gly-Arg-(Lys)2-(Arg)2-Gln-(Arg)3-NH2;

(SEQ ID NO: 170)
Ac-c(Cys-Glu-His-D-2-Nal-Arg-Trp-Ala-Cys)-(Pro)2-Lys-Asp-Doc-Tyr-

Gly-Arg-(Lys)2-(Arg)2-Gln-(Arg)3-NH2;

(SEQ ID NO: 171)
Ac-Nle-c(Asp-His-D-2-Nal-Arg-Trp-Lys)-(Doc)2-Tyr-Gly-Arg-(Lys)2-

(Arg)2-Gln-(Arg)3-NH2;
                                                 (SEQ ID NO: 172)
Ac-c(Cys-Glu-His-D-2-Nal-Arg-2-Nal-Ala-Cys)-(Pro)2-Lys-Asp-β-Ala-Tyr-

Gly-Arg-(Lys)2-(Arg)2-Gln-(Arg)3-NH2;

(SEQ ID NO: 173)
Ac-c(Cys-Glu-His-D-2-Nal-Arg-Bal-Ala-Cys)-(Pro)2-Lys-Asp-β-Ala-(Arg)5-

Gln-(Arg)3-NH2;

(SEQ ID NO: 174)
Ac-c(Cys-Glu-His-D-2-Nal-Arg-Bal-Ala-Cys)-(Pro)2-Lys-Asp-β-Ala-Gly- (Arg)5-(Arg)3-NH2;

(SEQ ID NO: 175)
Ac-c(Cys-Glu-His-D-2-Nal-Arg-Bal-Ala-Cys)-(Pro)2-Lys-Asp-β-Ala-Tyr-

Gly-(Arg)5-Gln-(Arg)3-NH2;

(SEQ ID NO: 176)
Ac-c(Cys-Glu-His-D-2-Nal-Arg-Trp-Ala-Cys)-(Pro)2-Lys-Asp-β-Ala-Tyr-

Gly-Arg-(Lys)2-Arg-Gln-(Arg)4-NH2;

(SEQ ID NO: 177)
Ac-c(Cys-Glu-His-D-2-Nal-Arg-Trp-Ala-Cys)-(Pro)2-Lys-Asp-β-Ala-Tyr-

Gly-Arg-(Lys)2-Gln-(Arg)5-NH2;
```

(SEQ ID NO: 178)
Ac-c(Cys-Glu-His-D-2-Nal-Arg-Trp-Ala-Cys)-(Pro)$_2$-Lys-Asp-β-Ala-Tyr-Gly-Arg-Lys-Gln-Lys-(Arg)$_5$-NH$_2$;

(SEQ ID NO: 179)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_4$-Gln-Arg-NH$_2$;

(SEQ ID NO: 180)
Ac-c(Cys-Glu-His-D-2-Nal-Arg-Bal-Ala-Cys)-(Pro)$_2$-Lys-Asp-β-Ala-Tyr-Aib-Arg-(Lys)$_2$-(Arg)$_2$-Gln-(Arg)$_3$-NH$_2$;

(SEQ ID NO: 181)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_3$-NH$_2$;

(SEQ ID NO: 182)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_3$-NH$_2$;

(SEQ ID NO: 183)
Ac-c(Cys-Glu-His-D-2-Nal-Arg-1-Nal-Ala-Cys)-(Pro)$_2$-Lys-Asp-β-Ala-(Arg)$_6$-Gln-(Arg)$_3$-NH$_2$;

(SEQ ID NO: 184)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_3$-NH$_2$;

(SEQ ID NO: 185)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_3$-NH$_2$;

(SEQ ID NO: 186)
Ac-c(Cys-Glu-His-D-2-Nal-Arg-2-Nal-Ala-Cys)-(Pro)$_2$-Lys-Asp-β-Ala-(Arg)$_6$-Gln-(Arg)$_3$-NH$_2$;

(SEQ ID NO: 187)
Ac-c(Cys-Glu-His-D-2-Nal-Arg-Bal-Ala-Cys)-(Pro)$_2$-Arg-Asp-β-Ala-(Arg)$_6$-Gln-(Arg)$_3$-NH$_2$;

(SEQ ID NO: 188)
Ac-c(Cys-Glu-His-D-2-Nal-Arg-Bal-Ala-Cys)-(Pro)$_2$-Arg-Asp-β-Ala-(Arg)$_5$-Gln-(Arg)$_3$-NH$_2$;

(SEQ ID NO: 189)
Ac-c(Cys-Glu-His-D-2-Nal-Arg-Bal-Ala-Cys)-(Pro)$_2$-Lys-Asp-β-Ala-(Arg)$_6$-Gln-(Arg)$_3$-NH$_2$;

(SEQ ID NO: 190)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_3$-Gln-(Arg)$_2$-NH$_2$;

(SEQ ID NO: 191)
Ac-c(Cys-Glu-His-D-2-Nal-Arg-Trp-Ala-Cys)-(Pro)$_2$-Lys-Asp-β-Ala-Tyr-Gly-Arg-Gln-(Lys)$_2$-(Arg)$_5$-NH$_2$;

(SEQ ID NO: 192)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_5$-Gln-NH$_2$;

(SEQ ID NO: 193)
Ac-c(Cys-Glu-His-D-2-Nal-Arg-1-Nal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

-continued (SEQ ID NO: 194)
Ac-c(Cys-Glu-His-D-2-Nal-Arg-Bal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 195)
Ac-c(Cys-Glu-His-D-2-Nal-Arg-1-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 196)
Ac-c(Cys-Glu-His-D-2-Nal-Arg-1-Nal-Ala-Cys)-(Pro)$_2$-Lys-Asp-β-Ala-Arg-Lys-(Arg)$_3$-Gln-(Arg)$_3$-NH$_2$;

(SEQ ID NO: 197)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 198)
Ac-c(Cys-Glu-His-D-2-Nal-Arg-2-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 199)
Ac-c(Cys-Glu-His-D-2-Nal-Arg-2-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 200)
Ac-c(Cys-Glu-His-D-2-Nal-Arg-2-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 201)
Ac-c(Cys-Glu-His-D-2-Nal-Arg-1-Nal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 202)
Ac-c(Cys-Glu-His-D-2-Nal-Arg-1-Nal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 203)
Ac-c(Cys-Glu-His-D-2-Nal-Arg-1-Nal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 204)
Ac-c(Cys-Glu-His-D-2-Nal-Arg-1-Nal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 205)
Ac-c(Cys-Glu-His-D-2-Nal-Arg-2-Nal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 206)
Ac-c(Cys-Glu-His-D-2-Nal-Arg-2-Nal-Ala-Cys)-(Pro)$_2$-Lys-Asp-β-Ala-Arg-Lys-(Arg)$_3$-Gln-(Arg)$_3$-NH$_2$;

(SEQ ID NO: 207)
Ac-c(Cys-Glu-His-D-2-Nal-Arg-2-Nal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 208)
Ac-c(Cys-Glu-His-D-2-Nal-Arg-Bal-Ala-Cys)-(Pro)$_2$-Lys-Asp-β-Ala-(Arg)$_2$-Lys-(Arg)$_2$-Gln-(Arg)$_3$-NH$_2$;

(SEQ ID NO: 209)
Ac-c(Cys-Glu-His-D-2-Nal-Arg-Bal-Ala-Cys)-(Pro)$_2$-Lys-Asp-β-Ala-Arg-Lys-(Arg)$_3$-Gln-(Arg)$_3$-NH$_2$;

-continued (SEQ ID NO: 210)
Ac-c(Cys-Glu-His-D-2-Nal-Arg-Bal-Ala-Cys)-(Pro)$_2$-Lys-Asp-β-Ala-Tyr-Gly-(Arg)$_2$-Lys-(Arg)$_2$-Gln-(Arg)$_3$-NH$_2$;

(SEQ ID NO: 211)
Ac-c(Cys-Glu-His-D-2-Nal-Arg-Bal-Ala-Cys)-(Pro)$_2$-Lys-Asp-β-Ala-Tyr-Gly-Arg-Lys-(Arg)$_3$-Gln-(Arg)$_3$-NH$_2$;

(SEQ ID NO: 212)
Ac-c(Cys-Glu-His-D-2-Nal-Arg-Bal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 213)
Ac-c(Cys-Glu-His-D-2-Nal-Arg-Bal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 214)
Ac-c(Cys-Glu-His-D-2-Nal-Arg-Trp-Ala-Cys)-(Pro)$_2$-Lys-Asp-β-Ala-(Arg)$_5$-Gln-(Arg)$_3$-NH$_2$;

(SEQ ID NO: 215)
Ac-c(Cys-Glu-His-D-2-Nal-Arg-Trp-Ala-Cys)-(Pro)$_2$-Arg-Asp-β-Ala-(Arg)$_5$-Gln-(Arg)$_3$-NH$_2$;

(SEQ ID NO: 216)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_3$-NH$_2$;

(SEQ ID NO: 217)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_3$-NH$_2$;

(SEQ ID NO: 218)
Ac-c(Cys-Glu-His-D-2-Nal-Arg-Trp-Ala-Cys)-(Pro)$_2$-Lys-Asp-β-Ala-(Arg)$_5$-Gln-(Arg)$_4$-NH$_2$;

(SEQ ID NO: 219)
Ac-c(Cys-Glu-His-D-2-Nal-Arg-Trp-Ala-Cys)-(Pro)$_2$-Arg-Asp-β-Ala-(Arg)$_5$-Gln-(Arg)$_4$-NH$_2$;

(SEQ ID NO: 220)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_4$-NH$_2$;

(SEQ ID NO: 221)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_4$-NH$_2$;

(SEQ ID NO: 222)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_4$-NH$_2$;

(SEQ ID NO: 223)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 224)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 225)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 226)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 227)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 228)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_4$-NH$_2$;

(SEQ ID NO: 229)
Ac-c(Cys-Glu-His-D-2-Nal-Arg-1-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 230)
Ac-c(Cys-Glu-His-D-2-Nal-Arg-1-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 231)
Ac-c(Cys-Glu-His-D-2-Nal-Arg-2-Nal-Ala-Cys)-(Pro)$_2$-Arg-Asp-β-Ala-(Arg)$_6$-Gln-(Arg)$_3$-NH$_2$;

(SEQ ID NO: 232)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_4$-NH$_2$;

(SEQ ID NO: 233)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_4$-NH$_2$;

(SEQ ID NO: 234)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 235)
Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 236)
Ac-c(Cys-Glu-His-D-2-Nal-Arg-2-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 237)
Ac-c(Cys-Glu-His-D-2-Nal-Arg-2-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 238)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 239)
Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_4$-NH$_2$;

(SEQ ID NO: 240)
Ac-c(Cys-Glu-His-D-2-Nal-Arg-Bal-Ala-Cys)-(Pro)$_2$-Lys-Asp-β-Ala-(Arg)$_5$-Gln-(Arg)$_4$-NH$_2$;

(SEQ ID NO: 241)
Ac-c(Cys-Glu-His-D-2-Nal-Arg-Bal-Ala-Cys)-(Pro)$_2$-Arg-Asp-β-Ala-(Arg)$_5$-Gln-(Arg)$_4$-NH$_2$;

(SEQ ID NO: 242)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_3$-NH$_2$;

(SEQ ID NO: 243)
Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_4$-NH$_2$;

(SEQ ID NO: 244)
Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_4$-NH$_2$;

(SEQ ID NO: 245)
Ac-c(Cys-Glu-His-D-2-Nal-Arg-Bal-Ala-Cys)-(Pro)$_2$-Lys-Asp-β-Ala-Tyr-Gly-(Arg)$_6$-Gln-(Arg)$_3$-NH$_2$;

(SEQ ID NO: 246)
Ac-c(Cys-Glu-His-D-2-Nal-Arg-Bal-Ala-Cys)-(Pro)$_2$-Arg-Asp-β-Ala-Tyr-Gly-(Arg)$_6$-Gln-(Arg)$_3$-NH$_2$;

(SEQ ID NO: 247)
Ac-Nle-c(Cys-D-Ala-His-D-Phe-Arg-Trp-Cys)-(Doc)$_2$-Tyr-Gly-Arg-(Lys)$_2$-(Arg)$_2$-Gln-(Arg)$_3$-NH$_2$;

(SEQ ID NO: 248)
Ac-Nle-c(Cys-D-Ala-His-D-Phe-Arg-Trp-Cys)-β-Ala-Tyr-Gly-Arg-(Lys)$_2$-Arg-Gln-(Arg)$_4$-NH$_2$;

(SEQ ID NO: 249)
Ac-Nle-c(Cys-D-Ala-His-D-Phe-Arg-Trp-Cys)-Doc-Tyr-Gly-Arg-(Lys)$_2$-(Arg)$_2$-Gln-(Arg)$_3$-NH$_2$;

(SEQ ID NO: 250)
Ac-Nle-c(Cys-D-Ala-His-D-Phe-Arg-Trp-Cys)-β-Ala-(Arg)$_5$-Gln-(Arg)$_3$-NH$_2$;

(SEQ ID NO: 251)
Ac-Nle-c(Cys-D-Ala-His-D-Phe-Arg-Trp-Cys)-β-Ala-Gly-(Arg)$_5$-Gln-(Arg)$_3$-NH$_2$;

(SEQ ID NO: 252)
Ac-Nle-c(Cys-D-Ala-His-D-Phe-Arg-Trp-Cys)-β-Ala-Tyr-Gly-(Arg)$_5$-Gln-(Arg)$_3$-NH$_2$;

(SEQ ID NO: 253)
Ac-Nle-c(Cys-D-Ala-His-D-Phe-Arg-Trp-Cys)-β-Ala-Gly-(Arg)$_5$-Gln-(Arg)$_4$-NH$_2$;

(SEQ ID NO: 254)
Ac-Nle-c(Cys-D-Ala-His-D-Phe-Arg-Trp-Cys)-β-Ala-Tyr-Gly-(Arg)$_2$-Lys-(Arg)$_2$-Gln-(Arg)$_3$-NH$_2$;

(SEQ ID NO: 255)
Ac-Nle-c(Cys-D-Ala-His-D-Phe-Arg-Trp-Cys)-β-Ala-Tyr-Gly-Arg-Lys-(Arg)$_3$-Gln-(Arg)$_3$-NH$_2$;

(SEQ ID NO: 256)
Ac-Nle-c(Cys-D-Ala-His-D-Phe-Arg-Trp-Cys)-β-Ala-Gly-(Arg)$_2$-Lys-(Arg)$_2$-Gln-(Arg)$_3$-NH$_2$;

(SEQ ID NO: 257)
Ac-Nle-c(Cys-D-Ala-His-D-Phe-Arg-Trp-Cys)-β-Ala-Gly-Arg-Lys-(Arg)$_3$-Gln-(Arg)$_3$-NH$_2$;

-continued

```
                                             (SEQ ID NO: 258)
Ac-Nle-c(Cys-D-Ala-His-D-Phe-Arg-Trp-Cys)-β-Ala-(Arg)₂-Lys-(Arg)₂-

Gln-(Arg)₃-NH₂;

(SEQ ID NO: 259)
Ac-Nle-c(Cys-D-Ala-His-D-Phe-Arg-Trp-Cys)-β-Ala-Arg-Lys-(Arg)₃-Gln- (Arg)₃-NH₂;

(SEQ ID NO: 260)
Ac-Nle-c(Cys-D-Ala-His-D-Phe-Arg-Trp-Cys)-(β-Ala)₂-(Arg)₅-Gln-(Arg)₃-

NH₂;

(SEQ ID NO: 261)
Ac-Nle-c(Cys-D-Ala-His-D-Phe-Arg-Trp-Cys)-(β-Ala)₂-Gly-(Arg)₅-Gln- (Arg)₃-NH₂;

(SEQ ID NO: 262)
Ac-Nle-c(Cys-D-Ala-His-D-Phe-Arg-Trp-Cys)-(β-Ala)₂-Tyr-Gly-(Arg)₅-

Gln-(Arg)₃-NH₂;

(SEQ ID NO: 263)
Ac-Nle-c(Cys-D-Ala-His-D-Phe-Arg-Trp-Cys)-Doc-(Arg)₅-Gln-(Arg)₃-

NH₂;

(SEQ ID NO: 264)
Ac-Nle-c(Cys-D-Ala-His-D-Phe-Arg-Trp-Cys)-Doc-Gly-(Arg)₅-Gln-(Arg)₃-

NH₂;

(SEQ ID NO: 265)
Ac-Nle-c(Cys-D-Ala-His-D-Phe-Arg-Trp-Cys)-Doc-Tyr-Gly-(Arg)₅-Gln- (Arg)₃-NH₂;

(SEQ ID NO: 266)
Ac-Nle-c(Cys-D-Ala-His-D-Phe-Arg-Trp-Cys)-(Doc)₂-(Arg)₅-Gln-(Arg)₃-

NH₂;

(SEQ ID NO: 267)
Ac-Nle-c(Cys-D-Ala-His-D-Phe-Arg-Trp-Cys)-(Doc)₂-Gly-(Arg)₅-Gln- (Arg)₃-NH₂;

(SEQ ID NO: 268)
Ac-Nle-c(Cys-D-Ala-His-D-Phe-Arg-Trp-Cys)-(Doc)₂-Tyr-Gly-(Arg)₅-

Gln-(Arg)₃-NH₂;

(SEQ ID NO: 269)
Ac-Nle-c(Cys-D-Ala-His-D-Phe-Arg-Trp-Cys)-β-Ala-(Arg)₅-Gln-(Arg)₄-

NH₂;

(SEQ ID NO: 270)
Ac-Nle-c(Cys-D-Ala-His-D-Phe-Arg-Trp-Cys)-β-Ala-Tyr-Gly-(Arg)₅-Gln- (Arg)₄-NH₂;

(SEQ ID NO: 271)
Ac-Nle-c(Cys-D-Ala-His-D-Phe-Arg-Trp-Cys)-(β-Ala)₂-(Arg)₅-Gln-(Arg)₄-

NH₂;

(SEQ ID NO: 272)
Ac-Nle-c(Cys-D-Ala-His-D-Phe-Arg-Trp-Cys)-(β-Ala)₂-Gly-(Arg)₅-Gln- (Arg)₄-NH₂;

(SEQ ID NO: 273)
Ac-Nle-c(Cys-D-Ala-His-D-Phe-Arg-Trp-Cys)-(β-Ala)₂-Tyr-Gly-(Arg)₅-

Gln-(Arg)₄-NH₂;
```

-continued

Ac-Nle-c(Cys-D-Ala-His-D-Phe-Arg-Trp-Cys)-Doc-(Arg)$_5$-Gln-(Arg)$_4$-NH$_2$; (SEQ ID NO: 274)

Ac-Nle-c(Cys-D-Ala-His-D-Phe-Arg-Trp-Cys)-Doc-Gly-(Arg)$_5$-Gln-(Arg)$_4$-NH$_2$; (SEQ ID NO: 275)

Ac-Nle-c(Cys-D-Ala-His-D-Phe-Arg-Trp-Cys)-Doc-Tyr-Gly-(Arg)$_5$-Gln-(Arg)$_4$-NH$_2$; (SEQ ID NO: 276)

Ac-Nle-c(Cys-D-Ala-His-D-Phe-Arg-Trp-Cys)-(Doc)$_2$-(Arg)$_5$-Gln-(Arg)$_4$-NH$_2$; (SEQ ID NO: 277)

Ac-Nle-c(Cys-D-Ala-His-D-Phe-Arg-Trp-Cys)-(Doc)$_2$-Gly-(Arg)$_5$-Gln-(Arg)$_4$-NH$_2$; (SEQ ID NO: 278)

Ac-Nle-c(Cys-D-Ala-His-D-Phe-Arg-Trp-Cys)-(Doc)$_2$-Tyr-Gly-(Arg)$_5$-Gln-(Arg)$_4$-NH$_2$; (SEQ ID NO: 279)

Ac-Nle-c(Cys-His-D-Phe-Arg-Trp-Gaba-Cys)-β-Ala-Tyr-Gly-(Arg)$_5$-Gln-(Arg)$_3$-NH$_2$; (SEQ ID NO: 280)

Ac-Nle-c(Cys-His-D-Phe-Arg-Trp-Gaba-Cys)-β-Ala-(Arg)$_5$-Gln-(Arg)$_3$-NH$_2$; (SEQ ID NO: 281)

Ac-Nle-c(Asp-His-D-Phe-Arg-Trp-Ala-Lys)-β-Ala-Tyr-Gly-(Arg)$_5$-Gln-(Arg)$_3$-NH$_2$; (SEQ ID NO: 282)

Ac-Nle-c(Asp-His-D-Phe-Arg-Trp-Ala-Lys)-β-Ala-(Arg)$_5$-Gln-(Arg)$_3$-NH$_2$; (SEQ ID NO: 283)

Ac-Nle-c(Asp-His-D-Phe-Arg-Trp-Lys)-β-Ala-Tyr-Gly-(Arg)$_5$-Gln-(Arg)$_3$-NH$_2$; (SEQ ID NO: 284)

Ac-Nle-c(Asp-His-D-Phe-Arg-Trp-Lys)-β-Ala-Gly-(Arg)$_5$-Gln-(Arg)$_3$-NH$_2$; (SEQ ID NO: 285)

Ac-Nle-c(Asp-His-D-Phe-Arg-Trp-Lys)-β-Ala-(Arg)$_5$-Gln-(Arg)$_3$-NH$_2$; (SEQ ID NO: 286)

Ac-Nle-c(Asp-His-D-Phe-Arg-Trp-Lys)-(β-Ala)$_2$-Tyr-Gly-(Arg)$_5$-Gln-(Arg)$_3$-NH$_2$; (SEQ ID NO: 287)

Ac-Nle-c(Asp-His-D-Phe-Arg-Trp-Lys)-(β-Ala)$_2$-Gly-(Arg)$_5$-Gln-(Arg)$_3$-NH$_2$; (SEQ ID NO: 288)

Ac-Nle-c(Asp-His-D-Phe-Arg-Trp-Lys)-(β-Ala)$_2$-(Arg)$_5$-Gln-(Arg)$_3$-NH$_2$; (SEQ ID NO: 289)

Ac-Nle-c(Asp-His-D-Phe-Arg-Trp-Lys)-Doc-Tyr-Gly-(Arg)$_5$-Gln-(Arg)$_3$-NH$_2$; (SEQ ID NO: 290)

Ac-Nle-c(Asp-His-D-Phe-Arg-Trp-Lys)-Doc-Gly-(Arg)$_5$-Gln-(Arg)$_3$-NH$_2$; (SEQ ID NO: 291)

-continued

Ac-Nle-c(Asp-His-D-Phe-Arg-Trp-Lys)-Doc-(Arg)$_5$-Gln-(Arg)$_3$-NH$_2$; (SEQ ID NO: 292)

Ac-Nle-c(Asp-His-D-Phe-Arg-Trp-Lys)-(Doc)$_2$-Tyr-Gly-(Arg)$_5$-Gln-(Arg)$_3$-NH$_2$; (SEQ ID NO: 293)

Ac-Nle-c(Asp-His-D-Phe-Arg-Trp-Lys)-(Doc)$_2$-Gly-(Arg)$_5$-Gln-(Arg)$_3$-NH$_2$; (SEQ ID NO: 294)

Ac-Nle-c(Asp-His-D-Phe-Arg-Trp-Lys)-(Doc)$_2$-(Arg)$_5$-Gln-(Arg)$_3$-NH$_2$; (SEQ ID NO: 295)

Ac-Nle-c(Asp-His-D-Phe-Arg-Trp-Lys)-β-Ala-Tyr-Gly-(Arg)$_5$-Gln-(Arg)$_4$-NH$_2$; (SEQ ID NO: 296)

Ac-Nle-c(Asp-His-D-Phe-Arg-Trp-Lys)-β-Ala-Gly-(Arg)$_5$-Gln-(Arg)$_4$-NH$_2$; (SEQ ID NO: 297)

Ac-Nle-c(Asp-His-D-Phe-Arg-Trp-Lys)-β-Ala-(Arg)$_5$-Gln-(Arg)$_4$-NH$_2$; (SEQ ID NO: 298)

Ac-Nle-c(Asp-His-D-Phe-Arg-Trp-Lys)-(β-Ala)$_2$-Tyr-Gly-(Arg)$_5$-Gln-(Arg)$_4$-NH$_2$; (SEQ ID NO: 299)

Ac-Nle-c(Asp-His-D-Phe-Arg-Trp-Lys)-(β-Ala)$_2$-Gly-(Arg)$_5$-Gln-(Arg)$_4$-NH$_2$; (SEQ ID NO: 300)

Ac-Nle-c(Asp-His-D-Phe-Arg-Trp-Lys)-(β-Ala)$_2$-(Arg)$_5$-Gln-(Arg)$_4$-NH$_2$; (SEQ ID NO: 301)

Ac-Nle-c(Asp-His-D-Phe-Arg-Trp-Lys)-Doc-Tyr-Gly-(Arg)$_5$-Gln-(Arg)$_4$-NH$_2$; (SEQ ID NO: 302)

Ac-Nle-c(Asp-His-D-Phe-Arg-Trp-Lys)-Doc-Gly-(Arg)$_5$-Gln-(Arg)$_4$-NH$_2$; (SEQ ID NO: 303)

Ac-Nle-c(Asp-His-D-Phe-Arg-Trp-Lys)-Doc-(Arg)$_5$-Gln-(Arg)$_4$-NH$_2$; (SEQ ID NO: 304)

Ac-Nle-c(Asp-His-D-Phe-Arg-Trp-Lys)-(Doc)$_2$-Tyr-Gly-(Arg)$_5$-Gln-(Arg)$_4$-NH$_2$; (SEQ ID NO: 305)

Ac-Nle-c(Asp-His-D-Phe-Arg-Trp-Lys)-(Doc)$_2$-Gly-(Arg)$_5$-Gln-(Arg)$_4$-NH$_2$; (SEQ ID NO: 306)

Ac-Nle-c(Asp-His-D-Phe-Arg-Trp-Lys)-(Doc)$_2$-(Arg)$_5$-Gln-(Arg)$_4$-NH$_2$; (SEQ ID NO: 307)

Ac-Nle-c(Asp-His-D-Phe-Arg-Trp-β-Ala-Lys)-β-Ala-Tyr-Gly-(Arg)$_5$-Gln-(Arg)$_3$-NH$_2$; (SEQ ID NO: 308)

Ac-Nle-c(Asp-His-D-Phe-Arg-Trp-β-Ala-Lys)-β-Ala-(Arg)$_5$-Gln-(Arg)$_3$-NH$_2$; (SEQ ID NO: 309)

Ac-Nle-c(Cys-His-D-Phe-Arg-Trp-Ahx-Cys)-β-Ala-Tyr-Gly-(Arg)$_5$-Gln-(Arg)$_3$-NH$_2$; (SEQ ID NO: 310)

-continued (SEQ ID NO: 311)
Ac-Nle-c(Cys-His-D-Phe-Arg-Trp-Ahx-Cys)-β-Ala-(Arg)$_5$-Gln-(Arg)$_3$-NH$_2$;

(SEQ ID NO: 312)
D-Phe-c(Cys-His-D-Phe-Arg-Trp-β-Ala-D-Cys)-Thr-β-Ala-Tyr-Gly-(Arg)$_5$-Gln-(Arg)$_3$-NH$_2$;

(SEQ ID NO: 313)
D-Phe-c(Cys-His-D-Phe-Arg-Trp-β-Ala-D-Cys)-Thr-β-Ala-(Arg)$_5$-Gln-(Arg)$_3$-NH$_2$;

(SEQ ID NO: 314)
Ac-Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 315)
Ac-Nle-c(Cys-His-D-Phe-Arg-Trp-Apn-Cys)-β-Ala-(Arg)$_5$-Gln-(Arg)$_3$-NH$_2$;

(SEQ ID NO: 316)
Ac-Cha-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 317)
Ac-Cha-c(Asp-His-D-Phe-Arg-Trp-Gaba-Lys)-β-Ala-(Arg)$_5$-Gln-(Arg)$_3$-NH$_2$;

(SEQ ID NO: 318)
Ac-Nle-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 319)
Ac-Nle-c(Asp-His-D-Phe-Arg-Trp-Gaba-Lys)-β-Ala-(Arg)$_5$-Gln-(Arg)$_3$-NH$_2$;

(SEQ ID NO: 320)
Ac-Chg-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 321)
Ac-Chg-c(Asp-His-D-Phe-Arg-Trp-Gaba-Lys)-β-Ala-(Arg)$_5$-Gln-(Arg)$_3$-NH$_2$;

(SEQ ID NO: 322)
Ac-hCha-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 323)
Ac-hCha-c(Asp-His-D-Phe-Arg-Trp-Gaba-Lys)-β-Ala-(Arg)$_5$-Gln-(Arg)$_3$-NH$_2$;

(SEQ ID NO: 324)
Ac-hCha-c(Asp-His-D-Phe-Arg-Trp-Gaba-Lys)-(β-Ala)$_2$-Tyr-Gly-(Arg)$_5$-Gln-(Arg)$_3$-NH$_2$;

(SEQ ID NO: 325)
Ac-hCha-c(Asp-His-D-Phe-Arg-Trp-Gaba-Lys)-(β-Ala)$_2$-(Arg)$_5$-Gln-(Arg)$_3$-NH$_2$;

-continued

```
                                           (SEQ ID NO: 326)
Ac-hCha-c(Asp-His-D-Phe-Arg-Trp-Gaba-Lys)-Doc-Tyr-Gly-(Arg)5-Gln-
(Arg)3-NH2;

(SEQ ID NO: 327)
Ac-hCha-c(Asp-His-D-Phe-Arg-Trp-Gaba-Lys)-Doc-(Arg)5-Gln-(Arg)3-
NH2;

(SEQ ID NO: 328)
Ac-hCha-c(Asp-His-D-Phe-Arg-Trp-Gaba-Lys)-(Doc)2-Tyr-Gly-(Arg)5-
Gln-(Arg)3-NH2;

(SEQ ID NO: 329)
Ac-hCha-c(Asp-His-D-Phe-Arg-Trp-Gaba-Lys)-(Doc)2-(Arg)5-Gln-(Arg)3-
NH2;

(SEQ ID NO: 330)
Ac-hCha-c(Asp-His-D-Phe-Arg-Trp-Gaba-Lys)-β-Ala-Tyr-Gly-(Arg)5-Gln-
(Arg)4-NH2;

(SEQ ID NO: 331)
Ac-hCha-c(Asp-His-D-Phe-Arg-Trp-Gaba-Lys)-β-Ala-(Arg)5-Gln-(Arg)4-
NH2;

(SEQ ID NO: 332)
Ac-hCha-c(Asp-His-D-Phe-Arg-Trp-Gaba-Lys)-(β-Ala)2-Tyr-Gly-(Arg)5-
Gln-(Arg)4-NH2;

(SEQ ID NO: 333)
Ac-hCha-c(Asp-His-D-Phe-Arg-Trp-Gaba-Lys)-(β-Ala)2-(Arg)5-Gln-(Arg)4-
NH2;

(SEQ ID NO: 334)
Ac-hCha-c(Asp-His-D-Phe-Arg-Trp-Gaba-Lys)-Doc-Tyr-Gly-(Arg)5-Gln-
(Arg)4-NH2;

(SEQ ID NO: 335)
Ac-hCha-c(Asp-His-D-Phe-Arg-Trp-Gaba-Lys)-Doc-(Arg)5-Gln-(Arg)4-
NH2;

(SEQ ID NO: 336)
Ac-hCha-c(Asp-His-D-Phe-Arg-Trp-Gaba-Lys)-(Doc)2-Tyr-Gly-(Arg)5-
Gln-(Arg)4-NH2;

(SEQ ID NO: 337)
Ac-hCha-c(Asp-His-D-Phe-Arg-Trp-Gaba-Lys)-(Doc)2-(Arg)5-Gln-(Arg)4-
NH2;

(SEQ ID NO: 338)
Ac-D-Chg-c(Asp-His-D-Phe-Arg-Trp-Gaba-Lys)-β-Ala-Tyr-Gly-(Arg)5-
Gln-(Arg)3-NH2;

(SEQ ID NO: 339)
Ac-D-Chg-c(Asp-His-D-Phe-Arg-Trp-Gaba-Lys)-β-Ala-(Arg)5-Gln-(Arg)3-
NH2;

(SEQ ID NO: 340)
Ac-hPhe-c(Asp-His-D-Phe-Arg-Trp-Gaba-Lys)-β-Ala-Tyr-Gly-(Arg)5-Gln-
(Arg)3-NH2;

(SEQ ID NO: 341)
Ac-hPhe-c(Asp-His-D-Phe-Arg-Trp-Gaba-Lys)-β-Ala-(Arg)5-Gln-(Arg)3-
NH2;
```

-continued

Ac-Nle-c(Cys-His-D-Phe-Arg-D-Trp-Apn-Cys)-β-Ala-Tyr-Gly-(Arg)$_5$-Gln-(Arg)$_3$-NH$_2$; (SEQ ID NO: 342)

Ac-Nle-c(Cys-His-D-Phe-Arg-D-Trp-Apn-Cys)-β-Ala-(Arg)$_5$-Gln-(Arg)$_3$-NH$_2$; (SEQ ID NO: 343)

Ac-Nle-c(Cys-His-D-Phe-Arg-D-Trp-Ahx-Cys)-β-Ala-Tyr-Gly-(Arg)$_5$-Gln-(Arg)$_3$-NH$_2$; (SEQ ID NO: 344)

Ac-Nle-c(Cys-His-D-Phe-Arg-D-Trp-Ahx-Cys)-β-Ala-(Arg)$_5$-Gln-(Arg)$_3$-NH$_2$; (SEQ ID NO: 345)

Ac-Nle-c(Cys-His-D-Phe-Arg-D-Trp-β-Ala-Cys)-β-Ala-Tyr-Gly-(Arg)$_5$-Gln-(Arg)$_3$-NH$_2$; (SEQ ID NO: 346)

Ac-Nle-c(Cys-His-D-Phe-Arg-D-Trp-β-Ala-Cys)-β-Ala-(Arg)$_5$-Gln-(Arg)$_3$-NH$_2$; (SEQ ID NO: 347)

Ac-Nle-c(Cys-D-Ala-His-D-Phe-Arg-Trp-Pen)-β-Ala-Tyr-Gly-(Arg)$_5$-Gln-(Arg)$_3$-NH$_2$; (SEQ ID NO: 348)

Ac-Nle-c(Cys-D-Ala-His-D-Phe-Arg-Trp-Pen)-β-Ala-Gly-(Arg)$_5$-Gln-(Arg)$_3$-NH$_2$; (SEQ ID NO: 349)

Ac-Nle-c(Cys-D-Ala-His-D-Phe-Arg-Trp-Pen)-β-Ala-(Arg)$_5$-Gln-(Arg)$_3$-NH$_2$; (SEQ ID NO: 350)

Ac-Nle-c(Cys-D-Ala-His-D-Phe-Arg-Trp-Pen)-(β-Ala)$_2$-Tyr-Gly-(Arg)$_5$-Gln-(Arg)$_3$-NH$_2$; (SEQ ID NO: 351)

Ac-Nle-c(Cys-D-Ala-His-D-Phe-Arg-Trp-Pen)-(β-Ala)$_2$-Gly-(Arg)$_5$-Gln-(Arg)$_3$-NH$_2$; (SEQ ID NO: 352)

Ac-Nle-c(Cys-D-Ala-His-D-Phe-Arg-Trp-Pen)-(β-Ala)$_2$-(Arg)$_5$-Gln-(Arg)$_3$-NH$_2$; (SEQ ID NO: 353)

Ac-Nle-c(Cys-D-Ala-His-D-Phe-Arg-Trp-Pen)-Doc-Tyr-Gly-(Arg)$_5$-Gln-(Arg)$_3$-NH$_2$; (SEQ ID NO: 354)

Ac-Nle-c(Cys-D-Ala-His-D-Phe-Arg-Trp-Pen)-Doc-Gly-(Arg)$_5$-Gln-(Arg)$_3$-NH$_2$; (SEQ ID NO: 355)

Ac-Nle-c(Cys-D-Ala-His-D-Phe-Arg-Trp-Pen)-Doc-(Arg)$_5$-Gln-(Arg)$_3$-NH$_2$; (SEQ ID NO: 356)

Ac-Nle-c(Cys-D-Ala-His-D-Phe-Arg-Trp-Pen)-(Doc)$_2$-Tyr-Gly-(Arg)$_5$-Gln-(Arg)$_3$-NH$_2$; (SEQ ID NO: 357)

-continued

Ac-Nle-c(Cys-D-Ala-His-D-Phe-Arg-Trp-Pen)-(Doc)$_2$-Gly-(Arg)$_5$-Gln-(Arg)$_3$-NH$_2$; (SEQ ID NO: 358)

Ac-Nle-c(Cys-D-Ala-His-D-Phe-Arg-Trp-Pen)-(Doc)$_2$-(Arg)$_5$-Gln-(Arg)$_3$-NH$_2$; (SEQ ID NO: 359)

D-Phe-c(Cys-His-D-(Et)Tyr-Arg-Trp-β-Ala-D-Cys)-β-Ala-Tyr-Gly-(Arg)$_5$-Gln-(Arg)$_3$-NH$_2$; (SEQ ID NO: 360)

D-Phe-c(Cys-His-D-(Et)Tyr-Arg-Trp-β-Ala-D-Cys)-β-Ala-(Arg)$_5$-Gln-(Arg)$_3$-NH$_2$; (SEQ ID NO: 361)

D-Phe-c(Cys-His-D-(Et)Tyr-Arg-Trp-β-Ala-D-Cys)-β-Ala-Gly-(Arg)$_5$-Gln-(Arg)$_3$-NH$_2$; (SEQ ID NO: 362)

D-Phe-c(Cys-His-D-(Et)Tyr-Arg-Trp-β-Ala-D-Cys)-β-Ala-(Arg)$_5$-Gln-(Arg)$_4$-NH$_2$; (SEQ ID NO: 363)

D-Phe-c(Cys-His-D-(Et)Tyr-Arg-Trp-β-Ala-D-Cys)-(β-Ala)$_2$-Tyr-Gly-(Arg)$_5$-Gln-(Arg)$_3$-NH$_2$; (SEQ ID NO: 364)

D-Phe-c(Cys-His-D-(Et)Tyr-Arg-Trp-β-Ala-D-Cys)-(β-Ala)$_2$-(Arg)$_5$-Gln-(Arg)$_3$-NH$_2$; (SEQ ID NO: 365)

D-Phe-c(Cys-His-D-(Et)Tyr-Arg-Trp-β-Ala-D-Cys)-(β-Ala)$_2$-Gly-(Arg)$_5$-Gln-(Arg)$_3$-NH$_2$; (SEQ ID NO: 366)

D-Phe-c(Cys-His-D-(Et)Tyr-Arg-Trp-β-Ala-D-Cys)-(β-Ala)$_2$-(Arg)$_5$-Gln-(Arg)$_4$-NH$_2$; (SEQ ID NO: 367)

D-Phe-c(Cys-His-D-(Et)Tyr-Arg-Trp-β-Ala-D-Cys)-Doc-Tyr-Gly-(Arg)$_5$-Gln-(Arg)$_3$-NH$_2$; (SEQ ID NO: 368)

D-Phe-c(Cys-His-D-(Et)Tyr-Arg-Trp-β-Ala-D-Cys)-Doc-(Arg)$_5$-Gln-(Arg)$_3$-NH$_2$; (SEQ ID NO: 369)

D-Phe-c(Cys-His-D-(Et)Tyr-Arg-Trp-β-Ala-D-Cys)-Doc-Gly-(Arg)$_5$-Gln-(Arg)$_3$-NH$_2$; (SEQ ID NO: 370)

D-Phe-c(Cys-His-D-(Et)Tyr-Arg-Trp-β-Ala-D-Cys)-Doc-(Arg)$_5$-Gln-(Arg)$_4$-NH$_2$; (SEQ ID NO: 371)

D-Phe-c(Cys-His-D-(Et)Tyr-Arg-Trp-β-Ala-D-Cys)-(Doc)$_2$-Tyr-Gly-(Arg)$_5$-Gln-(Arg)$_3$-NH$_2$; (SEQ ID NO: 372)

D-Phe-c(Cys-His-D-(Et)Tyr-Arg-Trp-β-Ala-D-Cys)-(Doc)$_2$-(Arg)$_5$-Gln-(Arg)$_3$-NH$_2$; (SEQ ID NO: 373)

-continued

```
                                           (SEQ ID NO: 374)
D-Phe-c(Cys-His-D-(Et)Tyr-Arg-Trp-β-Ala-D-Cys)-(Doc)2-Gly-(Arg)5-

Gln-(Arg)3-NH2;

(SEQ ID NO: 375)
D-Phe-c(Cys-His-D-(Et)Tyr-Arg-Trp-β-Ala-D-Cys)-(Doc)2-(Arg)5-Gln- (Arg)4-NH2;

(SEQ ID NO: 376)
D-Phe-c(Cys-His-D-(Et)Tyr-hArg-Trp-β-Ala-D-Cys)-Thr-β-Ala-Tyr-Gly- (Arg)5-Gln-(Arg)3-NH2;

(SEQ ID NO: 377)
D-Phe-c(Cys-His-D-(Et)Tyr-hArg-Trp-β-Ala-D-Cys)-Thr-β-Ala-(Arg)5-

Gln-(Arg)3-NH2;

(SEQ ID NO: 378)
D-Phe-c(Cys-His-D-(Et)Tyr-hArg-Trp-β-Ala-D-Cys)-Thr-(β-Ala)2-Tyr-Gly- (Arg)5-Gln-(Arg)3-NH2;

(SEQ ID NO: 379)
D-Phe-c(Cys-His-D-(Et)Tyr-hArg-Trp-β-Ala-D-Cys)-Thr-(β-Ala)2-(Arg)5-

Gln-(Arg)3-NH2;

(SEQ ID NO: 380)
D-Phe-c(Cys-His-D-(Et)Tyr-hArg-Trp-β-Ala-D-Cys)-Thr-Doc-Tyr-Gly- (Arg)5-Gln-(Arg)3-NH2;

(SEQ ID NO: 381)
D-Phe-c(Cys-His-D-(Et)Tyr-hArg-Trp-β-Ala-D-Cys)-Thr-Doc-(Arg)5-Gln- (Arg)3-NH2;

(SEQ ID NO: 382)
D-Phe-c(Cys-His-D-(Et)Tyr-hArg-Trp-β-Ala-D-Cys)-Thr-(Doc)2-Tyr-Gly- (Arg)5-Gln-(Arg)3-NH2;

(SEQ ID NO: 383)
D-Phe-c(Cys-His-D-(Et)Tyr-hArg-Trp-β-Ala-D-Cys)-Thr-β-Ala-Tyr-Gly- (Arg)5-Gln-(Arg)4-NH2;

(SEQ ID NO: 384)
D-Phe-c(Cys-His-D-(Et)Tyr-hArg-Trp-β-Ala-D-Cys)-Thr-β-Ala-(Arg)5-

Gln-(Arg)4-NH2;

(SEQ ID NO: 385)
D-Phe-c(Cys-His-D-(Et)Tyr-hArg-Trp-β-Ala-D-Cys)-Thr-(β-Ala)2-Tyr-Gly- (Arg)5-Gln-(Arg)4-NH2;

(SEQ ID NO: 386)
D-Phe-c(Cys-His-D-(Et)Tyr-hArg-Trp-β-Ala-D-Cys)-Thr-(β-Ala)2-(Arg)5-

Gln-(Arg)4-NH2;

(SEQ ID NO: 387)
D-Phe-c(Cys-His-D-(Et)Tyr-hArg-Trp-β-Ala-D-Cys)-Thr-Doc-Tyr-Gly- (Arg)5-Gln-(Arg)4-NH2;

(SEQ ID NO: 388)
D-Phe-c(Cys-His-D-(Et)Tyr-hArg-Trp-β-Ala-D-Cys)-Thr-Doc-(Arg)5-Gln- (Arg)4-NH2;
```

-continued (SEQ ID NO: 389)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_4$-NH$_2$;

(SEQ ID NO: 390)
D-Phe-c(Cys-His-D-(Et)Tyr-hArg-Trp-β-Ala-D-Cys)-Thr-(Doc)$_2$-(Arg)$_5$-Gln-(Arg)$_4$-NH$_2$;

(SEQ ID NO: 391)
D-Phe-c(Cys-His-D-(Et)Tyr-hArg-Bip-β-Ala-D-Cys)-Thr-β-Ala-Tyr-Gly-(Arg)$_5$-Gln-(Arg)$_3$-NH$_2$;

(SEQ ID NO: 392)
D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$;

(SEQ ID NO: 393)
D-Phe-c(Cys-His-D-(Et)Tyr-hArg-Bip-β-Ala-D-Cys)-Thr-β-Ala-(Arg)$_5$-Gln-(Arg)$_3$-NH$_2$;

(SEQ ID NO: 394)
D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$;

(SEQ ID NO: 395)
D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$;

(SEQ ID NO: 396)
D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$;

(SEQ ID NO: 397)
D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$;

(SEQ ID NO: 398)
D-Phe-c(Cys-His-D-(Et)Tyr-hArg-Bip-β-Ala-D-Cys)-Thr-Doc-(Arg)$_5$-Gln-(Arg)$_3$-NH$_2$;

(SEQ ID NO: 399)
D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$;

(SEQ ID NO: 400)
D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$;

(SEQ ID NO: 401)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 402)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 403)
Nle-c(Cys-His-D-Phe-Arg-Trp-Apn-Cys)-β-Ala-Tyr-Gly-(Arg)$_5$-Gln-(Arg)$_3$-NH$_2$;

-continued

```
                                           (SEQ ID NO: 404)
Nle-c(Cys-His-D-Phe-Arg-Trp-Apn-Cys)-β-Ala-(Arg)5-Gln-(Arg)3-NH2;

(SEQ ID NO: 405)
Nle-c(Cys-His-D-Phe-Arg-Trp-Apn-Cys)-(β-Ala)2-Tyr-Gly-(Arg)5-Gln- (Arg)3-NH2;

(SEQ ID NO: 406)
Nle-c(Cys-His-D-Phe-Arg-Trp-Apn-Cys)-(β-Ala)2-(Arg)5-Gln-(Arg)3-NH2;

(SEQ ID NO: 407)
Nle-c(Cys-His-D-Phe-Arg-Trp-Apn-Cys)-β-Ala-Tyr-Gly-(Arg)5-Gln-(Arg)4-

NH2;

(SEQ ID NO: 408)
Nle-c(Cys-His-D-Phe-Arg-Trp-Apn-Cys)-β-Ala-(Arg)5-Gln-(Arg)4-NH2;

(SEQ ID NO: 409)
Nle-c(Cys-His-D-Phe-Arg-Trp-Apn-Cys)-(β-Ala)2-Tyr-Gly-(Arg)5-Gln- (Arg)4-NH2;

(SEQ ID NO: 410)
Nle-c(Cys-His-D-Phe-Arg-Trp-Apn-Cys)-(β-Ala)2-(Arg)5-Gln-(Arg)4-NH2;

(SEQ ID NO: 411)
Nle-c(Cys-His-D-Phe-Arg-Trp-Apn-Cys)-Doc-Tyr-Gly-(Arg)5-Gln-(Arg)3-

NH2;

(SEQ ID NO: 412)
Nle-c(Cys-His-D-Phe-Arg-Trp-Apn-Cys)-Doc-(Arg)5-Gln-(Arg)3-NH2;

(SEQ ID NO: 413)
Nle-c(Cys-His-D-Phe-Arg-Trp-Apn-Cys)-(Doc)2-Tyr-Gly-(Arg)5-Gln- (Arg)3-NH2;

(SEQ ID NO: 414)
Nle-c(Cys-His-D-Phe-Arg-Trp-Apn-Cys)-(Doc)2-(Arg)5-Gln-(Arg)3-NH2;

(SEQ ID NO: 415)
Nle-c(Cys-His-D-Phe-Arg-Trp-Apn-Cys)-Doc-Tyr-Gly-(Arg)5-Gln-(Arg)4-

NH2;

(SEQ ID NO: 416)
Nle-c(Cys-His-D-Phe-Arg-Trp-Apn-Cys)-Doc-(Arg)5-Gln-(Arg)4-NH2;

(SEQ ID NO: 417)
Nle-c(Cys-His-D-Phe-Arg-Trp-Apn-Cys)-(Doc)2-Tyr-Gly-(Arg)5-Gln- (Arg)4-NH2;

(SEQ ID NO: 418)
Nle-c(Cys-His-D-Phe-Arg-Trp-Apn-Cys)-(Doc)2-(Arg)5-Gln-(Arg)4-NH2;

(SEQ ID NO: 419)
Ac-Nle-c(Cys-D-Leu-His-D-Phe-Arg-Trp-Cys)-β-Ala-Tyr-Gly-(Arg)5-Gln- (Arg)3-NH2;

(SEQ ID NO: 420)
Ac-Nle-c(Cys-D-Leu-His-D-Phe-Arg-Trp-Cys)-β-Ala-(Arg)5-Gln-(Arg)3-

NH2;

(SEQ ID NO: 421)
Ac-Nle-c(Cys-D-Leu-His-D-Phe-Arg-Trp-Cys)-(β-Ala)2-Tyr-Gly-(Arg)5-

Gln-(Arg)3-NH2;

(SEQ ID NO: 422)
Ac-Nle-c(Cys-D-Leu-His-D-Phe-Arg-Trp-Cys)-(β-Ala)2-(Arg)5-Gln-(Arg)3-

NH2;
```

-continued

```
                                              (SEQ ID NO: 423)
Ac-Nle-c(Cys-D-Leu-His-D-Phe-Arg-Trp-Cys)-Doc-Tyr-Gly-(Arg)5-Gln- (Arg)3-NH2;

(SEQ ID NO: 424)
Ac-Nle-c(Cys-D-Leu-His-D-Phe-Arg-Trp-Cys)-Doc-(Arg)5-Gln-(Arg)3-

NH2;

(SEQ ID NO: 425)
Ac-Nle-c(Cys-D-Leu-His-D-Phe-Arg-Trp-Cys)-(Doc)2-Tyr-Gly-(Arg)5-

Gln-(Arg)3-NH2;

(SEQ ID NO: 426)
Ac-Nle-c(Cys-D-Leu-His-D-Phe-Arg-Trp-Cys)-(Doc)2-(Arg)5-Gln-(Arg)3-

NH2;

(SEQ ID NO: 427)
Ac-Nle-c(Cys-D-Leu-His-D-Phe-Arg-Trp-Cys)-β-Ala-Tyr-Gly-(Arg)5-Gln- (Arg)4-NH2;

(SEQ ID NO: 428)
Ac-Nle-c(Cys-D-Leu-His-D-Phe-Arg-Trp-Cys)-β-Ala-(Arg)5-Gln-(Arg)4-

NH2;

(SEQ ID NO: 429)
Ac-Nle-c(Cys-D-Leu-His-D-Phe-Arg-Trp-Cys)-(β-Ala)2-Tyr-Gly-(Arg)5-

Gln-(Arg)4-NH2;

(SEQ ID NO: 430)
Ac-Nle-c(Cys-D-Leu-His-D-Phe-Arg-Trp-Cys)-(β-Ala)2-(Arg)5-Gln-(Arg)4-

NH2;

(SEQ ID NO: 431)
Ac-Nle-c(Cys-D-Leu-His-D-Phe-Arg-Trp-Cys)-Doc-Tyr-Gly-(Arg)5-Gln- (Arg)4-NH2;

(SEQ ID NO: 432)
Ac-Nle-c(Cys-D-Leu-His-D-Phe-Arg-Trp-Cys)-Doc-(Arg)5-Gln-(Arg)4-

NH2;

(SEQ ID NO: 433)
Ac-Nle-c(Cys-D-Leu-His-D-Phe-Arg-Trp-Cys)-(Doc)2-Tyr-Gly-(Arg)5-

Gln-(Arg)4-NH2;

(SEQ ID NO: 434)
Ac-Nle-c(Cys-D-Leu-His-D-Phe-Arg-Trp-Cys)-(Doc)2-(Arg)5-Gln-(Arg)4-

NH2;

(SEQ ID NO: 435)
Ac-Nle-c(Cys-D-Cha-His-D-Phe-Arg-Trp-Cys)-β-Ala-Tyr-Gly-(Arg)5-Gln- (Arg)3-NH2;

(SEQ ID NO: 436)
Ac-Nle-c(Cys-D-Cha-His-D-Phe-Arg-Trp-Cys)-β-Ala-(Arg)5-Gln-(Arg)3-

NH2;

(SEQ ID NO: 437)
Ac-Nle-c(Cys-D-Cha-His-D-Phe-Arg-Trp-Cys)-(β-Ala)2-Tyr-Gly-(Arg)5-

Gln-(Arg)3-NH2;

(SEQ ID NO: 438)
Ac-Nle-c(Cys-D-Cha-His-D-Phe-Arg-Trp-Cys)-(β-Ala)2-(Arg)5-Gln-(Arg)3-

NH2;
```

-continued (SEQ ID NO: 439)
Ac-Nle-c(Cys-D-Cha-His-D-Phe-Arg-Trp-Cys)-Doc-Tyr-Gly-(Arg)$_5$-Gln-(Arg)$_3$-NH$_2$;

(SEQ ID NO: 440)
Ac-Nle-c(Cys-D-Cha-His-D-Phe-Arg-Trp-Cys)-Doc-(Arg)$_5$-Gln-(Arg)$_3$-NH$_2$;

(SEQ ID NO: 441)
Ac-Nle-c(Cys-D-Cha-His-D-Phe-Arg-Trp-Cys)-(Doc)$_2$-Tyr-Gly-(Arg)$_5$-Gln-(Arg)$_3$-NH$_2$;

(SEQ ID NO: 442)
Ac-Nle-c(Cys-D-Cha-His-D-Phe-Arg-Trp-Cys)-(Doc)$_2$-(Arg)$_5$-Gln-(Arg)$_3$-NH$_2$;

(SEQ ID NO: 443)
Ac-Nle-c(Cys-D-Cha-His-D-Phe-Arg-Trp-Cys)-β-Ala-Tyr-Gly-(Arg)$_5$-Gln-(Arg)$_4$-NH$_2$;

(SEQ ID NO: 444)
Ac-Nle-c(Cys-D-Cha-His-D-Phe-Arg-Trp-Cys)-β-Ala-(Arg)$_5$-Gln-(Arg)$_4$-NH$_2$;

(SEQ ID NO: 445)
Ac-Nle-c(Cys-D-Cha-His-D-Phe-Arg-Trp-Cys)-(β-Ala)$_2$-Tyr-Gly-(Arg)$_5$-Gln-(Arg)$_4$-NH$_2$;

(SEQ ID NO: 446)
Ac-Nle-c(Cys-D-Cha-His-D-Phe-Arg-Trp-Cys)-(β-Ala)$_2$-(Arg)$_5$-Gln-(Arg)$_4$-NH$_2$;

(SEQ ID NO: 447)
Ac-Nle-c(Cys-D-Cha-His-D-Phe-Arg-Trp-Cys)-Doc-Tyr-Gly-(Arg)$_5$-Gln-(Arg)$_4$-NH$_2$;

(SEQ ID NO: 448)
Ac-Nle-c(Cys-D-Cha-His-D-Phe-Arg-Trp-Cys)-Doc-(Arg)$_5$-Gln-(Arg)$_4$-NH$_2$;

(SEQ ID NO: 449)
Ac-Nle-c(Cys-D-Cha-His-D-Phe-Arg-Trp-Cys)-(Doc)$_2$-Tyr-Gly-(Arg)$_5$-Gln-(Arg)$_4$-NH$_2$;

(SEQ ID NO: 450)
Ac-Nle-c(Cys-D-Cha-His-D-Phe-Arg-Trp-Cys)-(Doc)$_2$-(Arg)$_5$-Gln-(Arg)$_4$-NH$_2$;

(SEQ ID NO: 451)
Nle-c(Cys-His-D-Phe-Arg-Trp-Gaba-Cys)-β-Ala-Tyr-Gly-(Arg)$_5$-Gln-(Arg)$_3$-NH$_2$;

(SEQ ID NO: 452)
Nle-c(Cys-His-D-Phe-Arg-Trp-Gaba-Cys)-β-Ala-(Arg)$_5$-Gln-(Arg)$_3$-NH$_2$;

(SEQ ID NO: 453)
Nle-c(Cys-His-D-Phe-Arg-Trp-Gaba-Cys)-(β-Ala)$_2$-Tyr-Gly-(Arg)$_5$-Gln-(Arg)$_3$-NH$_2$;

(SEQ ID NO: 454)
Nle-c(Cys-His-D-Phe-Arg-Trp-Gaba-Cys)-(β-Ala)$_2$-(Arg)$_5$-Gln-(Arg)$_3$-NH$_2$;

(SEQ ID NO: 455)
Nle-c(Cys-His-D-Phe-Arg-Trp-Gaba-Cys)-β-Ala-Tyr-Gly-(Arg)$_5$-Gln-(Arg)$_4$-NH$_2$;

Nle-c(Cys-His-D-Phe-Arg-Trp-Gaba-Cys)-β-Ala-(Arg)$_5$-Gln-(Arg)$_4$-NH$_2$; (SEQ ID NO: 456)

Nle-c(Cys-His-D-Phe-Arg-Trp-Gaba-Cys)-(β-Ala)$_2$-Tyr-Gly-(Arg)$_5$-Gln-(Arg)$_4$-NH$_2$; (SEQ ID NO: 457)

Nle-c(Cys-His-D-Phe-Arg-Trp-Gaba-Cys)-(β-Ala)$_2$-(Arg)$_5$-Gln-(Arg)$_4$-NH$_2$; (SEQ ID NO: 458)

Nle-c(Cys-His-D-Phe-Arg-Trp-Gaba-Cys)-Doc-Tyr-Gly-(Arg)$_5$-Gln-(Arg)$_3$-NH$_2$; (SEQ ID NO: 459)

Nle-c(Cys-His-D-Phe-Arg-Trp-Gaba-Cys)-Doc-(Arg)$_5$-Gln-(Arg)$_3$-NH$_2$; (SEQ ID NO: 460)

Nle-c(Cys-His-D-Phe-Arg-Trp-Gaba-Cys)-(Doc)$_2$-Tyr-Gly-(Arg)$_5$-Gln-(Arg)$_3$-NH$_2$; (SEQ ID NO: 461)

Nle-c(Cys-His-D-Phe-Arg-Trp-Gaba-Cys)-(Doc)$_2$-(Arg)$_5$-Gln-(Arg)$_3$-NH$_2$; (SEQ ID NO: 462)

Nle-c(Cys-His-D-Phe-Arg-Trp-Gaba-Cys)-Doc-Tyr-Gly-(Arg)$_5$-Gln-(Arg)$_4$-NH$_2$; (SEQ ID NO: 463)

Nle-c(Cys-His-D-Phe-Arg-Trp-Gaba-Cys)-Doc-(Arg)$_5$-Gln-(Arg)$_4$-NH$_2$; (SEQ ID NO: 464)

Nle-c(Cys-His-D-Phe-Arg-Trp-Gaba-Cys)-(Doc)$_2$-Tyr-Gly-(Arg)$_5$-Gln-(Arg)$_4$-NH$_2$; (SEQ ID NO: 465)

or

Nle-c(Cys-His-D-Phe-Arg-Trp-Gaba-Cys)-(Doc)$_2$-(Arg)$_5$-Gln-(Arg)$_4$-NH$_2$, (SEQ ID NO: 466)

or pharmaceutically acceptable salts thereof.

In an example embodiment, the compounds useful for practicing the methods described herein are the compounds of Formula (IV):

$$\text{Ac-}c(\text{Cys-Glu-His-A}^1\text{-Arg-A}^2\text{-A}^3\text{-Cys})\text{-(Pro)}_2\text{-Lys-Asp-NH}_2 \quad (IV)$$

or pharmaceutically acceptable salts thereof. In Formula (IV):

A$^1$ is the D-isomer of X-Phe or 2-Nal where X is halogen;
A$^2$ is Bal, 1-Nal, 2-Nal, or Trp; and
A$^3$ is Aib, Ala, β-Ala or Gly, In an example embodiments, the at least on eof the following compounds is used:

Ac-c(Cys-Glu-His-D-4-Br-Phe-Arg-Trp-Gly-Cys)-(Pro)$_2$-Lys-Asp-NH$_2$; (SEQ ID NO: 467)

Ac-c(Cys-Glu-His-D-2-Nal-Arg-Trp-Ala-Cys)-(Pro)$_2$-Lys-Asp-NH$_2$; (SEQ ID NO: 468)

Ac-c(Cys-Glu-His-D-2-Nal-Arg-2-Nal-Ala-Cys)-(Pro)$_2$-Lys-Asp-NH$_2$; (SEQ ID NO: 469)

Ac-c(Cys-Glu-His-D-2-Nal-Arg-1-Nal-Ala-Cys)-(Pro)$_2$-Lys-Asp-NH$_2$; (SEQ ID NO: 470)

Ac-c(Cys-Glu-His-D-2-Nal-Arg-Bal-Ala-Cys)-(Pro)$_2$-Lys-Asp-NH$_2$; (SEQ ID NO: 471)

Ac-c(Cys-Glu-His-D-2-Nal-Arg-2-Nal-β-Ala-Cys)-(Pro)$_2$-Lys-Asp-NH$_2$; (SEQ ID NO: 472)

or

Ac-c(Cys-Glu-His-D-2-Nal-Arg-2-Nal-Aib-Cys)-(Pro)$_2$-Lys-Asp-NH$_2$; (SEQ ID NO: 473)

or pharmaceutically acceptable salts thereof.

In example embodiments, an MC4R agonist useful for practicing the methods described herein is at least one compound modified with a hydantoin moiety according to Formula (V), (VI) or (VII), or a pharmaceutically acceptable salt, hydrate, solvate or a prodrug thereof.

Formula (V) is described below: (see International Patent Application Number PCT/US08/06675 incorporated herein by reference in its entirety).

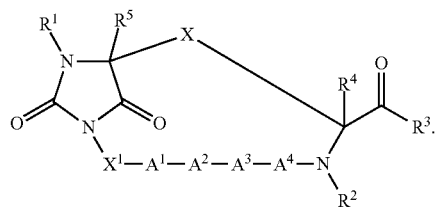

(V)

In Formula (V):

X is selected from the group consisting of —CH₂—S—S—CH₂—, —C(CH₃)₂—S—S—CH₂—, —CH₂—S—S—C(CH₃)₂—, —C(CH₃)₂—S—S—C(CH₃)₂—, —(CH₂)₂—S—S—CH₂—, —CH₂—S—S—(CH₂)₂—, —(CH₂)₂—S—S—(CH₂)₂—, —C(CH₃)₂—S—S—(CH₂)₂—, —(CH₂)₂—S—S—C(CH₃)₂—, —(CH₂)ᵣ—C(O)—NR⁸—(CH₂)ᵣ— and —(CH₂)ᵣ—NR⁸—C(O)—(CH₂)ᵣ—;

R² each is, independently, H, (C₁-C₁₀)alkyl or substituted (C₁-C₁₀)alkyl;

R³ is —OH or —NH₂;

R⁴ and R⁵ each is, independently, H, (C₁-C₁₀)alkyl or substituted (C₁-C₁₀)alkyl;

X¹ is

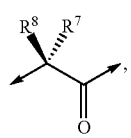

A¹ is H is, 2-Pal, 3-Pal, 4-Pal, (X¹, X², X³, X⁴, X⁵)Phe, Taz, 2-Thi, 3-Thi or is deleted;

A² is D-Bal, D-1-Nal, D-2-Nal, D-Phe or D-(X¹, X², X³, X⁴, X⁵)Phe;

A³ is Arg, hArg, Dab, Dap, Lys or Orn;

A⁴ is Bal, 1-Nal, 2-Nal, (X¹, X², X³, X⁴, X⁵)Phe or Trp;

R⁶ and R⁷ each is, independently for each occurrence thereof, H, (C₁-C₁₀)heteroalkyl, aryl(C₁-C₅)alkyl, substituted (C₁-C₁₀)alkyl, substituted (C₁-C₁₀)heteroalkyl or substituted aryl(C₁-C₅)alkyl provided that R⁶ and R⁷ may be joined together to form a ring;

R⁸ is H, (C₁-C₁₀)alkyl or substituted (C₁-C₁₀)alkyl;

r is, independently for each occurrence thereof, 1, 2, 3, 4 or 5; and t is, independently for each occurrence thereof, 1 or 2.

Compounds according the foregoing formula can include compounds wherein X¹ is selected from the group consisting of:

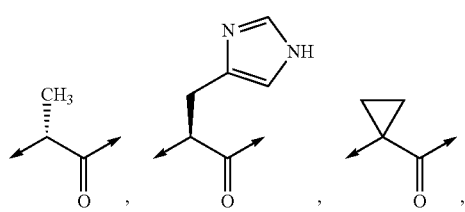

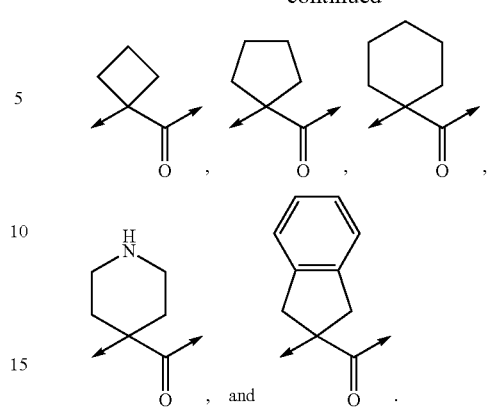

Representative embodiments of the foregoing class of compounds are as follows:

c[Hydantoin(C(O)-(Cys-D-Ala))-His-D-Phe-Arg-Trp-Cys]-NH₂; (SEQ ID NO: 474)

c[Hydantoin(C(O)-(hCys-D-Ala))-His-D-Phe-Arg-Trp-Cys]-NH₂; (SEQ ID NO: 475)

c[Hydantoin(C(O)-(Cys-D-Ala))-His-D-2-Nal-Arg-Trp-Cys]-NH₂; (SEQ ID NO: 476)

c[Hydantoin(C(O)-(hCys-D-Ala))-His-D-2-Nal-Arg-Trp-Cys]-NH₂; (SEQ ID NO: 477)

c[Hydantoin(C(O)-(Asp-D-Ala))-His-D-Phe-Arg-Trp-Lys]-NH₂; (SEQ ID NO: 478)

c[Hydantoin(C(O)-(Asp-D-Ala))-His-D-Phe-Arg-Trp-Orn]-NH₂; (SEQ ID NO: 479)

c[Hydantoin(C(O)-(Asp-D-Ala))-His-D-Phe-Arg-Trp-Dab]-NH₂; (SEQ ID NO: 480)

c[Hydantoin(C(O)-(Asp-D-Ala))-His-D-Phe-Arg-Trp-Dap]-NH₂; (SEQ ID NO: 481)

c[Hydantoin(C(O)-(Asp-His))-D-2-Nal-Arg-Trp-Lys]-NH₂; (SEQ ID NO: 482)

c[Hydantoin(C(O)-(Asp-His))-D-Phe-Arg-Trp-Lys]-NH₂; (SEQ ID NO: 483)

c[Hydantoin(C(O)-(Asp-A3c))-D-Phe-Arg-Trp-Lys]-NH₂; (SEQ ID NO: 484)

c[Hydantoin(C(O)-(Asp-A5c))-D-Phe-Arg-Trp-  (SEQ ID NO: 485)
Lys]-NH₂;

c[Hydantoin(C(O)-(Asp-A6c))-D-Phe-Arg-Trp-  (SEQ ID NO: 486)
Lys]-NH₂;

c[Hydantoin(C(O)-(Asp-A3c))-D-2-Nal-Arg-Trp-  (SEQ ID NO: 487)
Lys]-NH₂;

c[Hydantoin(C(O)-(Asp-A5c))-D-2-Nal-Arg-Trp-  (SEQ ID NO: 488)
Lys]-NH₂;

c[Hydantoin(C(O)-(Asp-A6c))-D-2-Nal-Arg-Trp-  (SEQ ID NO: 489)
Lys]-NH₂;

c[Hydantoin(C(O)-(Asp-Aic))-D-Phe-Arg-Trp-  (SEQ ID NO: 490)
Lys]-NH₂;

c[Hydantoin(C(O)-(Asp-Apc))-D-Phe-Arg-Trp-  (SEQ ID NO: 491)
Lys]-NH₂;

c[Hydantoin(C(O)-(Asp-Aic))-D-2-Nal-Arg-Trp-  (SEQ ID NO: 492)
Lys]-NH₂;

c[Hydantoin(C(O)-(Asp-Apc))-D-2-Nal-Arg-Trp-  (SEQ ID NO: 493)
Lys]-NH₂;

c[Hydantoin(C(O)-(Glu-D-Ala))-His-D-Phe-Arg-  (SEQ ID NO: 494)
Trp-Orn]-NH₂;

c[Hydantoin(C(O)-(Glu-D-Ala))-His-D-Phe-Arg-  (SEQ ID NO: 495)
Trp-Dab]-NH₂;

c[Hydantoin(C(O)-(Glu-D-Ala))-His-D-Phe-Arg-  (SEQ ID NO: 496)
Trp-Dap]-NH₂;

c[Hydantoin(C(O)-(Glu-D-Ala))-His-D-Phe-Arg-  (SEQ ID NO: 497)
Trp-Lys]-NH₂;

c[Hydantoin(C(O)-(Glu-His))-D-Phe-Arg-Trp-  (SEQ ID NO: 498)
Dap]-NH₂;
or c[Hydantoin(C(O)-(Glu-His))-D-Phe-Arg-Trp-  (SEQ ID NO: 499)
Lys]-NH₂.

In an example embodiment, an MC4R agonist useful for practicing the methods described herein is at least one compound of Formula (VI), a pharmaceutically-acceptable salt, hydrate, solvate and/or prodrugs thereof (see International Patent Application Number PCT/US08/06675 which is incorporated herein by reference in its entirety):

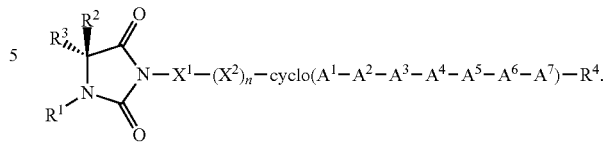

(VI)

In Formula (VI):
$X^1$ is

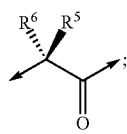

;

$X^2$ is

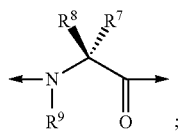

;

$A^1$ is Asp, Cys, D-Cys, Dab, Dap, Glu, Lys, Orn, Pen or D-Pen;
$A^2$ is an L- or D-amino acid;
$A^3$ is H is, 2-Pal, 3-Pal, 4-Pal, $(X^1, X^2, X^3, X^4, X^5)$Phe, Taz, 2-Thi or 3-Thi;
$A^4$ is D-Bal, D-1-Nal, D-2-Nal, D-Phe or D-$(X^1, X^2, X^3, X^4, X^5)$Phe;
$A^5$ is Arg, hArg, Dab, Dap, Lys or Orn;
$A^6$ is Bal, 1-Nal, 2-Nal, $(X^1, X^2, X^3, X^4, X^5)$Phe or Trp;
$A^7$ is Asp, Cys, D-Cys, Dab, Dap, Glu, Lys, Orn, Pen or D-Pen;
$R^1$ is H, $(C_1-C_{10})$alkyl or substituted $(C_1-C_{10})$alkyl;
$R^2$ and $R^3$ each is, independently, H, $(C_1-C_{10})$alkyl, $(C_1-C_{10})$heteroalkyl, aryl$(C_1-05)$alkyl, substituted $(C_1-C_{10})$alkyl, substituted $(C_1-C_{10})$hetero alkyl or substituted aryl$(C_1-05)$alkyl or $R^2$ and $R^3$ may be fused together form a cyclic moiety;
$R^4$ is $CO_2H$ or $C(O)NH_2$;
$R^5$ and $R^6$ each is, independently, H, $(C_1-00)$alkyl, $(C_1-C_{10})$heteroalkyl, aryl$(C_1-C_5)$alkyl, substituted $(C_1-C_{10})$alkyl, substituted $(C_1-C_{10})$hetero alkyl or substituted aryl$(C_1-C_5)$alkyl or $R^5$ and $R^6$ may be fused together form a cyclic moiety;
$R^7$ and $R^8$ each is, independently, H, $(C_1-C_{10})$alkyl, $(C_1-C_{10})$heteroalkyl, aryl$(C_1-C_5)$alkyl, substituted $(C_1-C_{10})$alkyl, substituted $(C_1-C_{10})$hetero alkyl or substituted aryl$(C_1-C_5)$alkyl; or $R^7$ and $R^8$ may be fused together form a cyclic moiety;
$R^9$ is H, $(C_1-C_{10})$alkyl or substituted $(C_1-C_{10})$alkyl; and
n is, independently for each occurrence thereof, 1, 2, 3, 4, 5, 6 or 7;
or a pharmaceutically acceptable salt thereof.

Exemplary embodiments of the compounds of Formula (VI) are those compounds wherein:
$A^1$ is Cys;
$A^2$ is D-Ala, Asn, Asp, Gln, Glu or D-Phe;
$A^3$ is H is;
$A^4$ is D-2-Nal or D-Phe;

A⁵ is Arg;

A⁶ is Trp; and

A⁷ is Cys or Pen;

each of $R^1$, $R^2$, $R^3$, and $R^9$ is, independently, H;

$R^4$ is C(O)NH$_2$;

each of $R^5$ and $R^6$ is, independently, H, (C$_1$-C$_{10}$)heteroalkyl, substituted (C$_1$-C$_{10}$)alkyl or substituted (C$_1$-C$_{10}$)heteroalkyl or $R^5$ and $R^6$ may be fused together form a cyclic moiety; and each of $R^7$ and $R^8$ is, independently, H, (C$_1$-C$_{10}$)alkyl, (C$_1$-C$_{10}$)heteroalkyl, substituted (C$_1$-C$_{10}$)alkyl or substituted (C$_1$-C$_{10}$)heteroalkyl; or pharmaceutically acceptable salts thereof.

Example compounds of the immediately foregoing Formula (VI) include:

```
                                           (SEQ ID NO: 500)
(Hydantoin(C(O)-(Arg-Gly))-c(Cys-Glu-His-D-Phe-
Arg-Trp-Cys)-NH2;

(SEQ ID NO: 501)
Hydantoin(C(O)-(Nle-Gly))-c(Cys-Glu-His-D-Phe-
Arg-Trp-Cys)-NH2;

(SEQ ID NO: 502)
Hydantoin(C(O)-(Gly-Gly))-c(Cys-Glu-His-D-Phe-
Arg-Trp-Cys)-NH2;

(SEQ ID NO: 503)
Hydantoin(C(O)-(Nle-Gly))-c(Cys-D-Ala-His-D-Phe-
Arg-Trp-Cys)-NH2;

(SEQ ID NO: 504)
Hydantoin(C(O)-(Gly-Gly))-c(Cys-D-Ala-His-D-Phe-
Arg-Trp-Cys)-NH2;

(SEQ ID NO: 505)
Hydantoin(C(O)-(Nle-Gly))-c(Cys-D-Ala-His-D-Phe-
Arg-Trp-Pen)-NH2;

(SEQ ID NO: 506)
Hydantoin(C(O)-(Gly-Gly))-c(Cys-D-Ala-His-D-Phe-
Arg-Trp-Pen)-NH2;

(SEQ ID NO: 507)
Hydantoin(C(O)-(Ala-Gly))-c(Cys-D-Ala-His-D-Phe-
Arg-Trp-Cys)-NH2;

(SEQ ID NO: 508)
Hydantoin(C(O)-(D-Ala-Gly))-c(Cys-D-Ala-His-D-Phe-
Arg-Trp-Cys)-NH2;

(SEQ ID NO: 509)
Hydantoin(C(O)-(Aib-Gly))-c(Cys-D-Ala-His-D-Phe-
Arg-Trp-Cys)-NH2;

(SEQ ID NO: 510)
Hydantoin(C(O)-(Val-Gly))-c(Cys-D-Ala-His-D-Phe-
Arg-Trp-Cys)-NH2;

(SEQ ID NO: 511)
Hydantoin(C(O)-(Ile-Gly))-c(Cys-D-Ala-His-D-Phe-
Arg-Trp-Cys)-NH2;

(SEQ ID NO: 512)
Hydantoin(C(O)-(Leu-Gly))-c(Cys-D-Ala-His-D-Phe-
Arg-Trp-Cys)-NH2;

(SEQ ID NO: 513)
Hydantoin(C(O)-(Gly-Gly))-c(Cys-Glu-His-D-2-Nal-
Arg-Trp-Cys)-NH2;

(SEQ ID NO: 514)
Hydantoin(C(O)-(Nle-Gly))-c(Cys-Glu-His-D-2-Nal-
Arg-Trp-Cys)-NH2;

(SEQ ID NO: 515)
Hydantoin(C(O)-(D-Arg-Gly))-c(Cys-Glu-His-D-Phe-
Arg-Trp-Cys)-NH2;

(SEQ ID NO: 516)
Hydantoin(C(O)-(D-Arg-Gly))-c(Cys-D-Ala-His-D-Phe-
Arg-Trp-Cys)-NH2;

(SEQ ID NO: 517)
Hydantoin(C(O)-(Arg-Gly))-c(Cys-D-Ala-His-D-Phe-
Arg-Trp-Cys)-NH2;

(SEQ ID NO: 518)
Hydantoin(C(O)-(D-Arg-Gly))-c(Cys-D-Ala-His-D-2-
Nal-Arg-Trp-Cys)-NH2;

(SEQ ID NO: 519)
Hydantoin(C(O)-(Arg-Gly))-c(Cys-D-Ala-His-D-2-Nal-
Arg-Trp-Cys)-NH2;

(SEQ ID NO: 520)
Hydantoin(C(O)-(Ala-Nle))-c(Cys-Glu-His-D-Phe-
Arg-Trp-Cys)-NH2;

(SEQ ID NO: 521)
Hydantoin(C(O)-(Val-Nle))-c(Cys-Glu-His-D-Phe-
Arg-Trp-Cys)-NH2;

(SEQ ID NO: 522)
Hydantoin(C(O)-(Gly-Nle))-c(Cys-Glu-His-D-Phe-
Arg-Trp-Cys)-NH2;

(SEQ ID NO: 523)
Hydantoin(C(O)-(A6c-Nle))-c(Cys-D-Ala-His-D-Phe-
Arg-Trp-Cys)-NH2;

(SEQ ID NO: 524)
Hydantoin(C(O)-(Gly-Nle))-c(Cys-D-Ala-His-D-Phe-
Arg-Trp-Cys)-NH2;

(SEQ ID NO: 525)
Hydantoin(C(O)-(Ala-Nle))-c(Cys-D-Ala-His-D-Phe-
Arg-Trp-Cys)-NH2;

(SEQ ID NO: 526)
Hydantoin(C(O)-(D-Ala-Nle))-c(Cys-D-Ala-His-D-Phe-
Arg-Trp-Cys)-NH2;

(SEQ ID NO: 527)
Hydantoin(C(O)-(Val-Nle))-c(Cys-D-Ala-His-D-Phe-
Arg-Trp-Cys)-NH2;
```

-continued (SEQ ID NO: 528)
Hydantoin(C(O)-(Leu-Nle))-c(Cys-D-Ala-His-D-Phe-Arg-Trp-Cys)-NH$_2$;

(SEQ ID NO: 529)
Hydantoin(C(O)-(Cha-Nle))-c(Cys-D-Ala-His-D-Phe-Arg-Trp-Cys)-NH$_2$;

(SEQ ID NO: 530)
Hydantoin(C(O)-(Aib-Nle))-c(Cys-D-Ala-His-D-Phe-Arg-Trp-Cys)-NH$_2$;

(SEQ ID NO: 531)
Hydantoin(C(O)-(Gly-Arg))-c(Cys-Glu-His-D-Phe-Arg-Trp-Cys)-NH$_2$;

(SEQ ID NO: 532)
Hydantoin(C(O)-(Gly-Arg))-c(Cys-Glu-His-D-2-Nal-Arg-Trp-Cys)-NH$_2$;

(SEQ ID NO: 533)
Hydantoin(C(O)-(Gly-Arg))-c(Cys-D-Ala-His-D-Phe-Arg-Trp-Cys)-NH$_2$;

(SEQ ID NO: 534)
Hydantoin(C(O)-(Gly-Arg))-c(Cys-D-Ala-His-D-2-Nal-Arg-Trp-Cys)-NH$_2$;

(SEQ ID NO: 535)
Hydantoin(C(O)-(Gly-D-Arg))-c(Cys-Glu-His-D-Phe-Arg-Trp-Cys)-NH$_2$;

(SEQ ID NO: 536)
Hydantoin(C(O)-(Gly-D-Arg))-c(Cys-D-Ala-His-D-Phe-Arg-Trp-Cys)-NH$_2$;

(SEQ ID NO: 537)
Hydantoin(C(O)-(Gly-D-Arg))-c(Cys-D-Ala-His-D-2-Nal-Arg-Trp-Cys)-NH$_2$;
or (SEQ ID NO: 538)
Hydantoin(C(O)-(Nle-Ala))-c(Cys-Glu-His-D-Phe-Arg-Trp-Cys)-NH$_2$;

or a pharmaceutically acceptable salt thereof.

In an example embodiment, the MC4R agonists useful for practicing the methods described herein are compounds having a structure according to Formula (VII) as depicted below (see International Patent Application Number PCT/US08/06675 which is incorporated herein by reference in its entirety):

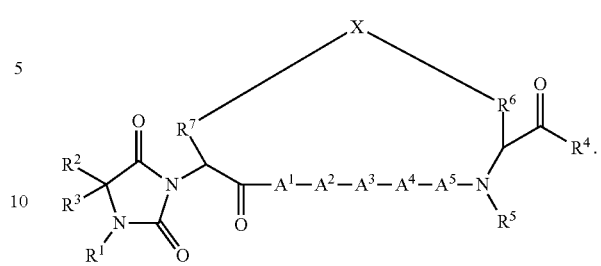

(VII)

wherein:

X is selected from the group consisting of —CH$_2$—S—S—CH$_2$—, —C(CH$_3$)$_2$SSCH$_2$—, —CH$_2$—S—S—C(CH$_3$)$_2$—, —C(CH$_3$)$_2$—S—S—C(CH$_3$)$_2$—, —(CH$_2$)$_2$—S—S—CH$_2$—, —CH$_2$—S—S—(CH$_2$)$_2$, (CH$_2$)$_2$—S—S—(CH$_2$)$_2$—, —C(CH$_3$)$_2$—S—S—(CH$_2$)$_2$—, —(CH$_2$)$_2$—S—S—C(CH$_3$)$_2$—, —(CH$_2$)$_t$—C(O)—NR$^8$—(CH$_2$)$_r$— and —(CH$_2$)$_r$—NR$^8$—C(O)—(CH$_2$);

each of IV and R$^5$ is, independently, H, (C$_1$-C$_{10}$)alkyl or substituted (C$_1$-C$_{10}$)alkyl;

each of R$^2$ and R$^3$ is, independently, H, (C$_1$-C$_{10}$)alkyl, (C$_1$-00)heteroalkyl, aryl(C$_1$-C$_5$)alkyl, substituted (C$_1$-C$_{10}$)alkyl, substituted (C$_1$-C$_{10}$)heteroalkyl or substituted aryl (C$_1$-C$_5$)alkyl or R$^2$ and R$^3$ may be fused together to form a ring;

R$^4$ is OH or NH$_2$;

each of R$^6$ and R$^7$ is, independently, H, (C$_1$-C$_{10}$)alkyl or substituted (C$_1$-C$_{10}$)alkyl;

A$^1$ is an L- or D-amino acid or deleted;

A$^2$ is H is, 2-Pal, 3-Pal, 4-Pal, (X$^1$, X$^2$, X$^3$, X$^4$, X$^5$)Phe, Taz, 2-Thi or 3-Thi;

A$^3$ is D-Bal, D-1-Nal, D-2-Nal, D-Phe or D-(X$^1$, X$^2$, X$^3$, X$^4$, X$^5$)Phe;

A$^4$ is Arg, hArg, Dab, Dap, Lys or Orn;

A$^5$ is Bal, 1-Nal, 2-Nal, (X$^1$, X$^2$, X$^3$, X$^4$, X$^5$)Phe or Trp;

r is, independently for each occurrence thereof, 1, 2, 3, 4 or 5; and t is, independently for each occurrence thereof, 1 or 2;

or pharmaceutically acceptable salts thereof.

In an example embodiment of the compounds of Formula (VII), A$^1$ is Ala, D-Ala, Asn, Asp, Gln, Glu or Gly.

Example compounds according to Formula (VII) include the following compounds:

(SEQ ID NO: 539)
c[Hydantoin(C(O)-(Nle-Cys))-D-Ala-His-D-Phe-Arg-Trp-Cys]-NH$_2$;

(SEQ ID NO: 540)
c[Hydantoin(C(O)-(Ala-Cys))-D-Ala-His-D-Phe-Arg-Trp-Cys]-NH$_2$;

(SEQ ID NO: 541)
c[Hydantoin(C(O)-(D-Ala-Cys))-D-Ala-His-D-Phe-Arg-Trp-Cys]-NH$_2$;

(SEQ ID NO: 542)
c[Hydantoin(C(O)-(Aib-Cys))-D-Ala-His-D-Phe-Arg-Trp-Cys]-NH$_2$;

c[Hydantoin(C(O)-(Val-Cys))-D-Ala-His-D-Phe-Arg-Trp-Cys]-NH$_2$; (SEQ ID NO: 543)

c[Hydantoin(C(O)-(Abu-Cys))-D-Ala-His-D-Phe-Arg-Trp-Cys]-NH$_2$; (SEQ ID NO: 544)

c[Hydantoin(C(O)-(Leu-Cys))-D-Ala-His-D-Phe-Arg-Trp-Cys]-NH$_2$; (SEQ ID NO: 545)

c[Hydantoin(C(O)-(Ile-Cys))-D-Ala-His-D-Phe-Arg-Trp-Cys]-NH$_2$; (SEQ ID NO: 546)

c[Hydantoin(C(O)-(Cha-Cys))-D-Ala-His-D-Phe-Arg-Trp-Cys]-NH$_2$; (SEQ ID NO: 547)

c[Hydantoin(C(O)-(A6c-Cys))-D-Ala-His-D-Phe-Arg-Trp-Cys]-NH$_2$; (SEQ ID NO: 548)

c[Hydantoin(C(O)-(Phe-Cys))-D-Ala-His-D-Phe-Arg-Trp-Cys]-NH$_2$; (SEQ ID NO: 549)

c[Hydantoin(C(O)-(Gly-Cys))-D-Ala-His-D-Phe-Arg-Trp-Cys]-NH$_2$; or (SEQ ID NO: 550)

c[Hydantoin(C(O)-(Gly-Cys))-Glu-His-D-Phe-Arg-Trp-Cys]-NH$_2$; (SEQ ID NO: 551)

or pharmaceutically acceptable salts thereof.

In an example embodiment, the MC4R agonist useful for practicing the methods described herein is at least one compound according to Formula (VIII) (see International Patent Application Number PCT/US08/07411, incorporated herein by reference in its entirety):

(VIII)

$(R^2R^3)-A^0-A^1-c(A^2-A^3-A^4-A^5-A^6-A^7-A^8-A^9)-A^{10}-R^1$

In Formula (VIII):
  $A^0$ is an aromatic amino acid
  $A^1$ is Acc, HN—(CH$_2$)$_m$—C(O), an L- or D-amino acid;
  $A^2$ is Asp, Cys, D-Cys, hCys, D-hCys, Glu, Pen, or D-Pen;
  $A^3$ is Aib, Ala, β-Ala, Gaba, Gly or a D-amino acid;
  $A^4$ is H is, 2-Pal, 3-Pal, 4-Pal, (X$^1$, X$^2$, X$^3$, X$^4$, X$^5$)Phe, Taz, 2-Thi, or 3-Thi;
  $A^5$ is D-Bal, D-1-Nal, D-2-Nal, D-Phe, L-Phe, D-(X$^1$, X$^2$, X$^3$, X$^4$, X$^5$)Phe, L-Phe, D-Trp or D-(Et)Tyr;
  $A^6$ is Arg, hArg, Dab, Dap, Lys, Orn, or HN—CH((CH$_2$)$_n$—N(R$^4$R$^5$))—C(O);
  $A^7$ is Bal, D-Bal, Bip, D-Bip, 1-Nal, D-1-Nal, 2-Nal, D-2-Nal, or D-Trp;
  $A^8$ is Acc, Aha, Ahx, Ala, D-Ala, Apn, Gaba, Gly, HN—(CH$_2$)$_s$—C(O), or deleted;
  $A^9$ is Cys, D-Cys, hCys, D-hCys, Dab, Dap, Lys, Orn, Pen, or D-Pen;
  $A^{10}$ is Acc, HN—(CH$_2$)$_t$—C(O), L- or D-amino acid, or deleted;
  $R^1$ is OH, or NH$_2$;
  each of $R^2$ and $R^3$ is, independently for each occurrence selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl;
  each of $R^4$ and $R^5$ is, independently for each occurrence, H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)allyl, substituted aryl(C$_1$-C$_{40}$)acyl, (C$_1$-C$_{40}$)alkylsulfonyl, or —C(NH)—NH$_2$;
  m is, independently for each occurrence, 1, 2, 3, 4, 5, 6 or 7;
  n is, independently for each occurrence, 1, 2, 3, 4 or 5;
  s is, independently for each occurrence, 1, 2, 3, 4, 5, 6, or 7;
  t is, independently for each occurrence, 1, 2, 3, 4, 5, 6, or 7;
  X$^1$, X$^2$, X$^3$, X$^4$, and V each is, independently for each occurrence, H, F, Cl, Br, I, (C$_{1-10}$)alkyl, substituted (C$_{1-10}$)alkyl, (C$_{2-10}$)alkenyl, substituted (C$_{2-10}$)alkenyl, (C$_{2-10}$)alkynyl, substituted (C$_{2-10}$)alkynyl, aryl, substituted aryl, OH, NH$_2$, NO$_2$, or CN.

In example embodiments of Formula (VIII),
  (I) when R$^4$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$)alkylsulfonyl, or —C(NH)—NH$_2$, then R$^5$ is H or (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$)alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;
  (II) when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;
  (III) when A$^2$ is Cys, D-Cys, hCys, D-hCys, Pen, or D-Pen, then A$^9$ is Cys, D-Cys, hCys, D-hCys, Pen, or D-Pen;
  (IV) when A$^2$ is Asp or Glu, then A$^9$ is Dab, Dap, Orn, or Lys;
  (V) when A$^8$ is Ala or Gly, then A$^1$ is not Nle; or pharmaceutically acceptable salts thereof.

In example embodiments of compounds of Formula (VIII):
  A$^0$ is 1-Nal, 2-Nal, H is, Pff, Phe, Trp, or Tyr;
  A$^1$ is Arg;
  A$^2$ is Cys;
  A$^3$ is D-Ala;
  A$^4$ is His;
  A$^5$ is D-Phe
  A$^6$ is Arg;
  A$^7$ is Trp
  A$^8$ is deleted;
  A$^9$ is Cys; and
  A$^{10}$ is deleted;
  or pharmaceutically acceptable salts thereof.

Particular compounds of the immediately foregoing group of compounds are of the formula:

Ac-Tyr-Arg-c(Cys-D-Ala-His-D-Phe-Arg-Trp-Cys)-NH$_2$; (SEQ ID NO: 552)

Ac-2-Nal-Arg-c(Cys-D-Ala-His-D-Phe-Arg-Trp-Cys)-NH$_2$; (SEQ ID NO: 553)

Ac-1-Nal-Arg-c(Cys-D-Ala-His-DPhe-Arg-Trp-Cys)-NH$_2$; (SEQ ID NO: 554)

Ac-Phe-Arg-c(Cys-D-Ala-His-D-Phe-Arg-Trp-Cys)-NH$_2$; (SEQ ID NO: 555)

Ac-Trp-Arg-c(Cys-D-Ala-His-D-Phe-Arg-Trp-Cys)-NH$_2$; (SEQ ID NO: 556)

Ac-Pff-Arg-c(Cys-D-Ala-His-D-Phe-Arg-Trp-Cys)-NH$_2$; (SEQ ID NO: 557)

H-His-Arg-c(Cys-D-Ala-His-D-Phe-Arg-Trp-Cys)-NH$_2$; or (SEQ ID NO: 558)

Ac-His-Arg-c(Cys-D-Ala-His-D-Phe-Arg-Trp-Cys)-NH$_2$; (SEQ ID NO: 559)

or a pharmaceutically acceptable salt thereof.

In one example embodiment, the MC4R agonist is Ac-Arg-c(Cys-D-Ala-His-D-Phe-Arg-Trp-Cys)-NH$_2$ (SEQ ID NO: 140) or a pharmaceutically acceptable salt thereof. In another example embodiment, the MC4R agonist is Hydantoin(C(O)-(Arg-Gly))-c(Cys-Glu-His-D-Phe-Arg-Trp-Cys)-NH$_2$ (SEQ ID NO: 500) or a pharmaceutically acceptable salt thereof.

Administration of a compound or pharmaceutically acceptable salt thereof or a composition comprising a compound or pharmaceutical salt of a compound of the invention useful to practice the methods described herein, can be continuous, hourly, four times daily, three time daily, twice daily, once daily, once every other day, twice weekly, once weekly, once every two weeks, once a month, or once every two months, or longer or some other intermittent dosing regimen.

Examples of administration of a compound or composition comprising a compound or pharmaceutical salt of a compound of the invention include peripheral administration. Examples of peripheral administration include oral, subcutaneous, intraperitoneal, intramuscular, intravenous, rectal, transdermal or intranasal forms of administration.

As used herein, peripheral administration includes all forms of administration of a compound or a composition comprising a compound of the instant invention which excludes intracranial administration. Examples of peripheral administration include, but are not limited to, oral, parenteral (e.g., intramuscular, intraperitoneal, intravenous or subcutaneous injection, extended release, slow release implant, depot and the like), nasal, vaginal, rectal, sublingual or topical routes of administration, including transdermal patch applications and the like.

The nomenclature used to define the peptides is that typically used in the art wherein the amino group at the N-terminus appears to the left and the carboxyl group at the C-terminus appears to the right. Where the amino acid has D and L isomeric forms, it is the L form of the amino acid that is represented unless otherwise explicitly indicated.

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention. For example, a claim to 2-hydroxypyridinyl would also cover its tautomeric form, α-pyridonyl.

Unless defined otherwise, all technical and scientific terms used herein have the same meaning as commonly understood by one of ordinary skill in the art to which this invention belongs. Also, all publications, patent applications, patents and other references mentioned herein are incorporated by reference in their entirety.

| Symbol | Meaning |
| --- | --- |
| Abu | α-aminobutyric acid |
| Ac | acyl group |
| Acc | 1-amino-1-cyclo(C$_3$—C$_9$)alkyl carboxylic acid |
| A3c | 1-amino-1cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Aic | 2-aminoindan-2-carboxylic acid |
| Ala or A | alanine |
| β-Ala | β-alanine |
| Apc | denotes the structure: |

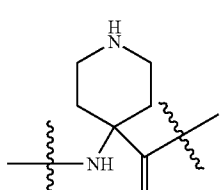

| | |
| --- | --- |
| Apn | 5-aminopentanoic acid (HN—(CH2)$_4$—C(O) |
| Arg or R | arginine |
| hArg | homoarginine |
| Asn or N | asparagine |
| Asp or D | aspartic acid |
| Bal | 3-benzothienylalanine |
| Bip | 4,4'-biphenylalanine, represented by the structure |

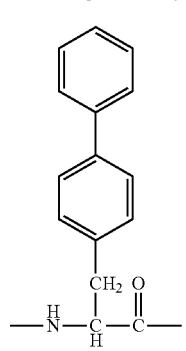 [SMILES: CNC(Cc1ccc(-c2ccccc2)cc1)C(C)=O]

| | |
| --- | --- |
| Bpa | 4-benzoylphenylalanine |
| 4-Br-Phe | 4-bromo-phenylalanine |

-continued

| Symbol | Meaning |
|---|---|
| Cha | β-cyclohexylalanine |
| hCha | homo-cyclohexylalanine |
| Chg | cyclohexylglycine |
| Cys or C | cysteine |
| hCys | homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: |
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-3-hydroxy-pyrrolidine-2-carboxylic acid |
| 4-Hyp | 4-hydroxyproline, i.e., (2S,4R)-4-hydorxypyrrolidine-2-carboxylic acid |
| Ile or I | isoleucine |
| Leu or L | leucine |
| hLeu | homoleucine |
| Lys or K | lysine |
| Met or M | methionine |
| β-hMet | β-homomethionine |
| 1-Nal | β-(1-naphthyl)alanine |
| 2-Nal | β-(2-naphthyl)alanine |
| Nip | nipecotic acid |
| Nle | norleucine |
| Ole | octahydroindole-2-carboxylic acid |
| Orn | ornithine |
| 2-Pal | β-(2-pyridiyl)alanine |
| 3-Pal | β-(3-pyridiyl)alanine |
| 4-Pal | β-(4-pyridiyl)alanine |
| Pen | penicillamine |
| Pff | (S)-pentafluorophenylalanine |
| Phe or F | phenylalanine |
| hPhe | homophenylalanine |
| Pro or P | proline |
| hProP | homoproline |
| Ser or S | Serine |
| Tle | tert-Leucine |
| Taz | β-(4-thiazolyl)alanine |
| 2-Thi | β-(2-thienyl)alanine |
| 3-Thi | β-(3-thienyl)alanine |
| Thr or T | threonine |
| Trp or W | tryptopham |
| Tyr or Y | tyrosine |
| D-(Et) Tyr | has a structure of 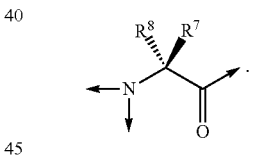 |
| Val or V | Valine |

Certain other abbreviations used herein are defined as follows:

| | |
|---|---|
| Boc: | tert-butyloxycarbonyl |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino}benzyl |
| DMAP: | 4-(dimethylamino)pyridine |
| DMF: | dimethylformamide |
| DNP: | 2,4-dinitrophenyl |
| Fm: | fluorenylmethyl |
| Fmoc: | fluorenylmethyloxycarbonyl |
| For: | formyl |
| HBTU: | 2-(1H-benzotriazole-1-yl)-1,1,3,3-tetramethyluronium hexafluorophosphate |
| cHex | cyclohexyl |
| HOAT: | O-(7-azabenzotriazol-1-yl)-1,1,3,3-tetramethyluronium hexafluorophosphate |
| HOBt: | 1-hydroxy-benzotriazole |
| MBNA | 4-methylbenzhydrylamine |
| Mmt: | 4-methoxytrityl |
| NMP: | N-methylpyrrolidone |
| O—tBu | oxy-tert-butyl |
| Pbf: | 2,2,4,6,7-pentamethyldihydrobenzofuran-5-sulfonyl |
| PyBroP | bromo-tris-pyrrolidino-phosphonium hexafluorophosphate |
| tBu: | tert-butyl |
| TIS: | triisopropylsilane |
| TOS: | tosyl |
| Trt | trityl |
| TFA: | trifluoro acetic acide |
| TFFH: | tetramethylfluoroforamidiaium hexafluorophosphate |
| Z: | benzyloxycarbonyl |

Unless otherwise indicated, with the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system.

For the N-terminal amino acid, the abbreviation stands for the structure of:

The designation "NH$_2$" in e.g., Ac-Nle-c(Cys-D-Ala-His-D-Phe-Arg-Trp-Cys)-NH$_2$ (SEQ ID NO:13), indicates that the C-terminus of the peptide is amidated. Ac-Nle-c(Cys-D-Ala-His-D-Phe-Arg-Trp-Cys) (SEQ ID NO:107), or alternatively Ac-Nle-c(Cys-D-Ala-His-D-Phe-Arg-Trp-Cys)-OH (SEQ ID NO:107), indicates that the C-terminus is the free acid.

"-c(Cys-Cys)-" or "-cyclo(Cys-Cys)-" denotes the structure:

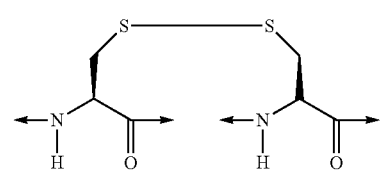

"-c(Cys-Pen)-" or "-cyclo(Cys-Pen)-" denotes the structure:

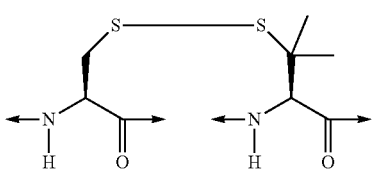

"-c(Asp-Lys)-" or "-cyclo(Asp-Lys)-" denotes the structure:

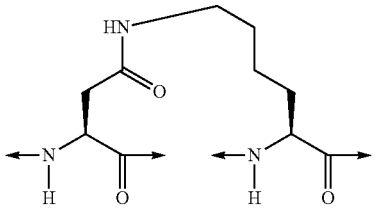

Applicants have devised the following shorthand used in naming the specific embodiments and/or species:

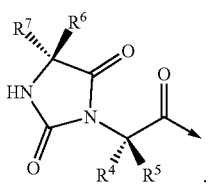

"HydantoinC(O)-($A^a$-$A^b$)" denotes the structure:
wherein amino acid "$A^a$" has the structure:

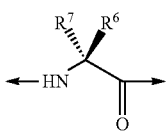

and amino acid "$A^b$" the structure:

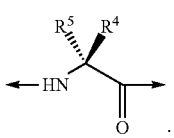

For example, a compound represented as "c[Hydantoin(C(O)-(Cys-$A^b$))-$A^1$-$A^2$-$A^3$-$A^4$-Cys]-" would have the following the structure:

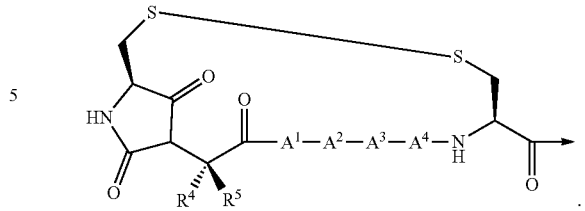

whereas a compound represented as "c[Hydantoin(C(O)-($A^b$-Cys))-$A^1$-$A^2$-$A^3$-$A^4$-Cys]-" would have the structure:

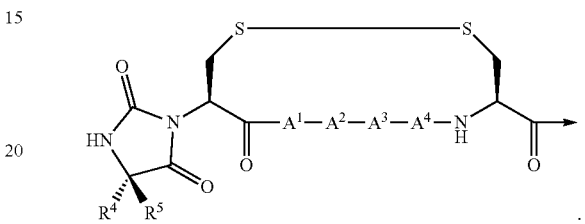

For further guidance, "c[Hydantoin(C(O)-(Asp-$A^b$))-$A^1$-$A^2$-$A^3$-$A^4$-Lys]-" represents the following compound:

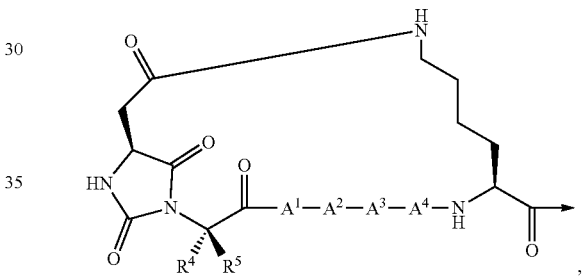

whereas "c[Hydantoin(C(O)-(Dap-$A^b$))-$A^1$-$A^2$-$A^3$-$A^4$-Asp]-" has the following formula:

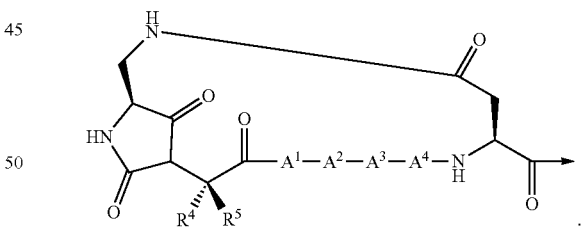

"Acyl" refers to R"—C(O)—, where R" is H, alkyl, substituted alkyl, heteroalkyl, substituted heteroalkyl, alkenyl, substituted alkenyl, aryl, alkylaryl, or substituted alklyaryl, and is indicated in the general formula of a particular embodiment as "Ac".

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Hydroxyalkyl" refers to an alkyl group wherein one or more hydrogen atoms of the hydrocarbon group are substituted with one or more hydroxy radicals, such as hydroxymethyl, hydroxyethyl, hydroxypropyl, hydroxybutyl, hydroxypentyl, hydroxyhexyl and the like.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Non-limiting examples of alkyl acids containing, or consisting of, —(CH$_2$)$_{0-20}$—COOH include 2-norbornane acetic acid, tert-butyric acid, 3-cyclopentyl propionic acid, and the like.

The term "halo" encompasses fluoro, chloro, bromo and iodo.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfur, oxygen, and/or nitrogen. Non-limiting examples of aryl include phenyl, 1-naphthyl, 2-naphthyl, indole, quinoline, 2-imidazole, 9-anthracene, and the like. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

The term "(C$_{1-12}$)hydrocarbon moiety" encompasses alkyl, alkenyl and alkynyl and in the case of alkenyl and alkynyl there is C$_2$-C$_{12}$.

For the avoidance of doubt, unless otherwise indicated, the term substituted means substituted by one or more defined groups. In the case where groups may be selected from a number of alternative groups, the selected groups may be the same or different. For the avoidance of doubt, the term independently means that where more than one substituent is selected from a number of possible substituents, those substituents may be the same or different.

The pharmaceutically acceptable salts of the compounds of the invention which contain a basic center are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically acceptable metal salts, in particular non-toxic alkali and alkaline earth metal salts, with bases. Examples include the sodium, potassium, aluminum, calcium, magnesium, zinc and diethanolamine salts (Berge, S. M. et al., *J. Pharm. Sci.*, 66:1-19 (1977); Gould, P. L., *Intl J. Pharmaceutics*, 33:201-17 (1986); and Bighley, L. D. et al., *Encyclo. Pharma. Tech.*, Marcel Dekker Inc, New York, 13:453-97 (1996).

The pharmaceutically acceptable solvates of the compounds of the invention include the hydrates thereof. Also included within the scope of the invention and various salts of the invention are polymorphs thereof. Hereinafter, compounds their pharmaceutically acceptable salts, their solvates or polymorphs, defined in any aspect of the invention (except intermediate compounds in chemical processes) are referred to as "compounds of the invention".

Designation "(amino acid)$_n$" means that an amino acid is repeated n times. For example, designation "(Pro)$_2$" or "(Arg)$_3$," mean that proline or arginine residues are repeated, respectively, two or three times.

MC4R agonists and pharmaceutically acceptable salts thereof described herein can also be used to treat individuals, including human subjects defective melanocortin receptor signaling, due to mutations/defects upstream of the MC4R. MC4R agonists and pharmaceutically acceptable salts thereof described herein can also be used to treat individuals, including human subjects that carry mutations in the genes coding for pro-opiomelanocortin (POMC) and leptin such that these mutations result in POMC haplo-insufficientcy or haplo-deficiency and/or leptin haplo-insufficiency or haplo-deficiency.

In one example embodiment, an MC4R agonist is a compound represented by structural formula (X):

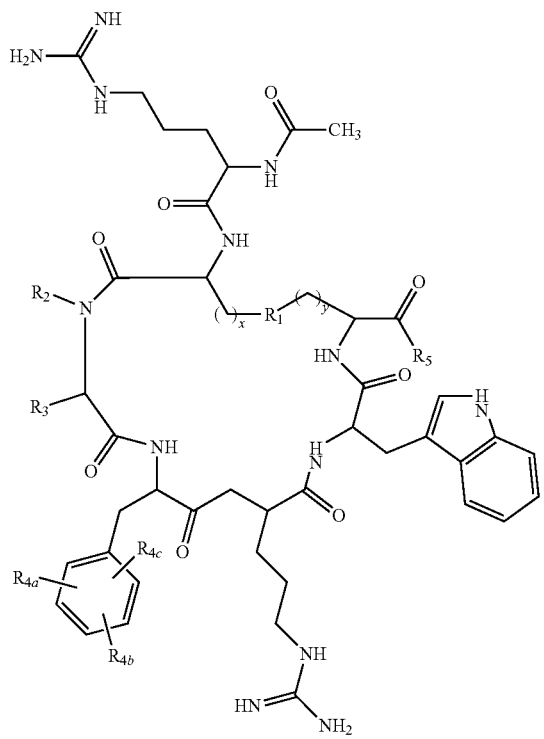

(X)

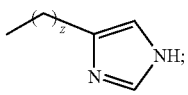

$R_{4a}$, $R_{4b}$, and $R_{4c}$ are each independently selected from hydrogen, halo, $(C_1\text{-}C_{10})$alkyl-halo, $(C_1\text{-}C_{10})$alkyl-trihalo, $(C_1\text{-}C_{10})$alkyl, $(C_1\text{-}C_{10})$alkoxy, $(C_1\text{-}C_{10})$alkylthio, aryl, aryloxy, nitro, nitrile, sulfonamide, amino, hydroxyl, carboxy, and alkoxy-carbonyl. In one example embodiment, $R_{4a}$, $R_{4b}$, and $R_{4c}$ is not hydrogen.

$R_5$ is —OH or —N(R6a)(R6b);

$R_{6a}$ and $R_{6b}$ are each independently H or $C_1$ to $C_4$ linear, branched or cyclic alkyl chain;

$R_7$ is —H or —C(O)—NH$_2$;

w is in each instance independently 0 to 5;

x is 1 to 5;

y is 1 to 5;

z is in each instance independently 1 to 5.

An example of a compound of structural formula (X) is a cyclic peptide defined by structural formula (XI):

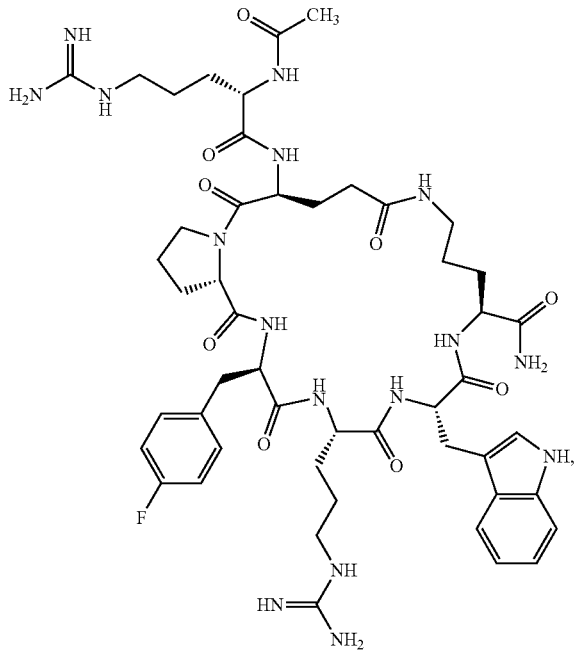 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@@H]2CCCN2C1=O]

or a pharmaceutically acceptable salt thereof. In structural formula (X), the chemical substituents are defined as follows:

$R_1$ is —NH—C(O)— or —C(O)—NH—;

$R_2$ is —H, —CH$_2$—, or, $R_2$, together with $R_3$, forms a pyrrolidine ring optionally substituted with —OH;

$R_3$ is —(CH$_2$)$_2$— if $R_2$ is —CH$_2$—, and otherwise $R_3$ is selected from

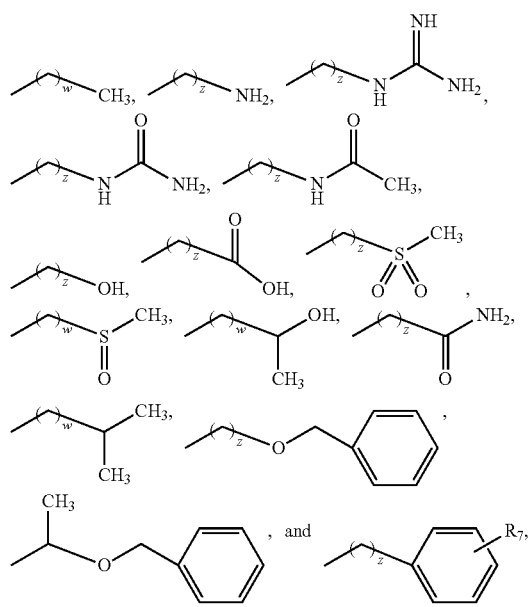

or a pharmaceutically acceptable salt thereof.

EXEMPLIFICATION

Example 1: Model for Evaluating Whether Obese MC4R+/− Heterozygotic Mice are Responsive to Treatment with Compound of SEQ ID NO: 140

The effect of MC4R agonist administration on a subject can be evaluated according to the following procedure.

The effects of a MC4 agonist in heterozygous MC4+/− mice and in weight-matched diet-induced-obesity (DIO) mice is evaluated. Heterozygous MC4+/− mice express a mild hyperphagic and obese phenotype when compared to the homozygous MC4−/− mice while retaining a putative response to MC4 stimulation. Weight-matched DIO mice are expressing the MC4 receptor (wild-type). In the course of the study, the effect of MC4 agonism on food intake and body weight in mice that are phenotypically obese but differ genetically in terms of the expression of the MC4 receptor is being characterized.

Pre-Study activities: C57BL/6 mice (N=50, males, 4 weeks of age) are pre-fed a high fat (HF) diet, commercially available from Research Diets Inc, New Brunswick, N.J., for 10 weeks prior to enrollment onto study. The HF diet (D12492) is fed to the animals ad libitum.

Species (number, sex, age/weight): C57BL/6 mice (N=40, males, 14 weeks of age at initiation of dose administration). Study criteria for animal enrollment based on body weight. B6-129/S-MC4+/− heterozygous mice (Jackson Labs or Taconic; N=40, males, body weight matching the DIO mice, 12-14 weeks of age).

Formulations: all test materials are formulated once weekly.

Treatment: All animals are surgically implanted with a subcutaneous osmotic minipump (infusion duration of 14 days).

The design of this study is summarized in Table A:

TABLE A

Study Design:

| Group No. | Mice | Animals per Group | Treatment | Dose Level and Volume | Treatment Regimen | Observation Period |
|---|---|---|---|---|---|---|
| 1 | MC4+/− | 10 | Vehicle | 0 | Chronic Constant Infusion by Osmotic Minipump (Option 2) | 14 days |
| 2 | DIO | 10 | | | | |
| 3 | MC4+/− | 10 | Peptide drug | Low | | |
| 4 | DIO | 10 | | | | |
| 5 | MC4+/− | 10 | | Mid | | |
| 6 | DIO | 10 | | | | |
| 7 | MC4+/− | 10 | | High | | |
| 8 | DIO | 10 | | | | |

Cage side and clinical observations are performed daily, clinical observations are noted per exception. Food intake by mice is permitted daily. Body Weights: All animals have body weights measured once weekly during the pre-feed and twice weekly during administration, initiating prior to the initial dose administration. Doses are based on most recently collected body weight.

Fasting Whole Blood Glucose Levels and Plasma Sample Collection: Following an overnight fast, all animals have a fasting whole blood glucose level (via glucometer) and blood sample collected (~100 μL) on Days −1 and 14.

Euthanasia and Tissue Collection: All animals are scheduled for euthanasia on Day 15 in the AM. All animals have a maximum terminal blood collection made. Blood samples are processed for plasma for insulin measurement. All animals have the retroperitoneal adipose tissue and liver excised and weighed.

Insulin measurement: Insulin levels are determined in terminal plasma samples using a mouse insulin ELISA assay by the testing facility.

Reporting: Data submission including clinical observations, food intakes, body weights, insulin levels, fasting blood glucose and plasma collections, mortality record (if applicable), the study protocol and associated amendments, and all protocol deviations.

Example 2: Models for Clinical Evaluation of the Efficacy of Treatment of MC4R-Mediated Obesity Using Compounds Disclosed Herein 1. Randomized, Double-Blind, Placebo-Controlled, Multiple Ascending Dose Study to Evaluate the Safety, Tolerability, Pharmacokinetics and Pharmacodynamics of Compounds of the Present Invention Administered to Healthy Obese Non-Diabetic Volunteers Objectives Primary:
  Investigate the safety and tolerability of multiple dose levels of the compounds of the present invention when given by continuous subcutaneous (SC) infusion for 14 or 28 days.

Secondary:
  Evaluate the pharmacokinetics (PK) of multiple dose levels of the compounds of the present invention when given by SC continuous infusion for 14 or 28 days.

Exploratory pharmacodynamic (PD) objectives of this study are to evaluate the effect of multiple dose levels of the compounds of the present invention when given by SC continuous infusion for 14 or 28 days on:
  Caloric intake, weight and waist circumference.
  Insulin sensitivity as measured by a Meal Tolerance Test (MTT).
  Hunger and satiety as measured by a Hunger/Satiety Questionnaire.
  Resting energy expenditure (REE) as measured by indirect calorimetry (to be performed at select centers with this capability).

Study Design

The study is designed to evaluate safety and tolerability of the compounds of the present invention administered up to 1 mg/kg/day for 14 or 28 days as a SC continuous infusion. The highest dose proposed to use in the study is no higher than 1 mg/kg. This is a randomized, double-blind, placebo-controlled, multiple ascending dose study during which 5 sequential cohorts of subjects will receive the compounds of the present invention or placebo by SC continuous infusion for 14 (Cohorts dosed for 14 days) or 28 days (Cohorts dosed for 28 days). Nine subjects will be enrolled in each cohort and subjects will be randomly allocated to receive the compounds of the present invention or placebo in a 6:3 ratio.

All subjects will remain confined to the Phase 1 clinical unit during treatment and under observation for at least 24 hours after the end of the study drug infusion.

A Clinical Safety Committee (CSC) will review blinded interim safety data from each dose level. Dose escalation will be recommended only if the previous dose level was deemed to be safe and well tolerated. Where appropriate, for safety reasons, additional interim dose levels (lower than the next scheduled dose) may be administered. Additionally, a sub-set of the general obese population may be enrolled. These subjects will meet all inclusion and exclusion criteria outlined in below, as well as one additional criterion: subjects must be heterozygous with a loss-of-function mutation in one of their two copies of the MC4 receptor gene. These subjects will have been pre-identified as having an MC4 receptor mutation. The rationale for this cohort is the lesser MC4 tone that is seen in heterozygous subjects, may give an altered sensitivity for these subjects to MC4 agonists such as the compounds of the present invention. If this cohort is enrolled, it is anticipated to be at a select site, nearer the end of the study.

Number of Subjects Planned

A sufficient number of healthy obese adult male and female subjects will be screened so that approximately 45 eligible subjects qualify for the study and are randomized. It is expected that approximately 45 subjects will be enrolled in approximately 5 dose groups to evaluate multiple days of dosing (14 or 28 days) of the compounds of the present invention administered by SC continuous infusion. Up to an additional 63 subjects may be enrolled to further characterize the compounds of the present invention with a maximum of approximately 108 subjects planned for treatment in the study. The additional subjects will be recruited in the event a subject needs to be replaced, a cohort is to be expanded or an intermediate dose is recommended by the CSC. It is intended that most cohorts will consist of 9 subjects (in a ratio of 2 active:1 placebo). However some cohorts may be increased in order to enhance the sample size and further define any prior findings.

Diagnosis and Main Criteria for Inclusion

Subjects must meet all of the following inclusion criteria to be eligible for the study.

Inclusion Criteria

Able to provide voluntary, written informed consent with comprehension of all aspects of the protocol, prior to any study procedures.

Healthy obese male and female volunteers aged 18 to 55 years, inclusive.

In good general health, without significant medical history, physical examination findings, or clinical laboratory abnormalities.

Body Mass Index of 30-40 kg/m$^2$, inclusive.

Stable body weight during the previous 6 months, based on Investigator judgment.

Blood pressure <140/90 mmHg at Screening and D-1. Measurement may be repeated once within 24 hours, based on Investigator judgment.

Females must not be pregnant and must have a negative serum pregnancy test result at the Screening Visit and Day −1.

Females of childbearing potential must agree to be abstinent or else use any two of the following medically acceptable forms of contraception from the Screening Period through the Final Study Visit: hormonal, condom with spermicidal jelly, diaphragm or cervical cap with spermicidal jelly, or IUD. Hormonal contraception must have started at least 3 months prior to screening. A female whose male partner has had a vasectomy must agree to use one additional form of medically acceptable contraception. Subjects must agree to practice the above birth control methods for 30 days from the final visit as a safety precaution.

Females of non-childbearing potential, defined as surgically sterile (status post hysterectomy, bilateral oophorectomy, or bilateral tubal ligation) or postmenopausal for at least 12 months (and confirmed with a screening FSH level in the post-menopausal range), do not require contraception during the study.

Males with female partners of childbearing potential must agree to use two medically acceptable forms of contraception as described above, with one of the two forms being condom with spermicide, from the Screening Period through the Final Study Visit. Males with female partners of childbearing potential who themselves are surgically sterile (status post vasectomy) must agree to use condoms with spermicide over the same period of time. Male subjects must agree to practice the above birth control methods for 30 days from the final visit as a safety precaution.

Additional Inclusion Criteria for Heterozygous MC4 Receptor Mutation Cohort:

Mutation of MC4R gene resulting in partial loss or complete loss of function of one of the MC4 receptor genes.

Exclusion Criteria

Fasting blood glucose >126 mg/dL at screening.

Resting heart rate <45 bpm or >90 bpm at screening.

Abnormal thyroid stimulating hormone (TSH) or thyroxine ($T_4$) levels on screening.

Elevated ALT or serum creatinine on screening or any clinically significant abnormalities on screening laboratory tests as determined by the Investigator.

History of diabetes or of treated or medically diagnosed hypertension.

Presence of a skin lesion suspicious for malignancy.

History of malignancy except for treated cervical carcinoma in situ in the past 5 years.

Active or history of any clinically significant medical condition including renal, hepatic, pulmonary, gastrointestinal, cardiovascular, genitourinary, endocrine, immunologic, metabolic, neurologic, psychiatric or hematological disease, based on Investigator judgment.

Acute illness or history of illness, which in the opinion of the Investigator, could pose a threat or harm to the subject or obscure interpretation of laboratory test results or interpretation of study data.

Positive hepatitis B surface antigen, positive hepatitis C antibody or positive HIV test at screening or a history of positive testing (e.g. liver biopsy, serology) suggesting acute or chronic hepatitis.

Abnormal 12-lead electrocardiogram (ECG) at screening or pre-dose (Day −1 or Day 1), except minor deviations deemed to be of no clinical significance by the Investigator.

Received any experimental drugs or devices within 30 days or 5 half lives, whichever is longer, prior to dosing.

Ongoing participation in a prior clinical study at the time of screening.

Blood donation within 60 days prior to screening or intent to donate within 60 days after Final Study Visit.

Hospitalization for major surgery including but not limited to abdominal, thoracic, or cardiovascular surgery within the past 3 months prior to screening, or for a clinically significant non-surgical illness, based on Investigator judgment, within the past 3 months.

Planned elective surgery within 30 days of the Final Study Visit.

Poor venous access or inability to tolerate venipuncture.

History of drug hypersensitivity or anaphylaxis.

History of hypersensitivity to proteins (e.g., allergy shots).

Use of prescription medications on a regular basis. The last use of any prescription medication must have been greater than 5 half-lives for the specific medication or at least 14 days prior to admission (Day −1), whichever is longer. Hormonal contraception is allowed for female subjects.

Use of a non-prescription drug and herbal substances during the study (through the Final Study Visit). The last dose of any non-prescription drug must have been taken greater than 5 half-lives for that drug before receiving study drug.

Inability to attend all study visits or to comply with protocol requirements including fasting and restrictions on alcohol, caffeine, nicotine and concomitant medication intake.

A significant history of drug/solvent abuse within 5 years of screening or a positive test for drugs of abuse test at screening or on Day −1.

Positive alcohol (breath test) or nicotine screen at Screening Visit or Day −1.

History of alcohol abuse (defined as average intake of three or more units of alcohol per day) within 5 years of the Screening Visit.

History of tobacco or tobacco product use unless abstinent for at least one year prior to the Screening Visit.

Previously randomized and dosed in this study.

Any other reason, which in the opinion of the Investigator would confound proper evaluation of the study.

Test Products, Doses, and Mode of Administration

The compounds of the present invention and the placebo are formulated for administration by SC continuous infusion using an infusion pump.

The 5 dose levels planned, in ascending order, are:
0.01 mg/kg/24 hrs
0.1 mg/kg/24 hrs
0.25 mg/kg/24 hrs
0.5 mg/kg/24 hrs
1.0 mg/kg/24 hrs The compounds of the present invention or placebo will be given by SC continuous infusion for 14 or 28 days. The dose levels evaluated may be modified based upon data from the single ascending dose study, or the prior MAD cohort.

Duration of Treatment

Overall study duration will be approximately 7 months. Individual subject participation in the study (screening, dosing, post-dosing assessments, follow-up) will be approximately 72 and 86 days for Cohorts dosed for 14 days and dosed for 28 days respectively.

The study will consist of a Screening Period, a Treatment Period and a Follow-up Period. The Screening Period will occur within 30 days prior to enrollment. The Treatment Period will consist of administration of a SC continuous infusion initiated on Day 1 and completed on Day 15 or Day 29 for Cohorts dosed for 14 days and Cohorts dosed for 28 days, respectively. Subjects will remain confined in the clinical research center (CRC) for approximately 24 hours following completion of the infusion and will be discharged from the CRC on Day 16 or 30 after all study procedures have been completed. Follow-up study visits are scheduled 1 and 4 weeks after the end of the study drug infusion.

Study Procedures

The procedures for each study period are briefly outlined below and are depicted in detail in the Schedule of Assessments (SOA).

Screening Period (Days −30 to −1)

After informed consent is obtained and eligibility assessed, screening assessments will be performed including: medical history; pregnancy test (all females); drug, nicotine and alcohol screen; safety laboratory tests (including clinical chemistry, hematology and urinalysis), HbA1c and fructosamine; full physical examination (including weight, waist circumference and height), comprehensive skin examination performed by a Dermatologist, vital signs (including supine systolic and diastolic blood pressure, pulse rate, respiratory rate and body temperature); 12-lead electrocardiogram (ECG); HBsAg, HCV-Ab, HIV screening; samples of antibodies against the compounds of the present invention; Fitzpatrick scale; dietary recall review, indirect calorimetry (within 3 days of Day 1); previous and concomitant medication use.

Treatment Period

Subjects will be admitted to the research unit on Day −1. After continued eligibility is confirmed, the following assessments will be performed: abbreviated physical exams including weight and waist circumference; vital signs; 12 lead ECG; safety laboratory tests (including clinical chemistry, hematology and urinalysis); lipid profile; level of antibodies against the compounds of the present invention; serum sample for storage; quantitative skin color measurement; photographic skin evaluation; Hunger/Satiety questionnaire; initiation of cardiac telemetry and ambulatory blood pressure (ABPM) monitoring; sample collection for 24 hour urine catecholamine and cortisol level determination; estimated caloric intake; Meal Tolerance Test (MTT), randomization; monitoring for AEs and concomitant medications.

Upon initiation of study treatment on Day 1, the following assessments will be performed on Days 1-16 (Cohorts dosed for 14 days) or Days 1-29 (Cohorts dosed for 28 days) according to the SOA: abbreviated physical exam including weight and waist circumference; vital signs; cardiac telemetry, ABPM, 12-lead ECG, safety laboratory tests; lipid profile; sample collection for 24 hour urine catecholamine and cortisol level determination; sample collection for plasma free metanephrine levels, PK blood and urine sampling, melanocortin receptor genotyping; infusion site evaluation; quantitative skin color measurement; photographic skin evaluation; estimated caloric intake; MTT; HbA1c and fructosamine; Hunger/Satiety questionnaire; indirect calorimetry, monitoring for AEs and concomitant medications. Prior to discharge from the research unit, a serum pregnancy test will be performed on all females, and a comprehensive skin evaluation will be performed by a Dermatologist.

Follow-Up Period

One and 4 weeks after completion of the study treatment infusion, subjects will return to the research unit for the following assessments: complete physical exam including weight and waist circumference; comprehensive skin exam performed by a Dermatologist, quantitative skin color measurement; photographic skin evaluation; infusion site evaluation; vital signs; safety laboratory tests; lipid profile; HbA1c and fructosamine; levels of antibodies against the compounds of the present invention; Hunger/Satiety questionnaire, monitoring for AEs and concomitant medications.

Study Endpoints

Safety

Safety will be evaluated by assessment of adverse events, ECGs, cardiac telemetry, ambulatory blood pressure monitoring, clinical laboratory evaluations (hematology, clinical chemistry including fasting blood glucose levels and urinalysis), lipid profile; levels of antibodies against the compounds of the present invention, urinary catecholamine levels, urinary free cortisol levels, plasma free metanephrine levels, vital signs (including blood pressure, respiratory rate, heart rate, and body temperature), physical examinations including infusion site evaluations and concomitant medication review.

Pharmacokinetic

Serial blood sampling and urine collections for measurement of plasma and urinary levels of the compounds of the present invention will be conducted. All samples will be assayed for the compounds of the present invention from which the following PK parameters will be computed for each subject: $AUC_{0-\tau}$, $C_{ave}$, $C_{max}$, $T_{max}$, $\lambda z$, $T_{1/2}$, CL/F, Vz/F, accumulation ratios, total urinary excretion and renal clearance.

Pharmacodynamic

Caloric intake, weight and waist circumference, insulin sensitivity (as measured by MTT), hunger and satiety (using a Hunger/Satiety Questionnaire) and REE (using indirect calorimetry) will be assessed as exploratory PD endpoints. HbAc1 and fructosamine levels will also be assessed.

Sample Size Determination

The sample size for this Phase 1 first multiple-dose study in humans was not based on formal statistical determinations. The sample size for this study was chosen in consideration of limiting exposure to this new compound while providing information to evaluate the safety and effect of the compounds of the present invention in a Phase 1 first multiple-dose study.

Statistical Methods

Continuous variables will be summarized by dose (all placebo pooled) with descriptive statistics (number of observations, mean, SD, median, maximum, and minimum). Categorical variables will be tabulated by frequency of subjects by dose (all placebo pooled) and for the active treatment doses combined. The PD endpoints may be analyzed via analysis of variance if appropriate. All subject information and safety measurements will be based on the Safety Population.

CSC Data Review and Stopping Rules

The study design is such that successively higher doses will be administered to different groups of subjects after the safety and tolerability of the preceding dose has been established. Dose escalation recommendations are to be made by the CSC based upon a review of clinical safety data through Day 16 (Cohorts dosed for 14 days) or Day 30 (Cohorts dosed for 28 days).

Rules for Suspension of Dosing for a Subject:
An increase in SBP, sustained for a minimum of 30 minutes, either to >35 mmHg above mean baseline pre-dose SBP, or to >165 mmHg;
An increase in DBP, sustained for a minimum of 30 minutes, either to >20 mmHg above mean baseline pre-dose DBP, or to >100 mmHg;
Any increase in BP that is judged to be symptomatic, per the Investigator, regardless of duration;
An increase in HR, sustained for a minimum of 30 minutes (or less in the judgment of the Investigator), to >35 bpm above mean baseline pre-dose HR;
A prolonged spontaneous erection lasting more than 60 minutes, or a spontaneous painful erection of any duration based on Investigator judgment;
Any other treatment-emergent AE that in the judgment of the Investigator poses a significant safety risk for that subject in the context of continued infusion of study drug.

Rules for Suspension or Termination of Dose Escalation:
An SAE that is deemed by the Investigator to be possibly or probably related to study drug occurs in any subject treated with the compounds of the present invention;
A CTCAE Grade 3 (severe treatment emergent AE) or higher that is possibly or probably related occurs in a subject treated with the compounds of the present invention;
A possibly or probably related treatment emergent AE not listed by the CTCAE occurs in a subject treated with the compounds of the present invention that is graded as severe or life threatening.

The CSC may also recommend suspension of the compounds of the present invention dose escalation based upon other conditions as deemed medically appropriate.

Rules for Suspension of Further Dosing:
The study may be immediately suspended and no additional doses administered if one or more subjects at any dose level develop any of the following adverse events deemed to be possibly or probably attributable to study drug:
Anaphylaxis (i.e., angioedema, hypotension, bronchospasm, hypoxia or respiratory distress) in a subject treated with the compounds of the present invention;
Any clinically significant treatment-related AE that poses an undue risk to subjects in the opinion of the CSC.

2. Randomized, Double-Blind, Placebo-Controlled Study to Evaluate the Safety and Efficacy of the Compound of the Present Invention in Patients with Obesity Due to an MC4R Mutation Objectives The primary objective is to assess the effect of the compounds of the present invention vs. placebo on mean percent body weight loss when administered for 90 days by continuous SC infusion.

Secondary objectives are to assess:
The mean body weight (BW) loss in the active treatment group compared to the placebo group from baseline to Day 90.
The proportion of patients who lose ≥5% of their baseline body weight in the active treatment group compared to the placebo group from baseline to Day 90.
The pharmacokinetics (PK) of the compounds of the present invention when given by continuous SC infusion for 90 days.
The safety and tolerability of the compounds of the present invention when given by continuous SC infusion for 90 days.
The effect of the compounds of the present invention versus placebo on ambulatory blood pressure monitoring parameters (ABPM) when given by continuous SC infusion for 90 days (sub-study).
The mean percent weight loss, mean weight loss, and proportion of patients who lose ≥5% of their baseline body weight in the active treatment group compared to the placebo group from baseline to Day 90 in patients who are severely obese (e.g., BMI≥40 $Kg/m^2$; sub-study).

Exploratory pharmacodynamic objectives of this study are to evaluate the effect of the compounds of the present invention when given by SC continuous infusion for 90 days in all patients, and those in the severely obese sub-study, on:
The proportion of patients who achieve a ≥10% decrease in body weight in the active treatment group compared to placebo from baseline to Day 90.
The change in glucose and insulin during a Meal Tolerance Test (MTT) from Baseline to Day 90.
Change in fasting glucose, insulin, insulin sensitivity, triglycerides, cholesterol, HDL, LDL, hs-CRP and HbA1c from Baseline to Day 90.
Change in waist circumference from Baseline to Day 90.
Change in body composition (assessed by Dual Energy X-Ray Absorptiometry (DXA)) from Baseline to Day 90 (sub-study).
Change in hunger and satiety from Baseline to Day 90.
Change in Impact of Weight on Quality of Life-Lite questionnaire (IWQOL-Lite) total score from Baseline to Day 90.

Change in depression/suicidality score (assessed by PHQ-9 and C-SSRS) from Baseline to Day 90.

Change in skin pigmentation (assessed by mexameter) from Baseline to Day 90.

Study Design

This is a randomized, double-blind, placebo-controlled study designed to evaluate the efficacy and safety of the compounds of the present invention when administered for 90 days to obese patients, inclusive of a sub-set of patients who are severely obese (BMI≥40 Kg/m$^2$).

Patients who are obese (BMI between 35-50 Kg/m$^2$), but otherwise healthy, will be enrolled. This study will be conducted on an outpatient basis. All patients will be required to self-administer study drug via an approved insulin infusion pump (OmniPod®) during the ~7 day placebo practice period. Patients with continued eligibility who have demonstrated the ability to successfully manage self-administration of placebo during the practice period will be randomized to the double blind 90 day Treatment Period. Number of Patients Planned Approximately 70 patients will be enrolled into the study. There will be three sub-studies within the protocol. The first will include those patients who are severely obese (BMI≥40 Kg/m$^2$, who will be stratified separately). Approximately 20 severely obese patients will be enrolled into this sub-study; these subjects will be recruited at all sites. The two remaining sub-studies will be enrolled at select sites. The first will be an ABPM sub-study where approximately 30 patients will be enrolled, and the final sub-study will include DXA scans on approximately 20 patients.

Diagnosis and Main Criteria for Inclusion

Patients must meet all of the following inclusion criteria to be eligible for the study:

1. MC4R heterozygous patients: mutation of MC4R gene.
2. Be between the age of 18 and 65.
3. Able to provide voluntary, written informed consent with comprehension of all aspects of the protocol, prior to any study procedures.
4. In good general health, without significant medical history, physical examination findings, or clinical laboratory abnormalities.
5. Body Mass Index: 35-50 Kg/m$^2$, inclusive. It is planned that approximately 20 of these patients will have a BMI≥40 Kg/m$^2$.
6. Stable body weight (+/−5 Kg) during previous 6 months.
7. Blood pressure (<140/90 mmHg); may include stable dose (≥30 days of use) of up to two anti-hypertensive medications to achieve control that are intended to remain on a stable dose during the protocol.
8. Willingness and demonstrates ability to self administer study medication subcutaneously via a continuous infusion pump during the placebo practice period.
9. Willing to maintain a healthy diet and exercise regime throughout study as recommended by counseling at study start.
10. Females of childbearing potential must agree to be abstinent or else use any two of the following medically acceptable forms of contraception from the Screening Period through the completion of study treatment: hormonal, condom with spermicidal jelly, diaphragm or cervical cap with spermicidal jelly, or IUD. Hormonal contraception must have started at least 3 months prior to screening. A female whose male partner has had a vasectomy must agree to use one additional form of medically acceptable contraception. Patients must agree to practice the above birth control methods for 30 days after completion of study treatment as a safety precaution.
11. Females of non-childbearing potential, defined as surgically sterile (status post hysterectomy, bilateral oophorectomy, or bilateral tubal ligation) or post-menopausal for at least 12 months (and confirmed with a screening FSH level in the post-menopausal range), do not require contraception during the study.
12. Males with female partners of childbearing potential must agree to use two medically acceptable forms of contraception as described above, with one of the two forms being condom with spermicide, from the Screening Period through 90 days after completion of study treatment. Males with female partners of childbearing potential who themselves are surgically sterile (status post vasectomy) must agree to use condoms with spermicide over the same period of time.

If any of the following exclusion criteria are met, the patient is not eligible for the study:

1. Fasting blood glucose greater than 140 mg/dL.
2. HbA1c≥6.5%.
3. TSH level outside the normal range.
4. Creatinine >1.5 times the upper limit of normal.
5. Liver function tests >2 times the upper limit of normal.
6. Active or history of any significant medical condition including renal, hepatic, pulmonary, gastrointestinal, cardiovascular, genitourinary, endocrine, immunologic, metabolic, neurologic or hematological disease.
7. Patients with a history of the following:
    a. Uncontrolled hypertension;
    b. Diabetes requiring medical treatment, presently or in the past;
    c. Major depressive disorder within the last 2 years;
    d. Any lifetime history of a suicide attempt;
    e. Any suicidal behavior in the last month;
    f. Other severe psychiatric disorders (e.g. schizophrenia, bipolar disorder, severe eating disorders including bulimia).
8. A PHQ-9 score of ≥15.
9. Any suicidal ideation of type 4 or 5 on the C-SSRS.
10. Prior bariatric surgery.
11. History or close family history (parents or siblings) of melanoma.
12. Significant dermatologic findings as part of the Screening comprehensive skin evaluation performed by the dermatologist. Any concerning lesions identified during the screening period will be biopsied and results known to be benign prior to randomization. If the pre-treatment biopsy results are of concern, the patient will be excluded from the study.
13. Treated with anorectic agents or drugs with anorexia as a frequent side event.
14. Taking 3 or more anti-hypertensive medications.
15. Acute illness or history of illness, which in the opinion of the Investigator, could pose a threat or harm to the patient or obscure interpretation of laboratory test results or interpretation of study data.
16. History of any malignancy, past or present, including skin cancer, multiple severely dysplastic nevi, or nevoid basal cell carcinoma.
17. History of HIV infection.
18. History of significant drug hypersensitivity or anaphylaxis.
19. History of hypersensitivity to proteins (e.g., allergy shots).
20. Any clinically significant abnormalities on screening laboratories as determined by the Investigator.

21. Abnormal 12-lead electrocardiogram (ECG) at screening or pre-dose (Day 1), except minor deviations deemed to be of no clinical significance by the Investigator. QTc must be <450 ms.
22. Received any experimental drugs or devices or have participated in a clinical study within 30 days prior to dosing.
23. Blood donation within 60 days prior to screening or intent to donate up to 60 days after Final Study Visit.
24. Hospitalization for surgery within the 3 months prior to screening except for minor outpatient procedures, or any planned hospitalizations during the study period.
25. Poor venous access or inability to tolerate venipuncture.
26. Inability to attend all study visits or comply with protocol requirements including fasting and restrictions on concomitant medication intake.
27. Participation in weight loss programs during the study period, including nutritional supplements/replacements other than as recommended by nutritional counseling provided at study start.
28. Use of prescription medications on a regular basis with the following exceptions:
    a. Contraceptives (must be on for ≥3 months);
    b. Hormone replacement therapy (must be on stable dose for ≥3 months);
    c. Antihypertensives (<3 medications on a stable dose for ≥30 days);
    d. Statins (dose must be ≤half the maximum dose; must be on a stable dose ≥3 months);
    e. Fibrates (must be on stable dose for ≥3 months);
    f. Niacin (must be on stable dose for ≥3 months);
    g. Thyroxin (stable dose for ≥30 days);
    h. The last use of any other prescription medication must have been greater than 5 half-lives for the specific medication or at least 14 days prior to randomization, whichever is longer.
29. Women who are pregnant or are breast feeding.
30. Previously randomized and dosed in this study or previously exposed to the compounds of the present invention.
31. History of alcohol or drug abuse within 5 years of Screening Visit.
32. Any other reason, which in the opinion of the Investigator would confound proper evaluation of the study.

Test Products, Doses, and Mode of Administration

The compounds of the present invention will be supplied as sterile solutions for infusion. The product will be manufactured at a concentration of 2.0 mg/mL at pH 5 with a fill volume of 11 mL/vial. Placebo will be vehicle. Drug products and placebo consist of sodium phosphate and citric acid, including 0.5% phenol as a preservative. Both the compounds of the present invention and placebo multiuse vials may be punctured multiple times under sterile conditions. The compounds of the present invention and placebo will be administered as a continuous subcutaneous infusion using the FDA approved insulin infusion pump, Insulet's Omni-Pod® (infusion pump which is wireless/tubeless and does not require a traditional infusion set, inclusive of an auto-injector whereby the patient never sees the needle or cannula). A total daily dose of 1 mg/24 hours of the compounds of the present invention, or equivalent volume of placebo, will be self-administered via continuous SC infusion during the treatment period.

Duration of Treatment

The overall study duration will be approximately 9 months, as currently planned. Individual patient participation in the study (Screening Period, Treatment Period and Follow-up Period) will be approximately 7 months.

Screening, inclusive of the placebo practice period, will occur within 30 days prior to randomization. Patients who successfully complete the open label placebo practice period will be randomized to double blind treatment for 90 days. The Final Visit will occur approximately 90 days after the last dose of study drug is administered (Day 180).

Study Procedures

The study will consist of a Screening Period inclusive of 2 visits. Patients who demonstrate compliance with the continuous infusion will be randomized to a double-blind treatment regimen (at Visit 3) and will begin 90 days of double-blind, self-administered SC continuous infusion, outpatient treatment. Additional clinic visits are scheduled on approximately Day 7 (Visit 4), Day 14 (Visit 5), Day 28 (Visit 6), Day 56 (Visit 7) and at the end of treatment (Day 90, Visit 8). Patients will also be contacted by telephone weekly during the first month of treatment, followed by bi-weekly contact during the remaining Treatment Period to encourage compliance and to assess adverse events. Follow up Visits will be scheduled monthly for 3 months after completion of the 90-day Treatment Period. The Final Visit will occur ~90 days after the last dose of study drug is administered (Day 180, Visit 11).

Screening Period (Days −30 to −1)

The Screening Period consists of 2 visits; the first where patients will be assessed for study qualification. Eligible patients will then proceed onto the second screening visit which will consist of an open label placebo practice period to ensure study patients can self-administer placebo drug via an FDA approved SC insulin infusion pump for approximately 1 week.

Visit 1

During Visit 1, following signed, written informed consent, confirmation of eligibility will be performed. Medical history, physical examination (including vital signs, height and weight and waist circumference measurements), a comprehensive skin exam will be conducted by the Dermatologist, quantitative skin measurement, Fitzpatrick scale and Edmond Obesity Staging System (EOSS) assessments, concomitant medication review, clinical laboratory tests including HbA1c, serum pregnancy test or follicle-stimulating hormone test, and a 12-lead ECG will be performed at this visit. The PHQ-9 and C-SSRS will be administered. Hunger and satiety questionnaire will also be administered.

Visit 2

During visit 2, patients confirmed to be eligible at Visit 1 and who continue to meet the inclusion and exclusion criteria upon review of medical history since the prior visit as well as AE and concomitant medication review, will have their weight and waist circumference measured and vital signs measured. Study staff will train patients and instruct them on proper technique of how to use the OmniPod® at this visit. Patients will be required to demonstrate understanding by successfully filling the OmniPod® with placebo, successfully placing the pod on an appropriate body area, and starting the infusion while at site. The study patients will change the OmniPod® approximately 2-3 times during the ~7 day period between Visits 2 and 3.

For those patients participating in the ABPM sub-study, an additional clinic visit will be necessary.

Treatment Period (Days 1-90)

Patients will return to the clinic approximately 7 days after starting the placebo practice period. Study patients who successfully complete the open label placebo practice period will return for Visit 3 (Day 1), and be randomized to 90 days of double-blind study treatment. Additional clinic visits are scheduled on approximately Day 7 (Visit 4), Day 14 (Visit 5), Day 28 (Visit 6), Day 56 (Visit 7) and at the end of treatment (Day 90, Visit 8). During these visits, a variety of efficacy, safety and exploratory assessments will be performed, according to the SOA.

Efficacy will be evaluated by measuring body weight. Safety will be evaluated by assessment of adverse events, vital signs (including blood pressure, respiratory rate, heart rate, and body temperature), ECGs, ABPM (sub-study), clinical laboratory evaluations (hematology, clinical chemistry including fasting blood glucose and insulin levels and urinalysis), lipid profile; levels of antibodies against the compounds of the present invention, quantitative skin assessments (mexameter) and photographic skin evaluation, protocol defined pigmented skin lesion biopsies, physical examinations including infusion site evaluations and concomitant medication review. Additionally, changes in depression/suicidality as assessed by the C-SSRS and PHQ-9 will be monitored. Plasma concentrations of the compounds of the present invention will be summarized and may be compared to PD parameters.

Exploratory measurements will be assessed by insulin sensitivity (as measured by MTT and HOMA-IR), effects on Hs-CRP and HbA1c, hunger and satiety (using a Hunger/Satiety Questionnaire), body composition (using DXA at select sites), changes in waist circumference, and changes in IWQOL-Lite, PHQ-9 and C-SSRS will be assessed as exploratory endpoints.

For patients who do not complete the full 90 day treatment period, attempts will be made to have the patient return for continued follow-up visits in order to monitor patient safety, as well as any effects on pharmacodynamic assessments.

Follow-up Period (Days 91-180)

Upon completion of the 90 day Treatment Period, Patients will enter a 90 day post-treatment Follow-up Period consisting of 3 monthly visits, where a variety of safety and efficacy assessments according to the SOA. The Final Study Visit will occur on approximately Day 180.

In the event an AE is ongoing at the time of the Final Visit, additional visits should be scheduled, at a frequency deemed appropriate by the Investigator, in order to follow the event to resolution. If a patient experiences a Serious Adverse Event for which follow-up laboratories and review are required, the Investigator will schedule additional post-treatment visits as necessary.

Study Endpoints

The primary endpoint will be evaluated by assessment of mean percent body weight loss. Secondary endpoints will be evaluated by assessments of weight, as well as safety and tolerability, including the ABPM sub-study. Plasma concentrations of the compounds of the present invention will be summarized and may be compared to various endpoints. In addition, weight loss parameters will be summarized in the severely obese patient sub-study.

Safety

Safety will be evaluated by assessment of adverse events, vital signs (including blood pressure, respiratory rate, heart rate, and body temperature), ECGs, clinical laboratory evaluations (hematology, clinical chemistry including fasting blood glucose and insulin levels and urinalysis), lipid profile; levels of antibodies against the compounds of the present invention, quantitative skin assessments (mexameter) and photographic skin evaluation, protocol defined pigmented skin lesion biopsies, physical examinations including infusion site evaluations and concomitant medication review. Additionally, changes in depression/suicidality as assessed by the C-SSRS and PHQ-9 will be monitored.

Pharmacokinetic

Plasma concentrations of the compounds of the present invention will summarized and may be compared to PD endpoints.

Exploratory

Exploratory measurements will be assessed by insulin sensitivity (as measured by MTT and HOMA-IR), effects on Hs-CRP and HbA1c, hunger and satiety (using a Hunger/Satiety Questionnaire), body composition (using DXA at select sites), changes in waist circumference, and changes in IWQOL-Lite and C-SSRS will be assessed as exploratory endpoints.

Sample Size Determination

Sample size per arm was calculated to target a 5 percentage point difference in mean weight change between a treatment arm and the placebo arm. From data reported by Gadde (2011), an SD of 5.7% was computed for weight change after 16 weeks of treatment. Assuming the SD in this study will be 5% to 6%, the sample size of N=30 completing subjects (accounting for 5 dropouts per dose group) has 97% power to yield a statistically significant (alpha=0.025, 1-sided) difference between an active dose group and placebo if the true underlying difference in means is 5 percentage points, and the SD is 5%. If the SD is 6%, there is 89% power.

Statistical Methods

Continuous variables will be summarized by dose group with descriptive statistics (e.g., number of observations, mean, SD, median, maximum, and minimum). Categorical variables will be tabulated by frequency of patients per dose group. All patient information and safety measurements will be based on the Safety Population, which will include all patients who receive a dose of study drug and have a post baseline observation.

Analyses will be based on observed data only; no data will be imputed.

Continuous efficacy endpoints will be assessed via a longitudinal mixed analysis of variance model which will include fixed effects terms for treatment, timepoint, treatment-by-timepoint interaction, and baseline covariate, and random effect for subjects. The assumption of normality will be assessed via the Shapiro-Wilk statistic. If substantial departure from normality is observed, a transformation such as log (post/pre) or rank may be used to analyze the data.

The comparison of the compounds of the present invention with placebo will be carried out via 1-sided statistical test at alpha=0.025.

Guidelines for Additional Safety Monitoring and Suspension of Dosing of a Patient Patients will be monitored carefully during the treatment period during on site clinic visits as well as periodic telephone calls made to the patients by the study staff. In the event a patient is withdrawn from treatment due to an AE, the patient should be encouraged to complete the remaining study visits in order to monitor the event to resolution and obtain additional protocol defined safety assessments. Additionally, guidance will be provided for any worsening of depression or suicidality during the study. At all times, this guidance is subject to the clinical judgment of the Investigator and study consultants (if applicable).

The Investigator shall notify the Medical Monitor in the event any study participant fulfills any of the criteria defined in the appendices noted above, or undergoes additional monitoring for any of the events defined herein.

Example 3: Treatment of Obese MC4R+/− Heterozygotic Mice with Compound of SEQ ID NO: 140

Diet induced obesity (DIO) littermate C57B1/6J mice that were either wild type with respect to MC4R gene (+/+), or heterozygous for the MC4R gene (+/−), or homozygous MC4R knockout mice that do not express the MC4R gene at all (−/−) were exposed to the compound of SEQ ID NO: 140: Ac-Arg-c(Cys-D-Ala-His-D-Phe-Arg-Trp-Cys)-NH$_2$ by Alzet pump infusion of at a concentration of 1200 nmol/kg/day for 8 days. Body weight was measured.

Figure 3:
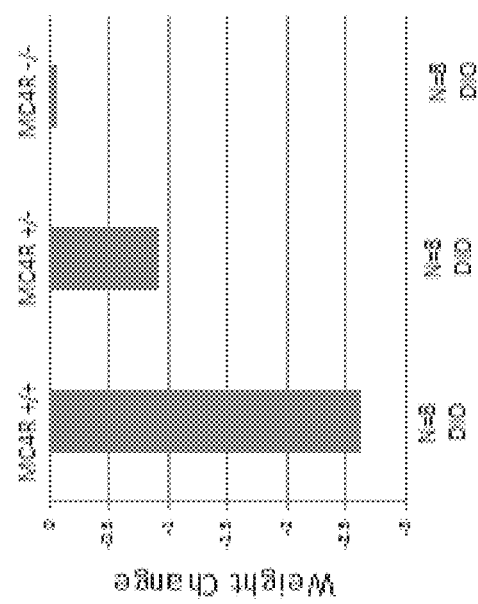
FIG. 3 is a bar plot showing the effect of administration of a compound of SEQ ID NO: 140 to mice as described in Example 1.

The data is presented in FIG. 3. The data shows that mice that were heterozygous for the MC4R gene (+/−) lost significant body weight (about 1 gram) over the treatment period while rodents that did not express the MC4R gene, did not show significant weight loss over this time period.

The weight change due to the exposure to the compound of SEQ ID NO: 140 in mice that are either wild type for the MC4R gene, or express only a single MC4R allele, or mice without any MC4R protein expression were compared. The data suggests that human patients with one functional MC4R allele, where their obesity is caused by the loss of function of the MC4R allele, will respond to the SEQ ID NO: 140, resulting in weight loss.

While this invention has been particularly shown and described with references to example embodiments thereof, it will be understood by those skilled in the art that various changes in form and details may be made therein without departing from the scope of the invention encompassed by the appended claims.

The invention claimed is:

1. A method of treating obesity in a subject in need thereof, comprising:
   administering to said subject an effective amount of an agonist of the melanocortin-4 receptor (MC4R), wherein the subject is a heterozygous carrier of an MC4R mutation.

2. The method of claim 1, wherein said MC4R agonist is Ac-Arg-c(Cys-D-Ala-His-D-Phe-Arg-Trp-Cys)-NH$_2$ (SEQ ID NO: 140) or a pharmaceutically acceptable salt thereof.

3. The method of claim 1, wherein said MC4R agonist is Hydantoin(C(O)-(Arg-Gly))-c(Cys-Glu-His-D-Phe-Arg-Trp-Cys)-NH$_2$ (SEQ ID NO: 500) or a pharmaceutically acceptable salt thereof.

4. The method of claim 1, wherein said MC4R agonist is a tripeptide D-Phe-Arg-Trp (SEQ ID NO: 560) or a pharmaceutical salt thereof.

5. The method of claim 1, wherein said MC4R agonist is a peptide that includes D-Phe-Arg-Trp (SEQ ID NO: 560) or a pharmaceutical salt thereof.

6. The method of claim 1, wherein said MC4R agonist is a peptide that includes an acetylated tripeptide Ac-D-Phe-Arg-Trp-NH$_2$ (SEQ ID NO: 561) or a pharmaceutical salt thereof.

7. The method of claim 1, wherein said MC4R agonist is a peptide selected form:

```
Ac-Nle-c(Asp-His-D-Phe-Arg-Trp-β-Ala-Lys)-NH2;                 (SEQ ID NO: 1)

Ac-Nle-c(Asp-His-D-Phe-Arg-Trp-A6c-Lys)-NH2;                   (SEQ ID NO: 2)

Ac-Nle-c(Cys-His-D-Phe-Arg-Trp-Ahx-Cys)-NH2;                   (SEQ ID NO: 3)

D-Phe-c(Cys-His-D-Phe-Arg-Trp-Ala-D-Cys)-Thr-NH2;              (SEQ ID NO: 4)

D-Phe-c(Cys-His-D-Phe-Arg-Trp-β-Ala-D-Cys)-Thr-NH2;            (SEQ ID NO: 5)

D-Phe-c(Cys-His-D-Phe-Arg-Trp-Gaba-D-Cys)-Thr-NH2;             (SEQ ID NO: 6)

Ac-Nle-c(Cys-His-D-Phe-Arg-Trp-Apn-Cys)-NH2;                   (SEQ ID NO: 7)

Ac-Nle-c(Asp-His-D-Phe-Arg-Trp-Apn-Lys)-NH2;                   (SEQ ID NO: 8)

Ac-A6c-c(Asp-His-D-Phe-Arg-Trp-Gaba-Lys)-NH2;                  (SEQ ID NO: 9)

Ac-D-2-Nal-c(Asp-His-D-Phe-Arg-Trp-Gaba-Lys)-NH2;              (SEQ ID NO: 10)

Ac-Cha-c(Asp-His-D-Phe-Arg-Trp-Gaba-Lys)-NH2;                  (SEQ ID NO: 11)

Ac-Nle-c(Asp-His-D-Phe-Arg-Trp-Gaba-Lys)-NH2;                  (SEQ ID NO: 12)

Ac-Nle-c(Cys-D-Ala-His-D-Phe-Arg-Trp-Cys)-NH2;                 (SEQ ID NO: 13)

Ac-Nle-c(Cys-β-Ala-His-D-Phe-Arg-Trp-Cys)-NH2;                 (SEQ ID NO: 14)

Ac-Nle-c(Cys-Gaba-His-D-Phe-Arg-Trp-Cys)-NH2;                  (SEQ ID NO: 15)

Ac-Nle-c(Cys-Aib-His-D-Phe-Arg-Trp-Cys)-NH2;                   (SEQ ID NO: 16)

Ac-Nle-c(Cys-Gly-His-D-Phe-Arg-Trp-Cys)-NH2;                   (SEQ ID NO: 17)

Ac-Nle-c(D-Cys-Ala-His-D-Phe-Arg-Trp-Cys)-NH2;                 (SEQ ID NO: 18)

(SEQ ID NO: 19)
```

-continued

Ac-Nle-c(D-Cys-D-Ala-His-D-Phe-Arg-Trp-Cys)-NH₂; (SEQ ID NO: 20)

Ac-Nle-c(D-Cys-β-Ala-His-D-Phe-Arg-Trp-Cys)-NH₂; (SEQ ID NO: 21)

Ac-Nle-c(D-Cys-Gaba-His-D-Phe-Arg-Trp-Cys)-NH₂; (SEQ ID NO: 22)

Ac-Nle-c(D-Cys-Aib-His-D-Phe-Arg-Trp-Cys)-NH₂; (SEQ ID NO: 23)

Ac-Nle-c(D-Cys-Gly-His-D-Phe-Arg-Trp-Cys)-NH₂; (SEQ ID NO: 24)

Ac-Nle-c(Cys-D-Ala-His-D-Phe-Arg-Trp-D-Cys)-NH₂; (SEQ ID NO: 25)

Ac-Nle-c(Cys-β-Ala-His-D-Phe-Arg-Trp-D-Cys)-NH₂; (SEQ ID NO: 26)

Ac-Nle-c(Cys-Gaba-His-D-Phe-Arg-Trp-D-Cys)-NH₂; (SEQ ID NO: 27)

Ac-Nle-c(Cys-Aib-His-D-Phe-Arg-Trp-D-Cys)-NH₂; (SEQ ID NO: 28)

Ac-Nle-c(Cys-Gly-His-D-Phe-Arg-Trp-D-Cys)-NH₂; (SEQ ID NO: 29)

Ac-Nle-c(D-Cys-Ala-His-D-Phe-Arg-Trp-D-Cys)-NH₂; (SEQ ID NO: 30)

Ac-Nle-c(D-Cys-D-Ala-His-D-Phe-Arg-Trp-D-Cys)-NH₂; (SEQ ID NO: 31)

Ac-Nle-c(D-Cys-β-Ala-His-D-Phe-Arg-Trp-D-Cys)-NH₂; (SEQ ID NO: 32)

Ac-Nle-c(D-Cys-Gaba-His-D-Phe-Arg-Trp-D-Cys)-NH₂; (SEQ ID NO: 33)

Ac-Nle-c(D-Cys-Aib-His-D-Phe-Arg-Trp-D-Cys)-NH₂; (SEQ ID NO: 34)

Ac-Oic-c(Asp-His-D-Phe-Arg-Trp-Gaba-Lys)-NH₂; (SEQ ID NO: 35)

Ac-Chg-c(Asp-His-D-Phe-Arg-Trp-Gaba-Lys)-NH₂; (SEQ ID NO: 36)

Ac-hCha-c(Asp-His-D-Phe-Arg-Trp-Gaba-Lys)-NH₂; (SEQ ID NO: 37)

Ac-D-Cha-c(Asp-His-D-Phe-Arg-Trp-Gaba-Lys)-NH₂; (SEQ ID NO: 38)

Ac-D-hCha-c(Asp-His-D-Phe-Arg-Trp-Gaba-Lys)-NH₂; (SEQ ID NO: 39)

Ac-Nip-c(Asp-His-D-Phe-Arg-Trp-Gaba-Lys)-NH₂; (SEQ ID NO: 40)

Ac-hPro-c(Asp-His-D-Phe-Arg-Trp-Gaba-Lys)-NH₂; (SEQ ID NO: 41)

Ac-hLeu-c(Asp-His-D-Phe-Arg-Trp-Gaba-Lys)-NH₂; (SEQ ID NO: 42)

Ac-Phe-c(Asp-His-D-Phe-Arg-Trp-Gaba-Lys)-NH₂; (SEQ ID NO: 43)

Ac-D-Phe-c(Asp-His-D-Phe-Arg-Trp-Gaba-Lys)-NH₂; (SEQ ID NO: 44)

Ac-D-Chg-c(Asp-His-D-Phe-Arg-Trp-Gaba-Lys)-NH₂; (SEQ ID NO: 45)

n-butanoyl-Cha-c(Asp-His-D-Phe-Arg-Trp-Gaba-Lys)-NH₂; (SEQ ID NO: 46)

-continued n-butyryl-Cha-c(Asp-His-D-Phe-Arg-Trp-Gaba-Lys)-NH$_2$;

(SEQ ID NO: 47)

Ac-hPhe-c(Asp-His-D-Phe-Arg-Trp-Gaba-Lys)-NH$_2$;

(SEQ ID NO: 48)

Ac-β-hMet-c(Asp-His-D-Phe-Arg-Trp-Gaba-Lys)-NH$_2$;

(SEQ ID NO: 49)

Ac-Gaba-c(Asp-His-D-Phe-Arg-Trp-Gaba-Lys)-NH$_2$;

(SEQ ID NO: 50)

Ac-Cha-c(Asp-His-D-Phe-Arg-D-Trp-Ala-Lys)-NH$_2$;

(SEQ ID NO: 51)

Ac-hCha-c(Asp-His-D-Phe-Arg-D-Trp-Ala-Lys)-NH$_2$;

(SEQ ID NO: 52)

Ac-Leu-c(Asp-His-D-Phe-Arg-D-Trp-Ala-Lys)-NH$_2$;

(SEQ ID NO: 53)

Ac-hLeu-c(Asp-His-D-Phe-Arg-D-Trp-Ala-Lys)-NH$_2$;

(SEQ ID NO: 54)

Ac-Phe-c(Asp-His-D-Phe-Arg-D-Trp-Ala-Lys)-NH$_2$;

(SEQ ID NO: 55)

Ac-Nle-c(Asp-His-D-Phe-Arg-D-Trp-D-Ala-Lys)-NH$_2$;

(SEQ ID NO: 56)

Ac-Nle-c(Asp-His-D-Phe-Arg-D-Trp-β-Ala-Lys)-NH$_2$;

(SEQ ID NO: 57)

Ac-Nle-c(Asp-His-D-Phe-Arg-D-Trp-Gaba-Lys)-NH$_2$;

(SEQ ID NO: 58)

Ac-Nle-c(Asp-His-D-Phe-Arg-D-Trp-Aha-Lys)-NH$_2$;

(SEQ ID NO: 59)

Ac-Nle-c(Asp-His-D-Phe-Arg-D-Trp-Apn-Lys)-NH$_2$;

(SEQ ID NO: 60)

Ac-Nle-c(Cys-His-D-Phe-Arg-D-Trp-Apn-Cys)-NH$_2$;

(SEQ ID NO: 61)

Ac-Nle-c(Cys-His-D-Phe-Arg-D-Trp-Gaba-Cys)-NH$_2$;

(SEQ ID NO: 62)

Ac-Nle-c(Cys-His-D-Phe-Arg-D-Trp-Ahx-Cys)-NH$_2$;

(SEQ ID NO: 63)

Ac-Nle-c(Cys-His-D-Phe-Arg-D-Trp-β-Ala-Cys)-NH$_2$;

(SEQ ID NO: 64)

Ac-Nle-c(Cys-His-D-Phe-Arg-D-Trp-D-Ala-Cys)-NH$_2$;

(SEQ ID NO: 65)

Ac-Nle-c(Cys-D-Ala-His-D-2-Nal-Arg-Trp-Cys)-NH$_2$;

(SEQ ID NO: 66)

Ac-Nle-c(Cys-D-Ala-His-D-2-Nal-Arg-2-Nal-Cys)-NH$_2$;

(SEQ ID NO: 67)

Ac-Nle-c(Cys-D-Ala-His-D-2-Nal-Arg-1-Nal-Cys)-NH$_2$;

(SEQ ID NO: 68)

n-butanoyl-Nle-c(Cys-D-Ala-His-D-Phe-Arg-2-Nal-Cys)-NH$_2$;

(SEQ ID NO: 69)

n-butanoyl-Nle-c(Cys-D-Ala-His-D-Phe-Arg-Trp-Cys)-NH$_2$;

(SEQ ID NO: 70)

Ac-Nle-c(Cys-D-Ala-His-D-Phe-Arg-2-Nal-Cys)-NH$_2$;

(SEQ ID NO: 71)

Ac-Nle-c(Cys-D-Ala-His-D-Phe-Arg-1-Nal-Cys)-NH$_2$;

(SEQ ID NO: 72)

Ac-Nle-c(Cys-D-Ala-His-D-Phe-Arg-Bal-Cys)-NH$_2$;

(SEQ ID NO: 73)

Ac-Nle-c(Cys-D-Glu-His-D-Phe-Arg-Trp-Cys)-NH$_2$;

(SEQ ID NO: 74)

Ac-Nle-c(Asp-His-D-Phe-Arg-Trp-D-Ala-Lys)-NH$_2$;

(SEQ ID NO: 75)

Ac-Nle-c(Cys-D-Ala-His-D-2-Nal-Arg-Bal-Cys)-NH$_2$;

(SEQ ID NO: 76)

Ac-Nle-c(Pen-D-Ala-His-D-Phe-Arg-Trp-Cys)-NH$_2$;

(SEQ ID NO: 77)

Ac-Nle-c(Cys-D-Ala-His-D-Phe-Arg-Trp-Pen)-NH$_2$;

(SEQ ID NO: 78)

Ac-Nle-c(Pen-D-Ala-His-D-Phe-Arg-Trp-Pen)-NH$_2$;

(SEQ ID NO: 79)

D-Phe-c(Cys-His-D-Phe-hArg-Trp-β-Ala-D-Cys)-Thr-NH$_2$;

(SEQ ID NO: 80)

D-Phe-c(Cys-His-D-(Et)Tyr-Arg-Trp-β-Ala-D-Cys)-Thr-NH$_2$;

(SEQ ID NO: 81)

D-Phe-c(Cys-His-D-Phe-Arg-Bip-β-Ala-D-Cys)-Thr-NH$_2$;

(SEQ ID NO: 82)

D-Phe-c(Cys-His-D-(Et)Tyr-hArg-Trp-β-Ala-D-Cys)-Thr-NH$_2$;

(SEQ ID NO: 83)

D-Phe-c(Cys-His-D-Phe-hArg-Bip-β-Ala-D-Cys)-Thr-NH$_2$;

(SEQ ID NO: 84)

D-Phe-c(Cys-His-D-(Et)Tyr-hArg-Bip-β-Ala-D-Cys)-Thr-NH$_2$;

(SEQ ID NO: 85)

Nle-c(Cys-His-D-Phe-Arg-Trp-Apn-Cys)-NH$_2$;

(SEQ ID NO: 86)

Ac-Nle-c(Asp-D-Ala-His-D-Phe-Arg-Trp-Lys)-NH$_2$;

(SEQ ID NO: 87)

Ac-Nle-c(Asp-D-Ala-His-D-Phe-Arg-Bal-Lys)-NH$_2$;

(SEQ ID NO: 88)

Ac-Nle-c(Cys-D-Ala-His-D-Phe-Arg-Trp-Pen)-OH;

(SEQ ID NO: 89)

Ac-Nle-c(Cys-D-Abu-His-D-Phe-Arg-Trp-Cys)-NH$_2$;

(SEQ ID NO: 90)

Ac-Nle-c(Cys-D-Val-His-D-Phe-Arg-Trp-Cys)-NH$_2$;

(SEQ ID NO: 91)

Ac-Nle-c(Cys-D-Ile-His-D-Phe-Arg-Trp-Cys)-NH$_2$;

(SEQ ID NO: 92)

Ac-Nle-c(Cys-D-Leu-His-D-Phe-Arg-Trp-Cys)-NH$_2$;

(SEQ ID NO: 93)

Ac-Nle-c(Cys-D-Tle-His-D-Phe-Arg-Trp-Cys)-NH$_2$;

(SEQ ID NO: 94)

Ac-Nle-c(Cys-D-Cha-His-D-Phe-Arg-Trp-Cys)-NH$_2$;

(SEQ ID NO: 95)

Ac-Nle-c(Pen-His-D-Phe-Arg-Trp-Gaba-Cys)-NH$_2$;

(SEQ ID NO: 96)

Ac-Nle-c(Cys-His-D-Phe-Arg-Trp-Gaba-Pen)-NH$_2$;

(SEQ ID NO: 97)

Ac-Nle-c(Pen-His-D-Phe-Arg-Trp-Gaba-Pen)-NH$_2$;

(SEQ ID NO: 98)

Ac-Leu-c(Cys-His-D-Phe-Arg-Trp-Gaba-Cys)-NH$_2$;

(SEQ ID NO: 99)

Ac-Cha-c(Cys-His-D-Phe-Arg-Trp-Gaba-Cys)-NH$_2$;

(SEQ ID NO: 100)

```
Ac-Ile-c(Cys-His-D-Phe-Arg-Trp-Gaba-Cys)-NH₂;

(SEQ ID NO: 101)
Ac-Phe-c(Cys-His-D-Phe-Arg-Trp-Gaba-Cys)-NH₂;

(SEQ ID NO: 102)
Ac-Val-c(Cys-His-D-Phe-Arg-Trp-Gaba-Cys)-NH₂;

(SEQ ID NO: 103)
Ac-2-Nal-c(Cys-His-D-Phe-Arg-Trp-Gaba-Cys)-NH₂;

(SEQ ID NO: 104)
Nle-c(Cys-His-D-Phe-Arg-Trp-Gaba-Cys)-NH₂;

(SEQ ID NO: 105)
Phe-c(Cys-His-D-Phe-Arg-Trp-Gaba-Cys)-NH₂;

(SEQ ID NO: 106)
Ac-Nle-c(Cys-3-Pal-D-Phe-Arg-Trp-Gaba-Cys)-NH₂;

(SEQ ID NO: 107)
Ac-Nle-c(Cys-D-Ala-His-D-Phe-Arg-Trp-Cys)-OH;

(SEQ ID NO: 108)
Ac-Nle-c(Cys-His-Phe-Arg-D-Trp-Gaba-Cys)-NH₂;

(SEQ ID NO: 109)
Ac-Nle-c(Asp-His-D-2-Nal-Arg-Trp-Ala-Lys)-NH₂;

(SEQ ID NO: 110)
Ac-Nle-c(Asp-His-D-2-Nal-Arg-Trp-β-Ala-Lys)-NH₂;

(SEQ ID NO: 111)
Ac-Nle-c(Cys-His-D-2-Nal-Arg-Trp-Gaba-Cys)-NH₂;

(SEQ ID NO: 112)
Ac-Nle-c(Cys-His-D-2-Nal-Arg-Trp-Ahx-Cys)-NH₂;

(SEQ ID NO: 113)
Ac-hPhe-c(Asp-His-D-2-Nal-Arg-Trp-Gaba-Lys)-NH₂;

(SEQ ID NO: 114)
Ac-Cha-c(Asp-His-D-2-Nal-Arg-Trp-Gaba-Lys)-NH₂;

(SEQ ID NO: 115)
Ac-Nle-c(Asp-His-D-Phe-Arg-Trp-β-Ala-Lys)-OH;

(SEQ ID NO: 116)
Ac-Nle-c(Cys-His-D-Phe-Arg-Trp-Ahx-Cys)-OH;

(SEQ ID NO: 117)
D-Phe-c(Cys-His-D-Phe-Arg-Trp-Ala-D-Cys)-Thr-OH;

(SEQ ID NO: 118)
D-Phe-c(Cys-His-D-Phe-Arg-Trp-β-Ala-D-Cys)-Thr-OH;

(SEQ ID NO: 119)
D-Phe-c(Cys-His-D-Phe-Arg-Trp-Gaba-D-Cys)-Thr-OH;

(SEQ ID NO: 120)
Ac-Nle-c(Cys-His-D-Phe-Arg-Trp-Apn-Cys)-OH;

(SEQ ID NO: 121)
Ac-Nle-c(Asp-His-D-Phe-Arg-Trp-Apn-Lys)-OH;

(SEQ ID NO: 122)
Ac-Cha-c(Asp-His-D-Phe-Arg-Trp-Gaba-Lys)-OH;

(SEQ ID NO: 123)
Ac-Nle-c(Asp-His-D-Phe-Arg-Trp-Gaba-Lys)-OH;

(SEQ ID NO: 124)
Ac-Chg-c(Asp-His-D-Phe-Arg-Trp-Gaba-Lys)-OH;

(SEQ ID NO: 125)
Ac-D-Cha-c(Asp-His-D-Phe-Arg-Trp-Gaba-Lys)-OH;

(SEQ ID NO: 126)
Ac-hCha-c(Asp-His-D-Phe-Arg-Trp-Gaba-Lys)-OH;

(SEQ ID NO: 127)
```

-continued

Ac-D-Chg-c(Asp-His-D-Phe-Arg-Trp-Gaba-Lys)-OH;

(SEQ ID NO: 128)

Ac-hPhe-c(Asp-His-D-Phe-Arg-Trp-Gaba-Lys)-OH;

(SEQ ID NO: 129)

Ac-Nle-c(Cys-His-D-Phe-Arg-D-Trp-Gaba-Cys)-OH;

(SEQ ID NO: 130)

Ac-Nle-c(Cys-His-D-Phe-Arg-D-Trp-Ahx-Cys)-OH;

(SEQ ID NO: 131)

Ac-Nle-c(Cys-His-D-Phe-Arg-D-Trp-β-Ala-Cys)-OH;

(SEQ ID NO: 132)

Ac-Nle-c(Cys-His-D-Phe-Arg-D-Trp-D-Ala-Cys)-OH;

(SEQ ID NO: 133)

Ac-Nle-c(Cys-D-Ala-His-D-2-Nal-Arg-Trp-Cys)-OH;

(SEQ ID NO: 134)

Ac-Nle-c(Cys-D-Ala-His-D-2-Nal-Arg-2-Nal-Cys)-OH;

(SEQ ID NO: 135)

Ac-Nle-c(Cys-D-Ala-His-D-2-Nal-Arg-1-Nal-Cys)-OH;

(SEQ ID NO: 136)

Ac-Nle-c(Cys-D-Ala-His-D-2-Nal-Arg-Bal-Cys)-OH;

(SEQ ID NO: 137)

Ac-Nle-c(Pen-D-Ala-His-D-Phe-Arg-Trp-Cys)-OH;

(SEQ ID NO: 138)

Ac-Nle-c(Cys-His-D-Phe-Arg-Trp-Gaba-Pen)-OH;

(SEQ ID NO: 139)

Ac-Arg-c(Cys-D-Ala-His-D-2-Nal-Arg-Trp-Cys)-NH$_2$;

(SEQ ID NO: 140)

Ac-Arg-c(Cys-D-Ala-His-D-Phe-Arg-Trp-Cys)-NH$_2$;

(SEQ ID NO: 141)

Ac-D-Arg-c(Cys-D-Ala-His-D-Phe-Arg-Trp-Cys)-NH$_2$;

(SEQ ID NO: 142)

Ac-D-Arg-c(Cys-D-Ala-His-D-Phe-Arg-Trp-Pen)-NH$_2$;

(SEQ ID NO: 143)

Ac-D-Arg-c(Cys-His-D-Phe-Arg-Trp-Gaba-Pen)-NH$_2$;

(SEQ ID NO: 144)

Ac-Arg-c(Cys-His-D-Phe-Arg-Trp-Gaba-Pen)-NH$_2$;

(SEQ ID NO: 145)

Ac-Arg-c(Cys-D-Ala-His-D-Phe-Arg-Trp-Pen)-NH$_2$;

(SEQ ID NO: 146)

Ac-D-Arg-c(Asp-His-D-Phe-Arg-Trp-Ala-Lys)-NH$_2$;

(SEQ ID NO: 147)

Ac-Arg-c(Asp-His-D-Phe-Arg-Trp-Ala-Lys)-NH$_2$;

(SEQ ID NO: 148)

Ac-Nle-c(Cys-D-Ala-His-D-Phe-Arg-Trp-Gly-Cys)-NH$_2$;

(SEQ ID NO: 149)

Ac-Nle-c(Cys-D-Ala-His-D-Phe-Arg-Trp-D-Ala-Cys)-NH$_2$;

(SEQ ID NO: 150)

Ac-Nle-c(Cys-D-Ala-His-D-Phe-Arg-Trp-β-Ala-Cys)-NH$_2$;

(SEQ ID NO: 151)

Ac-Nle-c(Cys-D-Ala-His-D-Phe-Arg-Trp-Gaba-Cys)-NH$_2$;

(SEQ ID NO: 152)

Ac-Nle-c(Cys-D-Ala-His-D-Phe-Arg-Trp-Apn-Cys)-NH$_2$;

(SEQ ID NO: 153)

Ac-c(Cys-Glu-His-D-Phe-Arg-Trp-Ala-Cys)-NH$_2$;

(SEQ ID NO: 154)

-continued

Ac-c(Cys-Glu-His-D-Phe-Arg-2-Nal-Ala-Cys)-NH$_2$;

(SEQ ID NO: 155)
Ac-c(Cys-D-Ala-His-D-Phe-Arg-Trp-Ala-Cys)-NH$_2$;

(SEQ ID NO: 156)
Ac-c(Cys-D-Ala-His-D-Phe-Arg-2-Nal-Ala-Cys)-NH$_2$;

(SEQ ID NO: 157)
Ac-Nle-c(Cys-D-Ala-His-D-Phe-Arg-Trp-Ala-Cys)-NH$_2$;

(SEQ ID NO: 158)
Ac-Nle-c(Asp-D-Ala-His-D-Phe-Arg-Bal-Ala-Lys)-NH$_2$;

(SEQ ID NO: 159)
Tyr-Gly-Arg-(Lys)$_2$-(Arg)$_2$-Gln-(Arg)$_3$-Nle-c(Asp-His-D-2-Nal-Arg-Trp-Lys)-NH$_2$;

(SEQ ID NO: 160)
Tyr-Gly-Arg-(Lys)$_2$-(Arg)$_2$-Gln-(Arg)$_3$-Doc-Nle-c(Asp-His-D-2-Nal-Arg-Trp-Lys)-NH$_2$;

(SEQ ID NO: 161)
Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

(SEQ ID NO: 162)
Ac-Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

(SEQ ID NO: 163)
Nle-c(Asp-His-D-2-Nal-Arg-Trp-Lys)-(Doc)$_2$-Tyr-Gly-Arg-(Lys)$_2$-(Arg)$_2$-Gln-(Arg)$_3$-NH$_2$;

(SEQ ID NO: 164)
Ac-Nle-c(Asp-His-D-2-Nal-Arg-Trp-Lys)-(Pro)$_2$-Lys-Asp-Tyr-Gly-Arg-(Lys)$_2$-(Arg)$_2$-Gln-(Arg)$_3$-NH$_2$;

(SEQ ID NO: 165)
Ac-c(Cys-Glu-His-D-2-Nal-Arg-Trp-Gly-Cys)-(Pro)$_2$-Lys-Asp-Tyr-Gly-Arg-(Lys)$_2$-(Arg)$_2$-Gln-(Arg)$_3$-NH$_2$;

(SEQ ID NO: 166)
Ac-Nle-c(Asp-His-D-2-Nal-Arg-Trp-Lys)-(β-Ala)$_2$-Tyr-Gly-Arg-(Lys)$_2$-(Arg)$_2$-Gln-(Arg)$_3$-NH$_2$;

(SEQ ID NO: 167)
Ac-Nle-c(Asp-His-D-2-Nal-Arg-Trp-Lys)-(Pro)$_2$-Lys-Asp-Doc-Tyr-Gly-Arg-(Lys)$_2$-(Arg)$_2$-Gln-(Arg)$_3$-NH$_2$;

(SEQ ID NO: 168)
Ac-c(Cys-Glu-His-D-2-Nal-Arg-Trp-Gly-Cys)-(Pro)$_2$-Lys-Asp-Doc-Tyr-Gly-Arg-(Lys)$_2$-(Arg)$_2$-Gln-(Arg)$_3$-NH$_2$;

(SEQ ID NO: 169)
Ac-c(Cys-Glu-His-D-2-Nal-Arg-Trp-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 170)
Ac-c(Cys-Glu-His-D-2-Nal-Arg-Trp-Ala-Cys)-(Pro)$_2$-Lys-Asp-Doc-Tyr-Gly-Arg-(Lys)$_2$-(Arg)$_2$-Gln-(Arg)$_3$-NH$_2$;

(SEQ ID NO: 171)
Ac-Nle-c(Asp-His-D-2-Nal-Arg-Trp-Lys)-(Doc)$_2$-Tyr-Gly-Arg-(Lys)$_2$-(Arg)$_2$-Gln-(Arg)$_3$-NH$_2$;

(SEQ ID NO: 172)
Ac-c(Cys-Glu-His-D-2-Nal-Arg-2-Nal-Ala-Cys)-(Pro)$_2$-Lys-Asp-β-Ala-Tyr-Gly-Arg-(Lys)$_2$-(Arg)$_2$-Gln-(Arg)$_3$-NH$_2$;

(SEQ ID NO: 173)
Ac-c(Cys-Glu-His-D-2-Nal-Arg-Bal-Ala-Cys)-(Pro)$_2$-Lys-Asp-β-Ala-(Arg)$_5$-Gln-(Arg)$_3$-NH$_2$;

(SEQ ID NO: 174)

-continued

```
Ac-c(Cys-Glu-His-D-2-Nal-Arg-Bal-Ala-Cys)-(Pro)₂-Lys-Asp-β-Ala-Gly-(Arg)₅-Gln-
(Arg)₃-NH₂;

(SEQ ID NO: 175)
Ac-c(Cys-Glu-His-D-2-Nal-Arg-Bal-Ala-Cys)-(Pro)₂-Lys-Asp-β-Ala-Tyr-Gly-(Arg)₅-Gln-
(Arg)₃-NH₂;

(SEQ ID NO: 176)
Ac-c(Cys-Glu-His-D-2-Nal-Arg-Trp-Ala-Cys)-(Pro)₂-Lys-Asp-β-Ala-Tyr-Gly-Arg-(Lys)₂-
Arg-Gln-(Arg)₄-NH₂;

(SEQ ID NO: 177)
Ac-c(Cys-Glu-His-D-2-Nal-Arg-Trp-Ala-Cys)-(Pro)₂-Lys-Asp-β-Ala-Tyr-Gly-Arg-(Lys)₂-
Gln-(Arg)₅-NH₂;

(SEQ ID NO: 178)
Ac-c(Cys-Glu-His-D-2-Nal-Arg-Trp-Ala-Cys)-(Pro)₂-Lys-Asp-β-Ala-Tyr-Gly-Arg-Lys-
Gln-Lys-(Arg)₅-NH₂;

(SEQ ID NO: 179)
Ac-c(Cys-Glu-His-D-2-Nal-Arg-Trp-Ala-Cys)-(Pro)₂-Lys-Asp-β-Ala-Tyr-Gly-Arg-(Lys)₂-
(Arg)₄-Gln-Arg-NH₂;

(SEQ ID NO: 180)
Ac-c(Cys-Glu-His-D-2-Nal-Arg-Bal-Ala-Cys)-(Pro)₂-Lys-Asp-β-Ala-Tyr-Aib-Arg-(Lys)₂-
(Arg)₂-Gln-(Arg)₃-NH₂;

(SEQ ID NO: 181)
Ac-c(Cys-Glu-His-D-2-Nal-Arg-1-Nal-Ala-Cys)-(Pro)₂-Arg-Asp-β-Ala-(Arg)₅-Gln-(Arg)₃-
NH₂;

(SEQ ID NO: 182)
Ac-c(Cys-Glu-His-D-2-Nal-Arg-1-Nal-Ala-Cys)-(Pro)₂-Lys-Asp-β-Ala-(Arg)₅-Gln-(Arg)₃-
NH₂;

(SEQ ID NO: 183)
Ac-c(Cys-Glu-His-D-2-Nal-Arg-1-Nal-Ala-Cys)-(Pro)₂-Lys-Asp-β-Ala-(Arg)₆-Gln-(Arg)₃-
NH₂;

(SEQ ID NO: 184)
Ac-c(Cys-Glu-His-D-2-Nal-Arg-2-Nal-Ala-Cys)-(Pro)₂-Arg-Asp-β-Ala-(Arg)₅-Gln-(Arg)₃-
NH₂;

(SEQ ID NO: 185)
Ac-c(Cys-Glu-His-D-2-Nal-Arg-2-Nal-Ala-Cys)-(Pro)₂-Lys-Asp-β-Ala-(Arg)₅-Gln-(Arg)₃-
NH₂;

(SEQ ID NO: 186)
Ac-c(Cys-Glu-His-D-2-Nal-Arg-2-Nal-Ala-Cys)-(Pro)₂-Lys-Asp-β-Ala-(Arg)₆-Gln-(Arg)₃-
NH₂;

(SEQ ID NO: 187)
Ac-c(Cys-Glu-His-D-2-Nal-Arg-Bal-Ala-Cys)-(Pro)₂-Arg-Asp-β-Ala-(Arg)₆-Gln-(Arg)₃-
NH₂;

(SEQ ID NO: 188)
Ac-c(Cys-Glu-His-D-2-Nal-Arg-Bal-Ala-Cys)-(Pro)₂-Arg-Asp-β-Ala-(Arg)₅-Gln-(Arg)₃-
NH₂;

(SEQ ID NO: 189)
Ac-c(Cys-Glu-His-D-2-Nal-Arg-Bal-Ala-Cys)-(Pro)₂-Lys-Asp-β-Ala-(Arg)₆-Gln-(Arg)₃-
NH₂;

(SEQ ID NO: 190)
Ac-c(Cys-Glu-His-D-2-Nal-Arg-Trp-Ala-Cys)-(Pro)₂-Lys-Asp-β-Ala-Tyr-Gly-Arg-(Lys)₂-
```

-continued (Arg)₃-Gln-(Arg)₂-NH₂;

(SEQ ID NO: 191)
Ac-c(Cys-Glu-His-D-2-Nal-Arg-Trp-Ala-Cys)-(Pro)₂-Lys-Asp-β-Ala-Tyr-Gly-Arg-Gln-(Lys)₂-(Arg)₅-NH₂;

(SEQ ID NO: 192)
Ac-c(Cys-Glu-His-D-2-Nal-Arg-Trp-Ala-Cys)-(Pro)₂-Lys-Asp-β-Ala-Tyr-Gly-Arg-(Lys)₂-(Arg)₅-Gln-NH₂;

(SEQ ID NO: 193)
Ac-c(Cys-Glu-His-D-2-Nal-Arg-1-Nal-Ala-Cys)-(Pro)₂-Lys-Asp-β-Ala-Tyr-Gly-Arg-(Lys)₂-(Arg)₂-Gln-(Arg)₃-NH₂;

(SEQ ID NO: 194)
Ac-c(Cys-Glu-His-D-2-Nal-Arg-Bal-Ala-Cys)-(Pro)₂-Lys-Asp-β-Ala-Tyr-Gly-Arg-(Lys)₂-(Arg)₂-Gln-(Arg)₃-NH₂;

(SEQ ID NO: 195)
Ac-c(Cys-Glu-His-D-2-Nal-Arg-1-Nal-Ala-Cys)-(Pro)₂-Lys-Asp-β-Ala-(Arg)₂-Lys-(Arg)₂-Gln-(Arg)₃-NH₂;

(SEQ ID NO: 196)
Ac-c(Cys-Glu-His-D-2-Nal-Arg-1-Nal-Ala-Cys)-(Pro)₂-Lys-Asp-β-Ala-Arg-Lys-(Arg)₃-Gln-(Arg)₃-NH₂;

(SEQ ID NO: 197)
Ac-c(Cys-Glu-His-D-2-Nal-Arg-2-Nal-Ala-Cys)-(Pro)₂-Lys-Asp-β-Ala-(Arg)₂-Lys-(Arg)₂-Gln-(Arg)₃-NH₂;

(SEQ ID NO: 198)
Ac-c(Cys-Glu-His-D-2-Nal-Arg-2-Nal-Ala-Cys)-(Pro)₂-Lys-Asp-β-Ala-Tyr-Gly-(Arg)₂-Lys-(Arg)₂-Gln-(Arg)₃-NH₂;

(SEQ ID NO: 199)
Ac-c(Cys-Glu-His-D-2-Nal-Arg-2-Nal-Ala-Cys)-(Pro)₂-Lys-Asp-β-Ala-Gly-(Arg)₂-Lys-(Arg)₂-Gln-(Arg)₃-NH₂;

(SEQ ID NO: 200)
Ac-c(Cys-Glu-His-D-2-Nal-Arg-2-Nal-Ala-Cys)-(Pro)₂-Lys-Asp-β-Ala-Gly-Arg-Lys-(Arg)₃-Gln-(Arg)₃-NH₂;

(SEQ ID NO: 201)
Ac-c(Cys-Glu-His-D-2-Nal-Arg-1-Nal-Ala-Cys)-(Pro)₂-Lys-Asp-β-Ala-Tyr-Gly-(Arg)₂-Lys-(Arg)₂-Gln-(Arg)₃-NH₂;

(SEQ ID NO: 202)
Ac-c(Cys-Glu-His-D-2-Nal-Arg-1-Nal-Ala-Cys)-(Pro)₂-Lys-Asp-β-Ala-Tyr-Gly-Arg-Lys-(Arg)₃-Gln-(Arg)₃-NH₂;

(SEQ ID NO: 203)
Ac-c(Cys-Glu-His-D-2-Nal-Arg-1-Nal-Ala-Cys)-(Pro)₂-Lys-Asp-β-Ala-Gly-(Arg)₂-Lys-(Arg)₂-Gln-(Arg)₃-NH₂;

(SEQ ID NO: 204)
Ac-c(Cys-Glu-His-D-2-Nal-Arg-1-Nal-Ala-Cys)-(Pro)₂-Lys-Asp-β-Ala-Gly-Arg-Lys-(Arg)₃-Gln-(Arg)₃-NH₂;

(SEQ ID NO: 205)
Ac-c(Cys-Glu-His-D-2-Nal-Arg-2-Nal-Ala-Cys)-(Pro)₂-Lys-Asp-β-Ala-(Arg)₂-Lys-(Arg)₂-Gln-(Arg)₃-NH₂;

(SEQ ID NO: 206)
Ac-c(Cys-Glu-His-D-2-Nal-Arg-2-Nal-Ala-Cys)-(Pro)₂-Lys-Asp-β-Ala-Arg-Lys-(Arg)₃-

-continued

Gln-(Arg)₃-NH₂;

(SEQ ID NO: 207)
Ac-c(Cys-Glu-His-D-2-Nal-Arg-2-Nal-Ala-Cys)-(Pro)₂-Lys-Asp-β-Ala-Tyr-Gly-Arg-Lys-(Arg)₃-Gln-(Arg)₃-NH₂;

(SEQ ID NO: 208)
Ac-c(Cys-Glu-His-D-2-Nal-Arg-Bal-Ala-Cys)-(Pro)₂-Lys-Asp-β-Ala-(Arg)₂-Lys-(Arg)₂-Gln-(Arg)₃-NH₂;

(SEQ ID NO: 209)
Ac-c(Cys-Glu-His-D-2-Nal-Arg-Bal-Ala-Cys)-(Pro)₂-Lys-Asp-β-Ala-Arg-Lys-(Arg)₃-Gln-(Arg)₃-NH₂;

(SEQ ID NO: 210)
Ac-c(Cys-Glu-His-D-2-Nal-Arg-Bal-Ala-Cys)-(Pro)₂-Lys-Asp-β-Ala-Tyr-Gly-(Arg)₂-Lys-(Arg)₂-Gln-(Arg)₃-NH₂;

(SEQ ID NO: 211)
Ac-c(Cys-Glu-His-D-2-Nal-Arg-Bal-Ala-Cys)-(Pro)₂-Lys-Asp-β-Ala-Tyr-Gly-Arg-Lys-(Arg)₃-Gln-(Arg)₃-NH₂;

(SEQ ID NO: 212)
Ac-c(Cys-Glu-His-D-2-Nal-Arg-Bal-Ala-Cys)-(Pro)₂-Lys-Asp-β-Ala-Gly-(Arg)₂-Lys-(Arg)₂-Gln-(Arg)₃-NH₂;

(SEQ ID NO: 213)
Ac-c(Cys-Glu-His-D-2-Nal-Arg-Bal-Ala-Cys)-(Pro)₂-Lys-Asp-β-Ala-Gly-Arg-Lys-(Arg)₃-Gln-(Arg)₃-NH₂;

(SEQ ID NO: 214)
Ac-c(Cys-Glu-His-D-2-Nal-Arg-Trp-Ala-Cys)-(Pro)₂-Lys-Asp-β-Ala-(Arg)₅-Gln-(Arg)₃-NH₂;

(SEQ ID NO: 215)
Ac-c(Cys-Glu-His-D-2-Nal-Arg-Trp-Ala-Cys)-(Pro)₂-Arg-Asp-β-Ala-(Arg)₅-Gln-(Arg)₃-NH₂;

(SEQ ID NO: 216)
Ac-c(Cys-Glu-His-D-2-Nal-Arg-Trp-Ala-Cys)-(Pro)₂-Lys-Asp-β-Ala-Tyr-Gly-(Arg)₅-Gln-(Arg)₃-NH₂;

(SEQ ID NO: 217)
Ac-c(Cys-Glu-His-D-2-Nal-Arg-Trp-Ala-Cys)-(Pro)₂-Arg-Asp-β-Ala-Tyr-Gly-(Arg)₅-Gln-(Arg)₃-NH₂;

(SEQ ID NO: 218)
Ac-c(Cys-Glu-His-D-2-Nal-Arg-Trp-Ala-Cys)-(Pro)₂-Lys-Asp-β-Ala-(Arg)₅-Gln-(Arg)₄-NH₂;

(SEQ ID NO: 219)
Ac-c(Cys-Glu-His-D-2-Nal-Arg-Trp-Ala-Cys)-(Pro)₂-Arg-Asp-β-Ala-(Arg)₅-Gln-(Arg)₄-NH₂;

(SEQ ID NO: 220)
Ac-c(Cys-Glu-His-D-2-Nal-Arg-Trp-Ala-Cys)-(Pro)₂-Lys-Asp-β-Ala-Tyr-Gly-(Arg)₅-Gln-(Arg)₄-NH₂;

(SEQ ID NO: 221)
Ac-c(Cys-Glu-His-D-2-Nal-Arg-Trp-Ala-Cys)-(Pro)₂-Arg-Asp-β-Ala-Tyr-Gly-(Arg)₅-Gln-(Arg)₄-NH₂;

(SEQ ID NO: 222)
Ac-c(Cys-Glu-His-D-2-Nal-Arg-1-Nal-Ala-Cys)-(Pro)₂-Lys-Asp-β-Ala-(Arg)₅-Gln-(Arg)₄-NH₂;

(SEQ ID NO: 223)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 224)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 225)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 226)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 227)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 228)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_4$-NH$_2$;

(SEQ ID NO: 229)
Ac-c(Cys-Glu-His-D-2-Nal-Arg-1-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 230)
Ac-c(Cys-Glu-His-D-2-Nal-Arg-1-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 231)
Ac-c(Cys-Glu-His-D-2-Nal-Arg-2-Nal-Ala-Cys)-(Pro)$_2$-Arg-Asp-β-Ala-(Arg)$_6$-Gln-(Arg)$_3$-NH$_2$;

(SEQ ID NO: 232)
Ac-c(Cys-Glu-His-D-2-Nal-Arg-2-Nal-Ala-Cys)-(Pro)$_2$-Lys-Asp-β-Ala-(Arg)$_5$-Gln-(Arg)$_4$-NH$_2$;

(SEQ ID NO: 233)
Ac-c(Cys-Glu-His-D-2-Nal-Arg-2-Nal-Ala-Cys)-(Pro)$_2$-Arg-Asp-β-Ala-(Arg)$_5$-Gln-(Arg)$_4$-NH$_2$;

(SEQ ID NO: 234)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 235)
Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 236)
Ac-c(Cys-Glu-His-D-2-Nal-Arg-2-Nal-Ala-Cys)-(Pro)$_2$-Lys-Asp-β-Ala-Tyr-Gly-(Arg)$_6$-Gln-(Arg)$_3$-NH$_2$;

(SEQ ID NO: 237)
Ac-c(Cys-Glu-His-D-2-Nal-Arg-2-Nal-Ala-Cys)-(Pro)$_2$-Arg-Asp-β-Ala-Tyr-Gly-(Arg)$_6$-Gln-(Arg)$_3$-NH$_2$;

(SEQ ID NO: 238)
Ac-c(Cys-Glu-His-D-2-Nal-Arg-2-Nal-Ala-Cys)-(Pro)$_2$-Lys-Asp-β-Ala-Tyr-Gly-(Arg)$_5$-Gln-(Arg)$_4$-NH$_2$;

-continued

Ac-c(Cys-Glu-His-D-2-Nal-Arg-2-Nal-Ala-Cys)-(Pro)$_2$-Arg-Asp-β-Ala-Tyr-Gly-(Arg)$_5$-Gln-(Arg)$_4$-NH$_2$; (SEQ ID NO: 239)

Ac-c(Cys-Glu-His-D-2-Nal-Arg-Bal-Ala-Cys)-(Pro)$_2$-Lys-Asp-β-Ala-(Arg)$_5$-Gln-(Arg)$_4$-NH$_2$; (SEQ ID NO: 240)

Ac-c(Cys-Glu-His-D-2-Nal-Arg-Bal-Ala-Cys)-(Pro)$_2$-Arg-Asp-β-Ala-(Arg)$_5$-Gln-(Arg)$_4$-NH$_2$; (SEQ ID NO: 241)

Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_3$-NH$_2$; (SEQ ID NO: 242)

Ac-c(Cys-Glu-His-D-2-Nal-Arg-Bal-Ala-Cys)-(Pro)$_2$-Lys-Asp-β-Ala-Tyr-Gly-(Arg)$_5$-Gln-(Arg)$_4$-NH$_2$; (SEQ ID NO: 243)

Ac-c(Cys-Glu-His-D-2-Nal-Arg-Bal-Ala-Cys)-(Pro)$_2$-Arg-Asp-β-Ala-Tyr-Gly-(Arg)$_5$-Gln-(Arg)$_4$-NH$_2$; (SEQ ID NO: 244)

Ac-c(Cys-Glu-His-D-2-Nal-Arg-Bal-Ala-Cys)-(Pro)$_2$-Lys-Asp-β-Ala-Tyr-Gly-(Arg)$_6$-Gln-(Arg)$_3$-NH$_2$; (SEQ ID NO: 245)

Ac-c(Cys-Glu-His-D-2-Nal-Arg-Bal-Ala-Cys)-(Pro)$_2$-Arg-Asp-β-Ala-Tyr-Gly-(Arg)$_6$-Gln-(Arg)$_3$-NH$_2$; (SEQ ID NO: 246)

Ac-Nle-c(Cys-D-Ala-His-D-Phe-Arg-Trp-Cys)-(Doc)$_2$-Tyr-Gly-Arg-(Lys)$_2$-(Arg)$_2$-Gln-(Arg)$_3$-NH$_2$; (SEQ ID NO: 247)

Ac-Nle-c(Cys-D-Ala-His-D-Phe-Arg-Trp-Cys)-β-Ala-Tyr-Gly-Arg-(Lys)$_2$-Arg-Gln-(Arg)$_4$-NH$_2$; (SEQ ID NO: 248)

Ac-Nle-c(Cys-D-Ala-His-D-Phe-Arg-Trp-Cys)-Doc-Tyr-Gly-Arg-(Lys)$_2$-(Arg)$_2$-Gln-(Arg)$_3$-NH$_2$; (SEQ ID NO: 249)

Ac-Nle-c(Cys-D-Ala-His-D-Phe-Arg-Trp-Cys)-β-Ala-(Arg)$_5$-Gln-(Arg)$_3$-NH$_2$; (SEQ ID NO: 250)

Ac-Nle-c(Cys-D-Ala-His-D-Phe-Arg-Trp-Cys)-β-Ala-Gly-(Arg)$_5$-Gln-(Arg)$_3$-NH$_2$; (SEQ ID NO: 251)

Ac-Nle-c(Cys-D-Ala-His-D-Phe-Arg-Trp-Cys)-β-Ala-Tyr-Gly-(Arg)$_5$-Gln-(Arg)$_3$-NH$_2$; (SEQ ID NO: 252)

Ac-Nle-c(Cys-D-Ala-His-D-Phe-Arg-Trp-Cys)-β-Ala-Gly-(Arg)$_5$-Gln-(Arg)$_4$-NH$_2$; (SEQ ID NO: 253)

Ac-Nle-c(Cys-D-Ala-His-D-Phe-Arg-Trp-Cys)-β-Ala-Tyr-Gly-(Arg)$_2$-Lys-(Arg)$_2$-Gln-(Arg)$_3$-NH$_2$; (SEQ ID NO: 254)

Ac-Nle-c(Cys-D-Ala-His-D-Phe-Arg-Trp-Cys)-β-Ala-Tyr-Gly-Arg-Lys-(Arg)$_3$-Gln-(Arg)$_3$-NH$_2$; (SEQ ID NO: 255)

Ac-Nle-c(Cys-D-Ala-His-D-Phe-Arg-Trp-Cys)-β-Ala-Gly-(Arg)$_2$-Lys-(Arg)$_2$-Gln-(Arg)$_3$-NH$_2$; (SEQ ID NO: 256)

```
                                                                 (SEQ ID NO: 257)
Ac-Nle-c(Cys-D-Ala-His-D-Phe-Arg-Trp-Cys)-β-Ala-Gly-Arg-Lys-(Arg)₃-Gln-(Arg)₃-NH₂;

(SEQ ID NO: 258)
Ac-Nle-c(Cys-D-Ala-His-D-Phe-Arg-Trp-Cys)-β-Ala-(Arg)₂-Lys-(Arg)₂-Gln-(Arg)₃-NH₂;

(SEQ ID NO: 259)
Ac-Nle-c(Cys-D-Ala-His-D-Phe-Arg-Trp-Cys)-β-Ala-Arg-Lys-(Arg)₃-Gln-(Arg)₃-NH₂;

(SEQ ID NO: 260)
Ac-Nle-c(Cys-D-Ala-His-D-Phe-Arg-Trp-Cys)-(β-Ala)₂-(Arg)₅-Gln-(Arg)₃-NH₂;

(SEQ ID NO: 261)
Ac-Nle-c(Cys-D-Ala-His-D-Phe-Arg-Trp-Cys)-(β-Ala)₂-Gly-(Arg)₅-Gln-(Arg)₃-NH₂;

(SEQ ID NO: 262)
Ac-Nle-c(Cys-D-Ala-His-D-Phe-Arg-Trp-Cys)-(β-Ala)₂-Tyr-Gly-(Arg)₅-Gln-(Arg)₃-NH₂;

(SEQ ID NO: 263)
Ac-Nle-c(Cys-D-Ala-His-D-Phe-Arg-Trp-Cys)-Doc-(Arg)₅-Gln-(Arg)₃-NH₂;

(SEQ ID NO: 264)
Ac-Nle-c(Cys-D-Ala-His-D-Phe-Arg-Trp-Cys)-Doc-Gly-(Arg)₅-Gln-(Arg)₃-NH₂;

(SEQ ID NO: 265)
Ac-Nle-c(Cys-D-Ala-His-D-Phe-Arg-Trp-Cys)-Doc-Tyr-Gly-(Arg)₅-Gln-(Arg)₃-NH₂;

(SEQ ID NO: 266)
Ac-Nle-c(Cys-D-Ala-His-D-Phe-Arg-Trp-Cys)-(Doc)₂-(Arg)₅-Gln-(Arg)₃-NH₂;

(SEQ ID NO: 267)
Ac-Nle-c(Cys-D-Ala-His-D-Phe-Arg-Trp-Cys)-(Doc)₂-Gly-(Arg)₅-Gln-(Arg)₃-NH₂;

(SEQ ID NO: 268)
Ac-Nle-c(Cys-D-Ala-His-D-Phe-Arg-Trp-Cys)-(Doc)₂-Tyr-Gly-(Arg)₅-Gln-(Arg)₃-NH₂;

(SEQ ID NO: 269)
Ac-Nle-c(Cys-D-Ala-His-D-Phe-Arg-Trp-Cys)-β-Ala-(Arg)₅-Gln-(Arg)₄-NH₂;

(SEQ ID NO: 270)
Ac-Nle-c(Cys-D-Ala-His-D-Phe-Arg-Trp-Cys)-β-Ala-Tyr-Gly-(Arg)₅-Gln-(Arg)₄-NH₂;

(SEQ ID NO: 271)
Ac-Nle-c(Cys-D-Ala-His-D-Phe-Arg-Trp-Cys)-(β-Ala)₂-(Arg)₅-Gln-(Arg)₄-NH₂;

(SEQ ID NO: 272)
Ac-Nle-c(Cys-D-Ala-His-D-Phe-Arg-Trp-Cys)-(β-Ala)₂-Gly-(Arg)₅-Gln-(Arg)₄-NH₂;

(SEQ ID NO: 273)
Ac-Nle-c(Cys-D-Ala-His-D-Phe-Arg-Trp-Cys)-(β-Ala)₂-Tyr-Gly-(Arg)₅-Gln-(Arg)₄-NH₂;

(SEQ ID NO: 274)
Ac-Nle-c(Cys-D-Ala-His-D-Phe-Arg-Trp-Cys)-Doc-(Arg)₅-Gln-(Arg)₄-NH₂;

(SEQ ID NO: 275)
Ac-Nle-c(Cys-D-Ala-His-D-Phe-Arg-Trp-Cys)-Doc-Gly-(Arg)₅-Gln-(Arg)₄-NH₂;

(SEQ ID NO: 276)
Ac-Nle-c(Cys-D-Ala-His-D-Phe-Arg-Trp-Cys)-Doc-Tyr-Gly-(Arg)₅-Gln-(Arg)₄-NH₂;

(SEQ ID NO: 277)
Ac-Nle-c(Cys-D-Ala-His-D-Phe-Arg-Trp-Cys)-(Doc)₂-(Arg)₅-Gln-(Arg)₄-NH₂;

(SEQ ID NO: 278)
Ac-Nle-c(Cys-D-Ala-His-D-Phe-Arg-Trp-Cys)-(Doc)₂-Gly-(Arg)₅-Gln-(Arg)₄-NH₂;

(SEQ ID NO: 279)
Ac-Nle-c(Cys-D-Ala-His-D-Phe-Arg-Trp-Cys)-(Doc)₂-Tyr-Gly-(Arg)₅-Gln-(Arg)₄-NH₂;

(SEQ ID NO: 280)
Ac-Nle-c(Cys-His-D-Phe-Arg-Trp-Gaba-Cys)-β-Ala-Tyr-Gly-(Arg)₅-Gln-(Arg)₃-NH₂;

(SEQ ID NO: 281)
Ac-Nle-c(Cys-His-D-Phe-Arg-Trp-Gaba-Cys)-β-Ala-(Arg)₅-Gln-(Arg)₃-NH₂;

(SEQ ID NO: 282)
Ac-Nle-c(Asp-His-D-Phe-Arg-Trp-Ala-Lys)-β-Ala-Tyr-Gly-(Arg)₅-Gln-(Arg)₃-NH₂;

(SEQ ID NO: 283)
Ac-Nle-c(Asp-His-D-Phe-Arg-Trp-Ala-Lys)-β-Ala-(Arg)₅-Gln-(Arg)₃-NH₂;
```

Ac-Nle-c(Asp-His-D-Phe-Arg-Trp-Lys)-β-Ala-Tyr-Gly-(Arg)$_5$-Gln-(Arg)$_3$-NH$_2$; (SEQ ID NO: 284)

Ac-Nle-c(Asp-His-D-Phe-Arg-Trp-Lys)-β-Ala-Gly-(Arg)$_5$-Gln-(Arg)$_3$-NH$_2$; (SEQ ID NO: 285)

Ac-Nle-c(Asp-His-D-Phe-Arg-Trp-Lys)-β-Ala-(Arg)$_5$-Gln-(Arg)$_3$-NH$_2$; (SEQ ID NO: 286)

Ac-Nle-c(Asp-His-D-Phe-Arg-Trp-Lys)-(β-Ala)$_2$-Tyr-Gly-(Arg)$_5$-Gln-(Arg)$_3$-NH$_2$; (SEQ ID NO: 287)

Ac-Nle-c(Asp-His-D-Phe-Arg-Trp-Lys)-(β-Ala)$_2$-Gly-(Arg)$_5$-Gln-(Arg)$_3$-NH$_2$; (SEQ ID NO: 288)

Ac-Nle-c(Asp-His-D-Phe-Arg-Trp-Lys)-(β-Ala)$_2$-(Arg)$_5$-Gln-(Arg)$_3$-NH$_2$; (SEQ ID NO: 289)

Ac-Nle-c(Asp-His-D-Phe-Arg-Trp-Lys)-Doc-Tyr-Gly-(Arg)$_5$-Gln-(Arg)$_3$-NH$_2$; (SEQ ID NO: 290)

Ac-Nle-c(Asp-His-D-Phe-Arg-Trp-Lys)-Doc-Gly-(Arg)$_5$-Gln-(Arg)$_3$-NH$_2$; (SEQ ID NO: 291)

Ac-Nle-c(Asp-His-D-Phe-Arg-Trp-Lys)-Doc-(Arg)$_5$-Gln-(Arg)$_3$-NH$_2$; (SEQ ID NO: 292)

Ac-Nle-c(Asp-His-D-Phe-Arg-Trp-Lys)-(Doc)$_2$-Tyr-Gly-(Arg)$_5$-Gln-(Arg)$_3$-NH$_2$; (SEQ ID NO: 293)

Ac-Nle-c(Asp-His-D-Phe-Arg-Trp-Lys)-(Doc)$_2$-Gly-(Arg)$_5$-Gln-(Arg)$_3$-NH$_2$; (SEQ ID NO: 294)

Ac-Nle-c(Asp-His-D-Phe-Arg-Trp-Lys)-(Doc)$_2$-(Arg)$_5$-Gln-(Arg)$_3$-NH$_2$; (SEQ ID NO: 295)

Ac-Nle-c(Asp-His-D-Phe-Arg-Trp-Lys)-β-Ala-Tyr-Gly-(Arg)$_5$-Gln-(Arg)$_4$-NH$_2$; (SEQ ID NO: 296)

Ac-Nle-c(Asp-His-D-Phe-Arg-Trp-Lys)-β-Ala-Gly-(Arg)$_5$-Gln-(Arg)$_4$-NH$_2$; (SEQ ID NO: 297)

Ac-Nle-c(Asp-His-D-Phe-Arg-Trp-Lys)-β-Ala-(Arg)$_5$-Gln-(Arg)$_4$-NH$_2$; (SEQ ID NO: 298)

Ac-Nle-c(Asp-His-D-Phe-Arg-Trp-Lys)-(β-Ala)$_2$-Tyr-Gly-(Arg)$_5$-Gln-(Arg)$_4$-NH$_2$; (SEQ ID NO: 299)

Ac-Nle-c(Asp-His-D-Phe-Arg-Trp-Lys)-(β-Ala)$_2$-Gly-(Arg)$_5$-Gln-(Arg)$_4$-NH$_2$; (SEQ ID NO: 300)

Ac-Nle-c(Asp-His-D-Phe-Arg-Trp-Lys)-(β-Ala)$_2$-(Arg)$_5$-Gln-(Arg)$_4$-NH$_2$; (SEQ ID NO: 301)

Ac-Nle-c(Asp-His-D-Phe-Arg-Trp-Lys)-Doc-Tyr-Gly-(Arg)$_5$-Gln-(Arg)$_4$-NH$_2$; (SEQ ID NO: 302)

Ac-Nle-c(Asp-His-D-Phe-Arg-Trp-Lys)-Doc-Gly-(Arg)$_5$-Gln-(Arg)$_4$-NH$_2$; (SEQ ID NO: 303)

Ac-Nle-c(Asp-His-D-Phe-Arg-Trp-Lys)-Doc-(Arg)$_5$-Gln-(Arg)$_4$-NH$_2$; (SEQ ID NO: 304)

Ac-Nle-c(Asp-His-D-Phe-Arg-Trp-Lys)-(Doc)$_2$-Tyr-Gly-(Arg)$_5$-Gln-(Arg)$_4$-NH$_2$; (SEQ ID NO: 305)

Ac-Nle-c(Asp-His-D-Phe-Arg-Trp-Lys)-(Doc)$_2$-Gly-(Arg)$_5$-Gln-(Arg)$_4$-NH$_2$; (SEQ ID NO: 306)

Ac-Nle-c(Asp-His-D-Phe-Arg-Trp-Lys)-(Doc)$_2$-(Arg)$_5$-Gln-(Arg)$_4$-NH$_2$; (SEQ ID NO: 307)

Ac-Nle-c(Asp-His-D-Phe-Arg-Trp-β-Ala-Lys)-β-Ala-Tyr-Gly-(Arg)$_5$-Gln-(Arg)$_3$-NH$_2$; (SEQ ID NO: 308)

Ac-Nle-c(Asp-His-D-Phe-Arg-Trp-β-Ala-Lys)-β-Ala-(Arg)$_5$-Gln-(Arg)$_3$-NH$_2$; (SEQ ID NO: 309)

Ac-Nle-c(Cys-His-D-Phe-Arg-Trp-Ahx-Cys)-β-Ala-Tyr-Gly-(Arg)$_5$-Gln-(Arg)$_3$-NH$_2$; (SEQ ID NO: 310)

-continued

```
                                                          (SEQ ID NO: 311)
Ac-Nle-c(Cys-His-D-Phe-Arg-Trp-Ahx-Cys)-β-Ala-(Arg)5-Gln-(Arg)3-NH2;

(SEQ ID NO: 312)
D-Phe-c(Cys-His-D-Phe-Arg-Trp-β-Ala-D-Cys)-Thr-β-Ala-Tyr-Gly-(Arg)5-Gln-(Arg)3-
NH2;

(SEQ ID NO: 313)
D-Phe-c(Cys-His-D-Phe-Arg-Trp-β-Ala-D-Cys)-Thr-β-Ala-(Arg)5-Gln-(Arg)3-NH2;

(SEQ ID NO: 314)
Ac-Nle-c(Cys-His-D-Phe-Arg-Trp-Apn-Cys)-β-Ala-Tyr-Gly-(Arg)5-Gln-(Arg)3-NH2;

(SEQ ID NO: 315)
Ac-Nle-c(Cys-His-D-Phe-Arg-Trp-Apn-Cys)-β-Ala-(Arg)5-Gln-(Arg)3-NH2;

(SEQ ID NO: 316)
Ac-Cha-c(Asp-His-D-Phe-Arg-Trp-Gaba-Lys)-β-Ala-Tyr-Gly-(Arg)5-Gln-(Arg)3-NH2;

(SEQ ID NO: 317)
Ac-Cha-c(Asp-His-D-Phe-Arg-Trp-Gaba-Lys)-β-Ala-(Arg)5-Gln-(Arg)3-NH2;

(SEQ ID NO: 318)
Ac-Nle-c(Asp-His-D-Phe-Arg-Trp-Gaba-Lys)-β-Ala-Tyr-Gly-(Arg)5-Gln-(Arg)3-NH2;

(SEQ ID NO: 319)
Ac-Nle-c(Asp-His-D-Phe-Arg-Trp-Gaba-Lys)-β-Ala-(Arg)5-Gln-(Arg)3-NH2;

(SEQ ID NO: 320)
Ac-Chg-c(Asp-His-D-Phe-Arg-Trp-Gaba-Lys)-β-Ala-Tyr-Gly-(Arg)5-Gln-(Arg)3-NH2;

(SEQ ID NO: 321)
Ac-Chg-c(Asp-His-D-Phe-Arg-Trp-Gaba-Lys)-β-Ala-(Arg)5-Gln-(Arg)3-NH2;

(SEQ ID NO: 322)
Ac-hCha-c(Asp-His-D-Phe-Arg-Trp-Gaba-Lys)-β-Ala-Tyr-Gly-(Arg)5-Gln-(Arg)3-NH2;

(SEQ ID NO: 323)
Ac-hCha-c(Asp-His-D-Phe-Arg-Trp-Gaba-Lys)-β-Ala-(Arg)5-Gln-(Arg)3-NH2;

(SEQ ID NO: 324)
Ac-hCha-c(Asp-His-D-Phe-Arg-Trp-Gaba-Lys)-(β-Ala)2-Tyr-Gly-(Arg)5-Gln-(Arg)3-
NH2;

(SEQ ID NO: 325)
Ac-hCha-c(Asp-His-D-Phe-Arg-Trp-Gaba-Lys)-(β-Ala)2-(Arg)5-Gln-(Arg)3-NH2;

(SEQ ID NO: 326)
Ac-hCha-c(Asp-His-D-Phe-Arg-Trp-Gaba-Lys)-Doc-Tyr-Gly-(Arg)5-Gln-(Arg)3-NH2;

(SEQ ID NO: 327)
Ac-hCha-c(Asp-His-D-Phe-Arg-Trp-Gaba-Lys)-Doc-(Arg)5-Gln-(Arg)3-NH2;

(SEQ ID NO: 328)
Ac-hCha-c(Asp-His-D-Phe-Arg-Trp-Gaba-Lys)-(Doc)2-Tyr-Gly-(Arg)5-Gln-(Arg)3-NH2;

(SEQ ID NO: 329)
Ac-hCha-c(Asp-His-D-Phe-Arg-Trp-Gaba-Lys)-(Doc)2-(Arg)5-Gln-(Arg)3-NH2;

(SEQ ID NO: 330)
Ac-hCha-c(Asp-His-D-Phe-Arg-Trp-Gaba-Lys)-β-Ala-Tyr-Gly-(Arg)5-Gln-(Arg)4-NH2;

(SEQ ID NO: 331)
Ac-hCha-c(Asp-His-D-Phe-Arg-Trp-Gaba-Lys)-β-Ala-(Arg)5-Gln-(Arg)4-NH2;

(SEQ ID NO: 332)
Ac-hCha-c(Asp-His-D-Phe-Arg-Trp-Gaba-Lys)-(β-Ala)2-Tyr-Gly-(Arg)5-Gln-(Arg)4-NH2;

(SEQ ID NO: 333)
Ac-hCha-c(Asp-His-D-Phe-Arg-Trp-Gaba-Lys)-(β-Ala)2-(Arg)5-Gln-(Arg)4-NH2;

(SEQ ID NO: 334)
Ac-hCha-c(Asp-His-D-Phe-Arg-Trp-Gaba-Lys)-Doc-Tyr-Gly-(Arg)5-Gln-(Arg)4-NH2;

(SEQ ID NO: 335)
Ac-hCha-c(Asp-His-D-Phe-Arg-Trp-Gaba-Lys)-Doc-(Arg)5-Gln-(Arg)4-NH2;

(SEQ ID NO: 336)
```

-continued

Ac-hCha-c(Asp-His-D-Phe-Arg-Trp-Gaba-Lys)-(Doc)$_2$-Tyr-Gly-(Arg)$_5$-Gln-(Arg)$_4$-NH$_2$;

(SEQ ID NO: 337)
Ac-hCha-c(Asp-His-D-Phe-Arg-Trp-Gaba-Lys)-(Doc)$_2$-(Arg)$_5$-Gln-(Arg)$_4$-NH$_2$;

(SEQ ID NO: 338)
Ac-D-Chg-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 339)
Ac-D-Chg-c(Asp-His-D-Phe-Arg-Trp-Gaba-Lys)-β-Ala-(Arg)$_5$-Gln-(Arg)$_3$-NH$_2$;

(SEQ ID NO: 340)
Ac-hPhe-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 341)
Ac-hPhe-c(Asp-His-D-Phe-Arg-Trp-Gaba-Lys)-β-Ala-(Arg)$_5$-Gln-(Arg)$_3$-NH$_2$;

(SEQ ID NO: 342)
Ac-Nle-c(Cys-His-D-Phe-Arg-D-Trp-Apn-Cys)-β-Ala-Tyr-Gly-(Arg)$_5$-Gln-(Arg)$_3$-NH$_2$;

(SEQ ID NO: 343)
Ac-Nle-c(Cys-His-D-Phe-Arg-D-Trp-Apn-Cys)-β-Ala-(Arg)$_5$-Gln-(Arg)$_3$-NH$_2$;

(SEQ ID NO: 344)
Ac-Nle-c(Cys-His-D-Phe-Arg-D-Trp-Ahx-Cys)-β-Ala-Tyr-Gly-(Arg)$_5$-Gln-(Arg)$_3$-NH$_2$;

(SEQ ID NO: 345)
Ac-Nle-c(Cys-His-D-Phe-Arg-D-Trp-Ahx-Cys)-β-Ala-(Arg)$_5$-Gln-(Arg)$_3$-NH$_2$;

(SEQ ID NO: 346)
Ac-Nle-c(Cys-His-D-Phe-Arg-D-Trp-β-Ala-Cys)-β-Ala-Tyr-Gly-(Arg)$_5$-Gln-(Arg)$_3$-NH$_2$;

(SEQ ID NO: 347)
Ac-Nle-c(Cys-His-D-Phe-Arg-D-Trp-β-Ala-Cys)-β-Ala-(Arg)$_5$-Gln-(Arg)$_3$-NH$_2$;

(SEQ ID NO: 348)
Ac-Nle-c(Cys-D-Ala-His-D-Phe-Arg-Trp-Pen)-β-Ala-Tyr-Gly-(Arg)$_5$-Gln-(Arg)$_3$-NH$_2$;

(SEQ ID NO: 349)
Ac-Nle-c(Cys-D-Ala-His-D-Phe-Arg-Trp-Pen)-β-Ala-Gly-(Arg)$_5$-Gln-(Arg)$_3$-NH$_2$;

(SEQ ID NO: 350)
Ac-Nle-c(Cys-D-Ala-His-D-Phe-Arg-Trp-Pen)-β-Ala-(Arg)$_5$-Gln-(Arg)$_3$-NH$_2$;

(SEQ ID NO: 351)
Ac-Nle-c(Cys-D-Ala-His-D-Phe-Arg-Trp-Pen)-(β-Ala)$_2$-Tyr-Gly-(Arg)$_5$-Gln-(Arg)$_3$-NH$_2$;

(SEQ ID NO: 352)
Ac-Nle-c(Cys-D-Ala-His-D-Phe-Arg-Trp-Pen)-(β-Ala)$_2$-Gly-(Arg)$_5$-Gln-(Arg)$_3$-NH$_2$;

(SEQ ID NO: 353)
Ac-Nle-c(Cys-D-Ala-His-D-Phe-Arg-Trp-Pen)-(β-Ala)$_2$-(Arg)$_5$-Gln-(Arg)$_3$-NH$_2$;

(SEQ ID NO: 354)
Ac-Nle-c(Cys-D-Ala-His-D-Phe-Arg-Trp-Pen)-Doc-Tyr-Gly-(Arg)$_5$-Gln-(Arg)$_3$-NH$_2$;

(SEQ ID NO: 355)
Ac-Nle-c(Cys-D-Ala-His-D-Phe-Arg-Trp-Pen)-Doc-Gly-(Arg)$_5$-Gln-(Arg)$_3$-NH$_2$;

(SEQ ID NO: 356)
Ac-Nle-c(Cys-D-Ala-His-D-Phe-Arg-Trp-Pen)-Doc-(Arg)$_5$-Gln-(Arg)$_3$-NH$_2$;

(SEQ ID NO: 357)
Ac-Nle-c(Cys-D-Ala-His-D-Phe-Arg-Trp-Pen)-(Doc)$_2$-Tyr-Gly-(Arg)$_5$-Gln-(Arg)$_3$-NH$_2$;

(SEQ ID NO: 358)
Ac-Nle-c(Cys-D-Ala-His-D-Phe-Arg-Trp-Pen)-(Doc)$_2$-Gly-(Arg)$_5$-Gln-(Arg)$_3$-NH$_2$;

(SEQ ID NO: 359)
Ac-Nle-c(Cys-D-Ala-His-D-Phe-Arg-Trp-Pen)-(Doc)$_2$-(Arg)$_5$-Gln-(Arg)$_3$-NH$_2$;

(SEQ ID NO: 360)
D-Phe-c(Cys-His-D-(Et)Tyr-Arg-Trp-β-Ala-D-Cys)-β-Ala-Tyr-Gly-(Arg)$_5$-Gln-(Arg)$_3$-NH$_2$;

(SEQ ID NO: 361)
D-Phe-c(Cys-His-D-(Et)Tyr-Arg-Trp-β-Ala-D-Cys)-β-Ala-(Arg)$_5$-Gln-(Arg)$_3$-NH$_2$;

(SEQ ID NO: 362)
D-Phe-c(Cys-His-D-(Et)Tyr-Arg-Trp-β-Ala-D-Cys)-β-Ala-Gly-(Arg)$_5$-Gln-(Arg)$_3$-NH$_2$;

```
                                                                  (SEQ ID NO: 363)
D-Phe-c(Cys-His-D-(Et)Tyr-Arg-Trp-β-Ala-D-Cys)-β-Ala-(Arg)₅-Gln-(Arg)₄-NH₂;

(SEQ ID NO: 364)
D-Phe-c(Cys-His-D-(Et)Tyr-Arg-Trp-β-Ala-D-Cys)-(β-Ala)₂-Tyr-Gly-(Arg)₅-Gln-(Arg)₃-
NH₂;

(SEQ ID NO: 365)
D-Phe-c(Cys-His-D-(Et)Tyr-Arg-Trp-β-Ala-D-Cys)-(β-Ala)₂-(Arg)₅-Gln-(Arg)₃-NH₂;

(SEQ ID NO: 366)
D-Phe-c(Cys-His-D-(Et)Tyr-Arg-Trp-β-Ala-D-Cys)-(β-Ala)₂-Gly-(Arg)₅-Gln-(Arg)₃-NH₂;

(SEQ ID NO: 367)
D-Phe-c(Cys-His-D-(Et)Tyr-Arg-Trp-β-Ala-D-Cys)-(β-Ala)₂-(Arg)₅-Gln-(Arg)₄-NH₂;

(SEQ ID NO: 368)
D-Phe-c(Cys-His-D-(Et)Tyr-Arg-Trp-β-Ala-D-Cys)-Doc-Tyr-Gly-(Arg)₅-Gln-(Arg)₃-NH₂;

(SEQ ID NO: 369)
D-Phe-c(Cys-His-D-(Et)Tyr-Arg-Trp-β-Ala-D-Cys)-Doc-(Arg)₅-Gln-(Arg)₃-NH₂;

(SEQ ID NO: 370)
D-Phe-c(Cys-His-D-(Et)Tyr-Arg-Trp-β-Ala-D-Cys)-Doc-Gly-(Arg)₅-Gln-(Arg)₃-NH₂;

(SEQ ID NO: 371)
D-Phe-c(Cys-His-D-(Et)Tyr-Arg-Trp-β-Ala-D-Cys)-Doc-(Arg)₅-Gln-(Arg)₄-NH₂;

(SEQ ID NO: 372)
D-Phe-c(Cys-His-D-(Et)Tyr-Arg-Trp-β-Ala-D-Cys)-(Doc)₂-Tyr-Gly-(Arg)₅-Gln-(Arg)₃-
NH₂;

(SEQ ID NO: 373)
D-Phe-c(Cys-His-D-(Et)Tyr-Arg-Trp-β-Ala-D-Cys)-(Doc)₂-(Arg)₅-Gln-(Arg)₃-NH₂;

(SEQ ID NO: 374)
D-Phe-c(Cys-His-D-(Et)Tyr-Arg-Trp-β-Ala-D-Cys)-(Doc)₂-Gly-(Arg)₅-Gln-(Arg)₃-NH₂;

(SEQ ID NO: 375)
D-Phe-c(Cys-His-D-(Et)Tyr-Arg-Trp-β-Ala-D-Cys)-(Doc)₂-(Arg)₅-Gln-(Arg)₄-NH₂;

(SEQ ID NO: 376)
D-Phe-c(Cys-His-D-(Et)Tyr-hArg-Trp-β-Ala-D-Cys)-Thr-β-Ala-Tyr-Gly-(Arg)₅-Gln-
(Arg)₃-NH₂;

(SEQ ID NO: 377)
D-Phe-c(Cys-His-D-(Et)Tyr-hArg-Trp-β-Ala-D-Cys)-Thr-β-Ala-(Arg)₅-Gln-(Arg)₃-NH₂;

(SEQ ID NO: 378)
D-Phe-c(Cys-His-D-(Et)Tyr-hArg-Trp-β-Ala-D-Cys)-Thr-(β-Ala)₂-Tyr-Gly-(Arg)₅-Gln-
(Arg)₃-NH₂;

(SEQ ID NO: 379)
D-Phe-c(Cys-His-D-(Et)Tyr-hArg-Trp-β-Ala-D-Cys)-Thr-(β-Ala)₂-(Arg)₅-Gln-(Arg)₃-NH₂;

(SEQ ID NO: 380)
D-Phe-c(Cys-His-D-(Et)Tyr-hArg-Trp-β-Ala-D-Cys)-Thr-Doc-Tyr-Gly-(Arg)₅-Gln-(Arg)₃-
NH₂;

(SEQ ID NO: 381)
D-Phe-c(Cys-His-D-(Et)Tyr-hArg-Trp-β-Ala-D-Cys)-Thr-Doc-(Arg)₅-Gln-(Arg)₃-NH₂;

(SEQ ID NO: 382)
D-Phe-c(Cys-His-D-(Et)Tyr-hArg-Trp-β-Ala-D-Cys)-Thr-(Doc)₂-Tyr-Gly-(Arg)₅-Gln-
(Arg)₃-NH₂;

(SEQ ID NO: 383)
D-Phe-c(Cys-His-D-(Et)Tyr-hArg-Trp-β-Ala-D-Cys)-Thr-β-Ala-Tyr-Gly-(Arg)₅-Gln-(Arg)₄-
NH₂;

(SEQ ID NO: 384)
D-Phe-c(Cys-His-D-(Et)Tyr-hArg-Trp-β-Ala-D-Cys)-Thr-β-Ala-(Arg)₅-Gln-(Arg)₄-NH₂;
```

-continued (SEQ ID NO: 385)
D-Phe-c(Cys-His-D-(Et)Tyr-hArg-Trp-β-Ala-D-Cys)-Thr-(β-Ala)$_2$-Tyr-Gly-(Arg)$_5$-Gln-(Arg)$_4$-NH$_2$;

(SEQ ID NO: 386)
D-Phe-c(Cys-His-D-(Et)Tyr-hArg-Trp-β-Ala-D-Cys)-Thr-(β-Ala)$_2$-(Arg)$_5$-Gln-(Arg)$_4$-NH$_2$;

(SEQ ID NO: 387)
D-Phe-c(Cys-His-D-(Et)Tyr-hArg-Trp-β-Ala-D-Cys)-Thr-Doc-Tyr-Gly-(Arg)$_5$-Gln-(Arg)$_4$-NH$_2$;

(SEQ ID NO: 388)
D-Phe-c(Cys-His-D-(Et)Tyr-hArg-Trp-β-Ala-D-Cys)-Thr-Doc-(Arg)$_5$-Gln-(Arg)$_4$-NH$_2$;

(SEQ ID NO: 389)
D-Phe-c(Cys-His-D-(Et)Tyr-hArg-Trp-β-Ala-D-Cys)-Thr-(Doc)$_2$-Tyr-Gly-(Arg)$_5$-Gln-(Arg)$_4$-NH$_2$;

(SEQ ID NO: 390)
D-Phe-c(Cys-His-D-(Et)Tyr-hArg-Trp-β-Ala-D-Cys)-Thr-(Doc)$_2$-(Arg)$_5$-Gln-(Arg)$_4$-NH$_2$;

(SEQ ID NO: 391)
D-Phe-c(Cys-His-D-(Et)Tyr-hArg-Bip-β-Ala-D-Cys)-Thr-β-Ala-Tyr-Gly-(Arg)$_5$-Gln-(Arg)$_3$-NH$_2$;

(SEQ ID NO: 392)
D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$;

(SEQ ID NO: 393)
D-Phe-c(Cys-His-D-(Et)Tyr-hArg-Bip-β-Ala-D-Cys)-Thr-β-Ala-(Arg)$_5$-Gln-(Arg)$_3$-NH$_2$;

(SEQ ID NO: 394)
D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$;

(SEQ ID NO: 395)
D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$;

(SEQ ID NO: 396)
D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$;

(SEQ ID NO: 397)
D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$;

(SEQ ID NO: 398)
D-Phe-c(Cys-His-D-(Et)Tyr-hArg-Bip-β-Ala-D-Cys)-Thr-Doc-(Arg)$_5$-Gln-(Arg)$_3$-NH$_2$;

(SEQ ID NO: 399)
D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$;

(SEQ ID NO: 400)
D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$;

(SEQ ID NO: 401)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 402)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 403)
Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 404)
Nle-c(Cys-His-D-Phe-Arg-Trp-Apn-Cys)-β-Ala-(Arg)$_5$-Gln-(Arg)$_3$-NH$_2$;

(SEQ ID NO: 405)
Nle-c(Cys-His-D-Phe-Arg-Trp-Apn-Cys)-(β-Ala)$_2$-Tyr-Gly-(Arg)$_5$-Gln-(Arg)$_3$-NH$_2$;

-continued

Nle-c(Cys-His-D-Phe-Arg-Trp-Apn-Cys)-(β-Ala)$_2$-(Arg)$_5$-Gln-(Arg)$_3$-NH$_2$; (SEQ ID NO: 406)

Nle-c(Cys-His-D-Phe-Arg-Trp-Apn-Cys)-β-Ala-Tyr-Gly-(Arg)$_5$-Gln-(Arg)$_4$-NH$_2$; (SEQ ID NO: 407)

Nle-c(Cys-His-D-Phe-Arg-Trp-Apn-Cys)-β-Ala-(Arg)$_5$-Gln-(Arg)$_4$-NH$_2$; (SEQ ID NO: 408)

Nle-c(Cys-His-D-Phe-Arg-Trp-Apn-Cys)-(β-Ala)$_2$-Tyr-Gly-(Arg)$_5$-Gln-(Arg)$_4$-NH$_2$; (SEQ ID NO: 409)

Nle-c(Cys-His-D-Phe-Arg-Trp-Apn-Cys)-(β-Ala)$_2$-(Arg)$_5$-Gln-(Arg)$_4$-NH$_2$; (SEQ ID NO: 410)

Nle-c(Cys-His-D-Phe-Arg-Trp-Apn-Cys)-Doc-Tyr-Gly-(Arg)$_5$-Gln-(Arg)$_3$-NH$_2$; (SEQ ID NO: 411)

Nle-c(Cys-His-D-Phe-Arg-Trp-Apn-Cys)-Doc-(Arg)$_5$-Gln-(Arg)$_3$-NH$_2$; (SEQ ID NO: 412)

Nle-c(Cys-His-D-Phe-Arg-Trp-Apn-Cys)-(Doc)$_2$-Tyr-Gly-(Arg)$_5$-Gln-(Arg)$_3$-NH$_2$; (SEQ ID NO: 413)

Nle-c(Cys-His-D-Phe-Arg-Trp-Apn-Cys)-(Doc)$_2$-(Arg)$_5$-Gln-(Arg)$_3$-NH$_2$; (SEQ ID NO: 414)

Nle-c(Cys-His-D-Phe-Arg-Trp-Apn-Cys)-Doc-Tyr-Gly-(Arg)$_5$-Gln-(Arg)$_4$-NH$_2$; (SEQ ID NO: 415)

Nle-c(Cys-His-D-Phe-Arg-Trp-Apn-Cys)-Doc-(Arg)$_5$-Gln-(Arg)$_4$-NH$_2$; (SEQ ID NO: 416)

Nle-c(Cys-His-D-Phe-Arg-Trp-Apn-Cys)-(Doc)$_2$-Tyr-Gly-(Arg)$_5$-Gln-(Arg)$_4$-NH$_2$; (SEQ ID NO: 417)

Nle-c(Cys-His-D-Phe-Arg-Trp-Apn-Cys)-(Doc)$_2$-(Arg)$_5$-Gln-(Arg)$_4$-NH$_2$; (SEQ ID NO: 418)

Ac-Nle-c(Cys-D-Leu-His-D-Phe-Arg-Trp-Cys)-β-Ala-Tyr-Gly-(Arg)$_5$-Gln-(Arg)$_3$-NH$_2$; (SEQ ID NO: 419)

Ac-Nle-c(Cys-D-Leu-His-D-Phe-Arg-Trp-Cys)-β-Ala-(Arg)$_5$-Gln-(Arg)$_3$-NH$_2$; (SEQ ID NO: 420)

Ac-Nle-c(Cys-D-Leu-His-D-Phe-Arg-Trp-Cys)-(β-Ala)$_2$-Tyr-Gly-(Arg)$_5$-Gln-(Arg)$_3$-NH$_2$; (SEQ ID NO: 421)

Ac-Nle-c(Cys-D-Leu-His-D-Phe-Arg-Trp-Cys)-(β-Ala)$_2$-(Arg)$_5$-Gln-(Arg)$_3$-NH$_2$; (SEQ ID NO: 422)

Ac-Nle-c(Cys-D-Leu-His-D-Phe-Arg-Trp-Cys)-Doc-Tyr-Gly-(Arg)$_5$-Gln-(Arg)$_3$-NH$_2$; (SEQ ID NO: 423)

Ac-Nle-c(Cys-D-Leu-His-D-Phe-Arg-Trp-Cys)-Doc-(Arg)$_5$-Gln-(Arg)$_3$-NH$_2$; (SEQ ID NO: 424)

Ac-Nle-c(Cys-D-Leu-His-D-Phe-Arg-Trp-Cys)-(Doc)$_2$-Tyr-Gly-(Arg)$_5$-Gln-(Arg)$_3$-NH$_2$; (SEQ ID NO: 425)

Ac-Nle-c(Cys-D-Leu-His-D-Phe-Arg-Trp-Cys)-(Doc)$_2$-(Arg)$_5$-Gln-(Arg)$_3$-NH$_2$; (SEQ ID NO: 426)

Ac-Nle-c(Cys-D-Leu-His-D-Phe-Arg-Trp-Cys)-β-Ala-Tyr-Gly-(Arg)$_5$-Gln-(Arg)$_4$-NH$_2$; (SEQ ID NO: 427)

Ac-Nle-c(Cys-D-Leu-His-D-Phe-Arg-Trp-Cys)-β-Ala-(Arg)$_5$-Gln-(Arg)$_4$-NH$_2$; (SEQ ID NO: 428)

Ac-Nle-c(Cys-D-Leu-His-D-Phe-Arg-Trp-Cys)-(β-Ala)$_2$-Tyr-Gly-(Arg)$_5$-Gln-(Arg)$_4$-NH$_2$; (SEQ ID NO: 429)

Ac-Nle-c(Cys-D-Leu-His-D-Phe-Arg-Trp-Cys)-(β-Ala)$_2$-(Arg)$_5$-Gln-(Arg)$_4$-NH$_2$; (SEQ ID NO: 430)

Ac-Nle-c(Cys-D-Leu-His-D-Phe-Arg-Trp-Cys)-Doc-Tyr-Gly-(Arg)$_5$-Gln-(Arg)$_4$-NH$_2$; (SEQ ID NO: 431)

Ac-Nle-c(Cys-D-Leu-His-D-Phe-Arg-Trp-Cys)-Doc-(Arg)$_5$-Gln-(Arg)$_4$-NH$_2$; (SEQ ID NO: 432)

-continued

Ac-Nle-c(Cys-D-Leu-His-D-Phe-Arg-Trp-Cys)-(Doc)$_2$-Tyr-Gly-(Arg)$_5$-Gln-(Arg)$_4$-NH$_2$; (SEQ ID NO: 433)

Ac-Nle-c(Cys-D-Leu-His-D-Phe-Arg-Trp-Cys)-(Doc)$_2$-(Arg)$_5$-Gln-(Arg)$_4$-NH$_2$; (SEQ ID NO: 434)

Ac-Nle-c(Cys-D-Cha-His-D-Phe-Arg-Trp-Cys)-β-Ala-Tyr-Gly-(Arg)$_5$-Gln-(Arg)$_3$-NH$_2$; (SEQ ID NO: 435)

Ac-Nle-c(Cys-D-Cha-His-D-Phe-Arg-Trp-Cys)-β-Ala-(Arg)$_5$-Gln-(Arg)$_3$-NH$_2$; (SEQ ID NO: 436)

Ac-Nle-c(Cys-D-Cha-His-D-Phe-Arg-Trp-Cys)-(β-Ala)$_2$-Tyr-Gly-(Arg)$_5$-Gln-(Arg)$_3$-NH$_2$; (SEQ ID NO: 437)

Ac-Nle-c(Cys-D-Cha-His-D-Phe-Arg-Trp-Cys)-(β-Ala)$_2$-(Arg)$_5$-Gln-(Arg)$_3$-NH$_2$; (SEQ ID NO: 438)

Ac-Nle-c(Cys-D-Cha-His-D-Phe-Arg-Trp-Cys)-Doc-Tyr-Gly-(Arg)$_5$-Gln-(Arg)$_3$-NH$_2$; (SEQ ID NO: 439)

Ac-Nle-c(Cys-D-Cha-His-D-Phe-Arg-Trp-Cys)-Doc-(Arg)$_5$-Gln-(Arg)$_3$-NH$_2$; (SEQ ID NO: 440)

Ac-Nle-c(Cys-D-Cha-His-D-Phe-Arg-Trp-Cys)-(Doc)$_2$-Tyr-Gly-(Arg)$_5$-Gln-(Arg)$_3$-NH$_2$; (SEQ ID NO: 441)

Ac-Nle-c(Cys-D-Cha-His-D-Phe-Arg-Trp-Cys)-(Doc)$_2$-(Arg)$_5$-Gln-(Arg)$_3$-NH$_2$; (SEQ ID NO: 442)

Ac-Nle-c(Cys-D-Cha-His-D-Phe-Arg-Trp-Cys)-β-Ala-Tyr-Gly-(Arg)$_5$-Gln-(Arg)$_4$-NH$_2$; (SEQ ID NO: 443)

Ac-Nle-c(Cys-D-Cha-His-D-Phe-Arg-Trp-Cys)-β-Ala-(Arg)$_5$-Gln-(Arg)$_4$-NH$_2$; (SEQ ID NO: 444)

Ac-Nle-c(Cys-D-Cha-His-D-Phe-Arg-Trp-Cys)-(β-Ala)$_2$-Tyr-Gly-(Arg)$_5$-Gln-(Arg)$_4$-NH$_2$; (SEQ ID NO: 445)

Ac-Nle-c(Cys-D-Cha-His-D-Phe-Arg-Trp-Cys)-(β-Ala)$_2$-(Arg)$_5$-Gln-(Arg)$_4$-NH$_2$; (SEQ ID NO: 446)

Ac-Nle-c(Cys-D-Cha-His-D-Phe-Arg-Trp-Cys)-Doc-Tyr-Gly-(Arg)$_5$-Gln-(Arg)$_4$-NH$_2$; (SEQ ID NO: 447)

Ac-Nle-c(Cys-D-Cha-His-D-Phe-Arg-Trp-Cys)-Doc-(Arg)$_5$-Gln-(Arg)$_4$-NH$_2$; (SEQ ID NO: 448)

Ac-Nle-c(Cys-D-Cha-His-D-Phe-Arg-Trp-Cys)-(Doc)$_2$-Tyr-Gly-(Arg)$_5$-Gln-(Arg)$_4$-NH$_2$; (SEQ ID NO: 449)

Ac-Nle-c(Cys-D-Cha-His-D-Phe-Arg-Trp-Cys)-(Doc)$_2$-(Arg)$_5$-Gln-(Arg)$_4$-NH$_2$; (SEQ ID NO: 450)

Nle-c(Cys-His-D-Phe-Arg-Trp-Gaba-Cys)-β-Ala-Tyr-Gly-(Arg)$_5$-Gln-(Arg)$_3$-NH$_2$; (SEQ ID NO: 451)

Nle-c(Cys-His-D-Phe-Arg-Trp-Gaba-Cys)-β-Ala-(Arg)$_5$-Gln-(Arg)$_3$-NH$_2$; (SEQ ID NO: 452)

Nle-c(Cys-His-D-Phe-Arg-Trp-Gaba-Cys)-(β-Ala)$_2$-Tyr-Gly-(Arg)$_5$-Gln-(Arg)$_3$-NH$_2$; (SEQ ID NO: 453)

Nle-c(Cys-His-D-Phe-Arg-Trp-Gaba-Cys)-(β-Ala)$_2$-(Arg)$_5$-Gln-(Arg)$_3$-NH$_2$; (SEQ ID NO: 454)

Nle-c(Cys-His-D-Phe-Arg-Trp-Gaba-Cys)-β-Ala-Tyr-Gly-(Arg)$_5$-Gln-(Arg)$_4$-NH$_2$; (SEQ ID NO: 455)

Nle-c(Cys-His-D-Phe-Arg-Trp-Gaba-Cys)-β-Ala-(Arg)$_5$-Gln-(Arg)$_4$-NH$_2$; (SEQ ID NO: 456)

Nle-c(Cys-His-D-Phe-Arg-Trp-Gaba-Cys)-(β-Ala)$_2$-Tyr-Gly-(Arg)$_5$-Gln-(Arg)$_4$-NH$_2$; (SEQ ID NO: 457)

Nle-c(Cys-His-D-Phe-Arg-Trp-Gaba-Cys)-(β-Ala)$_2$-(Arg)$_5$-Gln-(Arg)$_4$-NH$_2$; (SEQ ID NO: 458)

Nle-c(Cys-His-D-Phe-Arg-Trp-Gaba-Cys)-Doc-Tyr-Gly-(Arg)$_5$-Gln-(Arg)$_3$-NH$_2$; (SEQ ID NO: 459)

-continued

Nle-c(Cys-His-D-Phe-Arg-Trp-Gaba-Cys)-Doc-(Arg)$_5$-Gln-(Arg)$_3$-NH$_2$; (SEQ ID NO: 460)

Nle-c(Cys-His-D-Phe-Arg-Trp-Gaba-Cys)-(Doc)$_2$-Tyr-Gly-(Arg)$_5$-Gln-(Arg)$_3$-NH$_2$; (SEQ ID NO: 461)

Nle-c(Cys-His-D-Phe-Arg-Trp-Gaba-Cys)-(Doc)$_2$-(Arg)$_5$-Gln-(Arg)$_3$-NH$_2$; (SEQ ID NO: 462)

Nle-c(Cys-His-D-Phe-Arg-Trp-Gaba-Cys)-Doc-Tyr-Gly-(Arg)$_5$-Gln-(Arg)$_4$-NH$_2$; (SEQ ID NO: 463)

Nle-c(Cys-His-D-Phe-Arg-Trp-Gaba-Cys)-Doc-(Arg)$_5$-Gln-(Arg)$_4$-NH$_2$; (SEQ ID NO: 464)

Nle-c(Cys-His-D-Phe-Arg-Trp-Gaba-Cys)-(Doc)$_2$-Tyr-Gly-(Arg)$_5$-Gln-(Arg)$_4$-NH$_2$; (SEQ ID NO: 465)

Nle-c(Cys-His-D-Phe-Arg-Trp-Gaba-Cys)-(Doc)$_2$-(Arg)$_5$-Gln-(Arg)$_4$-NH$_2$; (SEQ ID NO: 466)

Ac-c(Cys-Glu-His-D-4-Br-Phe-Arg-Trp-Gly-Cys)-(Pro)$_2$-Lys-Asp-NH$_2$; (SEQ ID NO: 467)

Ac-c(Cys-Glu-His-D-2-Nal-Arg-Trp-Ala-Cys)-(Pro)$_2$-Lys-Asp-NH$_2$; (SEQ ID NO: 468)

Ac-c(Cys-Glu-His-D-2-Nal-Arg-2-Nal-Ala-Cys)-(Pro)$_2$-Lys-Asp-NH$_2$; (SEQ ID NO: 469)

Ac-c(Cys-Glu-His-D-2-Nal-Arg-1-Nal-Ala-Cys)-(Pro)$_2$-Lys-Asp-NH$_2$; (SEQ ID NO: 470)

Ac-c(Cys-Glu-His-D-2-Nal-Arg-Bal-Ala-Cys)-(Pro)$_2$-Lys-Asp-NH$_2$; (SEQ ID NO: 471)

Ac-c(Cys-Glu-His-D-2-Nal-Arg-2-Nal-β-Ala-Cys)-(Pro)$_2$-Lys-Asp-NH$_2$; (SEQ ID NO: 472)

Ac-c(Cys-Glu-His-D-2-Nal-Arg-2-Nal-Aib-Cys)-(Pro)$_2$-Lys-Asp-NH$_2$; (SEQ ID NO: 473)

c[Hydantoin(C(O)-(Cys-D-Ala))-His-D-Phe-Arg-Trp-Cys]-NH$_2$; (SEQ ID NO: 474)

c[Hydantoin(C(O)-(hCys-D-Ala))-His-D-Phe-Arg-Trp-Cys]-NH$_2$; (SEQ ID NO: 475)

c[Hydantoin(C(O)-(Cys-D-Ala))-His-D-2-Nal-Arg-Trp-Cys]-NH$_2$; (SEQ ID NO: 476)

c[Hydantoin(C(O)-(hCys-D-Ala))-His-D-2-Nal-Arg-Trp-Cys]-NH$_2$; (SEQ ID NO: 477)

c[Hydantoin(C(O)-(Asp-D-Ala))-His-D-Phe-Arg-Trp-Lys]-NH$_2$; (SEQ ID NO: 478)

c[Hydantoin(C(O)-(Asp-D-Ala))-His-D-Phe-Arg-Trp-Orn]-NH$_2$; (SEQ ID NO: 479)

c[Hydantoin(C(O)-(Asp-D-Ala))-His-D-Phe-Arg-Trp-Dab]-NH$_2$; (SEQ ID NO: 480)

c[Hydantoin(C(O)-(Asp-D-Ala))-His-D-Phe-Arg-Trp-Dap]-NH$_2$; (SEQ ID NO: 481)

c[Hydantoin(C(O)-(Asp-His))-D-2-Nal-Arg-Trp-Lys]-NH$_2$; (SEQ ID NO: 482)

c[Hydantoin(C(O)-(Asp-His))-D-Phe-Arg-Trp-Lys]-NH$_2$; (SEQ ID NO: 483)

c[Hydantoin(C(O)-(Asp-A3c))-D-Phe-Arg-Trp-Lys]-NH$_2$; (SEQ ID NO: 484)

c[Hydantoin(C(O)-(Asp-A5c))-D-Phe-Arg-Trp-Lys]-NH$_2$; (SEQ ID NO: 485)

c[Hydantoin(C(O)-(Asp-A6c))-D-Phe-Arg-Trp-Lys]-NH$_2$; (SEQ ID NO: 486)

-continued c[Hydantoin(C(O)-(Asp-A3c))-D-2-Nal-Arg-Trp-Lys]-NH$_2$; (SEQ ID NO: 487)

c[Hydantoin(C(O)-(Asp-A5c))-D-2-Nal-Arg-Trp-Lys]-NH$_2$; (SEQ ID NO: 488)

c[Hydantoin(C(O)-(Asp-A6c))-D-2-Nal-Arg-Trp-Lys]-NH$_2$; (SEQ ID NO: 489)

c[Hydantoin(C(O)-(Asp-Aic))-D-Phe-Arg-Trp-Lys]-NH$_2$; (SEQ ID NO: 490)

c[Hydantoin(C(O)-(Asp-Apc))-D-Phe-Arg-Trp-Lys]-NH$_2$; (SEQ ID NO: 491)

c[Hydantoin(C(O)-(Asp-Aic))-D-2-Nal-Arg-Trp-Lys]-NH$_2$; (SEQ ID NO: 492)

c[Hydantoin(C(O)-(Asp-Apc))-D-2-Nal-Arg-Trp-Lys]-NH$_2$; (SEQ ID NO: 493)

c[Hydantoin(C(O)-(Glu-D-Ala))-His-D-Phe-Arg-Trp-Orn]-NH$_2$; (SEQ ID NO: 494)

c[Hydantoin(C(O)-(Glu-D-Ala))-His-D-Phe-Arg-Trp-Dab]-NH$_2$; (SEQ ID NO: 495)

c[Hydantoin(C(O)-(Glu-D-Ala))-His-D-Phe-Arg-Trp-Dap]-NH$_2$; (SEQ ID NO: 496)

c[Hydantoin(C(O)-(Glu-D-Ala))-His-D-Phe-Arg-Trp-Lys]-NH$_2$; (SEQ ID NO: 497)

c[Hydantoin(C(O)-(Glu-His))-D-Phe-Arg-Trp-Dap]-NH$_2$; (SEQ ID NO: 498)

c[Hydantoin(C(O)-(Glu-His))-D-Phe-Arg-Trp-Lys]-NH$_2$; (SEQ ID NO: 499)

Hydantoin(C(O)-(Arg-Gly))-c(Cys-Glu-His-D-Phe-Arg-Trp-Cys)-NH$_2$; (SEQ ID NO: 500)

Hydantoin(C(O)-(Nle-Gly))-c(Cys-Glu-His-D-Phe-Arg-Trp-Cys)-NH$_2$; (SEQ ID NO: 501)

Hydantoin(C(O)-(Gly-Gly))-c(Cys-Glu-His-D-Phe-Arg-Trp-Cys)-NH$_2$; (SEQ ID NO: 502)

Hydantoin(C(O)-(Nle-Gly))-c(Cys-D-Ala-His-D-Phe-Arg-Trp-Cys)-NH$_2$; (SEQ ID NO: 503)

Hydantoin(C(O)-(Gly-Gly))-c(Cys-D-Ala-His-D-Phe-Arg-Trp-Cys)-NH$_2$; (SEQ ID NO: 504)

Hydantoin(C(O)-(Nle-Gly))-c(Cys-D-Ala-His-D-Phe-Arg-Trp-Pen)-NH$_2$; (SEQ ID NO: 505)

Hydantoin(C(O)-(Gly-Gly))-c(Cys-D-Ala-His-D-Phe-Arg-Trp-Pen)-NH$_2$; (SEQ ID NO: 506)

Hydantoin(C(O)-(Ala-Gly))-c(Cys-D-Ala-His-D-Phe-Arg-Trp-Cys)-NH$_2$; (SEQ ID NO: 507)

Hydantoin(C(O)-(D-Ala-Gly))-c(Cys-D-Ala-His-D-Phe-Arg-Trp-Cys)-NH$_2$; (SEQ ID NO: 508)

Hydantoin(C(O)-(Aib-Gly))-c(Cys-D-Ala-His-D-Phe-Arg-Trp-Cys)-NH$_2$; (SEQ ID NO: 509)

Hydantoin(C(O)-(Val-Gly))-c(Cys-D-Ala-His-D-Phe-Arg-Trp-Cys)-NH$_2$; (SEQ ID NO: 510)

Hydantoin(C(O)-(Ile-Gly))-c(Cys-D-Ala-His-D-Phe-Arg-Trp-Cys)-NH$_2$; (SEQ ID NO: 511)

Hydantoin(C(O)-(Leu-Gly))-c(Cys-D-Ala-His-D-Phe-Arg-Trp-Cys)-NH$_2$; (SEQ ID NO: 512)

Hydantoin(C(O)-(Gly-Gly))-c(Cys-Glu-His-D-2-Nal-Arg-Trp-Cys)-NH$_2$; (SEQ ID NO: 513)

-continued

Hydantoin(C(O)-(Nle-Gly))-c(Cys-Glu-His-D-2-Nal-Arg-Trp-Cys)-NH$_2$; (SEQ ID NO: 514)

Hydantoin(C(O)-(D-Arg-Gly))-c(Cys-Glu-His-D-Phe-Arg-Trp-Cys)-NH$_2$; (SEQ ID NO: 515)

Hydantoin(C(O)-(D-Arg-Gly))-c(Cys-D-Ala-His-D-Phe-Arg-Trp-Cys)-NH$_2$; (SEQ ID NO: 516)

Hydantoin(C(O)-(Arg-Gly))-c(Cys-D-Ala-His-D-Phe-Arg-Trp-Cys)-NH$_2$; (SEQ ID NO: 517)

Hydantoin(C(O)-(D-Arg-Gly))-c(Cys-D-Ala-His-D-2-Nal-Arg-Trp-Cys)-NH$_2$; (SEQ ID NO: 518)

Hydantoin(C(O)-(Arg-Gly))-c(Cys-D-Ala-His-D-2-Nal-Arg-Trp-Cys)-NH$_2$; (SEQ ID NO: 519)

Hydantoin(C(O)-(Ala-Nle))-c(Cys-Glu-His-D-Phe-Arg-Trp-Cys)-NH$_2$; (SEQ ID NO: 520)

Hydantoin(C(O)-(Val-Nle))-c(Cys-Glu-His-D-Phe-Arg-Trp-Cys)-NH$_2$; (SEQ ID NO: 521)

Hydantoin(C(O)-(Gly-Nle))-c(Cys-Glu-His-D-Phe-Arg-Trp-Cys)-NH$_2$; (SEQ ID NO: 522)

Hydantoin(C(O)-(A6c-Nle))-c(Cys-D-Ala-His-D-Phe-Arg-Trp-Cys)-NH$_2$; (SEQ ID NO: 523)

Hydantoin(C(O)-(Gly-Nle))-c(Cys-D-Ala-His-D-Phe-Arg-Trp-Cys)-NH$_2$; (SEQ ID NO: 524)

Hydantoin(C(O)-(Ala-Nle))-c(Cys-D-Ala-His-D-Phe-Arg-Trp-Cys)-NH$_2$; (SEQ ID NO: 525)

Hydantoin(C(O)-(D-Ala-Nle))-c(Cys-D-Ala-His-D-Phe-Arg-Trp-Cys)-NH$_2$; (SEQ ID NO: 526)

Hydantoin(C(O)-(Val-Nle))-c(Cys-D-Ala-His-D-Phe-Arg-Trp-Cys)-NH$_2$; (SEQ ID NO: 527)

Hydantoin(C(O)-(Leu-Nle))-c(Cys-D-Ala-His-D-Phe-Arg-Trp-Cys)-NH$_2$; (SEQ ID NO: 528)

Hydantoin(C(O)-(Cha-Nle))-c(Cys-D-Ala-His-D-Phe-Arg-Trp-Cys)-NH$_2$; (SEQ ID NO: 529)

Hydantoin(C(O)-(Aib-Nle))-c(Cys-D-Ala-His-D-Phe-Arg-Trp-Cys)-NH$_2$; (SEQ ID NO: 530)

Hydantoin(C(O)-(Gly-Arg))-c(Cys-Glu-His-D-Phe-Arg-Trp-Cys)-NH$_2$; (SEQ ID NO: 531)

Hydantoin(C(O)-(Gly-Arg))-c(Cys-Glu-His-D-2-Nal-Arg-Trp-Cys)-NH$_2$; (SEQ ID NO: 532)

Hydantoin(C(O)-(Gly-Arg))-c(Cys-D-Ala-His-D-Phe-Arg-Trp-Cys)-NH$_2$; (SEQ ID NO: 533)

Hydantoin(C(O)-(Gly-Arg))-c(Cys-D-Ala-His-D-2-Nal-Arg-Trp-Cys)-NH$_2$; (SEQ ID NO: 534)

Hydantoin(C(O)-(Gly-D-Arg))-c(Cys-Glu-His-D-Phe-Arg-Trp-Cys)-NH$_2$; (SEQ ID NO: 535)

Hydantoin(C(O)-(Gly-D-Arg))-c(Cys-D-Ala-His-D-Phe-Arg-Trp-Cys)-NH$_2$; (SEQ ID NO: 536)

Hydantoin(C(O)-(Gly-D-Arg))-c(Cys-D-Ala-His-D-2-Nal-Arg-Trp-Cys)-NH$_2$; (SEQ ID NO: 537)

Hydantoin(C(O)-(Nle-Ala))-c(Cys-Glu-His-D-Phe-Arg-Trp-Cys)-NH$_2$; (SEQ ID NO: 538)

c[Hydantoin(C(O)-(Nle-Cys))-D-Ala-His-D-Phe-Arg-Trp-Cys]-NH$_2$; (SEQ ID NO: 539)

c[Hydantoin(C(O)-(Ala-Cys))-D-Ala-His-D-Phe-Arg-Trp-Cys]-NH$_2$; (SEQ ID NO: 540)

| | |
|---|---|
| c[Hydantoin(C(O)-(D-Ala-Cys))-D-Ala-His-D-Phe-Arg-Trp-Cys]-NH$_2$; | (SEQ ID NO: 541) |
| c[Hydantoin(C(O)-(Aib-Cys))-D-Ala-His-D-Phe-Arg-Trp-Cys]-NH$_2$; | (SEQ ID NO: 542) |
| c[Hydantoin(C(O)-(Val-Cys))-D-Ala-His-D-Phe-Arg-Trp-Cys]-NH$_2$; | (SEQ ID NO: 543) |
| c[Hydantoin(C(O)-(Abu-Cys))-D-Ala-His-D-Phe-Arg-Trp-Cys]-NH$_2$; | (SEQ ID NO: 544) |
| c[Hydantoin(C(O)-(Leu-Cys))-D-Ala-His-D-Phe-Arg-Trp-Cys]-NH$_2$; | (SEQ ID NO: 545) |
| c[Hydantoin(C(O)-(Ile-Cys))-D-Ala-His-D-Phe-Arg-Trp-Cys]-NH$_2$; | (SEQ ID NO: 546) |
| c[Hydantoin(C(O)-(Cha-Cys))-D-Ala-His-D-Phe-Arg-Trp-Cys]-NH$_2$; | (SEQ ID NO: 547) |
| c[Hydantoin(C(O)-(A6c-Cys))-D-Ala-His-D-Phe-Arg-Trp-Cys]-NH$_2$; | (SEQ ID NO: 548) |
| c[Hydantoin(C(O)-(Phe-Cys))-D-Ala-His-D-Phe-Arg-Trp-Cys]-NH$_2$; | (SEQ ID NO: 549) |
| c[Hydantoin(C(O)-(Gly-Cys))-D-Ala-His-D-Phe-Arg-Trp-Cys]-NH$_2$; | (SEQ ID NO: 550) |
| c[Hydantoin(C(O)-(Gly-Cys))-Glu-His-D-Phe-Arg-Trp-Cys]-NH$_2$; | (SEQ ID NO: 551) |
| Ac-Tyr-Arg-c(Cys-D-Ala-His-D-Phe-Arg-Trp-Cys)-NH$_2$; | (SEQ ID NO: 552) |
| Ac-2-Nal-Arg-c(Cys-D-Ala-His-D-Phe-Arg-Trp-Cys)-NH$_2$; | (SEQ ID NO: 553) |
| Ac-1-Nal-Arg-c(Cys-D-Ala-His-DPhe-Arg-Trp-Cys)-NH$_2$; | (SEQ ID NO: 554) |
| Ac-Phe-Arg-c(Cys-D-Ala-His-D-Phe-Arg-Trp-Cys)-NH$_2$; | (SEQ ID NO: 555) |
| Ac-Trp-Arg-c(Cys-D-Ala-His-D-Phe-Arg-Trp-Cys)-NH$_2$; | (SEQ ID NO: 556) |
| Ac-Pff-Arg-c(Cys-D-Ala-His-D-Phe-Arg-Trp-Cys)-NH$_2$; | (SEQ ID NO: 557) |
| H-His-Arg-c(Cys-D-Ala-His-D-Phe-Arg-Trp-Cys)-NH$_2$; and | (SEQ ID NO: 558) |
| Ac-His-Arg-c(Cys-D-Ala-His-D-Phe-Arg-Trp-Cys)-NH$_2$. | (SEQ ID NO: 559) | or a pharmaceutically acceptable salt thereof.

8. The method of claim 1, wherein the obesity results from the attenuated response of MC4R to α-melanocortin stimulating hormone (α-MSH).

9. The method of claim 1, wherein the subject is a human.

10. A method of treating a metabolic syndrome in a subject in need thereof, comprising:
administering to said subject an effective amount of an agonist of the melanocortin-4 receptor (MC4R), wherein the subject is a heterozygous carrier of an MC4R mutation.

11. The method of claim 10, wherein said MC4R agonist is Ac-Arg-c(Cys-D-Ala-His-D-Phe-Arg-Trp-Cys)-NH$_2$ (SEQ ID NO: 140) or a pharmaceutically acceptable salt thereof.

12. The method of claim 10, wherein said MC4R agonist is Hydantoin(C(O)-(Arg-Gly))-c(Cys-Glu-His-D-Phe-Arg-Trp-Cys)-NH$_2$ (SEQ ID NO: 500) or a pharmaceutically acceptable salt thereof.

13. The method of claim 10, wherein said MC4R agonist is a tripeptide D-Phe-Arg-Trp (SEQ ID NO: 560) or a pharmaceutical salt thereof.

14. The method of claim 10, wherein said MC4R agonist is a peptide that includes D-Phe-Arg-Trp (SEQ ID NO: 560) or a pharmaceutical salt thereof.

15. The method of claim 10, wherein said MC4R agonist is a peptide that includes an acetylated tripeptide Ac-D-Phe-Arg-Trp-NH$_2$ (SEQ ID NO: 561) or a pharmaceutical salt thereof.

16. The method of claim 10, wherein said MC4R agonist is a peptide selected form:

(SEQ ID NO: 1)

-continued

| Sequence | |
|---|---|
| Ac-Nle-c(Asp-His-D-Phe-Arg-Trp-β-Ala-Lys)-NH$_2$; | (SEQ ID NO: 2) |
| Ac-Nle-c(Asp-His-D-Phe-Arg-Trp-A6c-Lys)-NH$_2$; | (SEQ ID NO: 3) |
| Ac-Nle-c(Cys-His-D-Phe-Arg-Trp-Ahx-Cys)-NH$_2$; | (SEQ ID NO: 4) |
| D-Phe-c(Cys-His-D-Phe-Arg-Trp-Ala-D-Cys)-Thr-NH$_2$; | (SEQ ID NO: 5) |
| D-Phe-c(Cys-His-D-Phe-Arg-Trp-β-Ala-D-Cys)-Thr-NH$_2$; | (SEQ ID NO: 6) |
| D-Phe-c(Cys-His-D-Phe-Arg-Trp-Gaba-D-Cys)-Thr-NH$_2$; | (SEQ ID NO: 7) |
| Ac-Nle-c(Cys-His-D-Phe-Arg-Trp-Apn-Cys)-NH$_2$; | (SEQ ID NO: 8) |
| Ac-Nle-c(Asp-His-D-Phe-Arg-Trp-Apn-Lys)-NH$_2$; | (SEQ ID NO: 9) |
| Ac-A6c-c(Asp-His-D-Phe-Arg-Trp-Gaba-Lys)-NH$_2$; | (SEQ ID NO: 10) |
| Ac-D-2-Nal-c(Asp-His-D-Phe-Arg-Trp-Gaba-Lys)-NH$_2$; | (SEQ ID NO: 11) |
| Ac-Cha-c(Asp-His-D-Phe-Arg-Trp-Gaba-Lys)-NH$_2$; | (SEQ ID NO: 12) |
| Ac-Nle-c(Asp-His-D-Phe-Arg-Trp-Gaba-Lys)-NH$_2$; | (SEQ ID NO: 13) |
| Ac-Nle-c(Cys-D-Ala-His-D-Phe-Arg-Trp-Cys)-NH$_2$; | (SEQ ID NO: 14) |
| Ac-Nle-c(Cys-β-Ala-His-D-Phe-Arg-Trp-Cys)-NH$_2$; | (SEQ ID NO: 15) |
| Ac-Nle-c(Cys-Gaba-His-D-Phe-Arg-Trp-Cys)-NH$_2$; | (SEQ ID NO: 16) |
| Ac-Nle-c(Cys-Aib-His-D-Phe-Arg-Trp-Cys)-NH$_2$; | (SEQ ID NO: 17) |
| Ac-Nle-c(Cys-Gly-His-D-Phe-Arg-Trp-Cys)-NH$_2$; | (SEQ ID NO: 18) |
| Ac-Nle-c(D-Cys-Ala-His-D-Phe-Arg-Trp-Cys)-NH$_2$; | (SEQ ID NO: 19) |
| Ac-Nle-c(D-Cys-D-Ala-His-D-Phe-Arg-Trp-Cys)-NH$_2$; | (SEQ ID NO: 20) |
| Ac-Nle-c(D-Cys-β-Ala-His-D-Phe-Arg-Trp-Cys)-NH$_2$; | (SEQ ID NO: 21) |
| Ac-Nle-c(D-Cys-Gaba-His-D-Phe-Arg-Trp-Cys)-NH$_2$; | (SEQ ID NO: 22) |
| Ac-Nle-c(D-Cys-Aib-His-D-Phe-Arg-Trp-Cys)-NH$_2$; | (SEQ ID NO: 23) |
| Ac-Nle-c(D-Cys-Gly-His-D-Phe-Arg-Trp-Cys)-NH$_2$; | (SEQ ID NO: 24) |
| Ac-Nle-c(Cys-D-Ala-His-D-Phe-Arg-Trp-D-Cys)-NH$_2$; | (SEQ ID NO: 25) |
| Ac-Nle-c(Cys-β-Ala-His-D-Phe-Arg-Trp-D-Cys)-NH$_2$; | (SEQ ID NO: 26) |
| Ac-Nle-c(Cys-Gaba-His-D-Phe-Arg-Trp-D-Cys)-NH$_2$; | (SEQ ID NO: 27) |
| Ac-Nle-c(Cys-Aib-His-D-Phe-Arg-Trp-D-Cys)-NH$_2$; | (SEQ ID NO: 28) |

-continued

Ac-Nle-c(Cys-Gly-His-D-Phe-Arg-Trp-D-Cys)-NH$_2$;

(SEQ ID NO: 29)

Ac-Nle-c(D-Cys-Ala-His-D-Phe-Arg-Trp-D-Cys)-NH$_2$;

(SEQ ID NO: 30)

Ac-Nle-c(D-Cys-D-Ala-His-D-Phe-Arg-Trp-D-Cys)-NH$_2$;

(SEQ ID NO: 31)

Ac-Nle-c(D-Cys-β-Ala-His-D-Phe-Arg-Trp-D-Cys)-NH$_2$;

(SEQ ID NO: 32)

Ac-Nle-c(D-Cys-Gaba-His-D-Phe-Arg-Trp-D-Cys)-NH$_2$;

(SEQ ID NO: 33)

Ac-Nle-c(D-Cys-Aib-His-D-Phe-Arg-Trp-D-Cys)-NH$_2$;

(SEQ ID NO: 34)

Ac-Oic-c(Asp-His-D-Phe-Arg-Trp-Gaba-Lys)-NH$_2$;

(SEQ ID NO: 35)

Ac-Chg-c(Asp-His-D-Phe-Arg-Trp-Gaba-Lys)-NH$_2$;

(SEQ ID NO: 36)

Ac-hCha-c(Asp-His-D-Phe-Arg-Trp-Gaba-Lys)-NH$_2$;

(SEQ ID NO: 37)

Ac-D-Cha-c(Asp-His-D-Phe-Arg-Trp-Gaba-Lys)-NH$_2$;

(SEQ ID NO: 38)

Ac-D-hCha-c(Asp-His-D-Phe-Arg-Trp-Gaba-Lys)-NH$_2$;

(SEQ ID NO: 39)

Ac-Nip-c(Asp-His-D-Phe-Arg-Trp-Gaba-Lys)-NH$_2$;

(SEQ ID NO: 40)

Ac-hPro-c(Asp-His-D-Phe-Arg-Trp-Gaba-Lys)-NH$_2$;

(SEQ ID NO: 41)

Ac-hLeu-c(Asp-His-D-Phe-Arg-Trp-Gaba-Lys)-NH$_2$;

(SEQ ID NO: 42)

Ac-Phe-c(Asp-His-D-Phe-Arg-Trp-Gaba-Lys)-NH$_2$;

(SEQ ID NO: 43)

Ac-D-Phe-c(Asp-His-D-Phe-Arg-Trp-Gaba-Lys)-NH$_2$;

(SEQ ID NO: 44)

Ac-D-Chg-c(Asp-His-D-Phe-Arg-Trp-Gaba-Lys)-NH$_2$;

(SEQ ID NO: 45)

n-butanoyl-Cha-c(Asp-His-D-Phe-Arg-Trp-Gaba-Lys)-NH$_2$;

(SEQ ID NO: 46)

n-butyryl-Cha-c(Asp-His-D-Phe-Arg-Trp-Gaba-Lys)-NH$_2$;

(SEQ ID NO: 47)

Ac-hPhe-c(Asp-His-D-Phe-Arg-Trp-Gaba-Lys)-NH$_2$;

(SEQ ID NO: 48)

Ac-β-hMet-c(Asp-His-D-Phe-Arg-Trp-Gaba-Lys)-NH$_2$;

(SEQ ID NO: 49)

Ac-Gaba-c(Asp-His-D-Phe-Arg-Trp-Gaba-Lys)-NH$_2$;

(SEQ ID NO: 50)

Ac-Cha-c(Asp-His-D-Phe-Arg-D-Trp-Ala-Lys)-NH$_2$;

(SEQ ID NO: 51)

Ac-hCha-c(Asp-His-D-Phe-Arg-D-Trp-Ala-Lys)-NH$_2$;

(SEQ ID NO: 52)

Ac-Leu-c(Asp-His-D-Phe-Arg-D-Trp-Ala-Lys)-NH$_2$;

(SEQ ID NO: 53)

Ac-hLeu-c(Asp-His-D-Phe-Arg-D-Trp-Ala-Lys)-NH$_2$;

(SEQ ID NO: 54)

Ac-Phe-c(Asp-His-D-Phe-Arg-D-Trp-Ala-Lys)-NH$_2$;

(SEQ ID NO: 55)

-continued

| | |
|---|---|
| Ac-Nle-c(Asp-His-D-Phe-Arg-D-Trp-D-Ala-Lys)-NH₂; | (SEQ ID NO: 56) |
| Ac-Nle-c(Asp-His-D-Phe-Arg-D-Trp-β-Ala-Lys)-NH₂; | (SEQ ID NO: 57) |
| Ac-Nle-c(Asp-His-D-Phe-Arg-D-Trp-Gaba-Lys)-NH₂; | (SEQ ID NO: 58) |
| Ac-Nle-c(Asp-His-D-Phe-Arg-D-Trp-Aha-Lys)-NH₂; | (SEQ ID NO: 59) |
| Ac-Nle-c(Asp-His-D-Phe-Arg-D-Trp-Apn-Lys)-NH₂; | (SEQ ID NO: 60) |
| Ac-Nle-c(Cys-His-D-Phe-Arg-D-Trp-Apn-Cys)-NH₂; | (SEQ ID NO: 61) |
| Ac-Nle-c(Cys-His-D-Phe-Arg-D-Trp-Gaba-Cys)-NH₂; | (SEQ ID NO: 62) |
| Ac-Nle-c(Cys-His-D-Phe-Arg-D-Trp-Ahx-Cys)-NH₂; | (SEQ ID NO: 63) |
| Ac-Nle-c(Cys-His-D-Phe-Arg-D-Trp-β-Ala-Cys)-NH₂; | (SEQ ID NO: 64) |
| Ac-Nle-c(Cys-His-D-Phe-Arg-D-Trp-D-Ala-Cys)-NH₂; | (SEQ ID NO: 65) |
| Ac-Nle-c(Cys-D-Ala-His-D-2-Nal-Arg-Trp-Cys)-NH₂; | (SEQ ID NO: 66) |
| Ac-Nle-c(Cys-D-Ala-His-D-2-Nal-Arg-2-Nal-Cys)-NH₂; | (SEQ ID NO: 67) |
| Ac-Nle-c(Cys-D-Ala-His-D-2-Nal-Arg-1-Nal-Cys)-NH₂; | (SEQ ID NO: 68) |
| n-butanoyl-Nle-c(Cys-D-Ala-His-D-Phe-Arg-2-Nal-Cys)-NH₂; | (SEQ ID NO: 69) |
| n-butanoyl-Nle-c(Cys-D-Ala-His-D-Phe-Arg-Trp-Cys)-NH₂; | (SEQ ID NO: 70) |
| Ac-Nle-c(Cys-D-Ala-His-D-Phe-Arg-2-Nal-Cys)-NH₂; | (SEQ ID NO: 71) |
| Ac-Nle-c(Cys-D-Ala-His-D-Phe-Arg-1-Nal-Cys)-NH₂; | (SEQ ID NO: 72) |
| Ac-Nle-c(Cys-D-Ala-His-D-Phe-Arg-Bal-Cys)-NH₂; | (SEQ ID NO: 73) |
| Ac-Nle-c(Cys-D-Glu-His-D-Phe-Arg-Trp-Cys)-NH₂; | (SEQ ID NO: 74) |
| Ac-Nle-c(Asp-His-D-Phe-Arg-Trp-D-Ala-Lys)-NH₂; | (SEQ ID NO: 75) |
| Ac-Nle-c(Cys-D-Ala-His-D-2-Nal-Arg-Bal-Cys)-NH₂; | (SEQ ID NO: 76) |
| Ac-Nle-c(Pen-D-Ala-His-D-Phe-Arg-Trp-Cys)-NH₂; | (SEQ ID NO: 77) |
| Ac-Nle-c(Cys-D-Ala-His-D-Phe-Arg-Trp-Pen)-NH₂; | (SEQ ID NO: 78) |
| Ac-Nle-c(Pen-D-Ala-His-D-Phe-Arg-Trp-Pen)-NH₂; | (SEQ ID NO: 79) |
| D-Phe-c(Cys-His-D-Phe-hArg-Trp-β-Ala-D-Cys)-Thr-NH₂; | (SEQ ID NO: 80) |
| D-Phe-c(Cys-His-D-(Et)Tyr-Arg-Trp-β-Ala-D-Cys)-Thr-NH₂; | (SEQ ID NO: 81) |
| D-Phe-c(Cys-His-D-Phe-Arg-Bip-β-Ala-D-Cys)-Thr-NH₂; | (SEQ ID NO: 82) |

-continued

D-Phe-c(Cys-His-D-(Et)Tyr-hArg-Trp-β-Ala-D-Cys)-Thr-NH₂;
(SEQ ID NO: 83)

D-Phe-c(Cys-His-D-Phe-hArg-Bip-β-Ala-D-Cys)-Thr-NH₂;
(SEQ ID NO: 84)

D-Phe-c(Cys-His-D-(Et)Tyr-hArg-Bip-β-Ala-D-Cys)-Thr-NH₂;
(SEQ ID NO: 85)

Nle-c(Cys-His-D-Phe-Arg-Trp-Apn-Cys)-NH₂;
(SEQ ID NO: 86)

Ac-Nle-c(Asp-D-Ala-His-D-Phe-Arg-Trp-Lys)-NH₂;
(SEQ ID NO: 87)

Ac-Nle-c(Asp-D-Ala-His-D-Phe-Arg-Bal-Lys)-NH₂;
(SEQ ID NO: 88)

Ac-Nle-c(Cys-D-Ala-His-D-Phe-Arg-Trp-Pen)-OH;
(SEQ ID NO: 89)

Ac-Nle-c(Cys-D-Abu-His-D-Phe-Arg-Trp-Cys)-NH₂;
(SEQ ID NO: 90)

Ac-Nle-c(Cys-D-Val-His-D-Phe-Arg-Trp-Cys)-NH₂;
(SEQ ID NO: 91)

Ac-Nle-c(Cys-D-Ile-His-D-Phe-Arg-Trp-Cys)-NH₂;
(SEQ ID NO: 92)

Ac-Nle-c(Cys-D-Leu-His-D-Phe-Arg-Trp-Cys)-NH₂;
(SEQ ID NO: 93)

Ac-Nle-c(Cys-D-Tle-His-D-Phe-Arg-Trp-Cys)-NH₂;
(SEQ ID NO: 94)

Ac-Nle-c(Cys-D-Cha-His-D-Phe-Arg-Trp-Cys)-NH₂;
(SEQ ID NO: 95)

Ac-Nle-c(Pen-His-D-Phe-Arg-Trp-Gaba-Cys)-NH₂;
(SEQ ID NO: 96)

Ac-Nle-c(Cys-His-D-Phe-Arg-Trp-Gaba-Pen)-NH₂;
(SEQ ID NO: 97)

Ac-Nle-c(Pen-His-D-Phe-Arg-Trp-Gaba-Pen)-NH₂;
(SEQ ID NO: 98)

Ac-Leu-c(Cys-His-D-Phe-Arg-Trp-Gaba-Cys)-NH₂;
(SEQ ID NO: 99)

Ac-Cha-c(Cys-His-D-Phe-Arg-Trp-Gaba-Cys)-NH₂;
(SEQ ID NO: 100)

Ac-Ile-c(Cys-His-D-Phe-Arg-Trp-Gaba-Cys)-NH₂;
(SEQ ID NO: 101)

Ac-Phe-c(Cys-His-D-Phe-Arg-Trp-Gaba-Cys)-NH₂;
(SEQ ID NO: 102)

Ac-Val-c(Cys-His-D-Phe-Arg-Trp-Gaba-Cys)-NH₂;
(SEQ ID NO: 103)

Ac-2-Nal-c(Cys-His-D-Phe-Arg-Trp-Gaba-Cys)-NH₂;
(SEQ ID NO: 104)

Nle-c(Cys-His-D-Phe-Arg-Trp-Gaba-Cys)-NH₂;
(SEQ ID NO: 105)

Phe-c(Cys-His-D-Phe-Arg-Trp-Gaba-Cys)-NH₂;
(SEQ ID NO: 106)

Ac-Nle-c(Cys-3-Pal-D-Phe-Arg-Trp-Gaba-Cys)-NH₂;
(SEQ ID NO: 107)

Ac-Nle-c(Cys-D-Ala-His-D-Phe-Arg-Trp-Cys)-OH;
(SEQ ID NO: 108)

Ac-Nle-c(Cys-His-Phe-Arg-D-Trp-Gaba-Cys)-NH₂;
(SEQ ID NO: 109)

-continued

Ac-Nle-c(Asp-His-D-2-Nal-Arg-Trp-Ala-Lys)-NH₂;
(SEQ ID NO: 110)

Ac-Nle-c(Asp-His-D-2-Nal-Arg-Trp-β-Ala-Lys)-NH₂;
(SEQ ID NO: 111)

Ac-Nle-c(Cys-His-D-2-Nal-Arg-Trp-Gaba-Cys)-NH₂;
(SEQ ID NO: 112)

Ac-Nle-c(Cys-His-D-2-Nal-Arg-Trp-Ahx-Cys)-NH₂;
(SEQ ID NO: 113)

Ac-hPhe-c(Asp-His-D-2-Nal-Arg-Trp-Gaba-Lys)-NH₂;
(SEQ ID NO: 114)

Ac-Cha-c(Asp-His-D-2-Nal-Arg-Trp-Gaba-Lys)-NH₂;
(SEQ ID NO: 115)

Ac-Nle-c(Asp-His-D-Phe-Arg-Trp-β-Ala-Lys)-OH;
(SEQ ID NO: 116)

Ac-Nle-c(Cys-His-D-Phe-Arg-Trp-Ahx-Cys)-OH;
(SEQ ID NO: 117)

D-Phe-c(Cys-His-D-Phe-Arg-Trp-Ala-D-Cys)-Thr-OH;
(SEQ ID NO: 118)

D-Phe-c(Cys-His-D-Phe-Arg-Trp-β-Ala-D-Cys)-Thr-OH;
(SEQ ID NO: 119)

D-Phe-c(Cys-His-D-Phe-Arg-Trp-Gaba-D-Cys)-Thr-OH;
(SEQ ID NO: 120)

Ac-Nle-c(Cys-His-D-Phe-Arg-Trp-Apn-Cys)-OH;
(SEQ ID NO: 121)

Ac-Nle-c(Asp-His-D-Phe-Arg-Trp-Apn-Lys)-OH;
(SEQ ID NO: 122)

Ac-Cha-c(Asp-His-D-Phe-Arg-Trp-Gaba-Lys)-OH;
(SEQ ID NO: 123)

Ac-Nle-c(Asp-His-D-Phe-Arg-Trp-Gaba-Lys)-OH;
(SEQ ID NO: 124)

Ac-Chg-c(Asp-His-D-Phe-Arg-Trp-Gaba-Lys)-OH;
(SEQ ID NO: 125)

Ac-D-Cha-c(Asp-His-D-Phe-Arg-Trp-Gaba-Lys)-OH;
(SEQ ID NO: 126)

Ac-hCha-c(Asp-His-D-Phe-Arg-Trp-Gaba-Lys)-OH;
(SEQ ID NO: 127)

Ac-D-Chg-c(Asp-His-D-Phe-Arg-Trp-Gaba-Lys)-OH;
(SEQ ID NO: 128)

Ac-hPhe-c(Asp-His-D-Phe-Arg-Trp-Gaba-Lys)-OH;
(SEQ ID NO: 129)

Ac-Nle-c(Cys-His-D-Phe-Arg-D-Trp-Gaba-Cys)-OH;
(SEQ ID NO: 130)

Ac-Nle-c(Cys-His-D-Phe-Arg-D-Trp-Ahx-Cys)-OH;
(SEQ ID NO: 131)

Ac-Nle-c(Cys-His-D-Phe-Arg-D-Trp-β-Ala-Cys)-OH;
(SEQ ID NO: 132)

Ac-Nle-c(Cys-His-D-Phe-Arg-D-Trp-D-Ala-Cys)-OH;
(SEQ ID NO: 133)

Ac-Nle-c(Cys-D-Ala-His-D-2-Nal-Arg-Trp-Cys)-OH;
(SEQ ID NO: 134)

Ac-Nle-c(Cys-D-Ala-His-D-2-Nal-Arg-2-Nal-Cys)-OH;
(SEQ ID NO: 135)

Ac-Nle-c(Cys-D-Ala-His-D-2-Nal-Arg-1-Nal-Cys)-OH;
(SEQ ID NO: 136)

-continued

Ac-Nle-c(Cys-D-Ala-His-D-2-Nal-Arg-Bal-Cys)-OH;

(SEQ ID NO: 137)
Ac-Nle-c(Pen-D-Ala-His-D-Phe-Arg-Trp-Cys)-OH;

(SEQ ID NO: 138)
Ac-Nle-c(Cys-His-D-Phe-Arg-Trp-Gaba-Pen)-OH;

(SEQ ID NO: 139)
Ac-Arg-c(Cys-D-Ala-His-D-2-Nal-Arg-Trp-Cys)-NH$_2$;

(SEQ ID NO: 140)
Ac-Arg-c(Cys-D-Ala-His-D-Phe-Arg-Trp-Cys)-NH$_2$;

(SEQ ID NO: 141)
Ac-D-Arg-c(Cys-D-Ala-His-D-Phe-Arg-Trp-Cys)-NH$_2$;

(SEQ ID NO: 142)
Ac-D-Arg-c(Cys-D-Ala-His-D-Phe-Arg-Trp-Pen)-NH$_2$;

(SEQ ID NO: 143)
Ac-D-Arg-c(Cys-His-D-Phe-Arg-Trp-Gaba-Pen)-NH$_2$;

(SEQ ID NO: 144)
Ac-Arg-c(Cys-His-D-Phe-Arg-Trp-Gaba-Pen)-NH$_2$;

(SEQ ID NO: 145)
Ac-Arg-c(Cys-D-Ala-His-D-Phe-Arg-Trp-Pen)-NH$_2$;

(SEQ ID NO: 146)
Ac-D-Arg-c(Asp-His-D-Phe-Arg-Trp-Ala-Lys)-NH$_2$;

(SEQ ID NO: 147)
Ac-Arg-c(Asp-His-D-Phe-Arg-Trp-Ala-Lys)-NH$_2$;

(SEQ ID NO: 148)
Ac-Nle-c(Cys-D-Ala-His-D-Phe-Arg-Trp-Gly-Cys)-NH$_2$;

(SEQ ID NO: 149)
Ac-Nle-c(Cys-D-Ala-His-D-Phe-Arg-Trp-D-Ala-Cys)-NH$_2$;

(SEQ ID NO: 150)
Ac-Nle-c(Cys-D-Ala-His-D-Phe-Arg-Trp-β-Ala-Cys)-NH$_2$;

(SEQ ID NO: 151)
Ac-Nle-c(Cys-D-Ala-His-D-Phe-Arg-Trp-Gaba-Cys)-NH$_2$;

(SEQ ID NO: 152)
Ac-Nle-c(Cys-D-Ala-His-D-Phe-Arg-Trp-Apn-Cys)-NH$_2$;

(SEQ ID NO: 153)
Ac-c(Cys-Glu-His-D-Phe-Arg-Trp-Ala-Cys)-NH$_2$;

(SEQ ID NO: 154)
Ac-c(Cys-Glu-His-D-Phe-Arg-2-Nal-Ala-Cys)-NH$_2$;

(SEQ ID NO: 155)
Ac-c(Cys-D-Ala-His-D-Phe-Arg-Trp-Ala-Cys)-NH$_2$;

(SEQ ID NO: 156)
Ac-c(Cys-D-Ala-His-D-Phe-Arg-2-Nal-Ala-Cys)-NH$_2$;

(SEQ ID NO: 157)
Ac-Nle-c(Cys-D-Ala-His-D-Phe-Arg-Trp-Ala-Cys)-NH$_2$;

(SEQ ID NO: 158)
Ac-Nle-c(Asp-D-Ala-His-D-Phe-Arg-Bal-Ala-Lys)-NH$_2$;

(SEQ ID NO: 159)
Tyr-Gly-Arg-(Lys)$_2$-(Arg)$_2$-Gln-(Arg)$_3$-Nle-c(Asp-His-D-2-Nal-Arg-Trp-Lys)-NH$_2$;

(SEQ ID NO: 160)
Tyr-Gly-Arg-(Lys)$_2$-(Arg)$_2$-Gln-(Arg)$_3$-Doc-Nle-c(Asp-His-D-2-Nal-Arg-Trp-Lys)-NH$_2$;

(SEQ ID NO: 161)
Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

(SEQ ID NO: 162)
Ac-Nle-c(Asp-His-D-2-Nal-Arg-Trp-Lys)-β-Ala-Tyr-Gly-Arg-(Lys)$_2$-(Arg)$_2$-Gln-(Arg)$_3$-NH$_2$;

```
                                                              (SEQ ID NO: 163)
Nle-c(Asp-His-D-2-Nal-Arg-Trp-Lys)-(Doc)2-Tyr-Gly-Arg-(Lys)2-(Arg)2-Gln-(Arg)3-NH2;

(SEQ ID NO: 164)
Ac-Nle-c(Asp-His-D-2-Nal-Arg-Trp-Lys)-(Pro)2-Lys-Asp-Tyr-Gly-Arg-(Lys)2-(Arg)2-Gln- (Arg)3-NH2;

(SEQ ID NO: 165)
Ac-c(Cys-Glu-His-D-2-Nal-Arg-Trp-Gly-Cys)-(Pro)2-Lys-Asp-Tyr-Gly-Arg-(Lys)2-(Arg)2-

Gln-(Arg)3-NH2;

(SEQ ID NO: 166)
Ac-Nle-c(Asp-His-D-2-Nal-Arg-Trp-Lys)-(β-Ala)2-Tyr-Gly-Arg-(Lys)2-(Arg)2-Gln-(Arg)3-

NH2;

(SEQ ID NO: 167)
Ac-Nle-c(Asp-His-D-2-Nal-Arg-Trp-Lys)-(Pro)2-Lys-Asp-Doc-Tyr-Gly-Arg-(Lys)2-(Arg)2-

Gln-(Arg)3-NH2;

(SEQ ID NO: 168)
Ac-c(Cys-Glu-His-D-2-Nal-Arg-Trp-Gly-Cys)-(Pro)2-Lys-Asp-Doc-Tyr-Gly-Arg-(Lys)2-

(Arg)2-Gln-(Arg)3-NH2;

(SEQ ID NO: 169)
Ac-c(Cys-Glu-His-D-2-Nal-Arg-Trp-Ala-Cys)-(Pro)2-Lys-Asp-β-Ala-Tyr-Gly-Arg-(Lys)2-

(Arg)2-Gln-(Arg)3-NH2;

(SEQ ID NO: 170)
Ac-c(Cys-Glu-His-D-2-Nal-Arg-Trp-Ala-Cys)-(Pro)2-Lys-Asp-Doc-Tyr-Gly-Arg-(Lys)2-
(Arg)2-Gln-(Arg)3-NH2;

(SEQ ID NO: 171)
Ac-Nle-c(Asp-His-D-2-Nal-Arg-Trp-Lys)-(Doc)2-Tyr-Gly-Arg-(Lys)2-(Arg)2-Gln-(Arg)3-

NH2;

(SEQ ID NO: 172)
Ac-c(Cys-Glu-His-D-2-Nal-Arg-2-Nal-Ala-Cys)-(Pro)2-Lys-Asp-β-Ala-Tyr-Gly-Arg- (Lys)2-(Arg)2-Gln-(Arg)3-NH2;

(SEQ ID NO: 173)
Ac-c(Cys-Glu-His-D-2-Nal-Arg-Bal-Ala-Cys)-(Pro)2-Lys-Asp-β-Ala-(Arg)5-Gln-(Arg)3-

NH2;

(SEQ ID NO: 174)
Ac-c(Cys-Glu-His-D-2-Nal-Arg-Bal-Ala-Cys)-(Pro)2-Lys-Asp-β-Ala-Gly-(Arg)5-Gln- (Arg)3-NH2;

(SEQ ID NO: 175)
Ac-c(Cys-Glu-His-D-2-Nal-Arg-Bal-Ala-Cys)-(Pro)2-Lys-Asp-β-Ala-Tyr-Gly-(Arg)5-Gln- (Arg)3-NH2;

(SEQ ID NO: 176)
Ac-c(Cys-Glu-His-D-2-Nal-Arg-Trp-Ala-Cys)-(Pro)2-Lys-Asp-β-Ala-Tyr-Gly-Arg-(Lys)2-

Arg-Gln-(Arg)4-NH2;

(SEQ ID NO: 177)
Ac-c(Cys-Glu-His-D-2-Nal-Arg-Trp-Ala-Cys)-(Pro)2-Lys-Asp-β-Ala-Tyr-Gly-Arg-(Lys)2-

Gln-(Arg)5-NH2;

(SEQ ID NO: 178)
Ac-c(Cys-Glu-His-D-2-Nal-Arg-Trp-Ala-Cys)-(Pro)2-Lys-Asp-β-Ala-Tyr-Gly-Arg-Lys-

Gln-Lys-(Arg)5-NH2;

(SEQ ID NO: 179)
Ac-c(Cys-Glu-His-D-2-Nal-Arg-Trp-Ala-Cys)-(Pro)2-Lys-Asp-β-Ala-Tyr-Gly-Arg-(Lys)2-
```

-continued (Arg)₄-Gln-Arg-NH₂;

(SEQ ID NO: 180)
Ac-c(Cys-Glu-His-D-2-Nal-Arg-Bal-Ala-Cys)-(Pro)₂-Lys-Asp-β-Ala-Tyr-Aib-Arg-(Lys)₂-(Arg)₂-Gln-(Arg)₃-NH₂;

(SEQ ID NO: 181)
Ac-c(Cys-Glu-His-D-2-Nal-Arg-1-Nal-Ala-Cys)-(Pro)₂-Arg-Asp-β-Ala-(Arg)₅-Gln-(Arg)₃-NH₂;

(SEQ ID NO: 182)
Ac-c(Cys-Glu-His-D-2-Nal-Arg-1-Nal-Ala-Cys)-(Pro)₂-Lys-Asp-β-Ala-(Arg)₅-Gln-(Arg)₃-NH₂;

(SEQ ID NO: 183)
Ac-c(Cys-Glu-His-D-2-Nal-Arg-1-Nal-Ala-Cys)-(Pro)₂-Lys-Asp-β-Ala-(Arg)₆-Gln-(Arg)₃-NH₂;

(SEQ ID NO: 184)
Ac-c(Cys-Glu-His-D-2-Nal-Arg-2-Nal-Ala-Cys)-(Pro)₂-Arg-Asp-β-Ala-(Arg)₅-Gln-(Arg)₃-NH₂;

(SEQ ID NO: 185)
Ac-c(Cys-Glu-His-D-2-Nal-Arg-2-Nal-Ala-Cys)-(Pro)₂-Lys-Asp-β-Ala-(Arg)₅-Gln-(Arg)₃-NH₂;

(SEQ ID NO: 186)
Ac-c(Cys-Glu-His-D-2-Nal-Arg-2-Nal-Ala-Cys)-(Pro)₂-Lys-Asp-β-Ala-(Arg)₆-Gln-(Arg)₃-NH₂;

(SEQ ID NO: 187)
Ac-c(Cys-Glu-His-D-2-Nal-Arg-Bal-Ala-Cys)-(Pro)₂-Arg-Asp-β-Ala-(Arg)₆-Gln-(Arg)₃-NH₂;

(SEQ ID NO: 188)
Ac-c(Cys-Glu-His-D-2-Nal-Arg-Bal-Ala-Cys)-(Pro)₂-Arg-Asp-β-Ala-(Arg)₅-Gln-(Arg)₃-NH₂;

(SEQ ID NO: 189)
Ac-c(Cys-Glu-His-D-2-Nal-Arg-Bal-Ala-Cys)-(Pro)₂-Lys-Asp-β-Ala-(Arg)₆-Gln-(Arg)₃-NH₂;

(SEQ ID NO: 190)
Ac-c(Cys-Glu-His-D-2-Nal-Arg-Trp-Ala-Cys)-(Pro)₂-Lys-Asp-β-Ala-Tyr-Gly-Arg-(Lys)₂-(Arg)₃-Gln-(Arg)₂-NH₂;

(SEQ ID NO: 191)
Ac-c(Cys-Glu-His-D-2-Nal-Arg-Trp-Ala-Cys)-(Pro)₂-Lys-Asp-β-Ala-Tyr-Gly-Arg-Gln-(Lys)₂-(Arg)₅-NH₂;

(SEQ ID NO: 192)
Ac-c(Cys-Glu-His-D-2-Nal-Arg-Trp-Ala-Cys)-(Pro)₂-Lys-Asp-β-Ala-Tyr-Gly-Arg-(Lys)₂-(Arg)₅-Gln-NH₂;

(SEQ ID NO: 193)
Ac-c(Cys-Glu-His-D-2-Nal-Arg-1-Nal-Ala-Cys)-(Pro)₂-Lys-Asp-β-Ala-Tyr-Gly-Arg-(Lys)₂-(Arg)₂-Gln-(Arg)₃-NH₂;

(SEQ ID NO: 194)
Ac-c(Cys-Glu-His-D-2-Nal-Arg-Bal-Ala-Cys)-(Pro)₂-Lys-Asp-β-Ala-Tyr-Gly-Arg-(Lys)₂-(Arg)₂-Gln-(Arg)₃-NH₂;

(SEQ ID NO: 195)
Ac-c(Cys-Glu-His-D-2-Nal-Arg-1-Nal-Ala-Cys)-(Pro)₂-Lys-Asp-β-Ala-(Arg)₂-Lys-(Arg)₂-Gln-(Arg)₃-NH₂;

```
                                                                (SEQ ID NO: 196)
Ac-c(Cys-Glu-His-D-2-Nal-Arg-1-Nal-Ala-Cys)-(Pro)₂-Lys-Asp-β-Ala-Arg-Lys-(Arg)₃-

Gln-(Arg)₃-NH₂;

(SEQ ID NO: 197)
Ac-c(Cys-Glu-His-D-2-Nal-Arg-2-Nal-Ala-Cys)-(Pro)₂-Lys-Asp-β-Ala-(Arg)₂-Lys-(Arg)₂-

Gln-(Arg)₃-NH₂;

(SEQ ID NO: 198)
Ac-c(Cys-Glu-His-D-2-Nal-Arg-2-Nal-Ala-Cys)-(Pro)₂-Lys-Asp-β-Ala-Tyr-Gly-(Arg)₂-

Lys-(Arg)₂-Gln-(Arg)₃-NH₂;

(SEQ ID NO: 199)
Ac-c(Cys-Glu-His-D-2-Nal-Arg-2-Nal-Ala-Cys)-(Pro)₂-Lys-Asp-β-Ala-Gly-(Arg)₂-Lys- (Arg)₂-Gln-(Arg)₃-NH₂;

(SEQ ID NO: 200)
Ac-c(Cys-Glu-His-D-2-Nal-Arg-2-Nal-Ala-Cys)-(Pro)₂-Lys-Asp-β-Ala-Gly-Arg-Lys- (Arg)₃-Gln-(Arg)₃-NH₂;

(SEQ ID NO: 201)
Ac-c(Cys-Glu-His-D-2-Nal-Arg-1-Nal-Ala-Cys)-(Pro)₂-Lys-Asp-β-Ala-Tyr-Gly-(Arg)₂-

Lys-(Arg)₂-Gln-(Arg)₃-NH₂;

(SEQ ID NO: 202)
Ac-c(Cys-Glu-His-D-2-Nal-Arg-1-Nal-Ala-Cys)-(Pro)₂-Lys-Asp-β-Ala-Tyr-Gly-Arg-Lys- (Arg)₃-Gln-(Arg)₃-NH₂;

(SEQ ID NO: 203)
Ac-c(Cys-Glu-His-D-2-Nal-Arg-1-Nal-Ala-Cys)-(Pro)₂-Lys-Asp-β-Ala-Gly-(Arg)₂-Lys- (Arg)₂-Gln-(Arg)₃-NH₂;

(SEQ ID NO: 204)
Ac-c(Cys-Glu-His-D-2-Nal-Arg-1-Nal-Ala-Cys)-(Pro)₂-Lys-Asp-β-Ala-Gly-Arg-Lys- (Arg)₃-Gln-(Arg)₃-NH₂;

(SEQ ID NO: 205)
Ac-c(Cys-Glu-His-D-2-Nal-Arg-2-Nal-Ala-Cys)-(Pro)₂-Lys-Asp-β-Ala-(Arg)₂-Lys-(Arg)₂-

Gln-(Arg)₃-NH₂;

(SEQ ID NO: 206)
Ac-c(Cys-Glu-His-D-2-Nal-Arg-2-Nal-Ala-Cys)-(Pro)₂-Lys-Asp-β-Ala-Arg-Lys-(Arg)₃-

Gln-(Arg)₃-NH₂;

(SEQ ID NO: 207)
Ac-c(Cys-Glu-His-D-2-Nal-Arg-2-Nal-Ala-Cys)-(Pro)₂-Lys-Asp-β-Ala-Tyr-Gly-Arg-Lys- (Arg)₃-Gln-(Arg)₃-NH₂;

(SEQ ID NO: 208)
Ac-c(Cys-Glu-His-D-2-Nal-Arg-Bal-Ala-Cys)-(Pro)₂-Lys-Asp-β-Ala-(Arg)₂-Lys-(Arg)₂-

Gln-(Arg)₃-NH₂;

(SEQ ID NO: 209)
Ac-c(Cys-Glu-His-D-2-Nal-Arg-Bal-Ala-Cys)-(Pro)₂-Lys-Asp-β-Ala-Arg-Lys-(Arg)₃-Gln- (Arg)₃-NH₂;

(SEQ ID NO: 210)
Ac-c(Cys-Glu-His-D-2-Nal-Arg-Bal-Ala-Cys)-(Pro)₂-Lys-Asp-β-Ala-Tyr-Gly-(Arg)₂-Lys- (Arg)₂-Gln-(Arg)₃-NH₂;

(SEQ ID NO: 211)
Ac-c(Cys-Glu-His-D-2-Nal-Arg-Bal-Ala-Cys)-(Pro)₂-Lys-Asp-β-Ala-Tyr-Gly-Arg-Lys- (Arg)₃-Gln-(Arg)₃-NH₂;
```

-continued (SEQ ID NO: 212)
Ac-c(Cys-Glu-His-D-2-Nal-Arg-Bal-Ala-Cys)-(Pro)$_2$-Lys-Asp-β-Ala-Gly-(Arg)$_2$-Lys-(Arg)$_2$-Gln-(Arg)$_3$-NH$_2$;

(SEQ ID NO: 213)
Ac-c(Cys-Glu-His-D-2-Nal-Arg-Bal-Ala-Cys)-(Pro)$_2$-Lys-Asp-β-Ala-Gly-Arg-Lys-(Arg)$_3$-Gln-(Arg)$_3$-NH$_2$;

(SEQ ID NO: 214)
Ac-c(Cys-Glu-His-D-2-Nal-Arg-Trp-Ala-Cys)-(Pro)$_2$-Lys-Asp-β-Ala-(Arg)$_5$-Gln-(Arg)$_3$-NH$_2$;

(SEQ ID NO: 215)
Ac-c(Cys-Glu-His-D-2-Nal-Arg-Trp-Ala-Cys)-(Pro)$_2$-Arg-Asp-β-Ala-(Arg)$_5$-Gln-(Arg)$_3$-NH$_2$;

(SEQ ID NO: 216)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_3$-NH$_2$;

(SEQ ID NO: 217)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_3$-NH$_2$;

(SEQ ID NO: 218)
Ac-c(Cys-Glu-His-D-2-Nal-Arg-Trp-Ala-Cys)-(Pro)$_2$-Lys-Asp-β-Ala-(Arg)$_5$-Gln-(Arg)$_4$-NH$_2$;

(SEQ ID NO: 219)
Ac-c(Cys-Glu-His-D-2-Nal-Arg-Trp-Ala-Cys)-(Pro)$_2$-Arg-Asp-β-Ala-(Arg)$_5$-Gln-(Arg)$_4$-NH$_2$;

(SEQ ID NO: 220)
Ac-c(Cys-Glu-His-D-2-Nal-Arg-Trp-Ala-Cys)-(Pro)$_2$-Lys-Asp-β-Ala-Tyr-Gly-(Arg)$_5$-Gln-(Arg)$_4$-NH$_2$;

(SEQ ID NO: 221)
Ac-c(Cys-Glu-His-D-2-Nal-Arg-Trp-Ala-Cys)-(Pro)$_2$-Arg-Asp-β-Ala-Tyr-Gly-(Arg)$_5$-Gln-(Arg)$_4$-NH$_2$;

(SEQ ID NO: 222)
Ac-c(Cys-Glu-His-D-2-Nal-Arg-1-Nal-Ala-Cys)-(Pro)$_2$-Lys-Asp-β-Ala-(Arg)$_5$-Gln-(Arg)$_4$-NH$_2$;

(SEQ ID NO: 223)
Ac-c(Cys-Glu-His-D-2-Nal-Arg-1-Nal-Ala-Cys)-(Pro)$_2$-Arg-Asp-β-Ala-(Arg)$_5$-Gln-(Arg)$_4$-NH$_2$;

(SEQ ID NO: 224)
Ac-c(Cys-Glu-His-D-2-Nal-Arg-1-Nal-Ala-Cys)-(Pro)$_2$-Arg-Asp-β-Ala-(Arg)$_6$-Gln-(Arg)$_3$-NH$_2$;

(SEQ ID NO: 225)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_3$-NH$_2$;

(SEQ ID NO: 226)
Ac-c(Cys-Glu-His-D-2-Nal-Arg-1-Nal-Ala-Cys)-(Pro)$_2$-Arg-Asp-β-Ala-Tyr-Gly-(Arg)$_5$-Gln-(Arg)$_3$-NH$_2$;

(SEQ ID NO: 227)
Ac-c(Cys-Glu-His-D-2-Nal-Arg-1-Nal-Ala-Cys)-(Pro)$_2$-Lys-Asp-β-Ala-Tyr-Gly-(Arg)$_5$-Gln-(Arg)$_4$-NH$_2$;

(SEQ ID NO: 228)

```
Ac-c(Cys-Glu-His-D-2-Nal-Arg-1-Nal-Ala-Cys)-(Pro)₂-Arg-Asp-β-Ala-Tyr-Gly-(Arg)₅-
Gln-(Arg)₄-NH₂;

(SEQ ID NO: 229)
Ac-c(Cys-Glu-His-D-2-Nal-Arg-1-Nal-Ala-Cys)-(Pro)₂-Lys-Asp-β-Ala-Tyr-Gly-(Arg)₆-
Gln-(Arg)₃-NH₂;

(SEQ ID NO: 230)
Ac-c(Cys-Glu-His-D-2-Nal-Arg-1-Nal-Ala-Cys)-(Pro)₂-Arg-Asp-β-Ala-Tyr-Gly-(Arg)₆-
Gln-(Arg)₃-NH₂;

(SEQ ID NO: 231)
Ac-c(Cys-Glu-His-D-2-Nal-Arg-2-Nal-Ala-Cys)-(Pro)₂-Arg-Asp-β-Ala-(Arg)₆-Gln-(Arg)₃-
NH₂;

(SEQ ID NO: 232)
Ac-c(Cys-Glu-His-D-2-Nal-Arg-2-Nal-Ala-Cys)-(Pro)₂-Lys-Asp-β-Ala-(Arg)₅-Gln-(Arg)₄-
NH₂;

(SEQ ID NO: 233)
Ac-c(Cys-Glu-His-D-2-Nal-Arg-2-Nal-Ala-Cys)-(Pro)₂-Arg-Asp-β-Ala-(Arg)₅-Gln-(Arg)₄-
NH₂;

(SEQ ID NO: 234)
Ac-c(Cys-Glu-His-D-2-Nal-Arg-2-Nal-Ala-Cys)-(Pro)₂-Lys-Asp-β-Ala-Tyr-Gly-(Arg)₅-
Gln-(Arg)₃-NH₂;

(SEQ ID NO: 235)
Ac-c(Cys-Glu-His-D-2-Nal-Arg-2-Nal-Ala-Cys)-(Pro)₂-Arg-Asp-β-Ala-Tyr-Gly-(Arg)₅-
Gln-(Arg)₃-NH₂;

(SEQ ID NO: 236)
Ac-c(Cys-Glu-His-D-2-Nal-Arg-2-Nal-Ala-Cys)-(Pro)₂-Lys-Asp-β-Ala-Tyr-Gly-(Arg)₆-
Gln-(Arg)₃-NH₂;

(SEQ ID NO: 237)
Ac-c(Cys-Glu-His-D-2-Nal-Arg-2-Nal-Ala-Cys)-(Pro)₂-Arg-Asp-β-Ala-Tyr-Gly-(Arg)₆-
Gln-(Arg)₃-NH₂;

(SEQ ID NO: 238)
Ac-c(Cys-Glu-His-D-2-Nal-Arg-2-Nal-Ala-Cys)-(Pro)₂-Lys-Asp-β-Ala-Tyr-Gly-(Arg)₅-
Gln-(Arg)₄-NH₂;

(SEQ ID NO: 239)
Ac-c(Cys-Glu-His-D-2-Nal-Arg-2-Nal-Ala-Cys)-(Pro)₂-Arg-Asp-β-Ala-Tyr-Gly-(Arg)₅-
Gln-(Arg)₄-NH₂;

(SEQ ID NO: 240)
Ac-c(Cys-Glu-His-D-2-Nal-Arg-Bal-Ala-Cys)-(Pro)₂-Lys-Asp-β-Ala-(Arg)₅-Gln-(Arg)₄-
NH₂;

(SEQ ID NO: 241)
Ac-c(Cys-Glu-His-D-2-Nal-Arg-Bal-Ala-Cys)-(Pro)₂-Arg-Asp-β-Ala-(Arg)₅-Gln-(Arg)₄-
NH₂;

(SEQ ID NO: 242)
Ac-c(Cys-Glu-His-D-2-Nal-Arg-Bal-Ala-Cys)-(Pro)₂-Arg-Asp-β-Ala-Tyr-Gly-(Arg)₅-Gln-
(Arg)₃-NH₂;

(SEQ ID NO: 243)
Ac-c(Cys-Glu-His-D-2-Nal-Arg-Bal-Ala-Cys)-(Pro)₂-Lys-Asp-β-Ala-Tyr-Gly-(Arg)₅-Gln-
(Arg)₄-NH₂;

(SEQ ID NO: 244)
Ac-c(Cys-Glu-His-D-2-Nal-Arg-Bal-Ala-Cys)-(Pro)₂-Arg-Asp-β-Ala-Tyr-Gly-(Arg)₅-Gln-
```

-continued (Arg)₄-NH₂;

(SEQ ID NO: 245)
Ac-c(Cys-Glu-His-D-2-Nal-Arg-Bal-Ala-Cys)-(Pro)₂-Lys-Asp-β-Ala-Tyr-Gly-(Arg)₆-Gln-(Arg)₃-NH₂;

(SEQ ID NO: 246)
Ac-c(Cys-Glu-His-D-2-Nal-Arg-Bal-Ala-Cys)-(Pro)₂-Arg-Asp-β-Ala-Tyr-Gly-(Arg)₆-Gln-(Arg)₃-NH₂;

(SEQ ID NO: 247)
Ac-Nle-c(Cys-D-Ala-His-D-Phe-Arg-Trp-Cys)-(Doc)₂-Tyr-Gly-Arg-(Lys)₂-(Arg)₂-Gln-(Arg)₃-NH₂;

(SEQ ID NO: 248)
Ac-Nle-c(Cys-D-Ala-His-D-Phe-Arg-Trp-Cys)-β-Ala-Tyr-Gly-Arg-(Lys)₂-Arg-Gln-(Arg)₄-NH₂;

(SEQ ID NO: 249)
Ac-Nle-c(Cys-D-Ala-His-D-Phe-Arg-Trp-Cys)-Doc-Tyr-Gly-Arg-(Lys)₂-(Arg)₂-Gln-(Arg)₃-NH₂;

(SEQ ID NO: 250)
Ac-Nle-c(Cys-D-Ala-His-D-Phe-Arg-Trp-Cys)-β-Ala-(Arg)₅-Gln-(Arg)₃-NH₂;

(SEQ ID NO: 251)
Ac-Nle-c(Cys-D-Ala-His-D-Phe-Arg-Trp-Cys)-β-Ala-Gly-(Arg)₅-Gln-(Arg)₃-NH₂;

(SEQ ID NO: 252)
Ac-Nle-c(Cys-D-Ala-His-D-Phe-Arg-Trp-Cys)-β-Ala-Tyr-Gly-(Arg)₅-Gln-(Arg)₃-NH₂;

(SEQ ID NO: 253)
Ac-Nle-c(Cys-D-Ala-His-D-Phe-Arg-Trp-Cys)-β-Ala-Gly-(Arg)₅-Gln-(Arg)₄-NH₂;

(SEQ ID NO: 254)
Ac-Nle-c(Cys-D-Ala-His-D-Phe-Arg-Trp-Cys)-β-Ala-Tyr-Gly-(Arg)₂-Lys-(Arg)₂-Gln-(Arg)₃-NH₂;

(SEQ ID NO: 255)
Ac-Nle-c(Cys-D-Ala-His-D-Phe-Arg-Trp-Cys)-β-Ala-Tyr-Gly-Arg-Lys-(Arg)₃-Gln-(Arg)₃-NH₂;

(SEQ ID NO: 256)
Ac-Nle-c(Cys-D-Ala-His-D-Phe-Arg-Trp-Cys)-β-Ala-Gly-(Arg)₂-Lys-(Arg)₂-Gln-(Arg)₃-NH₂;

(SEQ ID NO: 257)
Ac-Nle-c(Cys-D-Ala-His-D-Phe-Arg-Trp-Cys)-β-Ala-Gly-Arg-Lys-(Arg)₃-Gln-(Arg)₃-NH₂;

(SEQ ID NO: 258)
Ac-Nle-c(Cys-D-Ala-His-D-Phe-Arg-Trp-Cys)-β-Ala-(Arg)₂-Lys-(Arg)₂-Gln-(Arg)₃-NH₂;

(SEQ ID NO: 259)
Ac-Nle-c(Cys-D-Ala-His-D-Phe-Arg-Trp-Cys)-β-Ala-Arg-Lys-(Arg)₃-Gln-(Arg)₃-NH₂;

(SEQ ID NO: 260)
Ac-Nle-c(Cys-D-Ala-His-D-Phe-Arg-Trp-Cys)-(β-Ala)₂-(Arg)₅-Gln-(Arg)₃-NH₂;

(SEQ ID NO: 261)
Ac-Nle-c(Cys-D-Ala-His-D-Phe-Arg-Trp-Cys)-(β-Ala)₂-Gly-(Arg)₅-Gln-(Arg)₃-NH₂;

(SEQ ID NO: 262)
Ac-Nle-c(Cys-D-Ala-His-D-Phe-Arg-Trp-Cys)-(β-Ala)₂-Tyr-Gly-(Arg)₅-Gln-(Arg)₃-NH₂;

(SEQ ID NO: 263)
Ac-Nle-c(Cys-D-Ala-His-D-Phe-Arg-Trp-Cys)-Doc-(Arg)₅-Gln-(Arg)₃-NH₂;

(SEQ ID NO: 264)
Ac-Nle-c(Cys-D-Ala-His-D-Phe-Arg-Trp-Cys)-Doc-Gly-(Arg)₅-Gln-(Arg)₃-NH₂;

(SEQ ID NO: 265)
Ac-Nle-c(Cys-D-Ala-His-D-Phe-Arg-Trp-Cys)-Doc-Tyr-Gly-(Arg)₅-Gln-(Arg)₃-NH₂;

-continued

Ac-Nle-c(Cys-D-Ala-His-D-Phe-Arg-Trp-Cys)-(Doc)$_2$-(Arg)$_5$-Gln-(Arg)$_3$-NH$_2$; (SEQ ID NO: 266)

Ac-Nle-c(Cys-D-Ala-His-D-Phe-Arg-Trp-Cys)-(Doc)$_2$-Gly-(Arg)$_5$-Gln-(Arg)$_3$-NH$_2$; (SEQ ID NO: 267)

Ac-Nle-c(Cys-D-Ala-His-D-Phe-Arg-Trp-Cys)-(Doc)$_2$-Tyr-Gly-(Arg)$_5$-Gln-(Arg)$_3$-NH$_2$; (SEQ ID NO: 268)

Ac-Nle-c(Cys-D-Ala-His-D-Phe-Arg-Trp-Cys)-β-Ala-(Arg)$_5$-Gln-(Arg)$_4$-NH$_2$; (SEQ ID NO: 269)

Ac-Nle-c(Cys-D-Ala-His-D-Phe-Arg-Trp-Cys)-β-Ala-Tyr-Gly-(Arg)$_5$-Gln-(Arg)$_4$-NH$_2$; (SEQ ID NO: 270)

Ac-Nle-c(Cys-D-Ala-His-D-Phe-Arg-Trp-Cys)-(β-Ala)$_2$-(Arg)$_5$-Gln-(Arg)$_4$-NH$_2$; (SEQ ID NO: 271)

Ac-Nle-c(Cys-D-Ala-His-D-Phe-Arg-Trp-Cys)-(β-Ala)$_2$-Gly-(Arg)$_5$-Gln-(Arg)$_4$-NH$_2$; (SEQ ID NO: 272)

Ac-Nle-c(Cys-D-Ala-His-D-Phe-Arg-Trp-Cys)-(β-Ala)$_2$-Tyr-Gly-(Arg)$_5$-Gln-(Arg)$_4$-NH$_2$; (SEQ ID NO: 273)

Ac-Nle-c(Cys-D-Ala-His-D-Phe-Arg-Trp-Cys)-Doc-(Arg)$_5$-Gln-(Arg)$_4$-NH$_2$; (SEQ ID NO: 274)

Ac-Nle-c(Cys-D-Ala-His-D-Phe-Arg-Trp-Cys)-Doc-Gly-(Arg)$_5$-Gln-(Arg)$_4$-NH$_2$; (SEQ ID NO: 275)

Ac-Nle-c(Cys-D-Ala-His-D-Phe-Arg-Trp-Cys)-Doc-Tyr-Gly-(Arg)$_5$-Gln-(Arg)$_4$-NH$_2$; (SEQ ID NO: 276)

Ac-Nle-c(Cys-D-Ala-His-D-Phe-Arg-Trp-Cys)-(Doc)$_2$-(Arg)$_5$-Gln-(Arg)$_4$-NH$_2$; (SEQ ID NO: 277)

Ac-Nle-c(Cys-D-Ala-His-D-Phe-Arg-Trp-Cys)-(Doc)$_2$-Gly-(Arg)$_5$-Gln-(Arg)$_4$-NH$_2$; (SEQ ID NO: 278)

Ac-Nle-c(Cys-D-Ala-His-D-Phe-Arg-Trp-Cys)-(Doc)$_2$-Tyr-Gly-(Arg)$_5$-Gln-(Arg)$_4$-NH$_2$; (SEQ ID NO: 279)

Ac-Nle-c(Cys-His-D-Phe-Arg-Trp-Gaba-Cys)-β-Ala-Tyr-Gly-(Arg)$_5$-Gln-(Arg)$_3$-NH$_2$; (SEQ ID NO: 280)

Ac-Nle-c(Cys-His-D-Phe-Arg-Trp-Gaba-Cys)-β-Ala-(Arg)$_5$-Gln-(Arg)$_3$-NH$_2$; (SEQ ID NO: 281)

Ac-Nle-c(Asp-His-D-Phe-Arg-Trp-Ala-Lys)-β-Ala-Tyr-Gly-(Arg)$_5$-Gln-(Arg)$_3$-NH$_2$; (SEQ ID NO: 282)

Ac-Nle-c(Asp-His-D-Phe-Arg-Trp-Ala-Lys)-β-Ala-(Arg)$_5$-Gln-(Arg)$_3$-NH$_2$; (SEQ ID NO: 283)

Ac-Nle-c(Asp-His-D-Phe-Arg-Trp-Lys)-β-Ala-Tyr-Gly-(Arg)$_5$-Gln-(Arg)$_3$-NH$_2$; (SEQ ID NO: 284)

Ac-Nle-c(Asp-His-D-Phe-Arg-Trp-Lys)-β-Ala-Gly-(Arg)$_5$-Gln-(Arg)$_3$-NH$_2$; (SEQ ID NO: 285)

Ac-Nle-c(Asp-His-D-Phe-Arg-Trp-Lys)-β-Ala-(Arg)$_5$-Gln-(Arg)$_3$-NH$_2$; (SEQ ID NO: 286)

Ac-Nle-c(Asp-His-D-Phe-Arg-Trp-Lys)-(β-Ala)$_2$-Tyr-Gly-(Arg)$_5$-Gln-(Arg)$_3$-NH$_2$; (SEQ ID NO: 287)

Ac-Nle-c(Asp-His-D-Phe-Arg-Trp-Lys)-(β-Ala)$_2$-Gly-(Arg)$_5$-Gln-(Arg)$_3$-NH$_2$; (SEQ ID NO: 288)

Ac-Nle-c(Asp-His-D-Phe-Arg-Trp-Lys)-(β-Ala)$_2$-(Arg)$_5$-Gln-(Arg)$_3$-NH$_2$; (SEQ ID NO: 289)

Ac-Nle-c(Asp-His-D-Phe-Arg-Trp-Lys)-Doc-Tyr-Gly-(Arg)$_5$-Gln-(Arg)$_3$-NH$_2$; (SEQ ID NO: 290)

Ac-Nle-c(Asp-His-D-Phe-Arg-Trp-Lys)-Doc-Gly-(Arg)$_5$-Gln-(Arg)$_3$-NH$_2$; (SEQ ID NO: 291)

Ac-Nle-c(Asp-His-D-Phe-Arg-Trp-Lys)-Doc-(Arg)$_5$-Gln-(Arg)$_3$-NH$_2$; (SEQ ID NO: 292)

-continued

```
                                                                  (SEQ ID NO: 293)
Ac-Nle-c(Asp-His-D-Phe-Arg-Trp-Lys)-(Doc)₂-Tyr-Gly-(Arg)₅-Gln-(Arg)₃-NH₂;

(SEQ ID NO: 294)
Ac-Nle-c(Asp-His-D-Phe-Arg-Trp-Lys)-(Doc)₂-Gly-(Arg)₅-Gln-(Arg)₃-NH₂;

(SEQ ID NO: 295)
Ac-Nle-c(Asp-His-D-Phe-Arg-Trp-Lys)-(Doc)₂-(Arg)₅-Gln-(Arg)₃-NH₂;

(SEQ ID NO: 296)
Ac-Nle-c(Asp-His-D-Phe-Arg-Trp-Lys)-β-Ala-Tyr-Gly-(Arg)₅-Gln-(Arg)₄-NH₂;

(SEQ ID NO: 297)
Ac-Nle-c(Asp-His-D-Phe-Arg-Trp-Lys)-β-Ala-Gly-(Arg)₅-Gln-(Arg)₄-NH₂;

(SEQ ID NO: 298)
Ac-Nle-c(Asp-His-D-Phe-Arg-Trp-Lys)-β-Ala-(Arg)₅-Gln-(Arg)₄-NH₂;

(SEQ ID NO: 299)
Ac-Nle-c(Asp-His-D-Phe-Arg-Trp-Lys)-(β-Ala)₂-Tyr-Gly-(Arg)₅-Gln-(Arg)₄-NH₂;

(SEQ ID NO: 300)
Ac-Nle-c(Asp-His-D-Phe-Arg-Trp-Lys)-(β-Ala)₂-Gly-(Arg)₅-Gln-(Arg)₄-NH₂;

(SEQ ID NO: 301)
Ac-Nle-c(Asp-His-D-Phe-Arg-Trp-Lys)-(β-Ala)₂-(Arg)₅-Gln-(Arg)₄-NH₂;

(SEQ ID NO: 302)
Ac-Nle-c(Asp-His-D-Phe-Arg-Trp-Lys)-Doc-Tyr-Gly-(Arg)₅-Gln-(Arg)₄-NH₂;

(SEQ ID NO: 303)
Ac-Nle-c(Asp-His-D-Phe-Arg-Trp-Lys)-Doc-Gly-(Arg)₅-Gln-(Arg)₄-NH₂;

(SEQ ID NO: 304)
Ac-Nle-c(Asp-His-D-Phe-Arg-Trp-Lys)-Doc-(Arg)₅-Gln-(Arg)₄-NH₂;

(SEQ ID NO: 305)
Ac-Nle-c(Asp-His-D-Phe-Arg-Trp-Lys)-(Doc)₂-Tyr-Gly-(Arg)₅-Gln-(Arg)₄-NH₂;

(SEQ ID NO: 306)
Ac-Nle-c(Asp-His-D-Phe-Arg-Trp-Lys)-(Doc)₂-Gly-(Arg)₅-Gln-(Arg)₄-NH₂;

(SEQ ID NO: 307)
Ac-Nle-c(Asp-His-D-Phe-Arg-Trp-Lys)-(Doc)₂-(Arg)₅-Gln-(Arg)₄-NH₂;

(SEQ ID NO: 308)
Ac-Nle-c(Asp-His-D-Phe-Arg-Trp-β-Ala-Lys)-β-Ala-Tyr-Gly-(Arg)₅-Gln-(Arg)₃-NH₂;

(SEQ ID NO: 309)
Ac-Nle-c(Asp-His-D-Phe-Arg-Trp-β-Ala-Lys)-β-Ala-(Arg)₅-Gln-(Arg)₃-NH₂;

(SEQ ID NO: 310)
Ac-Nle-c(Cys-His-D-Phe-Arg-Trp-Ahx-Cys)-β-Ala-Tyr-Gly-(Arg)₅-Gln-(Arg)₃-NH₂;

(SEQ ID NO: 311)
Ac-Nle-c(Cys-His-D-Phe-Arg-Trp-Ahx-Cys)-β-Ala-(Arg)₅-Gln-(Arg)₃-NH₂;

(SEQ ID NO: 312)
D-Phe-c(Cys-His-D-Phe-Arg-Trp-β-Ala-D-Cys)-Thr-β-Ala-Tyr-Gly-(Arg)₅-Gln-(Arg)₃-
NH₂;

(SEQ ID NO: 313)
D-Phe-c(Cys-His-D-Phe-Arg-Trp-β-Ala-D-Cys)-Thr-β-Ala-(Arg)₅-Gln-(Arg)₃-NH₂;

(SEQ ID NO: 314)
Ac-Nle-c(Cys-His-D-Phe-Arg-Trp-Apn-Cys)-β-Ala-Tyr-Gly-(Arg)₅-Gln-(Arg)₃-NH₂;

(SEQ ID NO: 315)
Ac-Nle-c(Cys-His-D-Phe-Arg-Trp-Apn-Cys)-β-Ala-(Arg)₅-Gln-(Arg)₃-NH₂;

(SEQ ID NO: 316)
Ac-Cha-c(Asp-His-D-Phe-Arg-Trp-Gaba-Lys)-β-Ala-Tyr-Gly-(Arg)₅-Gln-(Arg)₃-NH₂;

(SEQ ID NO: 317)
Ac-Cha-c(Asp-His-D-Phe-Arg-Trp-Gaba-Lys)-β-Ala-(Arg)₅-Gln-(Arg)₃-NH₂;

(SEQ ID NO: 318)
Ac-Nle-c(Asp-His-D-Phe-Arg-Trp-Gaba-Lys)-β-Ala-Tyr-Gly-(Arg)₅-Gln-(Arg)₃-NH₂;
```

-continued (SEQ ID NO: 319)
Ac-Nle-c(Asp-His-D-Phe-Arg-Trp-Gaba-Lys)-β-Ala-(Arg)$_5$-Gln-(Arg)$_3$-NH$_2$;

(SEQ ID NO: 320)
Ac-Chg-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 321)
Ac-Chg-c(Asp-His-D-Phe-Arg-Trp-Gaba-Lys)-β-Ala-(Arg)$_5$-Gln-(Arg)$_3$-NH$_2$;

(SEQ ID NO: 322)
Ac-hCha-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 323)
Ac-hCha-c(Asp-His-D-Phe-Arg-Trp-Gaba-Lys)-β-Ala-(Arg)$_5$-Gln-(Arg)$_3$-NH$_2$;

(SEQ ID NO: 324)
Ac-hCha-c(Asp-His-D-Phe-Arg-Trp-Gaba-Lys)-(β-Ala)$_2$-Tyr-Gly-(Arg)$_5$-Gln-(Arg)$_3$-NH$_2$;

(SEQ ID NO: 325)
Ac-hCha-c(Asp-His-D-Phe-Arg-Trp-Gaba-Lys)-(β-Ala)$_2$-(Arg)$_5$-Gln-(Arg)$_3$-NH$_2$;

(SEQ ID NO: 326)
Ac-hCha-c(Asp-His-D-Phe-Arg-Trp-Gaba-Lys)-Doc-Tyr-Gly-(Arg)$_5$-Gln-(Arg)$_3$-NH$_2$;

(SEQ ID NO: 327)
Ac-hCha-c(Asp-His-D-Phe-Arg-Trp-Gaba-Lys)-Doc-(Arg)$_5$-Gln-(Arg)$_3$-NH$_2$;

(SEQ ID NO: 328)
Ac-hCha-c(Asp-His-D-Phe-Arg-Trp-Gaba-Lys)-(Doc)$_2$-Tyr-Gly-(Arg)$_5$-Gln-(Arg)$_3$-NH$_2$;

(SEQ ID NO: 329)
Ac-hCha-c(Asp-His-D-Phe-Arg-Trp-Gaba-Lys)-(Doc)$_2$-(Arg)$_5$-Gln-(Arg)$_3$-NH$_2$;

(SEQ ID NO: 330)
Ac-hCha-c(Asp-His-D-Phe-Arg-Trp-Gaba-Lys)-β-Ala-Tyr-Gly-(Arg)$_5$-Gln-(Arg)$_4$-NH$_2$;

(SEQ ID NO: 331)
Ac-hCha-c(Asp-His-D-Phe-Arg-Trp-Gaba-Lys)-β-Ala-(Arg)$_5$-Gln-(Arg)$_4$-NH$_2$;

(SEQ ID NO: 332)
Ac-hCha-c(Asp-His-D-Phe-Arg-Trp-Gaba-Lys)-(β-Ala)$_2$-Tyr-Gly-(Arg)$_5$-Gln-(Arg)$_4$-NH$_2$;

(SEQ ID NO: 333)
Ac-hCha-c(Asp-His-D-Phe-Arg-Trp-Gaba-Lys)-(β-Ala)$_2$-(Arg)$_5$-Gln-(Arg)$_4$-NH$_2$;

(SEQ ID NO: 334)
Ac-hCha-c(Asp-His-D-Phe-Arg-Trp-Gaba-Lys)-Doc-Tyr-Gly-(Arg)$_5$-Gln-(Arg)$_4$-NH$_2$;

(SEQ ID NO: 335)
Ac-hCha-c(Asp-His-D-Phe-Arg-Trp-Gaba-Lys)-Doc-(Arg)$_5$-Gln-(Arg)$_4$-NH$_2$;

(SEQ ID NO: 336)
Ac-hCha-c(Asp-His-D-Phe-Arg-Trp-Gaba-Lys)-(Doc)$_2$-Tyr-Gly-(Arg)$_5$-Gln-(Arg)$_4$-NH$_2$;

(SEQ ID NO: 337)
Ac-hCha-c(Asp-His-D-Phe-Arg-Trp-Gaba-Lys)-(Doc)$_2$-(Arg)$_5$-Gln-(Arg)$_4$-NH$_2$;

(SEQ ID NO: 338)
Ac-D-Chg-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 339)
Ac-D-Chg-c(Asp-His-D-Phe-Arg-Trp-Gaba-Lys)-β-Ala-(Arg)$_5$-Gln-(Arg)$_3$-NH$_2$;

(SEQ ID NO: 340)
Ac-hPhe-c(Asp-His-D-Phe-Arg-Trp-Gaba-Lys)-β-Ala-Tyr-Gly-(Arg)$_5$-Gln-(Arg)$_3$-NH$_2$;

(SEQ ID NO: 341)
Ac-hPhe-c(Asp-His-D-Phe-Arg-Trp-Gaba-Lys)-β-Ala-(Arg)$_5$-Gln-(Arg)$_3$-NH$_2$;

(SEQ ID NO: 342)
Ac-Nle-c(Cys-His-D-Phe-Arg-D-Trp-Apn-Cys)-β-Ala-Tyr-Gly-(Arg)$_5$-Gln-(Arg)$_3$-NH$_2$;

(SEQ ID NO: 343)
Ac-Nle-c(Cys-His-D-Phe-Arg-D-Trp-Apn-Cys)-β-Ala-(Arg)$_5$-Gln-(Arg)$_3$-NH$_2$;

(SEQ ID NO: 344)
Ac-Nle-c(Cys-His-D-Phe-Arg-D-Trp-Ahx-Cys)-β-Ala-Tyr-Gly-(Arg)$_5$-Gln-(Arg)$_3$-NH$_2$;

(SEQ ID NO: 345)

-continued

```
Ac-Nle-c(Cys-His-D-Phe-Arg-D-Trp-Ahx-Cys)-β-Ala-(Arg)₅-Gln-(Arg)₃-NH₂;

(SEQ ID NO: 346)
Ac-Nle-c(Cys-His-D-Phe-Arg-D-Trp-β-Ala-Cys)-β-Ala-Tyr-Gly-(Arg)₅-Gln-(Arg)₃-NH₂;

(SEQ ID NO: 347)
Ac-Nle-c(Cys-His-D-Phe-Arg-D-Trp-β-Ala-Cys)-β-Ala-(Arg)₅-Gln-(Arg)₃-NH₂;

(SEQ ID NO: 348)
Ac-Nle-c(Cys-D-Ala-His-D-Phe-Arg-Trp-Pen)-β-Ala-Tyr-Gly-(Arg)₅-Gln-(Arg)₃-NH₂;

(SEQ ID NO: 349)
Ac-Nle-c(Cys-D-Ala-His-D-Phe-Arg-Trp-Pen)-β-Ala-Gly-(Arg)₅-Gln-(Arg)₃-NH₂;

(SEQ ID NO: 350)
Ac-Nle-c(Cys-D-Ala-His-D-Phe-Arg-Trp-Pen)-β-Ala-(Arg)₅-Gln-(Arg)₃-NH₂;

(SEQ ID NO: 351)
Ac-Nle-c(Cys-D-Ala-His-D-Phe-Arg-Trp-Pen)-(β-Ala)₂-Tyr-Gly-(Arg)₅-Gln-(Arg)₃-NH₂;

(SEQ ID NO: 352)
Ac-Nle-c(Cys-D-Ala-His-D-Phe-Arg-Trp-Pen)-(β-Ala)₂-Gly-(Arg)₅-Gln-(Arg)₃-NH₂;

(SEQ ID NO: 353)
Ac-Nle-c(Cys-D-Ala-His-D-Phe-Arg-Trp-Pen)-(β-Ala)₂-(Arg)₅-Gln-(Arg)₃-NH₂;

(SEQ ID NO: 354)
Ac-Nle-c(Cys-D-Ala-His-D-Phe-Arg-Trp-Pen)-Doc-Tyr-Gly-(Arg)₅-Gln-(Arg)₃-NH₂;

(SEQ ID NO: 355)
Ac-Nle-c(Cys-D-Ala-His-D-Phe-Arg-Trp-Pen)-Doc-Gly-(Arg)₅-Gln-(Arg)₃-NH₂;

(SEQ ID NO: 356)
Ac-Nle-c(Cys-D-Ala-His-D-Phe-Arg-Trp-Pen)-Doc-(Arg)₅-Gln-(Arg)₃-NH₂;

(SEQ ID NO: 357)
Ac-Nle-c(Cys-D-Ala-His-D-Phe-Arg-Trp-Pen)-(Doc)₂-Tyr-Gly-(Arg)₅-Gln-(Arg)₃-NH₂;

(SEQ ID NO: 358)
Ac-Nle-c(Cys-D-Ala-His-D-Phe-Arg-Trp-Pen)-(Doc)₂-Gly-(Arg)₅-Gln-(Arg)₃-NH₂;

(SEQ ID NO: 359)
Ac-Nle-c(Cys-D-Ala-His-D-Phe-Arg-Trp-Pen)-(Doc)₂-(Arg)₅-Gln-(Arg)₃-NH₂;

(SEQ ID NO: 360)
D-Phe-c(Cys-His-D-(Et)Tyr-Arg-Trp-β-Ala-D-Cys)-β-Ala-Tyr-Gly-(Arg)₅-Gln-(Arg)₃-
NH₂;

(SEQ ID NO: 361)
D-Phe-c(Cys-His-D-(Et)Tyr-Arg-Trp-β-Ala-D-Cys)-β-Ala-(Arg)₅-Gln-(Arg)₃-NH₂;

(SEQ ID NO: 362)
D-Phe-c(Cys-His-D-(Et)Tyr-Arg-Trp-β-Ala-D-Cys)-β-Ala-Gly-(Arg)₅-Gln-(Arg)₃-NH₂;

(SEQ ID NO: 363)
D-Phe-c(Cys-His-D-(Et)Tyr-Arg-Trp-β-Ala-D-Cys)-β-Ala-(Arg)₅-Gln-(Arg)₄-NH₂;

(SEQ ID NO: 364)
D-Phe-c(Cys-His-D-(Et)Tyr-Arg-Trp-β-Ala-D-Cys)-(β-Ala)₂-Tyr-Gly-(Arg)₅-Gln-(Arg)₃-
NH₂;

(SEQ ID NO: 365)
D-Phe-c(Cys-His-D-(Et)Tyr-Arg-Trp-β-Ala-D-Cys)-(β-Ala)₂-(Arg)₅-Gln-(Arg)₃-NH₂;

(SEQ ID NO: 366)
D-Phe-c(Cys-His-D-(Et)Tyr-Arg-Trp-β-Ala-D-Cys)-(β-Ala)₂-Gly-(Arg)₅-Gln-(Arg)₃-NH₂;

(SEQ ID NO: 367)
D-Phe-c(Cys-His-D-(Et)Tyr-Arg-Trp-β-Ala-D-Cys)-(β-Ala)₂-(Arg)₅-Gln-(Arg)₄-NH₂;

(SEQ ID NO: 368)
D-Phe-c(Cys-His-D-(Et)Tyr-Arg-Trp-β-Ala-D-Cys)-Doc-Tyr-Gly-(Arg)₅-Gln-(Arg)₃-NH₂;

(SEQ ID NO: 369)
D-Phe-c(Cys-His-D-(Et)Tyr-Arg-Trp-β-Ala-D-Cys)-Doc-(Arg)₅-Gln-(Arg)₃-NH₂;

(SEQ ID NO: 370)
D-Phe-c(Cys-His-D-(Et)Tyr-Arg-Trp-β-Ala-D-Cys)-Doc-Gly-(Arg)₅-Gln-(Arg)₃-NH₂;
```

```
                                                          (SEQ ID NO: 371)
D-Phe-c(Cys-His-D-(Et)Tyr-Arg-Trp-β-Ala-D-Cys)-Doc-(Arg)5-Gln-(Arg)4-NH2;

(SEQ ID NO: 372)
D-Phe-c(Cys-His-D-(Et)Tyr-Arg-Trp-β-Ala-D-Cys)-(Doc)2-Tyr-Gly-(Arg)5-Gln-(Arg)3-
NH2;

(SEQ ID NO: 373)
D-Phe-c(Cys-His-D-(Et)Tyr-Arg-Trp-β-Ala-D-Cys)-(Doc)2-(Arg)5-Gln-(Arg)3-NH2;

(SEQ ID NO: 374)
D-Phe-c(Cys-His-D-(Et)Tyr-Arg-Trp-β-Ala-D-Cys)-(Doc)2-Gly-(Arg)5-Gln-(Arg)3-NH2;

(SEQ ID NO: 375)
D-Phe-c(Cys-His-D-(Et)Tyr-Arg-Trp-β-Ala-D-Cys)-(Doc)2-(Arg)5-Gln-(Arg)4-NH2;

(SEQ ID NO: 376)
D-Phe-c(Cys-His-D-(Et)Tyr-hArg-Trp-β-Ala-D-Cys)-Thr-β-Ala-Tyr-Gly-(Arg)5-Gln-
(Arg)3-NH2;

(SEQ ID NO: 377)
D-Phe-c(Cys-His-D-(Et)Tyr-hArg-Trp-β-Ala-D-Cys)-Thr-β-Ala-(Arg)5-Gln-(Arg)3-NH2;

(SEQ ID NO: 378)
D-Phe-c(Cys-His-D-(Et)Tyr-hArg-Trp-β-Ala-D-Cys)-Thr-(β-Ala)2-Tyr-Gly-(Arg)5-Gln-
(Arg)3-NH2;

(SEQ ID NO: 379)
D-Phe-c(Cys-His-D-(Et)Tyr-hArg-Trp-β-Ala-D-Cys)-Thr-(β-Ala)2-(Arg)5-Gln-(Arg)3-NH2;

(SEQ ID NO: 380)
D-Phe-c(Cys-His-D-(Et)Tyr-hArg-Trp-β-Ala-D-Cys)-Thr-Doc-Tyr-Gly-(Arg)5-Gln-(Arg)3-
NH2;

(SEQ ID NO: 381)
D-Phe-c(Cys-His-D-(Et)Tyr-hArg-Trp-β-Ala-D-Cys)-Thr-Doc-(Arg)5-Gln-(Arg)3-NH2;

(SEQ ID NO: 382)
D-Phe-c(Cys-His-D-(Et)Tyr-hArg-Trp-β-Ala-D-Cys)-Thr-(Doc)2-Tyr-Gly-(Arg)5-Gln-
(Arg)3-NH2;

(SEQ ID NO: 383)
D-Phe-c(Cys-His-D-(Et)Tyr-hArg-Trp-β-Ala-D-Cys)-Thr-β-Ala-Tyr-Gly-(Arg)5-Gln-(Arg)4-
NH2;

(SEQ ID NO: 384)
D-Phe-c(Cys-His-D-(Et)Tyr-hArg-Trp-β-Ala-D-Cys)-Thr-β-Ala-(Arg)5-Gln-(Arg)4-NH2;

(SEQ ID NO: 385)
D-Phe-c(Cys-His-D-(Et)Tyr-hArg-Trp-β-Ala-D-Cys)-Thr-(β-Ala)2-Tyr-Gly-(Arg)5-Gln-
(Arg)4-NH2;

(SEQ ID NO: 386)
D-Phe-c(Cys-His-D-(Et)Tyr-hArg-Trp-β-Ala-D-Cys)-Thr-(β-Ala)2-(Arg)5-Gln-(Arg)4-NH2;

(SEQ ID NO: 387)
D-Phe-c(Cys-His-D-(Et)Tyr-hArg-Trp-β-Ala-D-Cys)-Thr-Doc-Tyr-Gly-(Arg)5-Gln-(Arg)4-
NH2;

(SEQ ID NO: 388)
D-Phe-c(Cys-His-D-(Et)Tyr-hArg-Trp-β-Ala-D-Cys)-Thr-Doc-(Arg)5-Gln-(Arg)4-NH2;

(SEQ ID NO: 389)
D-Phe-c(Cys-His-D-(Et)Tyr-hArg-Trp-β-Ala-D-Cys)-Thr-(Doc)2-Tyr-Gly-(Arg)5-Gln-
(Arg)4-NH2;

(SEQ ID NO: 390)
D-Phe-c(Cys-His-D-(Et)Tyr-hArg-Trp-β-Ala-D-Cys)-Thr-(Doc)2-(Arg)5-Gln-(Arg)4-NH2;

(SEQ ID NO: 391)
D-Phe-c(Cys-His-D-(Et)Tyr-hArg-Bip-β-Ala-D-Cys)-Thr-β-Ala-Tyr-Gly-(Arg)5-Gln-
```

(Arg)$_3$-NH$_2$;

(SEQ ID NO: 392)
D-Phe-c(Cys-His-D-(Et)Tyr-hArg-Bip-β-Ala-D-Cys)-Thr-β-Ala-Tyr-Gly-(Arg)$_5$-Gln-(Arg)$_4$-NH$_2$;

(SEQ ID NO: 393)
D-Phe-c(Cys-His-D-(Et)Tyr-hArg-Bip-β-Ala-D-Cys)-Thr-β-Ala-(Arg)$_5$-Gln-(Arg)$_3$-NH$_2$;

(SEQ ID NO: 394)
D-Phe-c(Cys-His-D-(Et)Tyr-hArg-Bip-β-Ala-D-Cys)-Thr-(β-Ala)$_2$-Tyr-Gly-(Arg)$_5$-Gln-(Arg)$_3$-NH$_2$;

(SEQ ID NO: 395)
D-Phe-c(Cys-His-D-(Et)Tyr-hArg-Bip-β-Ala-D-Cys)-Thr-(β-Ala)$_2$-(Arg)$_5$-Gln-(Arg)$_3$-NH$_2$;

(SEQ ID NO: 396)
D-Phe-c(Cys-His-D-(Et)Tyr-hArg-Bip-β-Ala-D-Cys)-Thr-Doc-Tyr-Gly-(Arg)$_5$-Gln-(Arg)$_3$-NH$_2$;

(SEQ ID NO: 397)
D-Phe-c(Cys-His-D-(Et)Tyr-hArg-Bip-β-Ala-D-Cys)-Thr-Doc-Tyr-Gly-(Arg)$_5$-Gln-(Arg)$_4$-NH$_2$;

(SEQ ID NO: 398)
D-Phe-c(Cys-His-D-(Et)Tyr-hArg-Bip-β-Ala-D-Cys)-Thr-Doc-(Arg)$_5$-Gln-(Arg)$_3$-NH$_2$;

(SEQ ID NO: 399)
D-Phe-c(Cys-His-D-(Et)Tyr-hArg-Bip-β-Ala-D-Cys)-Thr-(Doc)$_2$-Tyr-Gly-(Arg)$_5$-Gln-(Arg)$_3$-NH$_2$;

(SEQ ID NO: 400)
D-Phe-c(Cys-His-D-(Et)Tyr-hArg-Bip-β-Ala-D-Cys)-Thr-(Doc)$_2$-(Arg)$_5$-Gln-(Arg)$_3$-NH$_2$;

(SEQ ID NO: 401)
Ac-Nle-c(Cys-D-Ala-His-D-Phe-Arg-Trp-Gly-Cys)-β-Ala-Tyr-Gly-(Arg)$_5$-Gln-(Arg)$_3$-NH$_2$;

(SEQ ID NO: 402)
Ac-Nle-c(Cys-D-Ala-His-D-Phe-Arg-Trp-Gly-Cys)-β-Ala-(Arg)$_5$-Gln-(Arg)$_3$-NH$_2$;

(SEQ ID NO: 403)
Nle-c(Cys-His-D-Phe-Arg-Trp-Apn-Cys)-β-Ala-Tyr-Gly-(Arg)$_5$-Gln-(Arg)$_3$-NH$_2$;

(SEQ ID NO: 404)
Nle-c(Cys-His-D-Phe-Arg-Trp-Apn-Cys)-β-Ala-(Arg)$_5$-Gln-(Arg)$_3$-NH$_2$;

(SEQ ID NO: 405)
Nle-c(Cys-His-D-Phe-Arg-Trp-Apn-Cys)-(β-Ala)$_2$-Tyr-Gly-(Arg)$_5$-Gln-(Arg)$_3$-NH$_2$;

(SEQ ID NO: 406)
Nle-c(Cys-His-D-Phe-Arg-Trp-Apn-Cys)-(β-Ala)$_2$-(Arg)$_5$-Gln-(Arg)$_3$-NH$_2$;

(SEQ ID NO: 407)
Nle-c(Cys-His-D-Phe-Arg-Trp-Apn-Cys)-β-Ala-Tyr-Gly-(Arg)$_5$-Gln-(Arg)$_4$-NH$_2$;

(SEQ ID NO: 408)
Nle-c(Cys-His-D-Phe-Arg-Trp-Apn-Cys)-β-Ala-(Arg)$_5$-Gln-(Arg)$_4$-NH$_2$;

(SEQ ID NO: 409)
Nle-c(Cys-His-D-Phe-Arg-Trp-Apn-Cys)-(β-Ala)$_2$-Tyr-Gly-(Arg)$_5$-Gln-(Arg)$_4$-NH$_2$;

(SEQ ID NO: 410)
Nle-c(Cys-His-D-Phe-Arg-Trp-Apn-Cys)-(β-Ala)$_2$-(Arg)$_5$-Gln-(Arg)$_4$-NH$_2$;

(SEQ ID NO: 411)
Nle-c(Cys-His-D-Phe-Arg-Trp-Apn-Cys)-Doc-Tyr-Gly-(Arg)$_5$-Gln-(Arg)$_3$-NH$_2$;

(SEQ ID NO: 412)
Nle-c(Cys-His-D-Phe-Arg-Trp-Apn-Cys)-Doc-(Arg)$_5$-Gln-(Arg)$_3$-NH$_2$;

(SEQ ID NO: 413)
Nle-c(Cys-His-D-Phe-Arg-Trp-Apn-Cys)-(Doc)$_2$-Tyr-Gly-(Arg)$_5$-Gln-(Arg)$_3$-NH$_2$;

(SEQ ID NO: 414)
Nle-c(Cys-His-D-Phe-Arg-Trp-Apn-Cys)-(Doc)$_2$-(Arg)$_5$-Gln-(Arg)$_3$-NH$_2$;

-continued

Nle-c(Cys-His-D-Phe-Arg-Trp-Apn-Cys)-Doc-Tyr-Gly-(Arg)$_5$-Gln-(Arg)$_4$-NH$_2$; (SEQ ID NO: 415)

Nle-c(Cys-His-D-Phe-Arg-Trp-Apn-Cys)-Doc-(Arg)$_5$-Gln-(Arg)$_4$-NH$_2$; (SEQ ID NO: 416)

Nle-c(Cys-His-D-Phe-Arg-Trp-Apn-Cys)-(Doc)$_2$-Tyr-Gly-(Arg)$_5$-Gln-(Arg)$_4$-NH$_2$; (SEQ ID NO: 417)

Nle-c(Cys-His-D-Phe-Arg-Trp-Apn-Cys)-(Doc)$_2$-(Arg)$_5$-Gln-(Arg)$_4$-NH$_2$; (SEQ ID NO: 418)

Ac-Nle-c(Cys-D-Leu-His-D-Phe-Arg-Trp-Cys)-β-Ala-Tyr-Gly-(Arg)$_5$-Gln-(Arg)$_3$-NH$_2$; (SEQ ID NO: 419)

Ac-Nle-c(Cys-D-Leu-His-D-Phe-Arg-Trp-Cys)-β-Ala-(Arg)$_5$-Gln-(Arg)$_3$-NH$_2$; (SEQ ID NO: 420)

Ac-Nle-c(Cys-D-Leu-His-D-Phe-Arg-Trp-Cys)-(β-Ala)$_2$-Tyr-Gly-(Arg)$_5$-Gln-(Arg)$_3$-NH$_2$; (SEQ ID NO: 421)

Ac-Nle-c(Cys-D-Leu-His-D-Phe-Arg-Trp-Cys)-(β-Ala)$_2$-(Arg)$_5$-Gln-(Arg)$_3$-NH$_2$; (SEQ ID NO: 422)

Ac-Nle-c(Cys-D-Leu-His-D-Phe-Arg-Trp-Cys)-Doc-Tyr-Gly-(Arg)$_5$-Gln-(Arg)$_3$-NH$_2$; (SEQ ID NO: 423)

Ac-Nle-c(Cys-D-Leu-His-D-Phe-Arg-Trp-Cys)-Doc-(Arg)$_5$-Gln-(Arg)$_3$-NH$_2$; (SEQ ID NO: 424)

Ac-Nle-c(Cys-D-Leu-His-D-Phe-Arg-Trp-Cys)-(Doc)$_2$-Tyr-Gly-(Arg)$_5$-Gln-(Arg)$_3$-NH$_2$; (SEQ ID NO: 425)

Ac-Nle-c(Cys-D-Leu-His-D-Phe-Arg-Trp-Cys)-(Doc)$_2$-(Arg)$_5$-Gln-(Arg)$_3$-NH$_2$; (SEQ ID NO: 426)

Ac-Nle-c(Cys-D-Leu-His-D-Phe-Arg-Trp-Cys)-β-Ala-Tyr-Gly-(Arg)$_5$-Gln-(Arg)$_4$-NH$_2$; (SEQ ID NO: 427)

Ac-Nle-c(Cys-D-Leu-His-D-Phe-Arg-Trp-Cys)-β-Ala-(Arg)$_5$-Gln-(Arg)$_4$-NH$_2$; (SEQ ID NO: 428)

Ac-Nle-c(Cys-D-Leu-His-D-Phe-Arg-Trp-Cys)-(β-Ala)$_2$-Tyr-Gly-(Arg)$_5$-Gln-(Arg)$_4$-NH$_2$; (SEQ ID NO: 429)

Ac-Nle-c(Cys-D-Leu-His-D-Phe-Arg-Trp-Cys)-(β-Ala)$_2$-(Arg)$_5$-Gln-(Arg)$_4$-NH$_2$; (SEQ ID NO: 430)

Ac-Nle-c(Cys-D-Leu-His-D-Phe-Arg-Trp-Cys)-Doc-Tyr-Gly-(Arg)$_5$-Gln-(Arg)$_4$-NH$_2$; (SEQ ID NO: 431)

Ac-Nle-c(Cys-D-Leu-His-D-Phe-Arg-Trp-Cys)-Doc-(Arg)$_5$-Gln-(Arg)$_4$-NH$_2$; (SEQ ID NO: 432)

Ac-Nle-c(Cys-D-Leu-His-D-Phe-Arg-Trp-Cys)-(Doc)$_2$-Tyr-Gly-(Arg)$_5$-Gln-(Arg)$_4$-NH$_2$; (SEQ ID NO: 433)

Ac-Nle-c(Cys-D-Leu-His-D-Phe-Arg-Trp-Cys)-(Doc)$_2$-(Arg)$_5$-Gln-(Arg)$_4$-NH$_2$; (SEQ ID NO: 434)

Ac-Nle-c(Cys-D-Cha-His-D-Phe-Arg-Trp-Cys)-β-Ala-Tyr-Gly-(Arg)$_5$-Gln-(Arg)$_3$-NH$_2$; (SEQ ID NO: 435)

Ac-Nle-c(Cys-D-Cha-His-D-Phe-Arg-Trp-Cys)-β-Ala-(Arg)$_5$-Gln-(Arg)$_3$-NH$_2$; (SEQ ID NO: 436)

Ac-Nle-c(Cys-D-Cha-His-D-Phe-Arg-Trp-Cys)-(β-Ala)$_2$-Tyr-Gly-(Arg)$_5$-Gln-(Arg)$_3$-NH$_2$; (SEQ ID NO: 437)

Ac-Nle-c(Cys-D-Cha-His-D-Phe-Arg-Trp-Cys)-(β-Ala)$_2$-(Arg)$_5$-Gln-(Arg)$_3$-NH$_2$; (SEQ ID NO: 438)

Ac-Nle-c(Cys-D-Cha-His-D-Phe-Arg-Trp-Cys)-Doc-Tyr-Gly-(Arg)$_5$-Gln-(Arg)$_3$-NH$_2$; (SEQ ID NO: 439)

Ac-Nle-c(Cys-D-Cha-His-D-Phe-Arg-Trp-Cys)-Doc-(Arg)$_5$-Gln-(Arg)$_3$-NH$_2$; (SEQ ID NO: 440)

Ac-Nle-c(Cys-D-Cha-His-D-Phe-Arg-Trp-Cys)-(Doc)$_2$-Tyr-Gly-(Arg)$_5$-Gln-(Arg)$_3$-NH$_2$; (SEQ ID NO: 441)

```
                                                                    (SEQ ID NO: 442)
Ac-Nle-c(Cys-D-Cha-His-D-Phe-Arg-Trp-Cys)-(Doc)₂-(Arg)₅-Gln-(Arg)₃-NH₂;

(SEQ ID NO: 443)
Ac-Nle-c(Cys-D-Cha-His-D-Phe-Arg-Trp-Cys)-β-Ala-Tyr-Gly-(Arg)₅-Gln-(Arg)₄-NH₂;

(SEQ ID NO: 444)
Ac-Nle-c(Cys-D-Cha-His-D-Phe-Arg-Trp-Cys)-β-Ala-(Arg)₅-Gln-(Arg)₄-NH₂;

(SEQ ID NO: 445)
Ac-Nle-c(Cys-D-Cha-His-D-Phe-Arg-Trp-Cys)-(β-Ala)₂-Tyr-Gly-(Arg)₅-Gln-(Arg)₄-NH₂;

(SEQ ID NO: 446)
Ac-Nle-c(Cys-D-Cha-His-D-Phe-Arg-Trp-Cys)-(β-Ala)₂-(Arg)₅-Gln-(Arg)₄-NH₂;

(SEQ ID NO: 447)
Ac-Nle-c(Cys-D-Cha-His-D-Phe-Arg-Trp-Cys)-Doc-Tyr-Gly-(Arg)₅-Gln-(Arg)₄-NH₂;

(SEQ ID NO: 448)
Ac-Nle-c(Cys-D-Cha-His-D-Phe-Arg-Trp-Cys)-Doc-(Arg)₅-Gln-(Arg)₄-NH₂;

(SEQ ID NO: 449)
Ac-Nle-c(Cys-D-Cha-His-D-Phe-Arg-Trp-Cys)-(Doc)₂-Tyr-Gly-(Arg)₅-Gln-(Arg)₄-NH₂;

(SEQ ID NO: 450)
Ac-Nle-c(Cys-D-Cha-His-D-Phe-Arg-Trp-Cys)-(Doc)₂-(Arg)₅-Gln-(Arg)₄-NH₂;

(SEQ ID NO: 451)
Nle-c(Cys-His-D-Phe-Arg-Trp-Gaba-Cys)-β-Ala-Tyr-Gly-(Arg)₅-Gln-(Arg)₃-NH₂;

(SEQ ID NO: 452)
Nle-c(Cys-His-D-Phe-Arg-Trp-Gaba-Cys)-β-Ala-(Arg)₅-Gln-(Arg)₃-NH₂;

(SEQ ID NO: 453)
Nle-c(Cys-His-D-Phe-Arg-Trp-Gaba-Cys)-(β-Ala)₂-Tyr-Gly-(Arg)₅-Gln-(Arg)₃-NH₂;

(SEQ ID NO: 454)
Nle-c(Cys-His-D-Phe-Arg-Trp-Gaba-Cys)-(β-Ala)₂-(Arg)₅-Gln-(Arg)₃-NH₂;

(SEQ ID NO: 455)
Nle-c(Cys-His-D-Phe-Arg-Trp-Gaba-Cys)-β-Ala-Tyr-Gly-(Arg)₅-Gln-(Arg)₄-NH₂;

(SEQ ID NO: 456)
Nle-c(Cys-His-D-Phe-Arg-Trp-Gaba-Cys)-β-Ala-(Arg)₅-Gln-(Arg)₄-NH₂;

(SEQ ID NO: 457)
Nle-c(Cys-His-D-Phe-Arg-Trp-Gaba-Cys)-(β-Ala)₂-Tyr-Gly-(Arg)₅-Gln-(Arg)₄-NH₂;

(SEQ ID NO: 458)
Nle-c(Cys-His-D-Phe-Arg-Trp-Gaba-Cys)-(β-Ala)₂-(Arg)₅-Gln-(Arg)₄-NH₂;

(SEQ ID NO: 459)
Nle-c(Cys-His-D-Phe-Arg-Trp-Gaba-Cys)-Doc-Tyr-Gly-(Arg)₅-Gln-(Arg)₃-NH₂;

(SEQ ID NO: 460)
Nle-c(Cys-His-D-Phe-Arg-Trp-Gaba-Cys)-Doc-(Arg)₅-Gln-(Arg)₃-NH₂;

(SEQ ID NO: 461)
Nle-c(Cys-His-D-Phe-Arg-Trp-Gaba-Cys)-(Doc)₂-Tyr-Gly-(Arg)₅-Gln-(Arg)₃-NH₂;

(SEQ ID NO: 462)
Nle-c(Cys-His-D-Phe-Arg-Trp-Gaba-Cys)-(Doc)₂-(Arg)₅-Gln-(Arg)₃-NH₂;

(SEQ ID NO: 463)
Nle-c(Cys-His-D-Phe-Arg-Trp-Gaba-Cys)-Doc-Tyr-Gly-(Arg)₅-Gln-(Arg)₄-NH₂;

(SEQ ID NO: 464)
Nle-c(Cys-His-D-Phe-Arg-Trp-Gaba-Cys)-Doc-(Arg)₅-Gln-(Arg)₄-NH₂;

(SEQ ID NO: 465)
Nle-c(Cys-His-D-Phe-Arg-Trp-Gaba-Cys)-(Doc)₂-Tyr-Gly-(Arg)₅-Gln-(Arg)₄-NH₂;

(SEQ ID NO: 466)
Nle-c(Cys-His-D-Phe-Arg-Trp-Gaba-Cys)-(Doc)₂-(Arg)₅-Gln-(Arg)₄-NH₂;

(SEQ ID NO: 467)
Ac-c(Cys-Glu-His-D-4-Br-Phe-Arg-Trp-Gly-Cys)-(Pro)₂-Lys-Asp-NH₂;

(SEQ ID NO: 468)
Ac-c(Cys-Glu-His-D-2-Nal-Arg-Trp-Ala-Cys)-(Pro)₂-Lys-Asp-NH₂;
```

-continued

Ac-c(Cys-Glu-His-D-2-Nal-Arg-2-Nal-Ala-Cys)-(Pro)$_2$-Lys-Asp-NH$_2$; (SEQ ID NO: 469)

Ac-c(Cys-Glu-His-D-2-Nal-Arg-1-Nal-Ala-Cys)-(Pro)$_2$-Lys-Asp-NH$_2$; (SEQ ID NO: 470)

Ac-c(Cys-Glu-His-D-2-Nal-Arg-Bal-Ala-Cys)-(Pro)$_2$-Lys-Asp-NH$_2$; (SEQ ID NO: 471)

Ac-c(Cys-Glu-His-D-2-Nal-Arg-2-Nal-β-Ala-Cys)-(Pro)$_2$-Lys-Asp-NH$_2$; (SEQ ID NO: 472)

Ac-c(Cys-Glu-His-D-2-Nal-Arg-2-Nal-Aib-Cys)-(Pro)$_2$-Lys-Asp-NH$_2$; (SEQ ID NO: 473)

c[Hydantoin(C(O)-(Cys-D-Ala))-His-D-Phe-Arg-Trp-Cys]-NH$_2$; (SEQ ID NO: 474)

c[Hydantoin(C(O)-(hCys-D-Ala))-His-D-Phe-Arg-Trp-Cys]-NH$_2$; (SEQ ID NO: 475)

c[Hydantoin(C(O)-(Cys-D-Ala))-His-D-2-Nal-Arg-Trp-Cys]-NH$_2$; (SEQ ID NO: 476)

c[Hydantoin(C(O)-(hCys-D-Ala))-His-D-2-Nal-Arg-Trp-Cys]-NH$_2$; (SEQ ID NO: 477)

c[Hydantoin(C(O)-(Asp-D-Ala))-His-D-Phe-Arg-Trp-Lys]-NH$_2$; (SEQ ID NO: 478)

c[Hydantoin(C(O)-(Asp-D-Ala))-His-D-Phe-Arg-Trp-Orn]-NH$_2$; (SEQ ID NO: 479)

c[Hydantoin(C(O)-(Asp-D-Ala))-His-D-Phe-Arg-Trp-Dab]-NH$_2$; (SEQ ID NO: 480)

c[Hydantoin(C(O)-(Asp-D-Ala))-His-D-Phe-Arg-Trp-Dap]-NH$_2$; (SEQ ID NO: 481)

c[Hydantoin(C(O)-(Asp-His))-D-2-Nal-Arg-Trp-Lys]-NH$_2$; (SEQ ID NO: 482)

c[Hydantoin(C(O)-(Asp-His))-D-Phe-Arg-Trp-Lys]-NH$_2$; (SEQ ID NO: 483)

c[Hydantoin(C(O)-(Asp-A3c))-D-Phe-Arg-Trp-Lys]-NH$_2$; (SEQ ID NO: 484)

c[Hydantoin(C(O)-(Asp-A5c))-D-Phe-Arg-Trp-Lys]-NH$_2$; (SEQ ID NO: 485)

c[Hydantoin(C(O)-(Asp-A6c))-D-Phe-Arg-Trp-Lys]-NH$_2$; (SEQ ID NO: 486)

c[Hydantoin(C(O)-(Asp-A3c))-D-2-Nal-Arg-Trp-Lys]-NH$_2$; (SEQ ID NO: 487)

c[Hydantoin(C(O)-(Asp-A5c))-D-2-Nal-Arg-Trp-Lys]-NH$_2$; (SEQ ID NO: 488)

c[Hydantoin(C(O)-(Asp-A6c))-D-2-Nal-Arg-Trp-Lys]-NH$_2$; (SEQ ID NO: 489)

c[Hydantoin(C(O)-(Asp-Aic))-D-Phe-Arg-Trp-Lys]-NH$_2$; (SEQ ID NO: 490)

c[Hydantoin(C(O)-(Asp-Apc))-D-Phe-Arg-Trp-Lys]-NH$_2$; (SEQ ID NO: 491)

c[Hydantoin(C(O)-(Asp-Aic))-D-2-Nal-Arg-Trp-Lys]-NH$_2$; (SEQ ID NO: 492)

c[Hydantoin(C(O)-(Asp-Apc))-D-2-Nal-Arg-Trp-Lys]-NH$_2$; (SEQ ID NO: 493)

c[Hydantoin(C(O)-(Glu-D-Ala))-His-D-Phe-Arg-Trp-Orn]-NH$_2$; (SEQ ID NO: 494)

c[Hydantoin(C(O)-(Glu-D-Ala))-His-D-Phe-Arg-Trp-Dab]-NH$_2$; (SEQ ID NO: 495)

-continued c[Hydantoin(C(O)-(Glu-D-Ala))-His-D-Phe-Arg-Trp-Dap]-NH$_2$;  (SEQ ID NO: 496)

c[Hydantoin(C(O)-(Glu-D-Ala))-His-D-Phe-Arg-Trp-Lys]-NH$_2$;  (SEQ ID NO: 497)

c[Hydantoin(C(O)-(Glu-His))-D-Phe-Arg-Trp-Dap]-NH$_2$;  (SEQ ID NO: 498)

c[Hydantoin(C(O)-(Glu-His))-D-Phe-Arg-Trp-Lys]-NH$_2$;  (SEQ ID NO: 499)

Hydantoin(C(O)-(Arg-Gly))-c(Cys-Glu-His-D-Phe-Arg-Trp-Cys)-NH$_2$;  (SEQ ID NO: 500)

Hydantoin(C(O)-(Nle-Gly))-c(Cys-Glu-His-D-Phe-Arg-Trp-Cys)-NH$_2$;  (SEQ ID NO: 501)

Hydantoin(C(O)-(Gly-Gly))-c(Cys-Glu-His-D-Phe-Arg-Trp-Cys)-NH$_2$;  (SEQ ID NO: 502)

Hydantoin(C(O)-(Nle-Gly))-c(Cys-D-Ala-His-D-Phe-Arg-Trp-Cys)-NH$_2$;  (SEQ ID NO: 503)

Hydantoin(C(O)-(Gly-Gly))-c(Cys-D-Ala-His-D-Phe-Arg-Trp-Cys)-NH$_2$;  (SEQ ID NO: 504)

Hydantoin(C(O)-(Nle-Gly))-c(Cys-D-Ala-His-D-Phe-Arg-Trp-Pen)-NH$_2$;  (SEQ ID NO: 505)

Hydantoin(C(O)-(Gly-Gly))-c(Cys-D-Ala-His-D-Phe-Arg-Trp-Pen)-NH$_2$;  (SEQ ID NO: 506)

Hydantoin(C(O)-(Ala-Gly))-c(Cys-D-Ala-His-D-Phe-Arg-Trp-Cys)-NH$_2$;  (SEQ ID NO: 507)

Hydantoin(C(O)-(D-Ala-Gly))-c(Cys-D-Ala-His-D-Phe-Arg-Trp-Cys)-NH$_2$;  (SEQ ID NO: 508)

Hydantoin(C(O)-(Aib-Gly))-c(Cys-D-Ala-His-D-Phe-Arg-Trp-Cys)-NH$_2$;  (SEQ ID NO: 509)

Hydantoin(C(O)-(Val-Gly))-c(Cys-D-Ala-His-D-Phe-Arg-Trp-Cys)-NH$_2$;  (SEQ ID NO: 510)

Hydantoin(C(O)-(Ile-Gly))-c(Cys-D-Ala-His-D-Phe-Arg-Trp-Cys)-NH$_2$;  (SEQ ID NO: 511)

Hydantoin(C(O)-(Leu-Gly))-c(Cys-D-Ala-His-D-Phe-Arg-Trp-Cys)-NH$_2$;  (SEQ ID NO: 512)

Hydantoin(C(O)-(Gly-Gly))-c(Cys-Glu-His-D-2-Nal-Arg-Trp-Cys)-NH$_2$;  (SEQ ID NO: 513)

Hydantoin(C(O)-(Nle-Gly))-c(Cys-Glu-His-D-2-Nal-Arg-Trp-Cys)-NH$_2$;  (SEQ ID NO: 514)

Hydantoin(C(O)-(D-Arg-Gly))-c(Cys-Glu-His-D-Phe-Arg-Trp-Cys)-NH$_2$;  (SEQ ID NO: 515)

Hydantoin(C(O)-(D-Arg-Gly))-c(Cys-D-Ala-His-D-Phe-Arg-Trp-Cys)-NH$_2$;  (SEQ ID NO: 516)

Hydantoin(C(O)-(Arg-Gly))-c(Cys-D-Ala-His-D-Phe-Arg-Trp-Cys)-NH$_2$;  (SEQ ID NO: 517)

Hydantoin(C(O)-(D-Arg-Gly))-c(Cys-D-Ala-His-D-2-Nal-Arg-Trp-Cys)-NH$_2$;  (SEQ ID NO: 518)

Hydantoin(C(O)-(Arg-Gly))-c(Cys-D-Ala-His-D-2-Nal-Arg-Trp-Cys)-NH$_2$;  (SEQ ID NO: 519)

Hydantoin(C(O)-(Ala-Nle))-c(Cys-Glu-His-D-Phe-Arg-Trp-Cys)-NH$_2$;  (SEQ ID NO: 520)

Hydantoin(C(O)-(Val-Nle))-c(Cys-Glu-His-D-Phe-Arg-Trp-Cys)-NH$_2$;  (SEQ ID NO: 521)

Hydantoin(C(O)-(Gly-Nle))-c(Cys-Glu-His-D-Phe-Arg-Trp-Cys)-NH$_2$;  (SEQ ID NO: 522)

Hydantoin(C(O)-(A6c-Nle))-c(Cys-D-Ala-His-D-Phe-Arg-Trp-Cys)-NH$_2$; (SEQ ID NO: 523)

Hydantoin(C(O)-(Gly-Nle))-c(Cys-D-Ala-His-D-Phe-Arg-Trp-Cys)-NH$_2$; (SEQ ID NO: 524)

Hydantoin(C(O)-(Ala-Nle))-c(Cys-D-Ala-His-D-Phe-Arg-Trp-Cys)-NH$_2$; (SEQ ID NO: 525)

Hydantoin(C(O)-(D-Ala-Nle))-c(Cys-D-Ala-His-D-Phe-Arg-Trp-Cys)-NH$_2$; (SEQ ID NO: 526)

Hydantoin(C(O)-(Val-Nle))-c(Cys-D-Ala-His-D-Phe-Arg-Trp-Cys)-NH$_2$; (SEQ ID NO: 527)

Hydantoin(C(O)-(Leu-Nle))-c(Cys-D-Ala-His-D-Phe-Arg-Trp-Cys)-NH$_2$; (SEQ ID NO: 528)

Hydantoin(C(O)-(Cha-Nle))-c(Cys-D-Ala-His-D-Phe-Arg-Trp-Cys)-NH$_2$; (SEQ ID NO: 529)

Hydantoin(C(O)-(Aib-Nle))-c(Cys-D-Ala-His-D-Phe-Arg-Trp-Cys)-NH$_2$; (SEQ ID NO: 530)

Hydantoin(C(O)-(Gly-Arg))-c(Cys-Glu-His-D-Phe-Arg-Trp-Cys)-NH$_2$; (SEQ ID NO: 531)

Hydantoin(C(O)-(Gly-Arg))-c(Cys-Glu-His-D-2-Nal-Arg-Trp-Cys)-NH$_2$; (SEQ ID NO: 532)

Hydantoin(C(O)-(Gly-Arg))-c(Cys-D-Ala-His-D-Phe-Arg-Trp-Cys)-NH$_2$; (SEQ ID NO: 533)

Hydantoin(C(O)-(Gly-Arg))-c(Cys-D-Ala-His-D-2-Nal-Arg-Trp-Cys)-NH$_2$; (SEQ ID NO: 534)

Hydantoin(C(O)-(Gly-D-Arg))-c(Cys-Glu-His-D-Phe-Arg-Trp-Cys)-NH$_2$; (SEQ ID NO: 535)

Hydantoin(C(O)-(Gly-D-Arg))-c(Cys-D-Ala-His-D-Phe-Arg-Trp-Cys)-NH$_2$; (SEQ ID NO: 536)

Hydantoin(C(O)-(Gly-D-Arg))-c(Cys-D-Ala-His-D-2-Nal-Arg-Trp-Cys)-NH$_2$; (SEQ ID NO: 537)

Hydantoin(C(O)-(Nle-Ala))-c(Cys-Glu-His-D-Phe-Arg-Trp-Cys)-NH$_2$; (SEQ ID NO: 538)

c[Hydantoin(C(O)-(Nle-Cys))-D-Ala-His-D-Phe-Arg-Trp-Cys]-NH$_2$; (SEQ ID NO: 539)

c[Hydantoin(C(O)-(Ala-Cys))-D-Ala-His-D-Phe-Arg-Trp-Cys]-NH$_2$; (SEQ ID NO: 540)

c[Hydantoin(C(O)-(D-Ala-Cys))-D-Ala-His-D-Phe-Arg-Trp-Cys]-NH$_2$; (SEQ ID NO: 541)

c[Hydantoin(C(O)-(Aib-Cys))-D-Ala-His-D-Phe-Arg-Trp-Cys]-NH$_2$; (SEQ ID NO: 542)

c[Hydantoin(C(O)-(Val-Cys))-D-Ala-His-D-Phe-Arg-Trp-Cys]-NH$_2$; (SEQ ID NO: 543)

c[Hydantoin(C(O)-(Abu-Cys))-D-Ala-His-D-Phe-Arg-Trp-Cys]-NH$_2$; (SEQ ID NO: 544)

c[Hydantoin(C(O)-(Leu-Cys))-D-Ala-His-D-Phe-Arg-Trp-Cys]-NH$_2$; (SEQ ID NO: 545)

c[Hydantoin(C(O)-(Ile-Cys))-D-Ala-His-D-Phe-Arg-Trp-Cys]-NH$_2$; (SEQ ID NO: 546)

c[Hydantoin(C(O)-(Cha-Cys))-D-Ala-His-D-Phe-Arg-Trp-Cys]-NH$_2$; (SEQ ID NO: 547)

c[Hydantoin(C(O)-(A6c-Cys))-D-Ala-His-D-Phe-Arg-Trp-Cys]-NH$_2$; (SEQ ID NO: 548)

c[Hydantoin(C(O)-(Phe-Cys))-D-Ala-His-D-Phe-Arg-Trp-Cys]-NH$_2$; (SEQ ID NO: 549)

c[Hydantoin(C(O)-(Gly-Cys))-D-Ala-His-D-Phe-Arg-Trp-Cys]-NH₂; (SEQ ID NO: 550)

c[Hydantoin(C(O)-(Gly-Cys))-Glu-His-D-Phe-Arg-Trp-Cys]-NH₂; (SEQ ID NO: 551)

Ac-Tyr-Arg-c(Cys-D-Ala-His-D-Phe-Arg-Trp-Cys)-NH₂; (SEQ ID NO: 552)

Ac-2-Nal-Arg-c(Cys-D-Ala-His-D-Phe-Arg-Trp-Cys)-NH₂; (SEQ ID NO: 553)

Ac-1-Nal-Arg-c(Cys-D-Ala-His-DPhe-Arg-Trp-Cys)-NH₂; (SEQ ID NO: 554)

Ac-Phe-Arg-c(Cys-D-Ala-His-D-Phe-Arg-Trp-Cys)-NH₂; (SEQ ID NO: 555)

Ac-Trp-Arg-c(Cys-D-Ala-His-D-Phe-Arg-Trp-Cys)-NH₂; (SEQ ID NO: 556)

Ac-Pff-Arg-c(Cys-D-Ala-His-D-Phe-Arg-Trp-Cys)-NH₂; (SEQ ID NO: 557)

H-His-Arg-c(Cys-D-Ala-His-D-Phe-Arg-Trp-Cys)-NH₂; (SEQ ID NO: 558)
and

Ac-His-Arg-c(Cys-D-Ala-His-D-Phe-Arg-Trp-Cys)-NH₂; (SEQ ID NO: 559)

or a pharmaceutically acceptable salt thereof.

17. The method of claim 10, wherein the metabolic syndrome results from the attenuated response of MC4R to α-melanocortin stimulating hormone (α-MSH).

18. The method of claim 10, wherein the subject is a human.

* * * * *

```
                           SEQUENCE LISTING

<160> NUMBER OF SEQ ID NOS: 559

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term NH2

<400> SEQUENCE: 1

Xaa Asp His Phe Arg Trp Ala Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (7)..(7)
<223> OTHER INFORMATION: A6c
<220> FEATURE:
<223> OTHER INFORMATION: C-term NH2

<400> SEQUENCE: 2

Xaa Asp His Phe Arg Trp Xaa Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
<220> FEATURE:
<223> OTHER INFORMATION: C-term NH2

<400> SEQUENCE: 3

Xaa Cys His Phe Arg Trp Xaa Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 4

Phe Cys His Phe Arg Trp Ala Cys Thr
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 5

Phe Cys His Phe Arg Trp Ala Cys Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 6

Phe Cys His Phe Arg Trp Xaa Cys Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<223> OTHER INFORMATION: C-term NH2

<400> SEQUENCE: 7

Xaa Cys His Phe Arg Trp Xaa Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<223> OTHER INFORMATION: C-term NH2

<400> SEQUENCE: 8

Xaa Asp His Phe Arg Trp Xaa Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: A6c
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 9

Xaa Asp His Phe Arg Trp Xaa Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-2-Nal
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 10

Xaa Asp His Phe Arg Trp Xaa Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2
```

```
<400> SEQUENCE: 11

Xaa Asp His Phe Arg Trp Xaa Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 12

Xaa Asp His Phe Arg Trp Xaa Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 13

Xaa Cys Ala His Phe Arg Trp Cys
1               5

<210> SEQ ID NO 14
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 14

Xaa Cys Ala His Phe Arg Trp Cys
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 15

Xaa Cys Xaa His Phe Arg Trp Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
```

```
<223> OTHER INFORMATION: Cyclic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 16

Xaa Cys Xaa His Phe Arg Trp Cys
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 17

Xaa Cys Gly His Phe Arg Trp Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 18

Xaa Cys Ala His Phe Arg Trp Cys
```

```
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 19

Xaa Cys Ala His Phe Arg Trp Cys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 20

Xaa Cys Ala His Phe Arg Trp Cys
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 21

Xaa Cys Xaa His Phe Arg Trp Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 22

Xaa Cys Xaa His Phe Arg Trp Cys
1               5

<210> SEQ ID NO 23
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 23

Xaa Cys Gly His Phe Arg Trp Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 24

Xaa Cys Ala His Phe Arg Trp Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 25

Xaa Cys Ala His Phe Arg Trp Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 26

Xaa Cys Xaa His Phe Arg Trp Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
```

-continued

```
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 27

Xaa Cys Xaa His Phe Arg Trp Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 28

Xaa Cys Gly His Phe Arg Trp Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
```

```
<223> OTHER INFORMATION: D-Cys
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 29

Xaa Cys Ala His Phe Arg Trp Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 30

Xaa Cys Ala His Phe Arg Trp Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Beta-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 31

Xaa Cys Ala His Phe Arg Trp Cys
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Gaba
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 32

Xaa Cys Xaa His Phe Arg Trp Cys
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
```

```
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: D-Cys
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 33

Xaa Cys Xaa His Phe Arg Trp Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Oic
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 34

Xaa Asp His Phe Arg Trp Xaa Lys
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 35

Xaa Asp His Phe Arg Trp Xaa Lys
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 36

Xaa Asp His Phe Arg Trp Xaa Lys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2
```

```
<400> SEQUENCE: 37

Xaa Asp His Phe Arg Trp Xaa Lys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 38

Xaa Asp His Phe Arg Trp Xaa Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nip
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 39

Xaa Asp His Phe Arg Trp Xaa Lys
1               5

<210> SEQ ID NO 40
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hPro
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 40

Pro Asp His Phe Arg Trp Xaa Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hLeu
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 41

Leu Asp His Phe Arg Trp Xaa Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 42

Phe Asp His Phe Arg Trp Xaa Lys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 43

Phe Asp His Phe Arg Trp Xaa Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 44

Xaa Asp His Phe Arg Trp Xaa Lys
```

-continued

```
<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term n-butanoyl
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 45

Xaa Asp His Phe Arg Trp Xaa Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term n-butyryl
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 46

Xaa Asp His Phe Arg Trp Xaa Lys
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<221> NAME/KEY: MOD_RES
<222> LOCATION: (1)..(1)
<223> OTHER INFORMATION: hPhe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 47

Phe Asp His Phe Arg Trp Xaa Lys
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Beta-hMet
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 48

Met Asp His Phe Arg Trp Xaa Lys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Gaba
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 49

Xaa Asp His Phe Arg Trp Xaa Lys
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<223> OTHER INFORMATION: C-term NH2

<400> SEQUENCE: 50

Xaa Asp His Phe Arg Trp Ala Lys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<223> OTHER INFORMATION: C-term NH2

<400> SEQUENCE: 51
```

```
Xaa Asp His Phe Arg Trp Ala Lys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<223> OTHER INFORMATION: C-term NH2

<400> SEQUENCE: 52

Leu Asp His Phe Arg Trp Ala Lys
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hLeu
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<223> OTHER INFORMATION: C-term NH2

<400> SEQUENCE: 53

Leu Asp His Phe Arg Trp Ala Lys
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<223> OTHER INFORMATION: C-term NH2

<400> SEQUENCE: 54

Phe Asp His Phe Arg Trp Ala Lys
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala
<220> FEATURE:
<223> OTHER INFORMATION: C-term NH2

<400> SEQUENCE: 55

Xaa Asp His Phe Arg Trp Ala Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term NH2

<400> SEQUENCE: 56

Xaa Asp His Phe Arg Trp Ala Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 57

Xaa Asp His Phe Arg Trp Xaa Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
```

```
<220> FEATURE:
<221> NAME/KEY: MOD_RES
<222> LOCATION: (7)..(7)
<223> OTHER INFORMATION: Aha
<220> FEATURE:
<223> OTHER INFORMATION: C-term NH2

<400> SEQUENCE: 58

Xaa Asp His Phe Arg Trp Xaa Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn
<220> FEATURE:
<223> OTHER INFORMATION: C-term NH2

<400> SEQUENCE: 59

Xaa Asp His Phe Arg Trp Xaa Lys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
```

```
<223> OTHER INFORMATION: Apn
<220> FEATURE:
<223> OTHER INFORMATION: C-term NH2

<400> SEQUENCE: 60

Xaa Cys His Phe Arg Trp Xaa Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 61

Xaa Cys His Phe Arg Trp Xaa Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<223> OTHER INFORMATION: C-term NH2
```

```
<400> SEQUENCE: 62

Xaa Cys His Phe Arg Trp Xaa Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term NH2

<400> SEQUENCE: 63

Xaa Cys His Phe Arg Trp Ala Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala
<220> FEATURE:
<223> OTHER INFORMATION: C-term NH2

<400> SEQUENCE: 64
```

Xaa Cys His Phe Arg Trp Ala Cys
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<223> OTHER INFORMATION: C-term NH2

<400> SEQUENCE: 65

Xaa Cys Ala His Xaa Arg Trp Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 2-Nal
<220> FEATURE:
<223> OTHER INFORMATION: C-term NH2

<400> SEQUENCE: 66

Xaa Cys Ala His Xaa Arg Xaa Cys
1               5

<210> SEQ ID NO 67
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 1-Nal
<220> FEATURE:
<223> OTHER INFORMATION: C-term NH2

<400> SEQUENCE: 67

Xaa Cys Ala His Xaa Arg Xaa Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term n-butanoyl
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 2-Nal
<220> FEATURE:
<223> OTHER INFORMATION: C-term NH2

<400> SEQUENCE: 68

Xaa Cys Ala His Phe Arg Xaa Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term n-butanoyl
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 69

Xaa Cys Ala His Phe Arg Trp Cys
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 2-Nal
<220> FEATURE:
<223> OTHER INFORMATION: C-term NH2

<400> SEQUENCE: 70

Xaa Cys Ala His Phe Arg Xaa Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
```

```
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: 1-Nal
<220> FEATURE:
<223> OTHER INFORMATION: C-term NH2

<400> SEQUENCE: 71

Xaa Cys Ala His Phe Arg Xaa Cys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal
<220> FEATURE:
<223> OTHER INFORMATION: C-term NH2

<400> SEQUENCE: 72

Xaa Cys Ala His Phe Arg Xaa Cys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
```

<223> OTHER INFORMATION: Cyclic
<220> FEATURE:
<221> NAME/KEY: MOD_RES
<222> LOCATION: (3)..(3)
<223> OTHER INFORMATION: D-Glu
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 73

Xaa Cys Glu His Phe Arg Trp Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: D-Ala
<220> FEATURE:
<223> OTHER INFORMATION: C-term NH2

<400> SEQUENCE: 74

Xaa Asp His Phe Arg Trp Ala Lys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES

```
<222> LOCATION: (7)..(7)
<223> OTHER INFORMATION: Bal
<220> FEATURE:
<223> OTHER INFORMATION: C-term NH2

<400> SEQUENCE: 75

Xaa Cys Ala His Xaa Arg Xaa Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 76

Xaa Xaa Ala His Phe Arg Trp Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
```

```
<223> OTHER INFORMATION: C-term NH2

<400> SEQUENCE: 77

Xaa Cys Ala His Phe Arg Trp Xaa
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 78

Xaa Xaa Ala His Phe Arg Trp Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
```

```
<222> LOCATION: (8)..(8)
<223> OTHER INFORMATION: D-Cys
<220> FEATURE:
<223> OTHER INFORMATION: C-term NH2

<400> SEQUENCE: 79

Phe Cys His Phe Arg Trp Ala Cys Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 80

Phe Cys His Tyr Arg Trp Ala Cys Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
```

```
<223> OTHER INFORMATION: C-term NH2

<400> SEQUENCE: 81

Phe Cys His Phe Arg Xaa Ala Cys Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 82

Phe Cys His Tyr Arg Trp Ala Cys Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
```

```
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 83

Phe Cys His Phe Arg Xaa Ala Cys Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term NH2

<400> SEQUENCE: 84

Phe Cys His Tyr Arg Xaa Ala Cys Thr
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: Apn
<220> FEATURE:
<223> OTHER INFORMATION: C-term NH2

<400> SEQUENCE: 85

Xaa Cys His Phe Arg Trp Xaa Cys
 1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 86

Xaa Asp Ala His Phe Arg Trp Lys
 1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal
<220> FEATURE:
<223> OTHER INFORMATION: C-term NH2

<400> SEQUENCE: 87

Xaa Asp Ala His Phe Arg Xaa Lys
```

```
1               5
```

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term OH

<400> SEQUENCE: 88

```
Xaa Cys Ala His Phe Arg Trp Xaa
1               5
```

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Abu
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 89

```
Xaa Cys Xaa His Phe Arg Trp Cys
1               5
```

<210> SEQ ID NO 90
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Val
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 90

Xaa Cys Val His Phe Arg Trp Cys
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ile
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 91

Xaa Cys Ile His Phe Arg Trp Cys
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 92

Xaa Cys Leu His Phe Arg Trp Cys
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Tle
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 93

Xaa Cys Xaa His Phe Arg Trp Cys
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
```

```
<223> OTHER INFORMATION: C-term NH2

<400> SEQUENCE: 94

Xaa Cys Xaa His Phe Arg Trp Cys
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 95

Xaa Xaa His Phe Arg Trp Xaa Cys
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 96
```

```
Xaa Cys His Phe Arg Trp Xaa Xaa
1               5
```

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 97

```
Xaa Xaa His Phe Arg Trp Xaa Xaa
1               5
```

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 98

```
Leu Cys His Phe Arg Trp Xaa Cys
1               5
```

<210> SEQ ID NO 99
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 99

Xaa Cys His Phe Arg Trp Xaa Cys
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 100

Ile Cys His Phe Arg Trp Xaa Cys
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
```

```
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 101

Phe Cys His Phe Arg Trp Xaa Cys
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 102

Val Cys His Phe Arg Trp Xaa Cys
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 2-Nal
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 103

Xaa Cys His Phe Arg Trp Xaa Cys
1               5

<210> SEQ ID NO 104
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 104

Xaa Cys His Phe Arg Trp Xaa Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 105

Phe Cys His Phe Arg Trp Xaa Cys
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: 3-Pal
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 106

Xaa Cys Xaa Phe Arg Trp Xaa Cys
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term OH

<400> SEQUENCE: 107

Xaa Cys Ala His Phe Arg Trp Cys
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2
```

```
<400> SEQUENCE: 108

Xaa Cys His Phe Arg Trp Xaa Cys
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 109

Xaa Asp His Xaa Arg Trp Ala Lys
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term NH2

<400> SEQUENCE: 110

Xaa Asp His Xaa Arg Trp Ala Lys
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 111

Xaa Cys His Xaa Arg Trp Xaa Cys
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Ahx
<220> FEATURE:
<223> OTHER INFORMATION: C-term NH2

<400> SEQUENCE: 112

Xaa Cys His Xaa Arg Trp Xaa Cys
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hPhe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
```

```
<223> OTHER INFORMATION: D-2-Nal
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 113

Phe Asp His Xaa Arg Trp Xaa Lys
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term NH2

<400> SEQUENCE: 114

Xaa Asp His Xaa Arg Trp Xaa Lys
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term OH

<400> SEQUENCE: 115

Xaa Asp His Phe Arg Trp Ala Lys
```

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
<220> FEATURE:
<223> OTHER INFORMATION: C-term OH

<400> SEQUENCE: 116

Xaa Cys His Phe Arg Trp Xaa Cys
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term OH

<400> SEQUENCE: 117

Phe Cys His Phe Arg Trp Ala Cys Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term OH

<400> SEQUENCE: 118

Phe Cys His Phe Arg Trp Ala Cys Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: D-Cys
<220> FEATURE:
<223> OTHER INFORMATION: C-term OH

<400> SEQUENCE: 119

Phe Cys His Phe Arg Trp Xaa Cys Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<223> OTHER INFORMATION: C-term OH

<400> SEQUENCE: 120

Xaa Cys His Phe Arg Trp Xaa Cys
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<223> OTHER INFORMATION: C-term OH

<400> SEQUENCE: 121

Xaa Asp His Phe Arg Trp Xaa Lys
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH
```

```
<400> SEQUENCE: 122

Xaa Asp His Phe Arg Trp Xaa Lys
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 123

Xaa Asp His Phe Arg Trp Xaa Lys
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 124

Xaa Asp His Phe Arg Trp Xaa Lys
1               5

<210> SEQ ID NO 125
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 125

Xaa Asp His Phe Arg Trp Xaa Lys
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 126

Xaa Asp His Phe Arg Trp Xaa Lys
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Chg
<220> FEATURE:
<221> NAME/KEY: DOMAIN
<222> LOCATION: (2)..(8)
```

```
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 127

Xaa Asp His Phe Arg Trp Xaa Lys
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hPhe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<223> OTHER INFORMATION: C-term OH

<400> SEQUENCE: 128

Phe Asp His Phe Arg Trp Xaa Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
```

```
<222> LOCATION: (7)..(7)
<223> OTHER INFORMATION: Gaba
<220> FEATURE:
<223> OTHER INFORMATION: C-term OH

<400> SEQUENCE: 129

Xaa Cys His Phe Arg Trp Xaa Cys
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<223> OTHER INFORMATION: C-term OH

<400> SEQUENCE: 130

Xaa Cys His Phe Arg Trp Xaa Cys
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
```

```
<223> OTHER INFORMATION: C-term OH

<400> SEQUENCE: 131

Xaa Cys His Phe Arg Trp Ala Cys
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: D-Ala
<220> FEATURE:
<223> OTHER INFORMATION: C-term OH

<400> SEQUENCE: 132

Xaa Cys His Phe Arg Trp Ala Cys
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<223> OTHER INFORMATION: C-term OH

<400> SEQUENCE: 133

Xaa Cys Ala His Xaa Arg Trp Cys
1               5
```

```
<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 2-Nal
<220> FEATURE:
<223> OTHER INFORMATION: C-term OH

<400> SEQUENCE: 134

Xaa Cys Ala His Xaa Arg Xaa Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: 1-Nal
<220> FEATURE:
<223> OTHER INFORMATION: C-term OH

<400> SEQUENCE: 135

Xaa Cys Ala His Xaa Arg Xaa Cys
1               5

<210> SEQ ID NO 136
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<221> NAME/KEY: MOD_RES
<222> LOCATION: (7)..(7)
<223> OTHER INFORMATION: Bal
<220> FEATURE:
<223> OTHER INFORMATION: C-term OH

<400> SEQUENCE: 136

Xaa Cys Ala His Xaa Arg Xaa Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term OH

<400> SEQUENCE: 137

Xaa Xaa Ala His Phe Arg Trp Cys
1               5

<210> SEQ ID NO 138
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term OH

<400> SEQUENCE: 138

Xaa Cys His Phe Arg Trp Xaa Xaa
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-2-Nal
<220> FEATURE:
<223> OTHER INFORMATION: C-term NH2

<400> SEQUENCE: 139

Arg Cys Ala His Xaa Arg Trp Cys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
```

```
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 140

Arg Cys Ala His Phe Arg Trp Cys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Arg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 141

Arg Cys Ala His Phe Arg Trp Cys
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Arg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2
```

```
<400> SEQUENCE: 142

Arg Cys Ala His Phe Arg Trp Xaa
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Arg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 143

Arg Cys His Phe Arg Trp Xaa Xaa
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 144

Arg Cys His Phe Arg Trp Xaa Xaa
1               5
```

```
<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<223> OTHER INFORMATION: C-term NH2

<400> SEQUENCE: 145

Arg Cys Ala His Phe Arg Trp Xaa
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Arg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 146

Arg Asp His Phe Arg Trp Ala Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (4)..(4)
<223> OTHER INFORMATION: D-Phe
<220> FEATURE:
<223> OTHER INFORMATION: C-term NH2

<400> SEQUENCE: 147

Arg Asp His Phe Arg Trp Ala Lys
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 148

Xaa Cys Ala His Phe Arg Trp Gly Cys
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: D-Ala
<220> FEATURE:
<223> OTHER INFORMATION: C-term NH2

<400> SEQUENCE: 149
```

```
Xaa Cys Ala His Phe Arg Trp Ala Cys
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 150

Xaa Cys Ala His Phe Arg Trp Ala Cys
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Gaba
<220> FEATURE:
<223> OTHER INFORMATION: C-term NH2

<400> SEQUENCE: 151

Xaa Cys Ala His Phe Arg Trp Xaa Cys
1               5
```

```
<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Apn
<220> FEATURE:
<223> OTHER INFORMATION: C-term NH2

<400> SEQUENCE: 152

Xaa Cys Ala His Phe Arg Trp Xaa Cys
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 153

Cys Glu His Phe Arg Trp Ala Cys
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
```

```
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: 2-Nal
<220> FEATURE:
<223> OTHER INFORMATION: C-term NH2

<400> SEQUENCE: 154

Cys Glu His Phe Arg Xaa Ala Cys
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 155

Cys Ala His Phe Arg Trp Ala Cys
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: 2-Nal
<220> FEATURE:
<223> OTHER INFORMATION: C-term NH2

<400> SEQUENCE: 156

Cys Ala His Phe Arg Xaa Ala Cys
1               5
```

```
<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-term NH2

<400> SEQUENCE: 157

Xaa Cys Ala His Phe Arg Trp Ala Cys
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (7)..(7)
<223> OTHER INFORMATION: Bal
<220> FEATURE:
<223> OTHER INFORMATION: C-term NH2

<400> SEQUENCE: 158

Xaa Asp Ala His Phe Arg Xaa Ala Lys
1               5

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (12)..(12)
<223> OTHER INFORMATION: Nle
<220> FEATURE:
<221> NAME/KEY: DOMAIN
<222> LOCATION: (13)..(18)
<223> OTHER INFORMATION: Cyclic
<220> FEATURE:
<221> NAME/KEY: MOD_RES
<222> LOCATION: (15)..(15)
<223> OTHER INFORMATION: D-2-Nal
<220> FEATURE:
<223> OTHER INFORMATION: C-term NH2

<400> SEQUENCE: 159

Tyr Gly Arg Lys Lys Arg Arg Gln Arg Arg Xaa Asp His Xaa Arg
1               5                   10                  15

Trp Lys

<210> SEQ ID NO 160
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (12)..(12)
<223> OTHER INFORMATION: Doc
<220> FEATURE:
<221> NAME/KEY: MOD_RES
<222> LOCATION: (13)..(13)
<223> OTHER INFORMATION: Nle
<220> FEATURE:
<221> NAME/KEY: DOMAIN
<222> LOCATION: (14)..(19)
<223> OTHER INFORMATION: Cyclic
<220> FEATURE:
<221> NAME/KEY: MOD_RES
<222> LOCATION: (16)..(16)
<223> OTHER INFORMATION: D-2-Nal
<220> FEATURE:
<223> OTHER INFORMATION: C-term NH2

<400> SEQUENCE: 160

Tyr Gly Arg Lys Lys Arg Arg Gln Arg Arg Xaa Xaa Asp His Xaa
1               5                   10                  15

Arg Trp Lys

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
```

```
<222> LOCATION: (8)..(8)
<223> OTHER INFORMATION: Beta-Ala
<220> FEATURE:
<223> OTHER INFORMATION: C-term NH2

<400> SEQUENCE: 161

Xaa Asp His Xaa Arg Trp Lys Ala Tyr Gly Arg Lys Lys Arg Arg Gln
1               5                   10                  15

Arg Arg Arg

<210> SEQ ID NO 162
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 162

Xaa Asp His Xaa Arg Trp Lys Ala Tyr Gly Arg Lys Lys Arg Arg Gln
1               5                   10                  15

Arg Arg Arg

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 163

Xaa Asp His Xaa Arg Trp Lys Xaa Xaa Tyr Gly Arg Lys Lys Arg Arg
1               5                   10                  15
```

Gln Arg Arg Arg
            20

<210> SEQ ID NO 164
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 164

Xaa Asp His Xaa Arg Trp Lys Pro Pro Lys Asp Tyr Gly Arg Lys Lys
1               5                   10                  15

Arg Arg Gln Arg Arg Arg
            20

<210> SEQ ID NO 165
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 165

Cys Glu His Xaa Arg Trp Gly Cys Pro Pro Lys Asp Tyr Gly Arg Lys
1               5                   10                  15

Lys Arg Arg Gln Arg Arg Arg
            20

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)

```
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 166

Xaa Asp His Xaa Arg Trp Lys Ala Ala Tyr Gly Arg Lys Lys Arg Arg
1               5                   10                  15

Gln Arg Arg
            20

<210> SEQ ID NO 167
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (12)..(12)
<223> OTHER INFORMATION: Doc
<220> FEATURE:
<223> OTHER INFORMATION: C-term NH2

<400> SEQUENCE: 167

Xaa Asp His Xaa Arg Trp Lys Pro Pro Lys Asp Xaa Tyr Gly Arg Lys
1               5                   10                  15

Lys Arg Arg Gln Arg Arg Arg
            20

<210> SEQ ID NO 168
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
```

```
<220> FEATURE:
<221> NAME/KEY: MOD_RES
<222> LOCATION: (13)..(13)
<223> OTHER INFORMATION: Doc
<220> FEATURE:
<223> OTHER INFORMATION: C-term NH2

<400> SEQUENCE: 168

Cys Glu His Xaa Arg Trp Gly Cys Pro Pro Lys Asp Xaa Tyr Gly Arg
1               5                   10                  15

Lys Lys Arg Arg Gln Arg Arg Arg
            20

<210> SEQ ID NO 169
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 169

Cys Glu His Xaa Arg Trp Ala Cys Pro Pro Lys Asp Ala Tyr Gly Arg
1               5                   10                  15

Lys Lys Arg Arg Gln Arg Arg Arg
            20

<210> SEQ ID NO 170
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Doc
<220> FEATURE:
<223> OTHER INFORMATION: C-term NH2

<400> SEQUENCE: 170

Cys Glu His Xaa Arg Trp Ala Cys Pro Pro Lys Asp Xaa Tyr Gly Arg
1               5                   10                  15

Lys Lys Arg Arg Gln Arg Arg Arg
```

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 171

Xaa Asp His Xaa Arg Trp Lys Xaa Xaa Tyr Gly Arg Lys Lys Arg Arg
1               5                   10                  15

Gln Arg Arg Arg
            20

<210> SEQ ID NO 172
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 172

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 173
<211> LENGTH: 22

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 173

Cys Glu His Xaa Arg Xaa Ala Cys Pro Pro Lys Asp Ala Arg Arg
1               5                   10                  15

Arg Arg Gln Arg Arg Arg
            20

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 174

Cys Glu His Xaa Arg Xaa Ala Cys Pro Pro Lys Asp Ala Gly Arg Arg
1               5                   10                  15

Arg Arg Arg Gln Arg Arg Arg
            20

<210> SEQ ID NO 175
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
-continued

<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 175

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 176
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 176

Cys Glu His Xaa Arg Trp Ala Cys Pro Pro Lys Asp Ala Tyr Gly Arg
1               5                   10                  15

Lys Lys Arg Gln Arg Arg Arg Arg
            20

<210> SEQ ID NO 177
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
```

```
<223> OTHER INFORMATION: Beta-Ala
<220> FEATURE:
<223> OTHER INFORMATION: C-term NH2

<400> SEQUENCE: 177

Cys Glu His Xaa Arg Trp Ala Cys Pro Pro Lys Asp Ala Tyr Gly Arg
1               5                   10                  15

Lys Lys Gln Arg Arg Arg Arg Arg
            20

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 178

Cys Glu His Xaa Arg Trp Ala Cys Pro Pro Lys Asp Ala Tyr Gly Arg
1               5                   10                  15

Lys Gln Lys Arg Arg Arg Arg Arg
            20

<210> SEQ ID NO 179
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 179

Cys Glu His Xaa Arg Trp Ala Cys Pro Pro Lys Asp Ala Tyr Gly Arg
1               5                   10                  15

Lys Lys Arg Arg Arg Arg Gln Arg
            20

<210> SEQ ID NO 180
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (15)..(15)
<223> OTHER INFORMATION: Aib
<220> FEATURE:
<223> OTHER INFORMATION: C-term NH2

<400> SEQUENCE: 180

Cys Glu His Xaa Arg Xaa Ala Cys Pro Pro Lys Asp Ala Tyr Xaa Arg
1               5                   10                  15

Lys Lys Arg Arg Gln Arg Arg Arg
            20

<210> SEQ ID NO 181
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 181

Cys Glu His Xaa Arg Xaa Ala Cys Pro Pro Arg Asp Ala Arg Arg Arg
1               5                   10                  15

Arg Arg Gln Arg Arg Arg
            20

<210> SEQ ID NO 182
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 182

Cys Glu His Xaa Arg Xaa Ala Cys Pro Pro Lys Asp Ala Arg Arg Arg
1               5                   10                  15

Arg Arg Gln Arg Arg Arg
            20

<210> SEQ ID NO 183
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 183

Cys Glu His Xaa Arg Xaa Ala Cys Pro Pro Lys Asp Ala Arg Arg Arg
1               5                   10                  15

Arg Arg Arg Gln Arg Arg Arg
            20

<210> SEQ ID NO 184
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 184

Cys Glu His Xaa Arg Xaa Ala Cys Pro Pro Arg Asp Ala Arg Arg
1               5                   10                  15

Arg Arg Gln Arg Arg Arg
            20

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 185

Cys Glu His Xaa Arg Xaa Ala Cys Pro Pro Lys Asp Ala Arg Arg
1               5                   10                  15

Arg Arg Gln Arg Arg Arg
            20

<210> SEQ ID NO 186
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
```

<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 186

Cys Glu His Xaa Arg Xaa Ala Cys Pro Pro Lys Asp Ala Arg Arg
1               5                   10                  15

Arg Arg Arg Gln Arg Arg Arg
            20

<210> SEQ ID NO 187
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 187

Cys Glu His Xaa Arg Xaa Ala Cys Pro Pro Arg Asp Ala Arg Arg
1               5                   10                  15

Arg Arg Arg Gln Arg Arg Arg
            20

<210> SEQ ID NO 188
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)

<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 188

Cys Glu His Xaa Arg Xaa Ala Cys Pro Pro Arg Asp Ala Arg Arg
1               5                   10                  15

Arg Arg Gln Arg Arg Arg
            20

<210> SEQ ID NO 189
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 189

Cys Glu His Xaa Arg Xaa Ala Cys Pro Pro Lys Asp Ala Arg Arg
1               5                   10                  15

Arg Arg Arg Gln Arg Arg Arg
            20

<210> SEQ ID NO 190
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 190

Cys Glu His Xaa Arg Trp Ala Cys Pro Pro Lys Asp Ala Tyr Gly Arg
1               5                   10                  15

Lys Lys Arg Arg Arg Gln Arg Arg
            20

<210> SEQ ID NO 191
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 191

Cys Glu His Xaa Arg Trp Ala Cys Pro Pro Lys Asp Ala Tyr Gly Arg
1               5                   10                  15

Gln Lys Lys Arg Arg Arg Arg Arg
            20

<210> SEQ ID NO 192
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 192

Cys Glu His Xaa Arg Trp Ala Cys Pro Pro Lys Asp Ala Tyr Gly Arg
1               5                   10                  15

Lys Lys Arg Arg Arg Arg Arg Gln
            20

<210> SEQ ID NO 193
<211> LENGTH: 24
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 193

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 194
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 194

Cys Glu His Xaa Arg Xaa Ala Cys Pro Pro Lys Asp Ala Tyr Gly Arg
1               5                   10                  15

Lys Lys Arg Arg Gln Arg Arg Arg
            20

<210> SEQ ID NO 195
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 195

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 196
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 196

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 197
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
```

```
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 197

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 198
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 198

Cys Glu His Xaa Arg Xaa Ala Cys Pro Pro Lys Asp Ala Tyr Gly Arg
1               5                   10                  15

Arg Lys Arg Arg Gln Arg Arg Arg
            20

<210> SEQ ID NO 199
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
```

```
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 199

Cys Glu His Xaa Arg Xaa Ala Cys Pro Pro Lys Asp Ala Gly Arg Arg
1               5                   10                  15

Lys Arg Arg Gln Arg Arg Arg
            20

<210> SEQ ID NO 200
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 200

Cys Glu His Xaa Arg Xaa Ala Cys Pro Pro Lys Asp Ala Gly Arg Lys
1               5                   10                  15

Arg Arg Arg Gln Arg Arg Arg
            20

<210> SEQ ID NO 201
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
```

<220> FEATURE:
<223> OTHER INFORMATION: C-term NH2

<400> SEQUENCE: 201

Cys Glu His Xaa Arg Xaa Ala Cys Pro Pro Lys Asp Ala Tyr Gly Arg
1               5                   10                  15

Arg Lys Arg Arg Gln Arg Arg Arg
            20

<210> SEQ ID NO 202
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 202

Cys Glu His Xaa Arg Xaa Ala Cys Pro Pro Lys Asp Ala Tyr Gly Arg
1               5                   10                  15

Lys Arg Arg Arg Gln Arg Arg Arg
            20

<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 203

Cys Glu His Xaa Arg Xaa Ala Cys Pro Pro Lys Asp Ala Gly Arg Arg
1               5                   10                  15

Lys Arg Arg Gln Arg Arg Arg
            20

<210> SEQ ID NO 204
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 204

Cys Glu His Xaa Arg Xaa Ala Cys Pro Pro Lys Asp Ala Gly Arg Lys
1               5                   10                  15

Arg Arg Arg Gln Arg Arg Arg
            20

<210> SEQ ID NO 205
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 205

Cys Glu His Xaa Arg Xaa Ala Cys Pro Pro Lys Asp Ala Arg Arg Lys
1               5                   10                  15

Arg Arg Gln Arg Arg Arg
            20

```
<210> SEQ ID NO 206
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 206

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 207
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 207

Cys Glu His Xaa Arg Xaa Ala Cys Pro Pro Lys Asp Ala Tyr Gly Arg
1               5                   10                  15

Lys Arg Arg Arg Gln Arg Arg Arg
            20

<210> SEQ ID NO 208
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 208

Cys Glu His Xaa Arg Xaa Ala Cys Pro Pro Lys Asp Ala Arg Arg Lys
1               5                   10                  15

Arg Arg Gln Arg Arg Arg
            20

<210> SEQ ID NO 209
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 209

Cys Glu His Xaa Arg Xaa Ala Cys Pro Pro Lys Asp Ala Arg Lys Arg
1               5                   10                  15

Arg Arg Gln Arg Arg Arg
            20

<210> SEQ ID NO 210
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 210

Cys Glu His Xaa Arg Xaa Ala Cys Pro Pro Lys Asp Ala Tyr Gly Arg
1               5                   10                  15

Arg Lys Arg Arg Gln Arg Arg Arg
            20

<210> SEQ ID NO 211
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 211

Cys Glu His Xaa Arg Xaa Ala Cys Pro Pro Lys Asp Ala Tyr Gly Arg
1               5                   10                  15

Lys Arg Arg Arg Gln Arg Arg Arg
            20

<210> SEQ ID NO 212
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 212

Cys Glu His Xaa Arg Xaa Ala Cys Pro Pro Lys Asp Ala Gly Arg Arg
1               5                   10                  15

Lys Arg Arg Gln Arg Arg Arg
            20

<210> SEQ ID NO 213
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 213

Cys Glu His Xaa Arg Xaa Ala Cys Pro Pro Lys Asp Ala Gly Arg Lys
1               5                   10                  15

Arg Arg Arg Gln Arg Arg Arg
            20

<210> SEQ ID NO 214
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
```

<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 214

Cys Glu His Xaa Arg Trp Ala Cys Pro Pro Lys Asp Ala Arg Arg Arg
1               5                   10                  15

Arg Arg Gln Arg Arg Arg
            20

<210> SEQ ID NO 215
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 215

Cys Glu His Xaa Arg Trp Ala Cys Pro Pro Arg Asp Ala Arg Arg Arg
1               5                   10                  15

Arg Arg Gln Arg Arg Arg
            20

<210> SEQ ID NO 216
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 216

Cys Glu His Xaa Arg Trp Ala Cys Pro Pro Lys Asp Ala Tyr Gly Arg
1               5                   10                  15

Arg Arg Arg Arg Gln Arg Arg Arg
            20

```
<210> SEQ ID NO 217
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 217

Cys Glu His Xaa Arg Trp Ala Cys Pro Pro Arg Asp Ala Tyr Gly Arg
1               5                   10                  15

Arg Arg Arg Arg Gln Arg Arg Arg
            20

<210> SEQ ID NO 218
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 218

Cys Glu His Xaa Arg Trp Ala Cys Pro Pro Lys Asp Ala Arg Arg Arg
1               5                   10                  15

Arg Arg Gln Arg Arg Arg Arg
            20

<210> SEQ ID NO 219
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
```

```
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 219

Cys Glu His Xaa Arg Trp Ala Cys Pro Pro Arg Asp Ala Arg Arg
1               5                   10                  15

Arg Arg Gln Arg Arg Arg Arg
            20

<210> SEQ ID NO 220
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 220

Cys Glu His Xaa Arg Trp Ala Cys Pro Pro Lys Asp Ala Tyr Gly Arg
1               5                   10                  15

Arg Arg Arg Arg Gln Arg Arg Arg Arg
            20                  25

<210> SEQ ID NO 221
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2
```

```
<400> SEQUENCE: 221

Cys Glu His Xaa Arg Trp Ala Cys Pro Pro Arg Asp Ala Tyr Gly Arg
1               5                   10                  15

Arg Arg Arg Arg Gln Arg Arg Arg
            20                  25

<210> SEQ ID NO 222
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 222

Cys Glu His Xaa Arg Xaa Ala Cys Pro Pro Lys Asp Ala Arg Arg Arg
1               5                   10                  15

Arg Arg Gln Arg Arg Arg Arg
            20

<210> SEQ ID NO 223
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 223

Cys Glu His Xaa Arg Xaa Ala Cys Pro Pro Arg Asp Ala Arg Arg Arg
1               5                   10                  15
```

Arg Arg Gln Arg Arg Arg Arg
            20

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 224

Cys Glu His Xaa Arg Xaa Ala Cys Pro Pro Arg Asp Ala Arg Arg
1               5                   10                  15

Arg Arg Arg Gln Arg Arg Arg
            20

<210> SEQ ID NO 225
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 225

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 226

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 226

Cys Glu His Xaa Arg Xaa Ala Cys Pro Pro Arg Asp Ala Tyr Gly Arg
1               5                   10                  15

Arg Arg Arg Arg Gln Arg Arg Arg
            20

<210> SEQ ID NO 227
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 227

Cys Glu His Xaa Arg Xaa Ala Cys Pro Pro Lys Asp Ala Tyr Gly Arg
1               5                   10                  15

Arg Arg Arg Arg Gln Arg Arg Arg Arg
            20                  25

<210> SEQ ID NO 228
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 228

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 229
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 229

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 230
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
```

```
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 230

Cys Glu His Xaa Arg Xaa Ala Cys Pro Pro Arg Asp Ala Tyr Gly Arg
1               5                   10                  15

Arg Arg Arg Arg Arg Gln Arg Arg Arg
            20                  25

<210> SEQ ID NO 231
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 231

Cys Glu His Xaa Arg Xaa Ala Cys Pro Pro Arg Asp Ala Arg Arg Arg
1               5                   10                  15

Arg Arg Arg Gln Arg Arg Arg
            20

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
```

<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 232

Cys Glu His Xaa Arg Xaa Ala Cys Pro Pro Lys Asp Ala Arg Arg Arg
1               5                   10                  15

Arg Arg Gln Arg Arg Arg Arg
            20

<210> SEQ ID NO 233
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 233

Cys Glu His Xaa Arg Xaa Ala Cys Pro Pro Arg Asp Ala Arg Arg Arg
1               5                   10                  15

Arg Arg Gln Arg Arg Arg Arg
            20

<210> SEQ ID NO 234
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal

```
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 234

Cys Glu His Xaa Arg Xaa Ala Cys Pro Pro Lys Asp Ala Tyr Gly Arg
1               5                   10                  15

Arg Arg Arg Arg Gln Arg Arg Arg
            20

<210> SEQ ID NO 235
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 235

Cys Glu His Xaa Arg Xaa Ala Cys Pro Pro Arg Asp Ala Tyr Gly Arg
1               5                   10                  15

Arg Arg Arg Arg Gln Arg Arg Arg
            20

<210> SEQ ID NO 236
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
```

<223> OTHER INFORMATION: C-term NH2

<400> SEQUENCE: 236

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 237
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 237

Cys Glu His Xaa Arg Xaa Ala Cys Pro Pro Arg Asp Ala Tyr Gly Arg
1               5                   10                  15

Arg Arg Arg Arg Arg Gln Arg Arg Arg
            20                  25

<210> SEQ ID NO 238
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 238

Cys Glu His Xaa Arg Xaa Ala Cys Pro Pro Lys Asp Ala Tyr Gly Arg

```
1               5                   10                  15

Arg Arg Arg Arg Gln Arg Arg Arg
            20                  25

<210> SEQ ID NO 239
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 239

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 240
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 240

Cys Glu His Xaa Arg Xaa Ala Cys Pro Pro Lys Asp Ala Arg Arg Arg
1               5                   10                  15

Arg Arg Gln Arg Arg Arg Arg
            20
```

```
<210> SEQ ID NO 241
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 241

Cys Glu His Xaa Arg Xaa Ala Cys Pro Pro Arg Asp Ala Arg Arg
1               5                   10                  15

Arg Arg Gln Arg Arg Arg Arg
            20

<210> SEQ ID NO 242
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 242

Cys Glu His Xaa Arg Xaa Ala Cys Pro Pro Arg Asp Ala Tyr Gly Arg
1               5                   10                  15

Arg Arg Arg Arg Gln Arg Arg Arg
            20

<210> SEQ ID NO 243
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 243

Cys Glu His Xaa Arg Xaa Ala Cys Pro Pro Lys Asp Ala Tyr Gly Arg
1               5                   10                  15

Arg Arg Arg Arg Gln Arg Arg Arg Arg
            20                  25

<210> SEQ ID NO 244
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 244

Cys Glu His Xaa Arg Xaa Ala Cys Pro Pro Arg Asp Ala Tyr Gly Arg
1               5                   10                  15

Arg Arg Arg Arg Gln Arg Arg Arg Arg
            20                  25

<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 245

Cys Glu His Xaa Arg Xaa Ala Cys Pro Pro Lys Asp Ala Tyr Gly Arg
1               5                   10                  15

Arg Arg Arg Arg Arg Gln Arg Arg Arg
            20                  25

<210> SEQ ID NO 246
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<221> NAME/KEY: MOD_RES
<222> LOCATION: (13)..(13)
<223> OTHER INFORMATION: Beta-Ala
<220> FEATURE:
<223> OTHER INFORMATION: C-term NH2

<400> SEQUENCE: 246

Cys Glu His Xaa Arg Xaa Ala Cys Pro Pro Arg Asp Ala Tyr Gly Arg
1               5                   10                  15

Arg Arg Arg Arg Arg Gln Arg Arg Arg
            20                  25

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:

```
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 247

Xaa Cys Ala His Phe Arg Trp Cys Xaa Xaa Tyr Gly Arg Lys Lys Arg
1               5                   10                  15

Arg Gln Arg Arg Arg
            20

<210> SEQ ID NO 248
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 248

Xaa Cys Ala His Phe Arg Trp Cys Ala Tyr Gly Arg Lys Lys Arg Gln
1               5                   10                  15

Arg Arg Arg Arg
            20

<210> SEQ ID NO 249
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 249

Xaa Cys Ala His Phe Arg Trp Cys Xaa Tyr Gly Arg Lys Lys Arg Arg
1               5                   10                  15

Gln Arg Arg Arg
            20

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 250

Xaa Cys Ala His Phe Arg Trp Cys Ala Arg Arg Arg Arg Arg Gln Arg
1               5                   10                  15

Arg Arg

<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 251

Xaa Cys Ala His Phe Arg Trp Cys Ala Gly Arg Arg Arg Arg Gln
1               5                   10                  15

Arg Arg Arg

<210> SEQ ID NO 252
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 252

Xaa Cys Ala His Phe Arg Trp Cys Ala Tyr Gly Arg Arg Arg Arg
1               5                   10                  15

Gln Arg Arg Arg
            20

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 253

Xaa Cys Ala His Phe Arg Trp Cys Ala Gly Arg Arg Arg Arg Gln
1               5                   10                  15

Arg Arg Arg Arg
            20

<210> SEQ ID NO 254
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 254

Xaa Cys Ala His Phe Arg Trp Cys Ala Tyr Gly Arg Arg Lys Arg
1               5                   10                  15

Gln Arg Arg Arg
            20

<210> SEQ ID NO 255
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 255

Xaa Cys Ala His Phe Arg Trp Cys Ala Tyr Gly Arg Lys Arg Arg Arg
1               5                   10                  15

Gln Arg Arg Arg
            20

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 256

Xaa Cys Ala His Phe Arg Trp Cys Ala Gly Arg Arg Lys Arg Arg Gln
1               5                   10                  15

Arg Arg Arg

<210> SEQ ID NO 257
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 257

Xaa Cys Ala His Phe Arg Trp Cys Ala Gly Arg Lys Arg Arg Gln
1               5                   10                  15

Arg Arg Arg

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 258

Xaa Cys Ala His Phe Arg Trp Cys Ala Arg Arg Lys Arg Arg Gln Arg
1               5                   10                  15

Arg Arg

<210> SEQ ID NO 259
```

```
-continued

<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 259

Xaa Cys Ala His Phe Arg Trp Cys Ala Arg Lys Arg Arg Arg Gln Arg
1               5                   10                  15

Arg Arg

<210> SEQ ID NO 260
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 260

Xaa Cys Ala His Phe Arg Trp Cys Ala Ala Arg Arg Arg Arg Gln
1               5                   10                  15

Arg Arg Arg
```

```
<210> SEQ ID NO 261
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 261

Xaa Cys Ala His Phe Arg Trp Cys Ala Ala Gly Arg Arg Arg Arg
1               5                   10                  15

Gln Arg Arg Arg
            20

<210> SEQ ID NO 262
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 262

Xaa Cys Ala His Phe Arg Trp Cys Ala Ala Tyr Gly Arg Arg Arg
1               5                   10                  15

Arg Gln Arg Arg Arg
```

```
<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 263

Xaa Cys Ala His Phe Arg Trp Cys Xaa Arg Arg Arg Arg Arg Gln Arg
1               5                   10                  15

Arg Arg

<210> SEQ ID NO 264
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 264

Xaa Cys Ala His Phe Arg Trp Cys Xaa Gly Arg Arg Arg Arg Arg Gln
1               5                   10                  15
```

Arg Arg Arg

```
<210> SEQ ID NO 265
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 265
```

Xaa Cys Ala His Phe Arg Trp Cys Xaa Tyr Gly Arg Arg Arg Arg
1               5                   10                  15

Gln Arg Arg Arg
            20

```
<210> SEQ ID NO 266
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 266
```

```
Xaa Cys Ala His Phe Arg Trp Cys Xaa Xaa Arg Arg Arg Arg Gln
1               5                   10                  15

Arg Arg Arg

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 267

Xaa Cys Ala His Phe Arg Trp Cys Xaa Xaa Gly Arg Arg Arg Arg
1               5                   10                  15

Gln Arg Arg Arg
            20

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2
```

-continued

```
<400> SEQUENCE: 268

Xaa Cys Ala His Phe Arg Trp Cys Xaa Xaa Tyr Gly Arg Arg Arg
1               5                   10                  15

Arg Gln Arg Arg Arg
            20

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 269

Xaa Cys Ala His Phe Arg Trp Cys Ala Arg Arg Arg Arg Gln Arg
1               5                   10                  15

Arg Arg Arg

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
```

<223> OTHER INFORMATION: C-term NH2

<400> SEQUENCE: 270

Xaa Cys Ala His Phe Arg Trp Cys Ala Tyr Gly Arg Arg Arg Arg
1               5                   10                  15

Gln Arg Arg Arg Arg
            20

<210> SEQ ID NO 271
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 271

Xaa Cys Ala His Phe Arg Trp Cys Ala Ala Arg Arg Arg Arg Gln
1               5                   10                  15

Arg Arg Arg Arg
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES

```
<222> LOCATION: (9)..(10)
<223> OTHER INFORMATION: Beta-Ala
<220> FEATURE:
<223> OTHER INFORMATION: C-term NH2

<400> SEQUENCE: 272

Xaa Cys Ala His Phe Arg Trp Cys Ala Ala Gly Arg Arg Arg Arg
1               5                   10                  15

Gln Arg Arg Arg Arg
            20

<210> SEQ ID NO 273
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 273

Xaa Cys Ala His Phe Arg Trp Cys Ala Ala Tyr Gly Arg Arg Arg
1               5                   10                  15

Arg Gln Arg Arg Arg Arg
            20

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
```

```
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 274

Xaa Cys Ala His Phe Arg Trp Cys Xaa Arg Arg Arg Arg Gln Arg
1               5                   10                  15

Arg Arg Arg

<210> SEQ ID NO 275
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 275

Xaa Cys Ala His Phe Arg Trp Cys Xaa Gly Arg Arg Arg Arg Gln
1               5                   10                  15

Arg Arg Arg Arg
            20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
```

```
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 276

Xaa Cys Ala His Phe Arg Trp Cys Xaa Tyr Gly Arg Arg Arg Arg
1               5                   10                  15

Gln Arg Arg Arg Arg
            20

<210> SEQ ID NO 277
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 277

Xaa Cys Ala His Phe Arg Trp Cys Xaa Xaa Arg Arg Arg Arg Gln
1               5                   10                  15

Arg Arg Arg Arg
            20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 278

Xaa Cys Ala His Phe Arg Trp Cys Xaa Xaa Gly Arg Arg Arg Arg
1               5                   10                  15

Gln Arg Arg Arg Arg
            20

<210> SEQ ID NO 279
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 279

Xaa Cys Ala His Phe Arg Trp Cys Xaa Xaa Tyr Gly Arg Arg Arg
1               5                   10                  15

Arg Gln Arg Arg Arg Arg
            20

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
```

```
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 280

Xaa Cys His Phe Arg Trp Xaa Cys Ala Tyr Gly Arg Arg Arg Arg
1               5                   10                  15

Gln Arg Arg Arg
            20

<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 281

Xaa Cys His Phe Arg Trp Xaa Cys Ala Arg Arg Arg Arg Gln Arg
1               5                   10                  15

Arg Arg

<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
```

```
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 282

Xaa Asp His Phe Arg Trp Ala Lys Ala Tyr Gly Arg Arg Arg Arg
1               5                   10                  15

Gln Arg Arg Arg
            20

<210> SEQ ID NO 283
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 283

Xaa Asp His Phe Arg Trp Ala Lys Ala Arg Arg Arg Arg Gln Arg
1               5                   10                  15

Arg Arg

<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
```

```
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 284

Xaa Asp His Phe Arg Trp Lys Ala Tyr Gly Arg Arg Arg Arg Gln
1               5                   10                  15

Arg Arg Arg

<210> SEQ ID NO 285
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 285

Xaa Asp His Phe Arg Trp Lys Ala Gly Arg Arg Arg Arg Gln Arg
1               5                   10                  15

Arg Arg

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2
```

```
<400> SEQUENCE: 286

Xaa Asp His Phe Arg Trp Lys Ala Arg Arg Arg Arg Gln Arg Arg
1               5                   10                  15

Arg

<210> SEQ ID NO 287
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 287

Xaa Asp His Phe Arg Trp Lys Ala Ala Tyr Gly Arg Arg Arg Arg
1               5                   10                  15

Gln Arg Arg Arg
            20

<210> SEQ ID NO 288
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 288

Xaa Asp His Phe Arg Trp Lys Ala Ala Gly Arg Arg Arg Arg Gln
1               5                   10                  15
```

Arg Arg Arg

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 289

Xaa Asp His Phe Arg Trp Lys Ala Ala Arg Arg Arg Arg Gln Arg
1               5                   10                  15

Arg Arg

<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 290

Xaa Asp His Phe Arg Trp Lys Xaa Tyr Gly Arg Arg Arg Arg Gln
1               5                   10                  15

Arg Arg Arg

<210> SEQ ID NO 291
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 291

Xaa Asp His Phe Arg Trp Lys Xaa Gly Arg Arg Arg Arg Gln Arg
1               5                   10                  15

Arg Arg

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 292

Xaa Asp His Phe Arg Trp Lys Xaa Arg Arg Arg Arg Gln Arg Arg
1               5                   10                  15

Arg

<210> SEQ ID NO 293
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 293

Xaa Asp His Phe Arg Trp Lys Xaa Xaa Tyr Gly Arg Arg Arg Arg
1               5                   10                  15

Gln Arg Arg Arg
            20

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 294

Xaa Asp His Phe Arg Trp Lys Xaa Xaa Gly Arg Arg Arg Arg Gln
1               5                   10                  15

Arg Arg Arg

<210> SEQ ID NO 295
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 295

Xaa Asp His Phe Arg Trp Lys Xaa Xaa Arg Arg Arg Arg Gln Arg
1               5                   10                  15

Arg Arg

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 296

Xaa Asp His Phe Arg Trp Lys Ala Tyr Gly Arg Arg Arg Arg Gln
1               5                   10                  15

Arg Arg Arg Arg
            20

<210> SEQ ID NO 297
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
```

```
<222> LOCATION: (8)..(8)
<223> OTHER INFORMATION: Beta-Ala
<220> FEATURE:
<223> OTHER INFORMATION: C-term NH2

<400> SEQUENCE: 297

Xaa Asp His Phe Arg Trp Lys Ala Gly Arg Arg Arg Arg Gln Arg
1               5                   10                  15

Arg Arg Arg

<210> SEQ ID NO 298
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Beta-Ala
<220> FEATURE:
<223> OTHER INFORMATION: C-term NH2

<400> SEQUENCE: 298

Xaa Asp His Phe Arg Trp Lys Ala Arg Arg Arg Arg Arg Gln Arg Arg
1               5                   10                  15

Arg Arg

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 299
```

-continued

```
Xaa Asp His Phe Arg Trp Lys Ala Ala Tyr Gly Arg Arg Arg Arg
1               5                   10                  15

Gln Arg Arg Arg Arg
            20

<210> SEQ ID NO 300
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 300

Xaa Asp His Phe Arg Trp Lys Ala Ala Gly Arg Arg Arg Arg Gln
1               5                   10                  15

Arg Arg Arg Arg
            20

<210> SEQ ID NO 301
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Beta-Ala
<220> FEATURE:
<223> OTHER INFORMATION: C-term NH2

<400> SEQUENCE: 301

Xaa Asp His Phe Arg Trp Lys Ala Ala Arg Arg Arg Arg Gln Arg
1               5                   10                  15

Arg Arg Arg
```

```
<210> SEQ ID NO 302
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 302

Xaa Asp His Phe Arg Trp Lys Xaa Tyr Gly Arg Arg Arg Arg Gln
1               5                   10                  15

Arg Arg Arg Arg
            20

<210> SEQ ID NO 303
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 303

Xaa Asp His Phe Arg Trp Lys Xaa Gly Arg Arg Arg Arg Gln Arg
1               5                   10                  15

Arg Arg Arg

<210> SEQ ID NO 304
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(8)
<223> OTHER INFORMATION: Doc
<220> FEATURE:
<223> OTHER INFORMATION: C-term NH2

<400> SEQUENCE: 304

Xaa Asp His Phe Arg Trp Lys Xaa Arg Arg Arg Arg Gln Arg Arg
1               5                   10                  15

Arg Arg

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 305

Xaa Asp His Phe Arg Trp Lys Xaa Xaa Tyr Gly Arg Arg Arg Arg
1               5                   10                  15

Gln Arg Arg Arg Arg
            20

<210> SEQ ID NO 306
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 306

Xaa Asp His Phe Arg Trp Lys Xaa Xaa Gly Arg Arg Arg Arg Gln
1               5                  10                  15

Arg Arg Arg Arg
            20

<210> SEQ ID NO 307
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (8)..(9)
<223> OTHER INFORMATION: Doc
<220> FEATURE:
<223> OTHER INFORMATION: C-term NH2

<400> SEQUENCE: 307

Xaa Asp His Phe Arg Trp Lys Xaa Xaa Arg Arg Arg Arg Gln Arg
1               5                  10                  15

Arg Arg Arg

<210> SEQ ID NO 308
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 308

Xaa Asp His Phe Arg Trp Ala Lys Ala Tyr Gly Arg Arg Arg Arg
1               5                   10                  15

Gln Arg Arg Arg
            20

<210> SEQ ID NO 309
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 309

Xaa Asp His Phe Arg Trp Ala Lys Ala Arg Arg Arg Arg Gln Arg
1               5                   10                  15

Arg Arg

<210> SEQ ID NO 310
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 310

Xaa Cys His Phe Arg Trp Xaa Cys Ala Tyr Gly Arg Arg Arg Arg
1               5                   10                  15

Gln Arg Arg Arg
            20

<210> SEQ ID NO 311
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 311

Xaa Cys His Phe Arg Trp Xaa Cys Ala Arg Arg Arg Arg Gln Arg
1               5                   10                  15

Arg Arg

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 312

Phe Cys His Phe Arg Trp Ala Cys Thr Ala Tyr Gly Arg Arg Arg
1               5                   10                  15

Arg Gln Arg Arg Arg
            20

<210> SEQ ID NO 313
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 313

Phe Cys His Phe Arg Trp Ala Cys Thr Ala Arg Arg Arg Arg Gln
1               5                   10                  15

Arg Arg Arg

<210> SEQ ID NO 314
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 314

Xaa Cys His Phe Arg Trp Xaa Cys Ala Tyr Gly Arg Arg Arg Arg
1               5                   10                  15

Gln Arg Arg Arg
        20

<210> SEQ ID NO 315
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 315

Xaa Cys His Phe Arg Trp Xaa Cys Ala Arg Arg Arg Arg Gln Arg
1               5                   10                  15

Arg Arg

<210> SEQ ID NO 316
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 316

Xaa Asp His Phe Arg Trp Xaa Lys Ala Tyr Gly Arg Arg Arg Arg Arg
1               5                   10                  15

Gln Arg Arg Arg
            20

<210> SEQ ID NO 317
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Cha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 317

Xaa Asp His Phe Arg Trp Xaa Lys Ala Arg Arg Arg Arg Arg Gln Arg
1               5                   10                  15

Arg Arg

<210> SEQ ID NO 318
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 318

Xaa Asp His Phe Arg Trp Xaa Lys Ala Tyr Gly Arg Arg Arg Arg
1               5                   10                  15

Gln Arg Arg Arg
            20

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 319

Xaa Asp His Phe Arg Trp Xaa Lys Ala Arg Arg Arg Arg Arg Gln Arg
1               5                   10                  15

Arg Arg

<210> SEQ ID NO 320
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 320

Xaa Asp His Phe Arg Trp Xaa Lys Ala Tyr Gly Arg Arg Arg Arg
1               5                   10                  15

Gln Arg Arg Arg
            20

<210> SEQ ID NO 321
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 321

Xaa Asp His Phe Arg Trp Xaa Lys Ala Arg Arg Arg Arg Gln Arg
1               5                   10                  15

Arg Arg
```

```
<210> SEQ ID NO 322
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 322

Xaa Asp His Phe Arg Trp Xaa Lys Ala Tyr Gly Arg Arg Arg Arg
1               5                   10                  15

Gln Arg Arg Arg
            20

<210> SEQ ID NO 323
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 323

Xaa Asp His Phe Arg Trp Xaa Lys Ala Arg Arg Arg Arg Gln Arg
1               5                   10                  15
```

Arg Arg

```
<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 324

Xaa Asp His Phe Arg Trp Xaa Lys Ala Ala Tyr Gly Arg Arg Arg Arg
1               5                   10                  15

Arg Gln Arg Arg Arg
            20

<210> SEQ ID NO 325
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 325

Xaa Asp His Phe Arg Trp Xaa Lys Ala Ala Arg Arg Arg Arg Arg Gln
```

-continued

```
1               5                   10                  15

Arg Arg Arg

<210> SEQ ID NO 326
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 326

Xaa Asp His Phe Arg Trp Xaa Lys Xaa Tyr Gly Arg Arg Arg Arg
1               5                   10                  15

Gln Arg Arg Arg
            20

<210> SEQ ID NO 327
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 327
```

```
Xaa Asp His Phe Arg Trp Xaa Lys Xaa Arg Arg Arg Arg Gln Arg
1               5                   10                  15

Arg Arg

<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 328

Xaa Asp His Phe Arg Trp Xaa Lys Xaa Xaa Tyr Gly Arg Arg Arg
1               5                   10                  15

Arg Gln Arg Arg Arg
            20

<210> SEQ ID NO 329
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2
```

<400> SEQUENCE: 329

Xaa Asp His Phe Arg Trp Xaa Lys Xaa Xaa Arg Arg Arg Arg Gln
1               5                   10                  15

Arg Arg Arg

<210> SEQ ID NO 330
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 330

Xaa Asp His Phe Arg Trp Xaa Lys Ala Tyr Gly Arg Arg Arg Arg
1               5                   10                  15

Gln Arg Arg Arg Arg
                20

<210> SEQ ID NO 331
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala

```
<220> FEATURE:
<223> OTHER INFORMATION: C-term NH2

<400> SEQUENCE: 331

Xaa Asp His Phe Arg Trp Xaa Lys Ala Arg Arg Arg Arg Gln Arg
1               5                   10                  15

Arg Arg Arg

<210> SEQ ID NO 332
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 332

Xaa Asp His Phe Arg Trp Xaa Lys Ala Ala Tyr Gly Arg Arg Arg
1               5                   10                  15

Arg Gln Arg Arg Arg Arg
            20

<210> SEQ ID NO 333
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
```

```
<222> LOCATION: (9)..(10)
<223> OTHER INFORMATION: Beta-Ala
<220> FEATURE:
<223> OTHER INFORMATION: C-term NH2

<400> SEQUENCE: 333

Xaa Asp His Phe Arg Trp Xaa Lys Ala Ala Arg Arg Arg Arg Gln
1               5                   10                  15

Arg Arg Arg Arg
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 334

Xaa Asp His Phe Arg Trp Xaa Lys Xaa Tyr Gly Arg Arg Arg Arg
1               5                   10                  15

Gln Arg Arg Arg Arg
            20

<210> SEQ ID NO 335
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 335

Xaa Asp His Phe Arg Trp Xaa Lys Xaa Arg Arg Arg Arg Gln Arg
1               5                   10                  15

Arg Arg Arg

<210> SEQ ID NO 336
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 336

Xaa Asp His Phe Arg Trp Xaa Lys Xaa Xaa Tyr Gly Arg Arg Arg
1               5                   10                  15

Arg Gln Arg Arg Arg Arg
            20

<210> SEQ ID NO 337
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hCha
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 337

Xaa Asp His Phe Arg Trp Xaa Lys Xaa Xaa Arg Arg Arg Arg Gln
1               5                  10                  15

Arg Arg Arg Arg
            20

<210> SEQ ID NO 338
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 338

Xaa Asp His Phe Arg Trp Xaa Lys Ala Tyr Gly Arg Arg Arg Arg
1               5                  10                  15

Gln Arg Arg Arg
            20

<210> SEQ ID NO 339
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Chg
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 339

Xaa Asp His Phe Arg Trp Xaa Lys Ala Arg Arg Arg Arg Gln Arg
1               5                   10                  15

Arg Arg

<210> SEQ ID NO 340
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hPhe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 340

Phe Asp His Phe Arg Trp Xaa Lys Ala Tyr Gly Arg Arg Arg Arg
1               5                   10                  15

Gln Arg Arg Arg
            20

<210> SEQ ID NO 341
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: hPhe
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 341

Phe Asp His Phe Arg Trp Xaa Lys Ala Arg Arg Arg Arg Gln Arg
1               5                   10                  15

Arg Arg

<210> SEQ ID NO 342
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 342

Xaa Cys His Phe Arg Trp Xaa Cys Ala Tyr Gly Arg Arg Arg Arg
1               5                   10                  15

Gln Arg Arg Arg
            20

<210> SEQ ID NO 343
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 343

Xaa Cys His Phe Arg Trp Xaa Cys Ala Arg Arg Arg Arg Gln Arg
1               5                   10                  15

Arg Arg

<210> SEQ ID NO 344
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 344

Xaa Cys His Phe Arg Trp Xaa Cys Ala Tyr Gly Arg Arg Arg Arg
1               5                   10                  15

Gln Arg Arg Arg
            20

<210> SEQ ID NO 345
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Ahx
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 345

Xaa Cys His Phe Arg Trp Xaa Cys Ala Arg Arg Arg Arg Arg Gln Arg
1               5                   10                  15

Arg Arg

<210> SEQ ID NO 346
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2
```

<400> SEQUENCE: 346

Xaa Cys His Phe Arg Trp Ala Cys Ala Tyr Gly Arg Arg Arg Arg
1               5                   10                  15

Gln Arg Arg Arg
            20

<210> SEQ ID NO 347
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 347

Xaa Cys His Phe Arg Trp Ala Cys Ala Arg Arg Arg Arg Gln Arg
1               5                   10                  15

Arg Arg

<210> SEQ ID NO 348
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:

```
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 348

Xaa Cys Ala His Phe Arg Trp Xaa Ala Tyr Gly Arg Arg Arg Arg
1               5                   10                  15

Gln Arg Arg Arg
            20

<210> SEQ ID NO 349
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 349

Xaa Cys Ala His Phe Arg Trp Xaa Ala Gly Arg Arg Arg Arg Gln
1               5                   10                  15

Arg Arg Arg

<210> SEQ ID NO 350
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
```

```
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 350

Xaa Cys Ala His Phe Arg Trp Xaa Ala Arg Arg Arg Arg Gln Arg
1               5                   10                  15

Arg Arg

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 351

Xaa Cys Ala His Phe Arg Trp Xaa Ala Ala Tyr Gly Arg Arg Arg
1               5                   10                  15

Arg Gln Arg Arg Arg
            20

<210> SEQ ID NO 352
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 352

Xaa Cys Ala His Phe Arg Trp Xaa Ala Ala Gly Arg Arg Arg Arg
1               5                   10                  15

Gln Arg Arg Arg
            20

<210> SEQ ID NO 353
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 353

Xaa Cys Ala His Phe Arg Trp Xaa Ala Ala Arg Arg Arg Arg Gln
1               5                   10                  15
```

Arg Arg Arg

<210> SEQ ID NO 354
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 354

Xaa Cys Ala His Phe Arg Trp Xaa Xaa Tyr Gly Arg Arg Arg Arg
1               5                   10                  15

Gln Arg Arg Arg
            20

<210> SEQ ID NO 355
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:

```
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 355

Xaa Cys Ala His Phe Arg Trp Xaa Xaa Gly Arg Arg Arg Arg Gln
1               5                   10                  15

Arg Arg Arg

<210> SEQ ID NO 356
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 356

Xaa Cys Ala His Phe Arg Trp Xaa Xaa Arg Arg Arg Arg Gln Arg
1               5                   10                  15

Arg Arg

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
```

```
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 357

Xaa Cys Ala His Phe Arg Trp Xaa Xaa Xaa Tyr Gly Arg Arg Arg
1               5                   10                  15

Arg Gln Arg Arg Arg
            20

<210> SEQ ID NO 358
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 358

Xaa Cys Ala His Phe Arg Trp Xaa Xaa Xaa Gly Arg Arg Arg Arg
1               5                   10                  15

Gln Arg Arg Arg
            20

<210> SEQ ID NO 359
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Pen
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 359

Xaa Cys Ala His Phe Arg Trp Xaa Xaa Xaa Arg Arg Arg Arg Gln
1               5                   10                  15

Arg Arg Arg

<210> SEQ ID NO 360
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 360

Phe Cys His Tyr Arg Trp Ala Cys Ala Tyr Gly Arg Arg Arg Arg
1               5                   10                  15

Gln Arg Arg Arg
                20

<210> SEQ ID NO 361
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 361

Phe Cys His Tyr Arg Trp Ala Cys Ala Arg Arg Arg Arg Gln Arg
1               5                   10                  15

Arg Arg

<210> SEQ ID NO 362
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 362

Phe Cys His Tyr Arg Trp Ala Cys Ala Gly Arg Arg Arg Arg Gln
1               5                   10                  15
```

Arg Arg Arg

```
<210> SEQ ID NO 363
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 363
```

Phe Cys His Tyr Arg Trp Ala Cys Ala Arg Arg Arg Arg Gln Arg
1               5                   10                  15

Arg Arg Arg

```
<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2
```

```
<400> SEQUENCE: 364

Phe Cys His Tyr Arg Trp Ala Cys Ala Ala Tyr Gly Arg Arg Arg
1               5                   10                  15

Arg Gln Arg Arg Arg
            20

<210> SEQ ID NO 365
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 365

Phe Cys His Tyr Arg Trp Ala Cys Ala Ala Arg Arg Arg Arg Gln
1               5                   10                  15

Arg Arg Arg

<210> SEQ ID NO 366
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
```

```
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 366

Phe Cys His Tyr Arg Trp Ala Cys Ala Ala Gly Arg Arg Arg Arg
1               5                   10                  15

Gln Arg Arg Arg
            20

<210> SEQ ID NO 367
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 367

Phe Cys His Tyr Arg Trp Ala Cys Ala Ala Arg Arg Arg Arg Gln
1               5                   10                  15

Arg Arg Arg
            20

<210> SEQ ID NO 368
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
```

```
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 368

Phe Cys His Tyr Arg Trp Ala Cys Xaa Tyr Gly Arg Arg Arg Arg
1               5                   10                  15

Gln Arg Arg Arg
            20

<210> SEQ ID NO 369
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 369

Phe Cys His Tyr Arg Trp Ala Cys Xaa Arg Arg Arg Arg Gln Arg
1               5                   10                  15

Arg Arg

<210> SEQ ID NO 370
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 370

Phe Cys His Tyr Arg Trp Ala Cys Xaa Gly Arg Arg Arg Arg Gln
1               5                   10                  15

Arg Arg Arg

<210> SEQ ID NO 371
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 371

Phe Cys His Tyr Arg Trp Ala Cys Xaa Arg Arg Arg Arg Gln Arg
1               5                   10                  15

Arg Arg Arg

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 372

Phe Cys His Tyr Arg Trp Ala Cys Xaa Xaa Tyr Gly Arg Arg Arg Arg
1               5                   10                  15

Arg Gln Arg Arg Arg
            20

<210> SEQ ID NO 373
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 373

Phe Cys His Tyr Arg Trp Ala Cys Xaa Xaa Arg Arg Arg Arg Arg Gln
1               5                   10                  15

Arg Arg Arg

<210> SEQ ID NO 374
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 374

Phe Cys His Tyr Arg Trp Ala Cys Xaa Xaa Gly Arg Arg Arg Arg
1               5                   10                  15

Gln Arg Arg Arg
            20

<210> SEQ ID NO 375
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 375

Phe Cys His Tyr Arg Trp Ala Cys Xaa Xaa Arg Arg Arg Arg Arg Gln
1               5                   10                  15

Arg Arg Arg Arg
```

<210> SEQ ID NO 376
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 376

Phe Cys His Tyr Arg Trp Ala Cys Thr Ala Tyr Gly Arg Arg Arg
1               5                   10                  15

Arg Gln Arg Arg Arg
            20

<210> SEQ ID NO 377
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES

```
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 377

Phe Cys His Tyr Arg Trp Ala Cys Thr Ala Arg Arg Arg Arg Gln
1               5                   10                  15

Arg Arg Arg

<210> SEQ ID NO 378
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
<220> FEATURE:
<223> OTHER INFORMATION: C-term NH2

<400> SEQUENCE: 378

Phe Cys His Tyr Arg Trp Ala Cys Thr Ala Ala Tyr Gly Arg Arg
1               5                   10                  15

Arg Arg Gln Arg Arg Arg
            20

<210> SEQ ID NO 379
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
<220> FEATURE:
<223> OTHER INFORMATION: C-term NH2

<400> SEQUENCE: 379

Phe Cys His Tyr Arg Trp Ala Cys Thr Ala Ala Arg Arg Arg Arg
1               5                   10                  15

Gln Arg Arg Arg
            20

<210> SEQ ID NO 380
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 380

Phe Cys His Tyr Arg Trp Ala Cys Thr Xaa Tyr Gly Arg Arg Arg
1               5                   10                  15

Arg Gln Arg Arg Arg
            20
```

```
<210> SEQ ID NO 381
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 381

Phe Cys His Tyr Arg Trp Ala Cys Thr Xaa Arg Arg Arg Arg Gln
1               5                   10                  15

Arg Arg Arg

<210> SEQ ID NO 382
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
```

```
<222> LOCATION: (10)..(11)
<223> OTHER INFORMATION: Doc
<220> FEATURE:
<223> OTHER INFORMATION: C-term NH2

<400> SEQUENCE: 382

Phe Cys His Tyr Arg Trp Ala Cys Thr Xaa Xaa Tyr Gly Arg Arg Arg
1               5                   10                  15

Arg Arg Gln Arg Arg Arg
            20

<210> SEQ ID NO 383
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 383

Phe Cys His Tyr Arg Trp Ala Cys Thr Ala Tyr Gly Arg Arg Arg Arg
1               5                   10                  15

Arg Gln Arg Arg Arg Arg
            20

<210> SEQ ID NO 384
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
```

```
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 384

Phe Cys His Tyr Arg Trp Ala Cys Thr Ala Arg Arg Arg Arg Gln
1               5                   10                  15

Arg Arg Arg Arg
            20

<210> SEQ ID NO 385
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
<220> FEATURE:
<223> OTHER INFORMATION: C-term NH2

<400> SEQUENCE: 385

Phe Cys His Tyr Arg Trp Ala Cys Thr Ala Ala Tyr Gly Arg Arg
1               5                   10                  15

Arg Arg Gln Arg Arg Arg Arg
            20

<210> SEQ ID NO 386
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
<220> FEATURE:
<223> OTHER INFORMATION: C-term NH2

<400> SEQUENCE: 386

Phe Cys His Tyr Arg Trp Ala Cys Thr Ala Ala Arg Arg Arg Arg
1               5                   10                  15

Gln Arg Arg Arg Arg
            20

<210> SEQ ID NO 387
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
```

<220> FEATURE:
<223> OTHER INFORMATION: C-term NH2

<400> SEQUENCE: 387

Phe Cys His Tyr Arg Trp Ala Cys Thr Xaa Tyr Gly Arg Arg Arg Arg
1               5                   10                  15

Arg Gln Arg Arg Arg Arg
            20

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 388

Phe Cys His Tyr Arg Trp Ala Cys Thr Xaa Arg Arg Arg Arg Gln
1               5                   10                  15

Arg Arg Arg Arg
            20

<210> SEQ ID NO 389
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:

```
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Doc
<220> FEATURE:
<223> OTHER INFORMATION: C-term NH2

<400> SEQUENCE: 389

Phe Cys His Tyr Arg Trp Ala Cys Thr Xaa Xaa Tyr Gly Arg Arg Arg
1               5                   10                  15

Arg Arg Gln Arg Arg Arg Arg
                20

<210> SEQ ID NO 390
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Doc
<220> FEATURE:
<223> OTHER INFORMATION: C-term NH2

<400> SEQUENCE: 390

Phe Cys His Tyr Arg Trp Ala Cys Thr Xaa Xaa Arg Arg Arg Arg Arg
1               5                   10                  15

Gln Arg Arg Arg Arg
                20

<210> SEQ ID NO 391
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 391

Phe Cys His Tyr Arg Xaa Ala Cys Thr Ala Tyr Gly Arg Arg Arg
1               5                   10                  15

Arg Gln Arg Arg Arg
            20

<210> SEQ ID NO 392
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
```

```
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 392

Phe Cys His Tyr Arg Xaa Ala Cys Thr Ala Tyr Gly Arg Arg Arg
 1               5                  10                  15

Arg Gln Arg Arg Arg Arg
                20

<210> SEQ ID NO 393
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 393

Phe Cys His Tyr Arg Xaa Ala Cys Thr Ala Arg Arg Arg Arg Gln
 1               5                  10                  15

Arg Arg Arg

<210> SEQ ID NO 394
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
```

```
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
<220> FEATURE:
<223> OTHER INFORMATION: C-term NH2

<400> SEQUENCE: 394

Phe Cys His Tyr Arg Xaa Ala Cys Thr Ala Ala Tyr Gly Arg Arg Arg
1               5                   10                  15

Arg Arg Gln Arg Arg Arg
            20

<210> SEQ ID NO 395
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Beta-Ala
```

```
<220> FEATURE:
<223> OTHER INFORMATION: C-term NH2

<400> SEQUENCE: 395

Phe Cys His Tyr Arg Xaa Ala Cys Thr Ala Ala Arg Arg Arg Arg
1               5                   10                  15

Gln Arg Arg Arg
            20

<210> SEQ ID NO 396
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 396

Phe Cys His Tyr Arg Xaa Ala Cys Thr Xaa Tyr Gly Arg Arg Arg
1               5                   10                  15

Arg Gln Arg Arg Arg
            20

<210> SEQ ID NO 397
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
```

```
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 397

Phe Cys His Tyr Arg Xaa Ala Cys Thr Xaa Tyr Gly Arg Arg Arg
1               5                   10                  15

Arg Gln Arg Arg Arg Arg
            20

<210> SEQ ID NO 398
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(10)
<223> OTHER INFORMATION: Doc
<220> FEATURE:
<223> OTHER INFORMATION: C-term NH2

<400> SEQUENCE: 398
```

Phe Cys His Tyr Arg Xaa Ala Cys Thr Xaa Arg Arg Arg Arg Gln
1               5                   10                  15

Arg Arg Arg

<210> SEQ ID NO 399
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Doc
<220> FEATURE:
<223> OTHER INFORMATION: C-term NH2

<400> SEQUENCE: 399

Phe Cys His Tyr Arg Xaa Ala Cys Thr Xaa Xaa Tyr Gly Arg Arg
1               5                   10                  15

Arg Arg Gln Arg Arg Arg
            20

<210> SEQ ID NO 400
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-(Et)Tyr
<220> FEATURE:
<221> NAME/KEY: MOD_RES
<222> LOCATION: (5)..(5)

```
<223> OTHER INFORMATION: hArg
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Cys
<220> FEATURE:
<221> NAME/KEY: MOD_RES
<222> LOCATION: (10)..(11)
<223> OTHER INFORMATION: Doc
<220> FEATURE:
<223> OTHER INFORMATION: C-term NH2

<400> SEQUENCE: 400

Phe Cys His Tyr Arg Xaa Ala Cys Thr Xaa Xaa Arg Arg Arg Arg
1               5                   10                  15

Gln Arg Arg Arg
            20

<210> SEQ ID NO 401
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 401

Xaa Cys Ala His Phe Arg Trp Gly Cys Ala Tyr Gly Arg Arg Arg
1               5                   10                  15

Arg Gln Arg Arg Arg
            20

<210> SEQ ID NO 402
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(9)
<223> OTHER INFORMATION: Cyclic
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (10)..(10)
<223> OTHER INFORMATION: Beta-Ala
<220> FEATURE:
<223> OTHER INFORMATION: C-term NH2

<400> SEQUENCE: 402

Xaa Cys Ala His Phe Arg Trp Gly Cys Ala Arg Arg Arg Arg Gln
1               5                   10                  15

Arg Arg Arg

<210> SEQ ID NO 403
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 403

Xaa Cys His Phe Arg Trp Xaa Cys Ala Tyr Gly Arg Arg Arg Arg
1               5                   10                  15

Gln Arg Arg Arg
                20

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 404

Xaa Cys His Phe Arg Trp Xaa Cys Ala Arg Arg Arg Arg Gln Arg
1               5                   10                  15

Arg Arg

<210> SEQ ID NO 405
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 405

Xaa Cys His Phe Arg Trp Xaa Cys Ala Ala Tyr Gly Arg Arg Arg
1               5                   10                  15

Arg Gln Arg Arg Arg
            20

<210> SEQ ID NO 406
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
```

```
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 406

Xaa Cys His Phe Arg Trp Xaa Cys Ala Ala Arg Arg Arg Arg Gln
1               5                   10                  15

Arg Arg Arg

<210> SEQ ID NO 407
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 407

Xaa Cys His Phe Arg Trp Xaa Cys Ala Tyr Gly Arg Arg Arg Arg
1               5                   10                  15

Gln Arg Arg Arg Arg
            20

<210> SEQ ID NO 408
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 408

Xaa Cys His Phe Arg Trp Xaa Cys Ala Arg Arg Arg Arg Gln Arg
1               5                   10                  15

Arg Arg Arg

<210> SEQ ID NO 409
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 409

Xaa Cys His Phe Arg Trp Xaa Cys Ala Ala Tyr Gly Arg Arg Arg
1               5                   10                  15

Arg Gln Arg Arg Arg Arg
            20

<210> SEQ ID NO 410
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 410

Xaa Cys His Phe Arg Trp Xaa Cys Ala Ala Arg Arg Arg Arg Gln
1               5                   10                  15

Arg Arg Arg Arg
            20

<210> SEQ ID NO 411
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 411

Xaa Cys His Phe Arg Trp Xaa Cys Xaa Tyr Gly Arg Arg Arg Arg
1               5                   10                  15

Gln Arg Arg Arg
            20

<210> SEQ ID NO 412
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
```

<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 412

Xaa Cys His Phe Arg Trp Xaa Cys Xaa Arg Arg Arg Arg Gln Arg
1               5                   10                  15

Arg Arg

<210> SEQ ID NO 413
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 413

Xaa Cys His Phe Arg Trp Xaa Cys Xaa Xaa Tyr Gly Arg Arg Arg
1               5                   10                  15

Arg Gln Arg Arg Arg
            20

<210> SEQ ID NO 414
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)

```
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 414

Xaa Cys His Phe Arg Trp Xaa Cys Xaa Xaa Arg Arg Arg Arg Gln
1               5                  10                  15

Arg Arg Arg

<210> SEQ ID NO 415
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 415

Xaa Cys His Phe Arg Trp Xaa Cys Xaa Tyr Gly Arg Arg Arg Arg
1               5                  10                  15

Gln Arg Arg Arg Arg
            20

<210> SEQ ID NO 416
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 416

Xaa Cys His Phe Arg Trp Xaa Cys Xaa Arg Arg Arg Arg Gln Arg
1               5                   10                  15

Arg Arg Arg

<210> SEQ ID NO 417
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Apn
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 417

Xaa Cys His Phe Arg Trp Xaa Cys Xaa Xaa Tyr Gly Arg Arg Arg
1               5                   10                  15

Arg Gln Arg Arg Arg Arg
            20

<210> SEQ ID NO 418
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
```

```
<223> OTHER INFORMATION: Apn
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 418

Xaa Cys His Phe Arg Trp Xaa Cys Xaa Xaa Arg Arg Arg Arg Gln
1               5                   10                  15

Arg Arg Arg Arg
            20

<210> SEQ ID NO 419
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 419

Xaa Cys Leu His Phe Arg Trp Cys Ala Tyr Gly Arg Arg Arg Arg
1               5                   10                  15

Gln Arg Arg Arg
            20

<210> SEQ ID NO 420
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
```

```
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 420

Xaa Cys Leu His Phe Arg Trp Cys Ala Arg Arg Arg Arg Gln Arg
 1               5                  10                 15

Arg Arg

<210> SEQ ID NO 421
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 421

Xaa Cys Leu His Phe Arg Trp Cys Ala Ala Tyr Gly Arg Arg Arg
 1               5                  10                 15

Arg Gln Arg Arg Arg
                20

<210> SEQ ID NO 422
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
```

```
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 422

Xaa Cys Leu His Phe Arg Trp Cys Ala Ala Arg Arg Arg Arg Arg Gln
1               5                   10                  15

Arg Arg Arg

<210> SEQ ID NO 423
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 423

Xaa Cys Leu His Phe Arg Trp Cys Xaa Tyr Gly Arg Arg Arg Arg
1               5                   10                  15

Gln Arg Arg Arg
            20

<210> SEQ ID NO 424
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
```

```
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 424

Xaa Cys Leu His Phe Arg Trp Cys Xaa Arg Arg Arg Arg Gln Arg
1               5                   10                  15

Arg Arg

<210> SEQ ID NO 425
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 425

Xaa Cys Leu His Phe Arg Trp Cys Xaa Xaa Tyr Gly Arg Arg Arg
1               5                   10                  15

Arg Gln Arg Arg Arg
            20

<210> SEQ ID NO 426
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 426

Xaa Cys Leu His Phe Arg Trp Cys Xaa Xaa Arg Arg Arg Arg Gln
1               5                   10                  15

Arg Arg Arg

<210> SEQ ID NO 427
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 427

Xaa Cys Leu His Phe Arg Trp Cys Ala Tyr Gly Arg Arg Arg Arg
1               5                   10                  15

Gln Arg Arg Arg Arg
            20

<210> SEQ ID NO 428
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
```

```
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 428

Xaa Cys Leu His Phe Arg Trp Cys Ala Arg Arg Arg Arg Gln Arg
1               5                  10                 15

Arg Arg Arg

<210> SEQ ID NO 429
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 429

Xaa Cys Leu His Phe Arg Trp Cys Ala Ala Tyr Gly Arg Arg Arg
1               5                  10                 15

Arg Gln Arg Arg Arg Arg
            20

<210> SEQ ID NO 430
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 430

Xaa Cys Leu His Phe Arg Trp Cys Ala Ala Arg Arg Arg Arg Gln
1               5                   10                  15

Arg Arg Arg Arg
            20

<210> SEQ ID NO 431
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 431

Xaa Cys Leu His Phe Arg Trp Cys Xaa Tyr Gly Arg Arg Arg Arg
1               5                   10                  15

Gln Arg Arg Arg Arg
            20

<210> SEQ ID NO 432
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 432

Xaa Cys Leu His Phe Arg Trp Cys Xaa Arg Arg Arg Arg Gln Arg
1               5                   10                  15

Arg Arg Arg

<210> SEQ ID NO 433
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 433

Xaa Cys Leu His Phe Arg Trp Cys Xaa Xaa Tyr Gly Arg Arg Arg
1               5                   10                  15

Arg Gln Arg Arg Arg Arg
            20

<210> SEQ ID NO 434
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Leu
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 434

Xaa Cys Leu His Phe Arg Trp Cys Xaa Xaa Arg Arg Arg Arg Gln
1               5                   10                  15

Arg Arg Arg Arg
            20

<210> SEQ ID NO 435
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 435

Xaa Cys Xaa His Phe Arg Trp Cys Ala Tyr Gly Arg Arg Arg Arg
1               5                   10                  15

Gln Arg Arg Arg
            20

<210> SEQ ID NO 436
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 436

Xaa Cys Xaa His Phe Arg Trp Cys Ala Arg Arg Arg Arg Gln Arg
1               5                   10                  15

Arg Arg

<210> SEQ ID NO 437
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 437

Xaa Cys Xaa His Phe Arg Trp Cys Ala Ala Tyr Gly Arg Arg Arg
1               5                   10                  15

Arg Gln Arg Arg Arg
            20

<210> SEQ ID NO 438

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 438

Xaa Cys Xaa His Phe Arg Trp Cys Ala Ala Arg Arg Arg Arg Gln
1               5                   10                  15

Arg Arg Arg

<210> SEQ ID NO 439
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 439

Xaa Cys Xaa His Phe Arg Trp Cys Xaa Tyr Gly Arg Arg Arg Arg
1               5                   10                  15

Gln Arg Arg Arg
            20
```

```
<210> SEQ ID NO 440
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 440

Xaa Cys Xaa His Phe Arg Trp Cys Xaa Arg Arg Arg Arg Gln Arg
1               5                   10                  15

Arg Arg

<210> SEQ ID NO 441
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 441

Xaa Cys Xaa His Phe Arg Trp Cys Xaa Xaa Tyr Gly Arg Arg Arg
1               5                   10                  15

Arg Gln Arg Arg Arg
```

20

<210> SEQ ID NO 442
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 442

Xaa Cys Xaa His Phe Arg Trp Cys Xaa Xaa Arg Arg Arg Arg Arg Gln
1               5                   10                  15

Arg Arg Arg

<210> SEQ ID NO 443
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 443

Xaa Cys Xaa His Phe Arg Trp Cys Ala Tyr Gly Arg Arg Arg Arg Arg
1               5                   10                  15

Gln Arg Arg Arg Arg
            20

<210> SEQ ID NO 444
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 444

Xaa Cys Xaa His Phe Arg Trp Cys Ala Arg Arg Arg Arg Gln Arg
1               5                   10                  15

Arg Arg Arg

<210> SEQ ID NO 445
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 445

```
Xaa Cys Xaa His Phe Arg Trp Cys Ala Ala Tyr Gly Arg Arg Arg Arg
1               5                   10                  15

Arg Gln Arg Arg Arg Arg
            20

<210> SEQ ID NO 446
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 446

Xaa Cys Xaa His Phe Arg Trp Cys Ala Ala Arg Arg Arg Arg Arg Gln
1               5                   10                  15

Arg Arg Arg Arg
            20

<210> SEQ ID NO 447
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2
```

<400> SEQUENCE: 447

Xaa Cys Xaa His Phe Arg Trp Cys Xaa Tyr Gly Arg Arg Arg Arg
1               5                   10                  15

Gln Arg Arg Arg Arg
                20

<210> SEQ ID NO 448
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 448

Xaa Cys Xaa His Phe Arg Trp Cys Xaa Arg Arg Arg Arg Gln Arg
1               5                   10                  15

Arg Arg Arg

<210> SEQ ID NO 449
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc

```
<220> FEATURE:
<223> OTHER INFORMATION: C-term NH2

<400> SEQUENCE: 449

Xaa Cys Xaa His Phe Arg Trp Cys Xaa Xaa Tyr Gly Arg Arg Arg
1               5                   10                  15

Arg Gln Arg Arg Arg Arg
            20

<210> SEQ ID NO 450
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (3)..(3)
<223> OTHER INFORMATION: D-Cha
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 450

Xaa Cys Xaa His Phe Arg Trp Cys Xaa Xaa Arg Arg Arg Arg Gln
1               5                   10                  15

Arg Arg Arg Arg
            20

<210> SEQ ID NO 451
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
```

```
<223> OTHER INFORMATION: Beta-Ala
<220> FEATURE:
<223> OTHER INFORMATION: C-term NH2

<400> SEQUENCE: 451

Xaa Cys His Phe Arg Trp Xaa Cys Ala Tyr Gly Arg Arg Arg Arg
1               5                  10                  15

Gln Arg Arg Arg
            20

<210> SEQ ID NO 452
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 452

Xaa Cys His Phe Arg Trp Xaa Cys Ala Arg Arg Arg Arg Gln Arg
1               5                  10                  15

Arg Arg

<210> SEQ ID NO 453
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
```

```
<223> OTHER INFORMATION: C-term NH2

<400> SEQUENCE: 453

Xaa Cys His Phe Arg Trp Xaa Cys Ala Ala Tyr Gly Arg Arg Arg Arg
1               5                   10                  15

Arg Gln Arg Arg Arg
            20

<210> SEQ ID NO 454
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 454

Xaa Cys His Phe Arg Trp Xaa Cys Ala Ala Arg Arg Arg Arg Arg Gln
1               5                   10                  15

Arg Arg Arg

<210> SEQ ID NO 455
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2
```

-continued

```
<400> SEQUENCE: 455

Xaa Cys His Phe Arg Trp Xaa Cys Ala Tyr Gly Arg Arg Arg Arg
1               5                   10                  15

Gln Arg Arg Arg Arg
            20

<210> SEQ ID NO 456
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Beta-Ala
<220> FEATURE:
<223> OTHER INFORMATION: C-term NH2

<400> SEQUENCE: 456

Xaa Cys His Phe Arg Trp Xaa Cys Ala Arg Arg Arg Arg Gln Arg
1               5                   10                  15

Arg Arg Arg

<210> SEQ ID NO 457
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 457
```

```
Xaa Cys His Phe Arg Trp Xaa Cys Ala Ala Tyr Gly Arg Arg Arg Arg
1               5                   10                  15

Arg Gln Arg Arg Arg Arg
            20
```

```
<210> SEQ ID NO 458
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Beta-Ala
<220> FEATURE:
<223> OTHER INFORMATION: C-term NH2

<400> SEQUENCE: 458
```

```
Xaa Cys His Phe Arg Trp Xaa Cys Ala Ala Arg Arg Arg Arg Arg Gln
1               5                   10                  15

Arg Arg Arg Arg
            20
```

```
<210> SEQ ID NO 459
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 459
```

```
Xaa Cys His Phe Arg Trp Xaa Cys Xaa Tyr Gly Arg Arg Arg Arg Arg
```

```
1               5                   10                  15

Gln Arg Arg Arg
            20

<210> SEQ ID NO 460
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 460

Xaa Cys His Phe Arg Trp Xaa Cys Xaa Arg Arg Arg Arg Gln Arg
1               5                   10                  15

Arg Arg

<210> SEQ ID NO 461
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 461

Xaa Cys His Phe Arg Trp Xaa Cys Xaa Xaa Tyr Gly Arg Arg Arg
1               5                   10                  15
```

-continued

Arg Gln Arg Arg Arg
            20

<210> SEQ ID NO 462
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 462

Xaa Cys His Phe Arg Trp Xaa Cys Xaa Xaa Arg Arg Arg Arg Arg Gln
1               5                   10                  15

Arg Arg Arg

<210> SEQ ID NO 463
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 463

Xaa Cys His Phe Arg Trp Xaa Cys Xaa Tyr Gly Arg Arg Arg Arg
1               5                   10                  15

Gln Arg Arg Arg Arg
            20

```
<210> SEQ ID NO 464
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(9)
<223> OTHER INFORMATION: Doc
<220> FEATURE:
<223> OTHER INFORMATION: C-term NH2

<400> SEQUENCE: 464

Xaa Cys His Phe Arg Trp Xaa Cys Xaa Arg Arg Arg Arg Gln Arg
1               5                   10                  15

Arg Arg Arg

<210> SEQ ID NO 465
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 465

Xaa Cys His Phe Arg Trp Xaa Cys Xaa Xaa Tyr Gly Arg Arg Arg Arg
1               5                   10                  15

Arg Gln Arg Arg Arg Arg
            20
```

```
<210> SEQ ID NO 466
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Gaba
<220> FEATURE:
<221> NAME/KEY: MOD_RES
<222> LOCATION: (9)..(10)
<223> OTHER INFORMATION: Doc
<220> FEATURE:
<223> OTHER INFORMATION: C-term NH2

<400> SEQUENCE: 466

Xaa Cys His Phe Arg Trp Xaa Cys Xaa Xaa Arg Arg Arg Arg Arg Gln
1               5                   10                  15

Arg Arg Arg Arg
            20

<210> SEQ ID NO 467
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-4-Br-Phe
<220> FEATURE:
<223> OTHER INFORMATION: C-term NH2

<400> SEQUENCE: 467

Cys Glu His Phe Arg Trp Gly Cys Pro Pro Lys Asp
1               5                   10

<210> SEQ ID NO 468
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
```

```
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 468

Cys Glu His Xaa Arg Trp Ala Cys Pro Pro Lys Asp
1               5                   10

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<223> OTHER INFORMATION: C-term NH2

<400> SEQUENCE: 469

Cys Glu His Xaa Arg Xaa Ala Cys Pro Pro Lys Asp
1               5                   10

<210> SEQ ID NO 470
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 1-Nal
<220> FEATURE:
<223> OTHER INFORMATION: C-term NH2

<400> SEQUENCE: 470

Cys Glu His Xaa Arg Xaa Ala Cys Pro Pro Lys Asp
1               5                   10

<210> SEQ ID NO 471
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: Bal
<220> FEATURE:
<223> OTHER INFORMATION: C-term NH2

<400> SEQUENCE: 471

Cys Glu His Xaa Arg Xaa Ala Cys Pro Pro Lys Asp
1               5                   10

<210> SEQ ID NO 472
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
<221> NAME/KEY: MOD_RES
<222> LOCATION: (7)..(7)
<223> OTHER INFORMATION: Beta-Ala
<220> FEATURE:
<223> OTHER INFORMATION: C-term NH2

<400> SEQUENCE: 472

Cys Glu His Xaa Arg Xaa Ala Cys Pro Pro Lys Asp
1               5                   10

<210> SEQ ID NO 473
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (1)..(8)
<223> OTHER INFORMATION: Cyclic
<220> FEATURE:
<221> NAME/KEY: MOD_RES
<222> LOCATION: (4)..(4)
<223> OTHER INFORMATION: D-2-Nal
<220> FEATURE:
<221> NAME/KEY: MOD_RES
<222> LOCATION: (6)..(6)
<223> OTHER INFORMATION: 2-Nal
<220> FEATURE:
```

```
<221> NAME/KEY: MOD_RES
<222> LOCATION: (7)..(7)
<223> OTHER INFORMATION: Aib
<220> FEATURE:
<223> OTHER INFORMATION: C-term NH2

<400> SEQUENCE: 473

Cys Glu His Xaa Arg Xaa Xaa Cys Pro Pro Lys Asp
1               5                   10

<210> SEQ ID NO 474
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Cys-D-Ala))-His
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term NH2

<400> SEQUENCE: 474

His Phe Arg Trp Cys
1               5

<210> SEQ ID NO 475
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(hCys-D-Ala))-His
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term NH2

<400> SEQUENCE: 475

His Phe Arg Trp Cys
1               5

<210> SEQ ID NO 476
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
```

```
<220> FEATURE:
<221> NAME/KEY: MOD_RES
<222> LOCATION: (1)..(1)
<223> OTHER INFORMATION: Hydantoin(C(O)-(Cys-D-Ala))-His
<220> FEATURE:
<221> NAME/KEY: MOD_RES
<222> LOCATION: (2)..(2)
<223> OTHER INFORMATION: D-2-Nal
<220> FEATURE:
<223> OTHER INFORMATION: C-term NH2

<400> SEQUENCE: 476

His Xaa Arg Trp Cys
1               5

<210> SEQ ID NO 477
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(hCys-D-Ala))-His
<220> FEATURE:
<221> NAME/KEY: MOD_RES
<222> LOCATION: (2)..(2)
<223> OTHER INFORMATION: D-2-Nal
<220> FEATURE:
<223> OTHER INFORMATION: C-term NH2

<400> SEQUENCE: 477

His Xaa Arg Trp Cys
1               5

<210> SEQ ID NO 478
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-D-Ala))-His
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term NH2

<400> SEQUENCE: 478

His Phe Arg Trp Lys
1               5

<210> SEQ ID NO 479
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-D-Ala))-His
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-term NH2

<400> SEQUENCE: 479

His Phe Arg Trp Xaa
1               5

<210> SEQ ID NO 480
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-D-Ala))-His
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (5)..(5)
<223> OTHER INFORMATION: Dab
<220> FEATURE:
<223> OTHER INFORMATION: C-term NH2

<400> SEQUENCE: 480

His Phe Arg Trp Xaa
1               5

<210> SEQ ID NO 481
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-D-Ala))-His
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
```

```
<222> LOCATION: (5)..(5)
<223> OTHER INFORMATION: Dap
<220> FEATURE:
<223> OTHER INFORMATION: C-term NH2

<400> SEQUENCE: 481

His Phe Arg Trp Xaa
1               5

<210> SEQ ID NO 482
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-His))-D-2-Nal
<220> FEATURE:
<223> OTHER INFORMATION: C-term NH2

<400> SEQUENCE: 482

Xaa Arg Trp Lys
1

<210> SEQ ID NO 483
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-His))-D-Phe
<220> FEATURE:
<223> OTHER INFORMATION: C-term NH2

<400> SEQUENCE: 483

Phe Arg Trp Lys
1

<210> SEQ ID NO 484
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A3c))-D-Phe
<220> FEATURE:
<223> OTHER INFORMATION: C-term NH2

<400> SEQUENCE: 484
```

Phe Arg Trp Lys
1

<210> SEQ ID NO 485
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A5c))-D-Phe
<220> FEATURE:
<223> OTHER INFORMATION: C-term NH2

<400> SEQUENCE: 485

Phe Arg Trp Lys
1

<210> SEQ ID NO 486
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A6c))-D-Phe
<220> FEATURE:
<223> OTHER INFORMATION: C-term NH2

<400> SEQUENCE: 486

Phe Arg Trp Lys
1

<210> SEQ ID NO 487
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A3c))-D-2-Nal
<220> FEATURE:
<223> OTHER INFORMATION: C-term NH2

<400> SEQUENCE: 487

Xaa Arg Trp Lys
1

<210> SEQ ID NO 488
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A5c))-D-2-Nal
<220> FEATURE:
<223> OTHER INFORMATION: C-term NH2

<400> SEQUENCE: 488

Xaa Arg Trp Lys
1

<210> SEQ ID NO 489
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-A6c))-D-2-Nal
<220> FEATURE:
<223> OTHER INFORMATION: C-term NH2

<400> SEQUENCE: 489

Xaa Arg Trp Lys
1

<210> SEQ ID NO 490
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-Aic))-D-Phe
<220> FEATURE:
<223> OTHER INFORMATION: C-term NH2

<400> SEQUENCE: 490

Phe Arg Trp Lys
1

<210> SEQ ID NO 491
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
```

```
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-Apc))-D-Phe
<220> FEATURE:
<223> OTHER INFORMATION: C-term NH2

<400> SEQUENCE: 491

Phe Arg Trp Lys
1

<210> SEQ ID NO 492
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-Aic))-D-2-Nal
<220> FEATURE:
<223> OTHER INFORMATION: C-term NH2

<400> SEQUENCE: 492

Xaa Arg Trp Lys
1

<210> SEQ ID NO 493
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Asp-Apc))-D-2-Nal
<220> FEATURE:
<223> OTHER INFORMATION: C-term NH2

<400> SEQUENCE: 493

Xaa Arg Trp Lys
1

<210> SEQ ID NO 494
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-D-Ala))-His
<220> FEATURE:
<221> NAME/KEY: MOD_RES
```

```
<222> LOCATION: (2)..(2)
<223> OTHER INFORMATION: D-Phe
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-term NH2

<400> SEQUENCE: 494

His Phe Arg Trp Xaa
1               5

<210> SEQ ID NO 495
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-D-Ala))-His
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (5)..(5)
<223> OTHER INFORMATION: Dab
<220> FEATURE:
<223> OTHER INFORMATION: C-term NH2

<400> SEQUENCE: 495

His Phe Arg Trp Xaa
1               5

<210> SEQ ID NO 496
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-D-Ala))-His
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (5)..(5)
<223> OTHER INFORMATION: Dap
<220> FEATURE:
<223> OTHER INFORMATION: C-term NH2

<400> SEQUENCE: 496

His Phe Arg Trp Xaa
1               5
```

```
<210> SEQ ID NO 497
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-D-Ala))-His
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term NH2

<400> SEQUENCE: 497

His Phe Arg Trp Lys
1               5

<210> SEQ ID NO 498
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-His))-D-Phe
<220> FEATURE:
<221> NAME/KEY: MOD_RES
<222> LOCATION: (4)..(4)
<223> OTHER INFORMATION: Dap
<220> FEATURE:
<223> OTHER INFORMATION: C-term NH2

<400> SEQUENCE: 498

Phe Arg Trp Xaa
1

<210> SEQ ID NO 499
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(4)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Glu-His))-D-Phe
<220> FEATURE:
<223> OTHER INFORMATION: C-term NH2

<400> SEQUENCE: 499

Phe Arg Trp Lys
1
```

```
<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Arg-Gly))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 500

Cys Glu His Phe Arg Trp Cys
1               5

<210> SEQ ID NO 501
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Gly))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 501

Cys Glu His Phe Arg Trp Cys
1               5

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Gly))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2
```

```
<400> SEQUENCE: 502

Cys Glu His Phe Arg Trp Cys
1               5

<210> SEQ ID NO 503
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 503

Cys Ala His Phe Arg Trp Cys
1               5

<210> SEQ ID NO 504
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 504

Cys Ala His Phe Arg Trp Cys
1               5

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
```

<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Pen
<220> FEATURE:
<223> OTHER INFORMATION: C-term NH2

<400> SEQUENCE: 505

Cys Ala His Phe Arg Trp Xaa
1               5

<210> SEQ ID NO 506
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Pen
<220> FEATURE:
<223> OTHER INFORMATION: C-term NH2

<400> SEQUENCE: 506

Cys Ala His Phe Arg Trp Xaa
1               5

<210> SEQ ID NO 507
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ala-Gly))-Cys
<220> FEATURE:

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 507

Cys Ala His Phe Arg Trp Cys
1               5

<210> SEQ ID NO 508
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Ala-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 508

Cys Ala His Phe Arg Trp Cys
1               5

<210> SEQ ID NO 509
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Aib-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 509

Cys Ala His Phe Arg Trp Cys
1               5
```

```
<210> SEQ ID NO 510
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Val-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 510

Cys Ala His Phe Arg Trp Cys
1               5

<210> SEQ ID NO 511
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ile-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 511

Cys Ala His Phe Arg Trp Cys
1               5

<210> SEQ ID NO 512
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
```

```
<223> OTHER INFORMATION: Hydantoin(C(O)-(Leu-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 512

Cys Ala His Phe Arg Trp Cys
1               5

<210> SEQ ID NO 513
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Gly))-Cys
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 513

Cys Glu His Xaa Arg Trp Cys
1               5

<210> SEQ ID NO 514
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Gly))-Cys
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 514

Cys Glu His Xaa Arg Trp Cys
1               5

<210> SEQ ID NO 515
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Arg-Gly))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 515

Cys Glu His Phe Arg Trp Cys
1               5

<210> SEQ ID NO 516
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Arg-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 516

Cys Ala His Phe Arg Trp Cys
1               5

<210> SEQ ID NO 517
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Arg-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
```

<223> OTHER INFORMATION: C-term NH2

<400> SEQUENCE: 517

Cys Ala His Phe Arg Trp Cys
1               5

<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Arg-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 518

Cys Ala His Xaa Arg Trp Cys
1               5

<210> SEQ ID NO 519
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Arg-Gly))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 519

Cys Ala His Xaa Arg Trp Cys
1               5

<210> SEQ ID NO 520
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ala-Nle))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 520

Cys Glu His Phe Arg Trp Cys
1               5

<210> SEQ ID NO 521
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Val-Nle))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 521

Cys Glu His Phe Arg Trp Cys
1               5

<210> SEQ ID NO 522
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Nle))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 522

Cys Glu His Phe Arg Trp Cys
1               5

<210> SEQ ID NO 523
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(A6c-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 523

Cys Ala His Phe Arg Trp Cys
1               5

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 524

Cys Ala His Phe Arg Trp Cys
1               5

<210> SEQ ID NO 525
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ala-Nle))-Cys
<220> FEATURE:
<221> NAME/KEY: MOD_RES
```

```
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 525

Cys Ala His Phe Arg Trp Cys
1               5

<210> SEQ ID NO 526
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Ala-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 526

Cys Ala His Phe Arg Trp Cys
1               5

<210> SEQ ID NO 527
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Val-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 527

Cys Ala His Phe Arg Trp Cys
1               5
```

```
<210> SEQ ID NO 528
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Leu-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 528

Cys Ala His Phe Arg Trp Cys
1               5

<210> SEQ ID NO 529
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Cha-Nle))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 529

Cys Ala His Phe Arg Trp Cys
1               5

<210> SEQ ID NO 530
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Aib-Nle))-Cys
```

```
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 530

Cys Ala His Phe Arg Trp Cys
1               5

<210> SEQ ID NO 531
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Arg))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 531

Cys Glu His Phe Arg Trp Cys
1               5

<210> SEQ ID NO 532
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Arg))-Cys
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 532

Cys Glu His Xaa Arg Trp Cys
1               5

<210> SEQ ID NO 533
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Arg))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 533

Cys Ala His Phe Arg Trp Cys
1               5

<210> SEQ ID NO 534
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Arg))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 534

Cys Ala His Xaa Arg Trp Cys
1               5

<210> SEQ ID NO 535
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-D-Arg))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2
```

```
<400> SEQUENCE: 535

Cys Glu His Phe Arg Trp Cys
1               5

<210> SEQ ID NO 536
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-D-Arg))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 536

Cys Ala His Phe Arg Trp Cys
1               5

<210> SEQ ID NO 537
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-D-Arg))-Cys
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: D-2-Nal
<220> FEATURE:
<223> OTHER INFORMATION: C-term NH2

<400> SEQUENCE: 537

Cys Ala His Xaa Arg Trp Cys
1               5

<210> SEQ ID NO 538
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: DOMAIN
<222> LOCATION: (1)..(7)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Ala))-Cys
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-term NH2

<400> SEQUENCE: 538

Cys Glu His Phe Arg Trp Cys
1               5

<210> SEQ ID NO 539
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Nle-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 539

Ala His Phe Arg Trp Cys
1               5

<210> SEQ ID NO 540
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ala-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 540

Ala His Phe Arg Trp Cys
1               5

<210> SEQ ID NO 541
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(D-Ala-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 541

Ala His Phe Arg Trp Cys
1               5

<210> SEQ ID NO 542
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Aib-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 542

Ala His Phe Arg Trp Cys
1               5

<210> SEQ ID NO 543
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Val-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 543

Ala His Phe Arg Trp Cys
1               5
```

```
<210> SEQ ID NO 544
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Abu-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 544

Ala His Phe Arg Trp Cys
1               5

<210> SEQ ID NO 545
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Leu-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 545

Ala His Phe Arg Trp Cys
1               5

<210> SEQ ID NO 546
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Ile-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2
```

-continued

<400> SEQUENCE: 546

Ala His Phe Arg Trp Cys
1               5

<210> SEQ ID NO 547
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Cha-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 547

Ala His Phe Arg Trp Cys
1               5

<210> SEQ ID NO 548
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(A6c-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 548

Ala His Phe Arg Trp Cys
1               5

<210> SEQ ID NO 549
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Phe-Cys))-D-Ala
<220> FEATURE:

```
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 549

Ala His Phe Arg Trp Cys
1               5

<210> SEQ ID NO 550
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Cys))-D-Ala
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 550

Ala His Phe Arg Trp Cys
1               5

<210> SEQ ID NO 551
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DOMAIN
<222> LOCATION: (1)..(6)
<223> OTHER INFORMATION: Cyclic
<220> FEATURE:
<221> NAME/KEY: MOD_RES
<222> LOCATION: (1)..(1)
<223> OTHER INFORMATION: Hydantoin(C(O)-(Gly-Cys))-Glu
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-term NH2

<400> SEQUENCE: 551

Glu His Phe Arg Trp Cys
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
```

```
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 552

Tyr Arg Cys Ala His Phe Arg Trp Cys
1               5

<210> SEQ ID NO 553
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 2-Nal
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 553

Xaa Arg Cys Ala His Phe Arg Trp Cys
1               5

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 1-Nal
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
```

```
<223> OTHER INFORMATION: C-term NH2

<400> SEQUENCE: 554

Xaa Arg Cys Ala His Phe Arg Trp Cys
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 555

Phe Arg Cys Ala His Phe Arg Trp Cys
1               5

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 556

Trp Arg Cys Ala His Phe Arg Trp Cys
1               5

<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: Pff
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 557

Xaa Arg Cys Ala His Phe Arg Trp Cys
1               5

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 558

His Arg Cys Ala His Phe Arg Trp Cys
1               5

<210> SEQ ID NO 559
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: DOMAIN
<222> LOCATION: (3)..(9)
<223> OTHER INFORMATION: Cyclic
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-term NH2

<400> SEQUENCE: 559
```

```
His Arg Cys Ala His Phe Arg Trp Cys
1             5
```